United States Patent
Kusumoto et al.

(10) Patent No.: US 6,746,728 B1
(45) Date of Patent: Jun. 8, 2004

(54) COMPOUND HAVING TETRAHYDRONAPHTHALENE SKELETON AND LIQUID CRYSTAL COMPOSITION CONTAINING SAME

(75) Inventors: Tetsuo Kusumoto, Kitaadachi-gun (JP); Yoshitaka Saito, Iwatsuki (JP); Makoto Negishi, Tokyo (JP); Yutaka Nagashima, Ageo (JP); Sadao Takehara, Sakura (JP); Haruyoshi Takatsu, Tokyo (JP); Gerwald Grahe, Berlin (DE); Rainer Bruno Frings, Berlin (DE); Cornelia Pithart, Berlin (DE)

(73) Assignee: Dainippon Ink and Chemicals, Inc., Tokyo (JP)

( * ) Notice: Subject to any disclaimer, the term of this patent is extended or adjusted under 35 U.S.C. 154(b) by 0 days.

(21) Appl. No.: 09/926,838
(22) PCT Filed: Sep. 10, 1999
(86) PCT No.: PCT/JP99/04919
§ 371 (c)(1), (2), (4) Date: Dec. 28, 2001
(87) PCT Pub. No.: WO01/00548
PCT Pub. Date: Jan. 4, 2001

(30) Foreign Application Priority Data

Jun. 30, 1999 (JP) .......................................... 11/184786
Jul. 6, 1999 (JP) .......................................... 11/191670

(51) Int. Cl.[7] ..................... C09K 19/32; C07C 69/753; C07C 23/18; C07C 25/18
(52) U.S. Cl. ..................... 428/1.1; 252/299.62; 560/5; 560/6; 560/119; 570/129; 570/183; 570/187
(58) Field of Search ..................... 428/1.1; 252/299.62; 252/299.1; 560/5, 6, 119; 570/129, 183, 187

(56) References Cited

FOREIGN PATENT DOCUMENTS

| | | |
|---|---|---|
| DE | 196 07 996 | 9/1997 |
| DE | 196 11 096 | 9/1997 |
| DE | 196 52 247 | 6/1998 |
| DE | 196 52 250 | 6/1998 |
| DE | 197 48 438 | 5/1999 |
| DE | 197 48 440 | 5/1999 |
| EP | 0 047 817 | 3/1982 |
| GB | 2 070 593 A | 9/1981 |
| GB | 2 310 669 | 9/1997 |
| JP | 57-54130 | 3/1982 |
| JP | 60-199878 | 10/1985 |
| JP | 6-256284 | 9/1994 |
| JP | 6-279321 | 10/1994 |

OTHER PUBLICATIONS

Nishiyama et al. "Synthesis and properties of new antiferroelectric liquid crystals with tetrallin core"; vol. 180, No. 1–4, 1996, pp. 315–332, XP008007142.

Primary Examiner—Shean C. Wu
(74) Attorney, Agent, or Firm—Armstrong, Kratz, Quintos, Hanson & Brooks, LLP

(57) ABSTRACT

A tetrahydronaphthalene derivative represented by the general formula (I) and a liquid crystal composition containing the same.

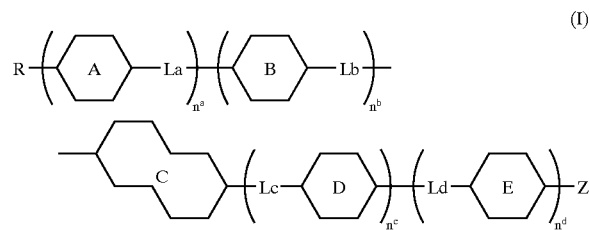

A compound represented by the general formula (I) shows superior liquid crystallinity and co-solubility with conventional liquid crystal compounds and compositions. Furthermore, addition of such a compound enables the threshold voltage to be significantly reduced with almost no deleterious effect on the responsiveness. In addition, a compound of the present invention can also be easily produced industrially, is colorless, and is chemically stable. Consequently, liquid crystal compositions containing such a compound are extremely useful as liquid crystals, and are particularly suitable for liquid crystal displays requiring a wide operating temperature range, low voltage driving and a high response speed.

27 Claims, No Drawings

US 6,746,728 B1

COMPOUND HAVING TETRAHYDRONAPHTHALENE SKELETON AND LIQUID CRYSTAL COMPOSITION CONTAINING SAME

TECHNICAL FIELD

The present invention relates to a novel liquid crystal compound comprising a tetrahydronaphthalene derivative which is useful as an electrooptical liquid crystal display material, as well as a liquid crystal composition containing such a compound and a liquid crystal display element utilizing the compound.

BACKGROUND ART

Liquid crystal display elements are now used not only in clocks and calculators, but also in various types of measuring instruments, automobile instrument panels, word processors, personal digital assistants, printers, computers and televisions. Typical examples of liquid crystal display methods include TN (twisted nematic) types, STN (super twisted nematic) types, DS (dynamic scattering) types, GH (guest host) types, or methods which enable high speed response such as FLC (ferroelectric liquid crystal) types or AFLC (antiferroelectric liquid crystal) types. In addition, multiplex driving is replacing the conventional static driving as the most common type of driving method, and moreover, simple matrix systems, and more recently, active matrix systems, have also come into practical use.

Extremely large numbers of different liquid crystal compounds have been synthesized for use as liquid crystal materials, and these are selected and used depending on the display method, the driving method and the final use of the display. However the demand for improved performance (such as improved display quality or increased display screen size) from liquid crystal display elements has grown stronger over the years, and development of new liquid crystal compounds to satisfy these demands is ongoing.

Liquid crystal compounds generally comprise a central skeleton part known as the core, with terminal portions on both sides. Typically, the most common ring structure that composes the core portion of the liquid crystal compound is a 1,4-phenylene group (which may be substituted with one or two halogen atoms, cyano groups, or methyl groups or the like) and a trans-1,4-cyclohexylene group. However, liquid crystal compounds composed solely of a 1,4-phenylene group and a trans-1,4-cyclohexylene group are limited in terms of the variety of possible compounds and the associated characteristics, and are currently unable to adequately accommodate the aforementioned demands.

Ring structures which have been investigated other than the 1,4-phenylene group and trans-1,4-cyclohexylene group described above include heterocyclic ring systems such as a pyridine-2,5-diyl group, pyrimidine-2,5-diyl group, and a 1,3-dioxane-trans-2,5-diyl group, and fused ring systems such as a trans-decahydronaphthalene-2,6-diyl group, naphthalene-2,6-diyl group, tetrahydronaphthalene-2,6-diyl group, bicyclo[2.2.2]octane-1,4-diyl group, and a spiro[3.3]heptane-2,6-diyl group, although production problems (including technical problems and cost) and stability problems mean that only a very small number are currently used in practical applications.

Of these fused ring systems, the tetrahydronaphthalene-2,6-diyl group is a ring structure that has been known for considerable time, although synthetic examples are extremely few, and furthermore, characteristics of the ring structure other than the liquid crystallinity (the phase transition temperature), in particular the characteristics of the structure as a nematic liquid crystal, are virtually unknown. (Recently, it was reported that an optically active alcohol ester of tetrahydronaphthalene-2-carboxylic acid showed smectic liquid crystal characteristics, and in particular highly interesting characteristics as a ferroelectric liquid crystal and an antiferroelectric liquid crystal. Furthermore, a ferroelectric liquid crystal skeleton comprising a fluorine containing tetrahydronaphthalene structure has also been recently reported.)

In a typical liquid crystal compound, at least one of the terminal portions is a chain like (side chain) group, and in cases in which the dielectric anisotropy is positive, so-called p-type liquid crystals, then the other terminal portion is usually a polar group.

In TN or STN display methods, in order to reduce the associated driving voltage, a w compound with a large positive dielectric anisotropy (p-type) is required. In order to satisfy this requirement, typically compounds with a cyano group at the molecule terminal, and moreover at least one fluorine atom in the same direction on the molecule are used. The reported tetrahydronaphthalene derivatives almost all have a dielectric anisotropy between 0 and a negative value, so-called n-type liquid crystals, and the only examples of p-type liquid crystals where a polar group has been introduced onto a tetrahydronaphthalene skeleton are limited to compounds with a phenyltetrahydronaphthalene skeleton or a phenyl tetrahydronaphthalene-2-carboxylate skeleton, and no comments have been made about the electrooptical characteristics, nor examples given of potential applications (Helv. Chim. Acta, 65, 1318–1330 (1992)).

Examples of p-type compounds for use with the aforementioned active matrix driving method include only compounds with a fluorine atom, a fluoroalkoxy group or a fluoroalkyl group as the polar group, and no reports have been made of a tetrahydronaphthalene compound. Furthermore, although many liquid crystal compounds which are tetrahydronaphthalene derivatives are not particularly co-soluble with other liquid crystal compounds, it is thought that introducing a side substituent (a fluorine atom is particularly desirable) into the tetrahydronaphthalene skeleton would be effective in alleviating this problem. In terms of application to the aforementioned active matrix system, it is thought that substitution with a fluorine group would also be effective in the case in which a polar group is introduced directly into the tetrahydronaphthalene ring. There are no actual synthetic examples of this type of fluorotetrahydronaphthalene derivative, and at present it is impossible to even estimate the properties of this type of compound.

In liquid crystal compounds, it is known that replacing the alkyl group typically used as the side chain portion with an alkenyl group, results in superior effects such as an improvement in liquid crystallinity, a reduction in viscosity, and improvements in the sharpness of the display characteristics. However, these alkenyl groups are usually introduced via direct bonding to a cyclohexane ring, and no compounds have been reported where such an introduction has occurred on an aromatic ring, or more particularly a tetrahydronaphthalene ring.

Similarly, tetrahydronaphthalene derivatives with a side chain such as an alkoxylalkyl group, a fluoroalkyl group, a fluoroalkenyl group, or a fluoroalkenyloxy group or the like, have also not been reported.

In terms of the ring structure linkage group within the core of a liquid crystal compound, in addition to single bonds and ester groups (—COO—, —OCO—), many bivalent organic groups such as a 1,2-ethylene group (—CH$_2$CH$_2$—), an ethynylene group (—C≡C—) or a difluoroethenylene group (—CF=CF—) are also known, although such groups are unknown within tetrahydronaphthalene derivatives.

DISCLOSURE OF INVENTION

The problem which the present invention attempts to resolve is to provide a novel compound with a tetrahydronaphthalene skeleton, and furthermore to provide a practical liquid crystal composition using such a compound.

As a result of intensive investigations aimed at resolving the above problem, the present inventors discovered compounds with a tetrahydronaphthalene skeleton which could be produced with ease, which in the main showed liquid crystallinity over a wide temperature range, and which regardless of the liquid crystallinity or otherwise of any single compound, upon addition to a composition, could be mixed with the composition without any lowering in the response speed (in a large number of cases the response speed improves), without any marked narrowing of the targeted liquid crystal temperature range (in a large number of cases the temperature range widens), and without any layer separation, and thereby completed the present invention.

Invention 1: A tetrahydronaphthalene derivative represented by a general formula (I)

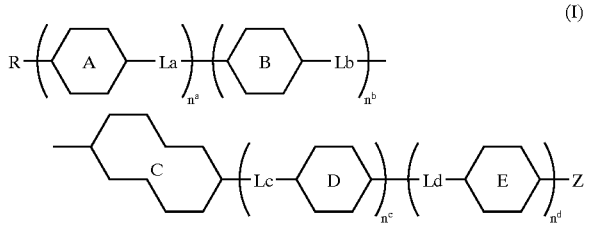

(wherein, R represents a saturated or unsaturated alkyl group or alkoxyl group of 1 to 20 carbon atoms which may incorporate a branched chain and may be substituted with 1 to 7 fluorine atoms or alkoxyl groups of 1 to 7 carbon atoms; the linkage groups La, Lb, Lc and Ld each represent independently a single bond, —CH$_2$CH$_2$—, —CH=CH—, —CH(CH$_3$)CH$_2$—, —CH$_2$CH(CH$_3$)—, —CH(CH$_3$)CH (CH$_3$)—, —CF$_2$CF$_2$—, —CF=CF—, —CH$_2$O—, —OCH$_2$—, —OCH(CH$_3$)—, —CH(CH$_3$)O—, —C≡C, CF$_2$O, OCF$_2$, COO, OCO, COS or SCO; Z represents a fluorine atom, chlorine atom, cyano group, cyanato group, trifluoromethoxy group or a difluoromethoxy group; ring A, ring B and ring D each represent independently a trans-1, 4-cyclohexylene group, trans-decahydronaphthalene-2,6-diyl group, trans-1,3-dioxane-2,4-diyl group, or a 1,4-phenylene group which may be substituted with one or two fluorine atoms, pyridine-2,5-diyl group, pyrimidine-2,5-diyl group, pyrazine-2,5-diyl group, a pyridazine-3,6-diyl group, and a naphthalene-2,6-diyl group which maybe substituted with one or two fluorine atoms; ring E represents independently a 1,4-phenylene group which may be substituted with one or two fluorine atoms, and a naphthalene-2,6-diyl group which may be substituted with one or two fluorine atoms; ring C represents either the general formula (IIa) or the general formula (IIb)

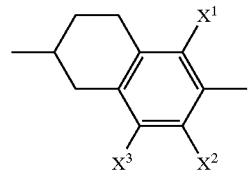

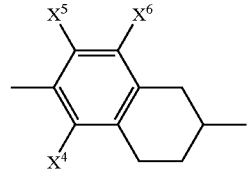

(wherein, X$^1$, X$^2$, X$^3$, X$^4$, X$^5$ and X$^6$ each represent independently a hydrogen atom or a fluorine atom); and n$^a$, n$^b$, n$^c$ and n$^d$ each represent independently either 0 or 1.

However, in the case in which n$^c$=1, n$^d$=0, the ring D represents a 1,4-phenylene group which may be substituted with one or two fluorine atoms and/or a naphthalene-2,6-diyl group which may be substituted with one or two fluorine atoms.

Furthermore, in the case in which Z is a cyano group, R is an unsubstituted and saturated alkyl group or alkoxyl group, n$^a$=n$^c$=n$^d$=0 and n$^b$=1, or n$^b$=n$^c$=n$^d$=0 and n$^a$=1, ring A and ring B are 1,4-phenylene groups, La and Lb are single bonds, and ring C is the general formula (IIa), then at least one of X$^1$, X$^2$ and X$^3$ represents a fluorine atom.

Furthermore, in the case in which Z is a cyano group, R is an unsubstituted and saturated alkyl group or alkoxyl group, n$^a$=n$^b$=n$^c$=0 and n$^d$=1, or n$^a$=n$^b$=n$^d$=0 and n$^c$=1, ring C and ring D are 1,4-phenylene groups, Lc and Ld are single bonds or —COO— linkages, and ring C is the general formula (IIa), then at least one of X$^1$, X$^2$ and X$^3$ represents a fluorine atom.

Furthermore, in the case in which Z is a cyano group, R is an unsubstituted and saturated alkyl group or alkoxyl group, n$^a$=n$^b$=n$^c$=0 and n$^d$=1, or n$^a$=n$^b$=n$^d$=0 and n$^c$=1, ring C and ring D are 1,4-phenylene groups, Lc and Ld are single bonds or —COO— linkages, and ring C is the general formula (IIb), then at least one of X$^4$, X$^5$ and X$^6$ represents a fluorine atom.

Furthermore, in the case in which Z is a fluorine atom, R is an unsubstituted and saturated alkyl group or alkoxyl group, n$^a$=n$^b$=n$^c$=0 and n$^d$=1, or n$^a$=n$^b$=n$^d$=0 and n$^c$=1, ring C and ring D are 1,4-phenylene groups, Lc and Ld are —COO— linkages, and ring C is the general formula (IIb), then at least one of X$^4$, X$^5$ and X$^6$ represents a fluorine atom.

In addition, in the case in which ring C is the general formula (IIb), at least one of n$^c$ and n$^d$ is 1.).

Invention 2: A tetrahydronaphthalene derivative according to Invention 1, wherein in ID the general formula (I), the ring C is represented by the formula (IIa).

Invention 3: A tetrahydronaphthalene derivative according to Invention 1, wherein in the general formula (I), the ring C is represented by the formula (IIb).

Invention 4: A tetrahydronaphthalene derivative according to any one of Inventions 1 through 3, wherein in the general formula (I), either n$^a$ or n$^b$ is 0.

Invention 5: A tetrahydronaphthalene derivative according to any one of Inventions 1 through 4, wherein in the general formula (I), either $n^c$ or $n^d$ is 0.

Invention 6: A tetrahydronaphthalene derivative according to any one of Inventions 1 through 5, wherein in the general formula (I), $n^a=n^b=0$.

Invention 7: A tetrahydronaphthalene derivative according to any one of Inventions 1, 2, 4 and 5, wherein in the general formula (I), $n^c=n^d=0$.

Invention 8: A tetrahydronaphthalene derivative according to any one of Inventions 1 through 7, wherein in the general formula (I), at least one of $n^a$, $n^b$, $n^c$ and $n^d$ is 1.

Invention 9: A tetrahydronaphthalene derivative according to any one of Inventions 1 through 8, wherein in the general formula (I), the linkage groups La, Lb, Lc and Ld are each selected independently from a group consisting of a single bond, —CH$_2$CH$_2$—, and —C≡C—.

Invention 10: A tetrahydronaphthalene derivative according to any one of Inventions 1 through 9, wherein in the general formula (I), the linkage groups La, Lb, Lc and Ld are each selected independently from a group consisting of a single bond and —CH$_2$CH$_2$—.

Invention 11: A tetrahydronaphthalene derivative according to any one of Inventions 1 through 10, wherein in the general formula (I), the linkage groups La, Lb, Lc and Ld are each a single bond.

Invention 12: A tetrahydronaphthalene derivative according to any one of Inventions 1 through 11, wherein in the general formula (I), the ring A, the ring B and the ring D are each independently selected from a group consisting of a trans-1,4-cyclohexylene group, a trans-decahydronaphthalene-2,6-diyl group, a trans-1,3-dioxane-2,4-diyl group, or a 1,4-phenylene group which may be substituted with one or two fluorine atoms, and a naphthalene-2,6-diyl group which may be substituted with one or two fluorine atoms.

Invention 13: A tetrahydronaphthalene derivative according to any one of Inventions 1 through 12, wherein in the general formula (I), Z is a fluorine atom.

Invention 14: A tetrahydronaphthalene derivative according to any one of Inventions 1 through 12, wherein in the general formula (I), Z is a cyano group.

Invention 15: A tetrahydronaphthalene derivative according to any one of Inventions 1 through 12, wherein in the general formula (I), Z is a trifluoromethoxy group.

Invention 16: A tetrahydronaphthalene derivative according to any one of Inventions 1 through 15, wherein in the general formula (I), R is a saturated or unsaturated alkyl group of 1 to 20 carbon atoms which may incorporate a branched chain and may be substituted with 1 to 7 fluorine atoms or alkoxyl groups of 1 to 7 carbon atoms.

Invention 17: A tetrahydronaphthalene derivative according to any one of Inventions 1 through 16, wherein in the general formula (I), R is a saturated or unsaturated straight chain alkyl group of 1 to 20 carbon atoms.

Invention 18: A tetrahydronaphthalene derivative according to any one of Inventions 1 through 17, wherein in the general formula (I), $X^3$, $X^4$ and $X^5$ in the formula (IIa) and the formula (IIb) are hydrogen atoms.

Invention 19: A tetrahydronaphthalene derivative according to any one of Inventions 1 through 18, wherein in the general formula (I), $X^2$ in the formula (IIa) is a hydrogen atom and $X^1$ is a fluorine atom.

Invention 20: A tetrahydronaphthalene derivative according to any one of Inventions 1 through 18, wherein in the general formula (I), $X^1$ in the formula (IIa) is a hydrogen atom and $X^2$ is a fluorine atom.

Invention 21: A tetrahydronaphthalene derivative according to any one of Inventions 1 through 20 which shows liquid crystallinity.

Invention 22: A tetrahydronaphthalene derivative according to any one of Inventions 1 through 21 which forms a nematic phase.

Invention 23: A tetrahydronaphthalene derivative according to any one of Inventions 1 through 22 which upon addition to a nematic liquid crystal composition forms a nematic phase.

Invention 24: A liquid crystal composition containing one or more compounds of the general formula (I) according to any one of Inventions 1 through 23.

Invention 25: A liquid crystal composition according to Invention 24 which can be used for active matrix driving.

Invention 26: A liquid crystal element comprising a liquid crystal composition according to Invention 25 as a structural element.

Invention 27: An active matrix driven liquid crystal display element utilizing a liquid crystal composition according to Invention 25.

BEST MODE FOR CARRYING OUT THE INVENTION

In the compound of the general formula (I) described above, suitable examples of the R, the linkage groups La, Lb, Lc and Ld, the polar group Z, the ring A, the ring B, the ring C, the ring D and the ring E, as well as $n^a$, $n^b$, $n^c$ and $n^d$ are described below.

$n^a$, $n^b$, $n^c$ and $n^d$ are either 0 or 1, and with the exception of the case in which ring C is represented by the formula (IIb), any combinations are possible, although in cases in which $n^a+n^b+n^c+n^d=3$ or 4 the melting point and the viscosity increase, and in the case in which $n^a+n^b+n^c+n^d=0$ the liquid crystallinity deteriorates, and so cases in which $n^a+n^b+n^c+n^d=1$ or 2 are preferred.

Examples of the group R include straight chain saturated alkyl groups such as a methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group and an eicosyl group; branched saturated alkyl groups such as a 1-methylethyl group, 1-methylpropyl group, 2-methylpropyl group, 1,2-dimethylpropyl group, 1-methylbutyl group, 2-methylbutyl group, 3-methylbutyl group, 1,2-dimethylbutyl group, 1,3-dimethylbutyl group, 2,3-dimethylbutyl group, 1-methylpentyl group, 2-methylpentyl group, 3-methylpentyl group, 4-methylpentyl group, 1,2-dimethylpentyl group, 1,3-dimethylpentyl group, 1-methylhexyl group, 2-methylhexyl group, 3-methylhexyl group, 4-methylhexyl group, 5-methylhexyl group, 1,2-dimethylhexyl group, 1,3-dimethylhexyl group, 1-methylheptyl group, 2-methylheptyl group, 3-methylheptyl group, 4-methylheptyl group, 5-methylheptyl group, 6-methylheptyl group, 1,2-dimethylheptyl group, 1,3-dimethylheptyl group, 1-methyloctyl group, 2-methyloctyl group, 3-methyloctyl group, 4-methyloctyl group, 5-methyloctyl group, 6-methyloctyl group, 7-methyloctyl group, 1,2-dimethyloctyl group, 1,3-dimethyloctyl group, 1-methylnonyl group, 2-methylnonyl group, 3-methylnonyl group, 4-methylnonyl group, 5-methylnonyl group, 6-methylnonyl group, 7-methylnonyl group, 8-methylnonyl group, 1,2-dimethylnonyl group, 1,3-dimethylnonyl group, 1-methyldecyl group, 2-methyldecyl group, 3-methyldecyl group, 1,2-dimethyldecyl group, 1,3-dimethyldecyl group, 1-methylundecyl group, 2-methylundecyl group, 3-methylundecyl group, 1,2-dimethylundecyl group, 1,3-dimethylundecyl group, 1-methyldodecyl group, 2-methyldodecyl group, 3-methyldodecyl group, 1,2-dimethyldodecyl group, 1,3-dimethyldodecyl group, 1-methyltridecyl group, 2-methyltridecyl group, 3-methyltridecyl group, 1,2-dimethyltridecyl group and a 1,3-dimethyltridecyl group; unsaturated alkyl groups such as a vinyl group, trans-1-propenyl group, 2-propenyl group, trans-1-butenyl group, trans-2-butenyl group, 3-butenyl group, trans-1-pentenyl group, trans-2-pentenyl group, trans-3-pentenyl group, 4-pentenyl group, trans-1-hexenyl group, trans-2-hexenyl group, trans-3-hexenyl group, trans-4-hexenyl group, 5-hexenyl group, trans-1-heptenyl group, trans-2-heptenyl group, trans-3-heptenyl group, trans-4-heptenyl group, trans-5-heptenyl group, 6-heptenyl group, trans-1-octenyl group, trans-2-octenyl group, trans-3-octenyl group, trans-4-octenyl group, trans-5-octenyl group, trans-6-octenyl group, 7-octenyl group, trans-1-nonenyl group, 8-nonenyl group, trans-1-decenyl group, 9-decenyl group, trans-1-undecenyl group, 10-undecenyl group, trans-1-dodecenyl group, 11-dodecenyl group, ethynyl group, 1-propynyl group, 2-propynyl group, 1-butynyl group, 2-butynyl group, 3-butynyl group, 1-pentynyl group, 2-pentynyl group, 3-pentynyl group, 4-pentynyl group, 1-hexynyl group, 2-hexynyl group, 3-hexynyl group, 4-hexynyl group, 5-hexynyl group, 1-heptynyl group, 2-heptynyl group, 3-heptynyl group, 4-heptynyl group, 5-heptynyl group, 6-heptynyl group, 1-octynyl group, 2-octynyl group, 3-octynyl group, 4-octynyl group, 5-octynyl group, 6-octynyl group, 7-octynyl group, 1-nonynyl group, 8-nonynyl group, 1-decynyl group, 9-decynyl group, 1-undecynyl group, 10-undecynyl group, 1-dodecynyl group, 11-dodecynyl group, 1-tridecynyl group and a 12-tridecynyl group; fluorine substituted alkyl groups such as a fluoromethyl group, difluoromethyl group, trifluoromethyl group, 2-fluoroethyl group, 2,2-difluoroethyl group, 2,2,2-trifluoroethyl group, 1,1,2,2,2-pentafluoroethyl group, 3-fluoropropyl group, 2-fluoropropyl group, 1-fluoropropyl group, 3,3-difluoropropyl group, 3,3,3-trifluoropropyl group, 2,2,3,3-tetrafluoropropyl group, 2,2,3,3,3-pentafluoropropyl group, 1,1,2,2,3,3,3-heptafluoropropyl group, 4-fluorobutyl group, 3-fluorobutyl group, 2-fluorobutyl group, 1-fluorobutyl group, 4,4-difluorobutyl group, 4,4,4-trifluorobutyl group, 3,3,4,4-tetrafluorobutyl group, 3,3,4,4,4-pentafluorobutyl group, 2,2,3,3,4,4,4-heptafluorobutyl group, 5-fluoropentyl group, 4-fluoropentyl group, 3-fluoropentyl group, 2-fluoropentyl group, 1-fluoropentyl group, 5,5-difluoropentyl group, 5,5,5-trifluoropentyl group, 4,4,5,5-tetrafluoropentyl group, 4,4,5,5,5-pentafluoropentyl group, 3,3,4,4,5,5,5-heptafluoropentyl group, 6-fluorohexyl group, 5-fluorohexyl group, 4-fluorohexyl group, 3-fluorohexyl group, 2-fluorohexyl group, 1-fluorohexyl group, 6,6-difluorohexyl group, 6,6,6-trifluorohexyl group, 5,5,6,6,6-pentafluorohexyl group, 4,4,5,5,6,6,6-heptafluorohexyl group, 7-fluoroheptyl group, 6-fluoroheptyl group, 5-fluoroheptyl group, 4-fluoroheptyl group, 3-fluoroheptyl group, 2-fluoroheptyl group, 1-fluoroheptyl group, 7,7-difluoroheptyl group, 7,7,7-trifluoroheptyl group, 6,6,7,7-tetrafluoroheptyl group, 6,6,7,7,7-pentafluoroheptyl group, 5,5,6,6,7,7,7-heptafluoroheptyl group, 8-fluorooctyl group, 7-fluorooctyl group, 6-fluorooctyl group, 5-fluorooctyl group, 4-fluorooctyl group, 3-fluorooctyl group, 2-fluorooctyl group, 1-fluorooctyl group, 8,8-difluorooctyl group, 8,8,8-trifluorooctyl group, 7,7,8,8-tetrafluorooctyl group, 7,7,8,8,8-pentafluorooctyl group and a 6,6,7,7,8,8,8-heptafluorooctyl group; fluorine substituted unsaturated alkyl groups such as a 2,2-difluoroethenyl group, (E)-1,2-difluoroethenyl group, (Z)-1,2-difluoroethenyl group, 3,3-difluoro-2-propenyl group, (E)-2,3-difluoro-2-propenyl group, (Z)-2,3-fluoro-2-propenyl group, 4,4-difluoro-3-butenyl group, (E)-3,4-difluoro-3-butenyl group, (Z)-3,4-difluoro-3-butenyl group, 5,5-difluoro-4-pentenyl group, (E)-4,5-difluoro-4-pentenyl group, (Z)-4,5-difluoro-4-pentenyl group, 6,6-difluoro-5-hexenyl group, (E)-5,6-difluoro-5-hexenyl group, (Z)-5,6-difluoro-5-hexenyl group, (E)-1,2-difluoro-1-propenyl group, (E)-1,2-difluoro-1-butenyl group, (E)-1,2-difluoro-1-pentenyl group, (E)-1,2-difluoro-1-hexenyl group, (Z)-1-fluoro-1-propenyl group, (Z)-1-fluoro-1-butenyl group, (Z)-1-fluoro-1-pentenyl group, (Z)-1-fluoro-1-hexenyl group, (Z)-2-fluoro-1-propenyl group, (Z)-2-fluoro-1-butenyl group, (Z)-2-fluoro-1-pentenyl group, (Z)-2-fluoro-1-hexenyl group, (E)-2,3-difluoro-2-butenyl group, (E)-2,3-difluoro-2-pentenyl group, (E)-2,3-difluoro-2-hexenyl group, (Z)-2-fluoro-2-butenyl group, (Z)-2-fluoro-2-pentenyl group, (Z)-2-fluoro-2-hexenyl group, (Z)-3-fluoro-2-butenyl group, (Z)-3-fluoro-2-pentenyl group and a (Z)-3-fluoro-2-hexenyl group; alkoxyl group substituted alkyl groups such as a methoxymethyl group, ethoxymethyl group, propoxymethyl group, butoxymethyl group, pentyloxymethyl group, hexyloxymethyl group, heptyloxymethyl group, 1-methoxyethyl group, 1-ethoxyethyl group, 1-propoxyethyl group, 1-butoxyethyl group, 1-pentyloxyethyl group, 1-hexyloxyethyl group, 1-heptyloxyethyl group, 2-methoxyethyl group, 2-ethoxyethyl group, 2-propoxyethyl group, 2-butoxyethyl group, 2-pentyloxyethyl group, 2-hexyloxyethyl group, 2-heptyloxyethyl group, 1-methoxypropyl group, 1-ethoxypropyl group, 1-propoxypropyl group, 1-butoxypropyl group, 1-pentyloxypropyl group, 1-hexyloxypropyl group, 1-heptyloxypropyl group, 2-methoxypropyl group, 2-ethoxypropyl group, 2-propoxypropyl group, 2-butoxypropyl group, 2-pentyloxypropyl group, 2-hexyloxypropyl group, 2-heptyloxypropyl group, 3-methoxypropyl group, 3-ethoxypropyl group, 3-propoxypropyl group, 3-butoxypropyl group, 3-pentyloxypropyl group, 3-hexyloxypropyl group, 3-heptyloxypropyl group, 4-methoxybutyl group, 4-ethoxybutyl group, 4-propoxybutyl group, 4-butoxybutyl group, 4-pentyloxybutyl group, 4-hexyloxybutyl group, 4-heptyloxybutyl group, 5-methoxypentyl group, 5-ethoxypentyl group, 5-propoxypentyl group, 5-butoxypentyl group, 5-pentyloxypentyl group, 5-hexyloxypentyl group, 5-heptyloxypentyl group, 6-methoxyhexyl group, 6-ethoxyhexyl group, 6-propoxyhexyl group, 6-butoxyhexyl group, 6-pentyloxyhexyl group, 6-hexyloxyhexyl group and a 6-heptyloxyhexyl group; and the alkoxyl groups thereof, although alkyl groups are preferred. Of such alkyl groups, straight chain saturated alkyl groups and unsaturated alkyl groups are preferred, and particularly desirable groups include a methyl group, ethyl group, propyl group, butyl group, pentyl group, hexyl group, heptyl group, octyl group, vinyl group, trans-1-propenyl group, 2-propenyl group, trans-1-butenyl group, trans-2-butenyl group, 3-butenyl group, trans-1-pentenyl group, trans-2-pentenyl group, trans-3-pentenyl group, 4-pentenyl group, trans-1-hexenyl group, trans-2-hexenyl group, trans-3-hexenyl group, trans-4-hexenyl group, 5-hexenyl group, trans-1-heptenyl group, trans-2-heptenyl group, trans-3-heptenyl group, trans-4-heptenyl group, trans-5-heptenyl group, and a 6-heptenyl group.

Examples of the linkage groups La, Lb, Lc and Ld include a single bond, —CH₂CH₂—, —CH=CH—, —CH(CH₃)CH₂—, —CH₂CH(CH₃)—, —CH(CH₃)CH(CH₃)—, —CF₂CF₂—, —CF=CF—, —CH₂O—, —OCH₂—, —OCH(CH₃)—, —CH(CH₃)O—, —C≡C—, —CF₂O—, —OCF₂—, —COO—, —OCO—, —COS— or —SCO—, and of these, a single bond, —CH₂CH₂— and —C≡C— are preferred, and a single bond is particularly preferred.

Examples of the group Z include a fluorine atom, chlorine atom, cyano group, cyanato group, trifluoromethoxy group or a difluoromethoxy group, although a fluorine atom, a cyano group, or a trifluoromethoxy group are preferred, and a fluorine atom or a trifluoromethoxy group are particularly desirable.

Examples of the ring A, the ring B and the ring D include the types of structures shown in the formulas group 1.

formulas group 1

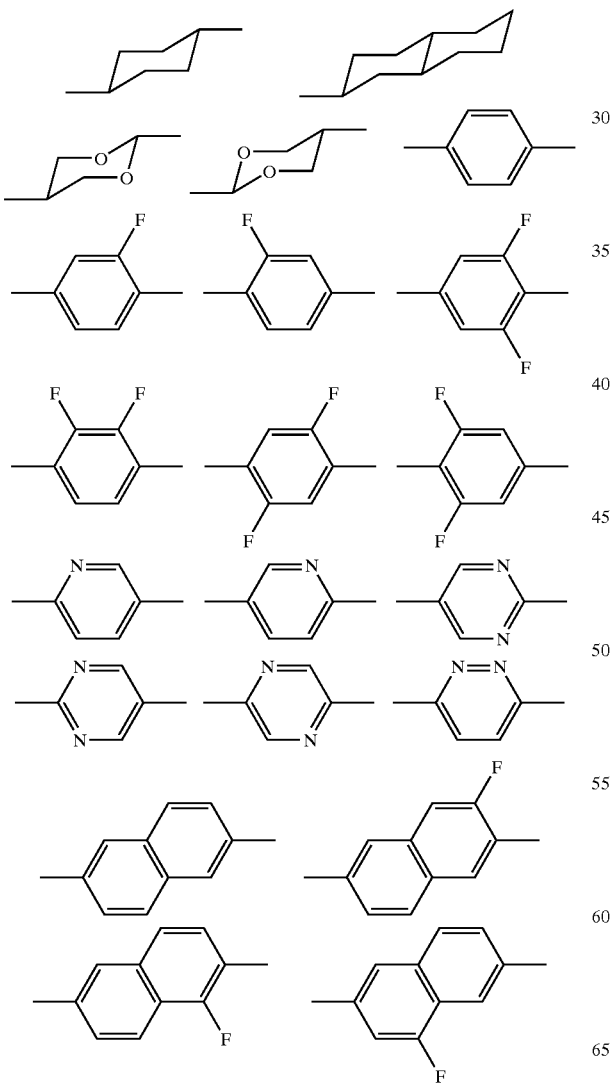

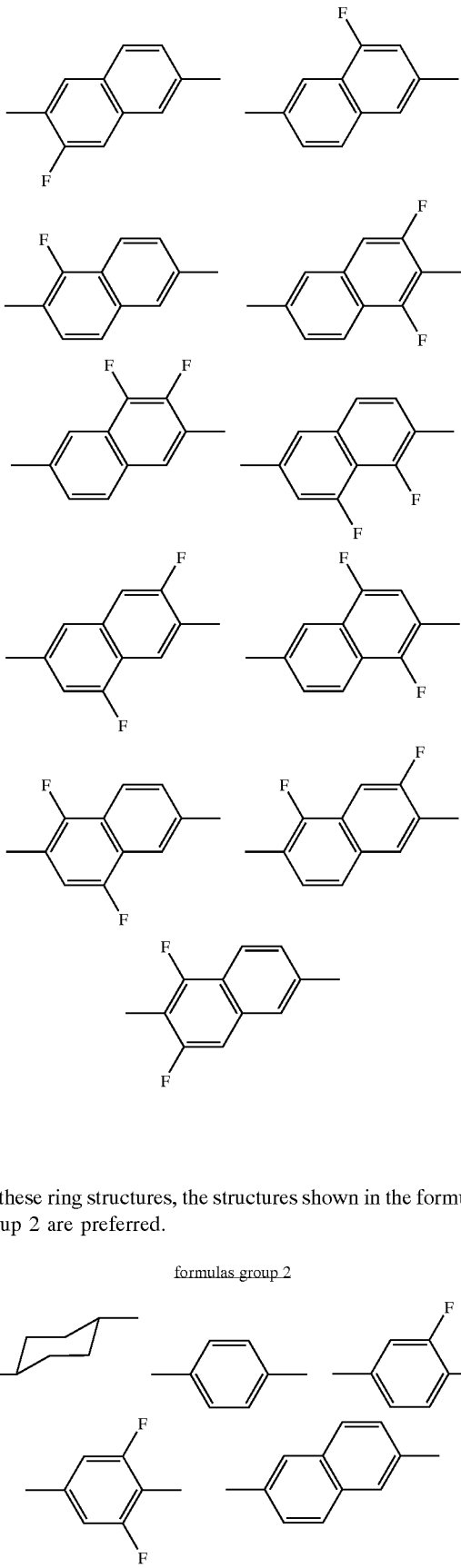

Of these ring structures, the structures shown in the formulas group 2 are preferred.

formulas group 2

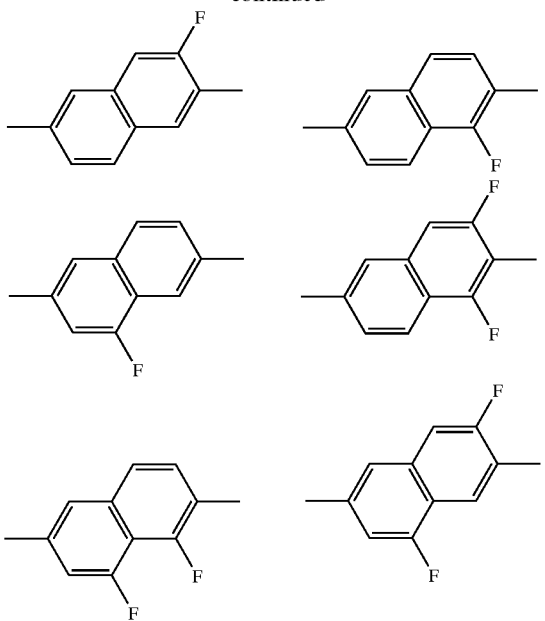
Of these ring structures, the structures shown in the formulas group 3 are particularly desirable.
formulas group 3
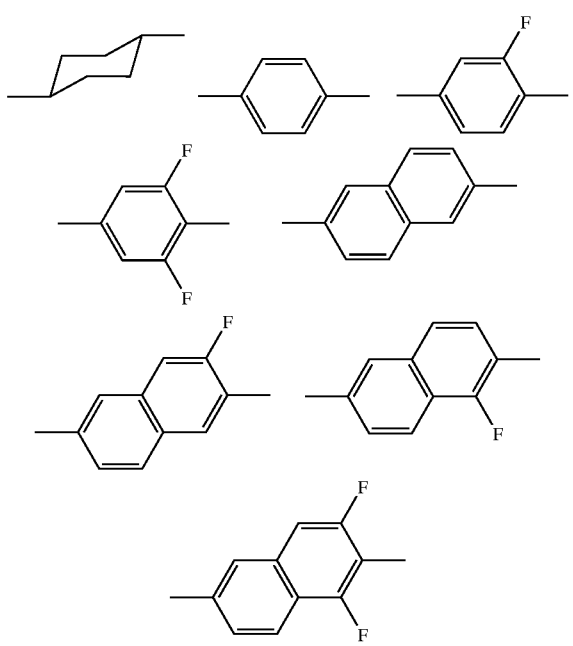
Examples of the ring E, and the ring D in the case in which $n^d=0$ include the types of structures shown in the formulas group 4.
formulas group 4
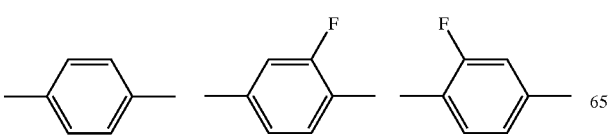
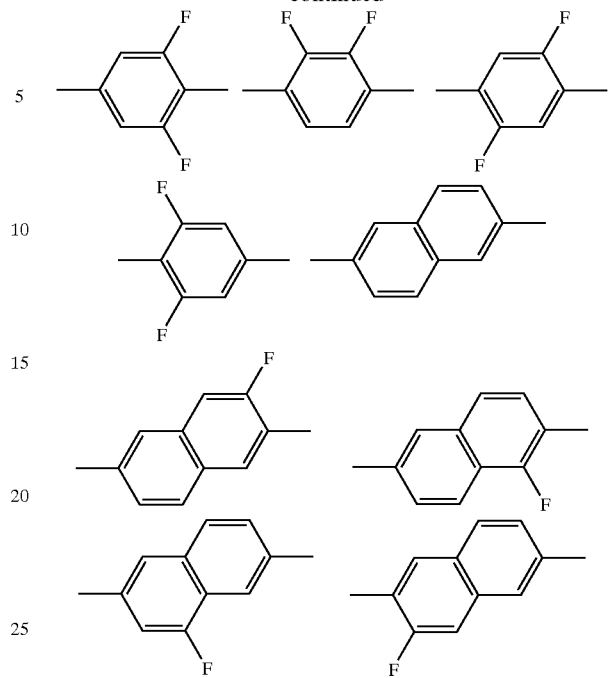
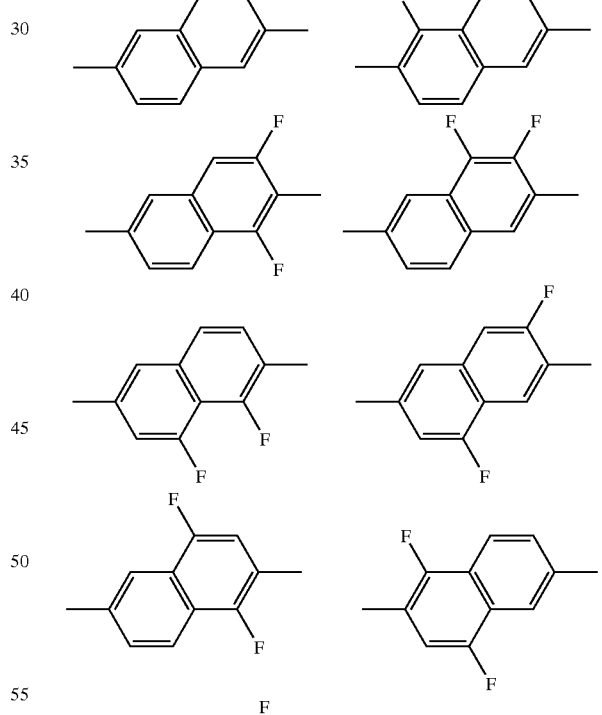
Of these ring structures, the structures shown in the formulas group 5 are preferred.

formulas group 5

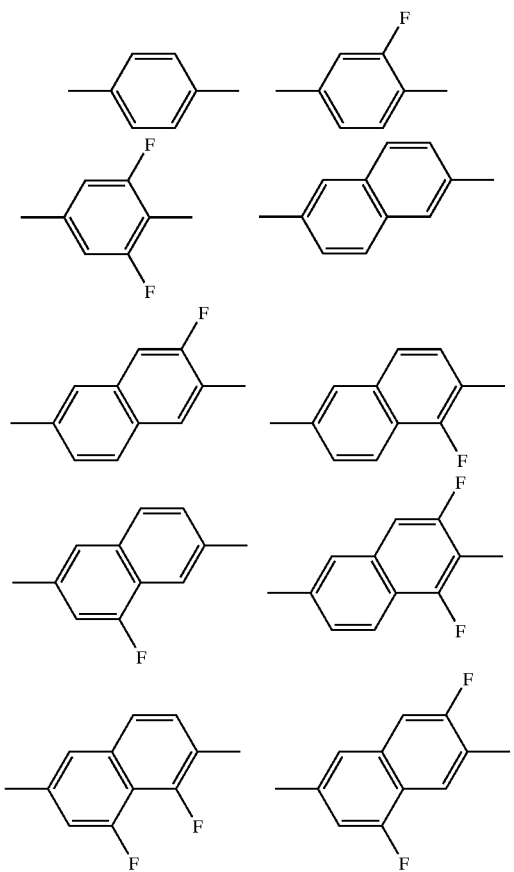

Of these ring structures, the structures shown in the formulas group 6 are particularly desirable.

formulas group 6

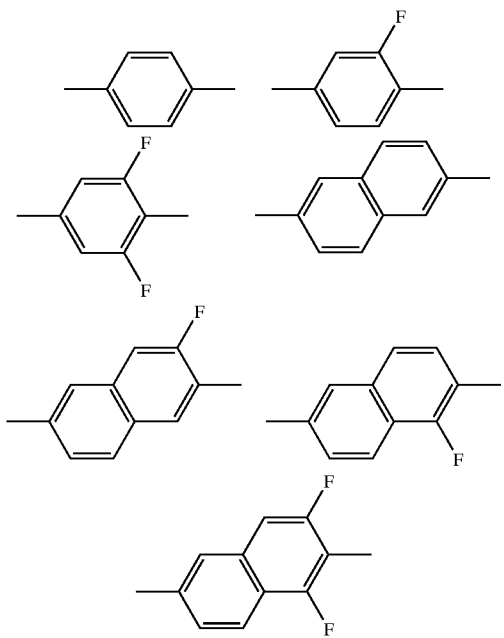

Examples of the formula (IIa) and the formula (IIb) of the ring C include the types of structures shown in the formulas group 7.

formulas group 7

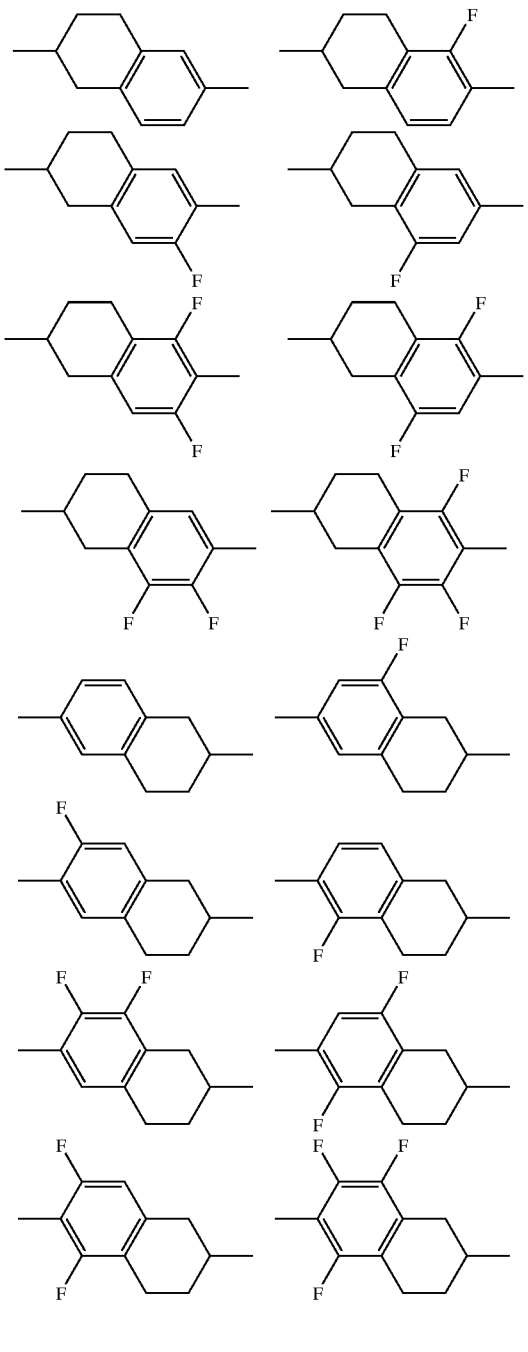

Of these ring structures, the structures shown in the formulas group 8 are preferred.

formulas group 8

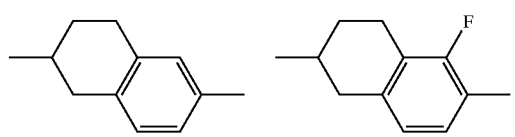

As described above, the compound of the aforementioned general formula (I) incorporates a very large variety of compounds depending on the selection of the group R, the linkage groups La, Lb, Lc and Ld, the polar group Z, the ring A, the ring B, the ring C, the ring D and the ring E, and $n^a$, $n^b$, $n^c$ and $n^d$, and by appropriate selection of each of these structural sites, compounds can be prepared which are applicable to a wide range of uses and fields. As a result, compounds of the general formula (I) show characteristics such as a broad nematic temperature range, good stability against light and heat, and a high voltage retention, that are extremely useful for electrooptical elements, and are particular preferable for STN-LCD and AM-LCD devices. Specifically, of the compounds represented by the general formula (I), particularly preferred compounds include those listed below.

In the compounds listed, the following abbreviations are used, so that $R^1$ represents any one of a methyl group, ethyl group, propyl group, butyl group, pentyl group, hexyl group, heptyl group, octyl group, vinyl group, trans-1-propenyl group, 2-propenyl group, trans-1-butenyl group, trans-2-butenyl group, 3-butenyl group, trans-1-pentenyl group, trans-2-pentenyl group, trans-3-pentenyl group, 4-pentenyl group, trans-1-hexenyl group, trans-2-hexenyl group, trans-3-hexenyl group, trans-4-hexenyl group, 5-hexenyl group, trans-1-heptenyl group, trans-2-heptenyl group, trans-3-heptenyl group, trans-4-heptenyl group, trans-5-heptenyl group, and a 6-heptenyl group.

Th4:
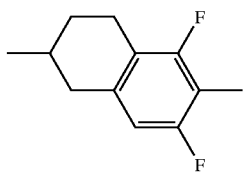

Te1:
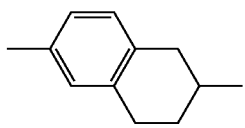

Te2:
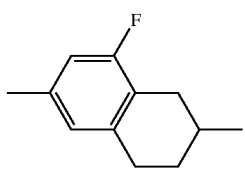

In the case in which ring C is the formula (IIa),
then in the case in which $n^a=1$, $n^b=0$ or $n^a=0$, $n^b=1$, and $n^c=n^d=0$, and Z is a fluorine atom,
$R^1$-Cy-Th1-F, $R^1$-Ph1-Th1-F, $R^1$-Ph2-Th1-F, $R^1$-Ph3-Th1-F, $R^1$-Np1-Th1-F,
$R^1$-Np2-Th1-F, $R^1$-Np3-Th1-F, $R^1$-Np4-Th1-F, $R^1$-Cy-Th2-F, $R^1$-Ph1-Th2-F,
$R^1$-Ph2-Th2-F, $R^1$-Ph3-Th2-F, $R^1$-Np1-Th2-F, $R^1$-Np2-Th2-F, $R^1$-Np3-Th2-F,
$R^1$-Np4-Th2-F, $R^1$-Cy-Th3-F, $R^1$-Ph1-Th3-F, $R^1$-Ph2-Th3-F, $R^1$-Ph3-Th3-F,
$R^1$-Np1-Th3-F, $R^1$-Np2-Th3-F, $R^1$-Np3-Th3-F, $R^1$-Np4-Th3-F, $R^1$-Cy-Th4-F,
$R^1$-Ph1-Th4-F, $R^1$-Ph2-Th4-F, $R^1$-Ph3-Th4-F, $R^1$-Np1-Th4-F, $R^1$-Np2-Th4-F,
$R^1$-Np3-Th4-F, $R^1$-Np4-Th4-F, $R^1$-Cy-CH$_2$CH$_2$-Th1-F, $R^1$-Ph1-CH$_2$CH$_2$-Th1-F,
$R^1$-Ph2-CH$_2$CH$_2$-Th1-F, $R^1$-Ph3-CH$_2$CH$_2$-Th1-F, $R^1$-Np1-CH$_2$CH$_2$-Th1-F,
$R^1$-Np2-CH$_2$CH$_2$-Th1-F, $R^1$-Np3-CH$_2$CH$_2$-Th1-F, $R^1$-Np4-CH$_2$CH$_2$-Th1-F,
$R^1$-Cy-CH$_2$CH$_2$-Th2-F, $R^1$-Ph1-CH$_2$CH$_2$-Th2-F, $R^1$-Ph2-CH$_2$CH$_2$-Th2-F,
$R^1$-Ph3-CH$_2$CH$_2$-Th2-F, $R^1$-Np1-CH$_2$CH$_2$-Th2-F, $R^1$-Np2-CH$_2$CH$_2$-Th2-F,
$R^1$-Np3-CH$_2$CH$_2$-Th2-F, $R^1$-Np4-CH$_2$CH$_2$-Th2-F, $R^1$-Cy-CH$_2$CH$_2$-Th3-F,
$R^1$-Ph1-CH$_2$CH$_2$-Th3-F, $R^1$-Ph2-CH$_2$CH$_2$-Th3-F, $R^1$-Ph3-CH$_2$CH$_2$-Th3-F,
$R^1$-Np1-CH$_2$CH$_2$-Th3-F, $R^1$-Np2-CH$_2$CH$_2$-Th3-F, $R^1$-Np3-CH$_2$CH$_2$-Th3-F,
$R^1$-Np4-CH$_2$CH$_2$-Th3-F, $R^1$-Cy-CH$_2$CH$_2$-Th4-F, $R^1$-Ph1-CH$_2$CH$_2$-Th4-F,
$R^1$-Ph2-CH$_2$CH$_2$-Th4-F, $R^1$-Ph3-CH$_2$CH$_2$-Th4-F, $R^1$-Np1-CH$_2$CH$_2$-Th4-F,
$R^1$-Np2-CH$_2$CH$_2$-Th4-F, $R^1$-Np3-CH$_2$CH$_2$-Th4-F, $R^1$-Np4-CH$_2$CH$_2$-Th4-F,
in the case in which $n^a=1$, $n^b=0$ or $n^a=0$, $n^b=1$, and $n^c=n^d=0$, and Z is a cyano group,
$R^1$-Cy-Th1-CN, $R^1$-Ph2-Th1-CN, $R^1$-Ph3-Th1-CN, $R^1$-Np1-Th1-CN, $R^1$-Np2-Th1-CN,
$R^1$-Np3-Th1-CN, $R^1$-Np4-Th1-CN, $R^1$-Cy-Th2-CN, $R^1$-Ph1-Th2-CN, $R^1$-Ph2-Th2-CN,
$R^1$-Ph3-Th2-CN, $R^1$-Np1-Th2-CN, $R^1$-Np2-Th2-CN, $R^1$-Np3-Th2-CN, $R^1$-Np4-Th2-CN,
$R^1$-Cy-Th3-CN, $R^1$-Ph1-Th3-CN, $R^1$-Ph2-Th3-CN, $R^1$-Ph3-Th3-CN, $R^1$-Np1-Th3-CN,
$R^1$-Np2-Th3-CN, $R^1$-Np3-Th3-CN, $R^1$-Np4-Th3-CN, $R^1$-Cy-Th4-CN, $R^1$-Ph1-Th4-CN,
$R^1$-Ph2-Th4-CN, $R^1$-Ph3-Th4-CN, $R^1$-Np1-Th4-CN, $R^1$-Np2-Th4-CN, $R^1$-Np3-Th4-CN,
$R^1$-Np4-Th4-CN,
$R^1$-Cy-CH$_2$CH$_2$-Th1-CN, $R^1$-Ph1-CH$_2$CH$_2$-Th1-CN, $R^1$-Ph2-CH$_2$CH$_2$-Th1-CN,
$R^1$-Ph3-CH$_2$CH$_2$-Th1-CN, $R^1$-Np1-CH$_2$CH$_2$-Th1-CN, $R^1$-Np2-CH$_2$CH$_2$-Th1-CN,
$R^1$-Np3-CH$_2$CH$_2$-Th1-CN, $R^1$-Np4-CH$_2$CH$_2$-Th1-CN, $R^1$-Cy-CH$_2$CH$_2$-Th2-CN,
$R^1$-Ph1-CH$_2$CH$_2$-Th2-CN, $R^1$-Ph2-CH$_2$CH$_2$-Th2-CN, $R^1$-Ph3-CH$_2$CH$_2$-Th2-CN,
$R^1$-Np1-CH$_2$CH$_2$-Th2-CN, $R^1$-Np2-CH$_2$CH$_2$-Th2-CN, $R^1$-Np3-CH$_2$CH$_2$-Th2-CN,
$R^1$-Np4-CH$_2$CH$_2$-Th2-CN, $R^1$-Cy-CH$_2$CH$_2$-Th3-CN, $R^1$-Ph1-CH$_2$CH$_2$-Th3-CN,
$R^1$-Ph2-CH$_2$CH$_2$-Th3-CN, $R^1$-Ph3-CH$_2$CH$_2$-Th3-CN, $R^1$-Np1-CH$_2$CH$_2$-Th3-CN,
$R^1$-Np2-CH$_2$CH$_2$-Th3-CN, $R^1$-Np3-CH$_2$CH$_2$-Th3-CN, $R^1$-Np4-CH$_2$CH$_2$-Th3-CN,
$R^1$-Cy-CH$_2$CH$_2$-Th4-CN, $R^1$-Ph1-CH$_2$CH$_2$-Th4-CN, $R^1$-Ph2-CH$_2$CH$_2$-Th4-CN,
$R^1$-Ph3-CH$_2$CH$_2$-Th4-CN, $R^1$-Np1-CH$_2$CH$_2$-Th4-CN, $R^1$-Np2-CH$_2$CH$_2$-Th4-CN,
$R^1$-Np3-CH$_2$CH$_2$-Th4-CN, $R^1$-Np4-CH$_2$CH$_2$-Th4-CN,
in the case in which $n^a=1$, $n^b=0$ or $n^a=0$, $n^b=1$, and $n^c=n^d=0$, and Z is a trifluoromethyl group,
$R^1$-Cy-Th1-OCF$_3$, $R^1$-Ph1-Th1-OCF$_3$, $R^1$-Ph2-Th1-OCF$_3$, $R^1$-Ph3-Th1-OCF$_3$,
$R^1$-Np1-Th1-OCF$_3$, $R^1$-Np2-Th1-OCF$_3$, $R^1$-Np3-Th1-OCF$_3$, $R^1$-Np4-Th1-OCF$_3$,
$R^1$-Cy-Th2-OCF$_3$, $R^1$-Ph1-Th2-OCF$_3$, $R^1$-Ph2-Th2-OCF$_3$, $R^1$-Ph3-Th2-OCF$_3$,
$R^1$-Np1-Th2-OCF$_3$, $R^1$-Np2-Th2-OCF$_3$, $R^1$-Np3-Th2-OCF$_3$, $R^1$-Np4-Th2-OCF$_3$,
$R^1$-Cy-Th3-OCF$_3$, $R^1$-Ph1-Th3-OCF$_3$, $R^1$-Ph2-Th3-OCF$_3$, $R^1$-Ph3-Th3-OCF$_3$,
$R^1$-Np1-Th3-OCF$_3$, $R^1$-Np2-Th3-OCF$_3$, $R^1$-Np3-Th3-OCF$_3$, $R^1$-Np4-Th3-OCF$_3$,
$R^1$-Cy-Th4-OCF$_3$, $R^1$-Ph1-Th4-OCF$_3$, $R^1$-Ph2-Th4-OCF$_3$, $R^1$-Ph3-Th4-OCF$_3$,
$R^1$-Np1-Th4-OCF$_3$, $R^1$-Np2-Th4-OCF$_3$, $R^1$-Np3-Th4-OCF$_3$, $R^1$-Np4-Th4-OCF$_3$,
$R^1$-Cy-CH$_2$CH$_2$-Th1-OCF$_3$, $R^1$-Ph1-CH$_2$CH$_2$-Th1-OCF$_3$, $R^1$-Ph2-CH$_2$CH$_2$-Th1-OCF$_3$,
$R^1$-Ph3-CH$_2$CH$_2$-Th1-OCF$_3$, $R^1$-Np1-CH$_2$CH$_2$-Th1-OCF$_3$, $R^1$-Np2-CH$_2$CH$_2$-Th1-OCF$_3$,
$R^1$-Np3-CH$_2$CH$_2$-Th1-OCF$_3$, $R^1$-Np4-CH$_2$CH$_2$-Th1-OCF$_3$, $R^1$-Cy-CH$_2$CH$_2$-Th2-OCF$_3$,
$R^1$-Ph1-CH$_2$CH$_2$-Th2-OCF$_3$, $R^1$-Ph2-CH$_2$CH$_2$-Th2-OCF$_3$, $R^1$-Ph3-CH$_2$CH$_2$-Th2-OCF$_3$,
$R^1$-Np1-CH$_2$CH$_2$-Th2-OCF$_3$, $R^1$-Np2-CH$_2$CH$_2$-Th2-OCF$_3$, $R^1$-Np3-CH$_2$CH$_2$-Th2-OCF$_3$,
$R^1$-Np4-CH$_2$CH$_2$-Th2-OCF$_3$, $R^1$-Cy-CH$_2$CH$_2$-Th3-OCF$_3$, $R^1$-Ph1-CH$_2$CH$_2$-Th3-OCF$_3$,
$R^1$-Ph2-CH$_2$CH$_2$-Th3-OCF$_3$, $R^1$-Ph3-CH$_2$CH$_2$-Th3-OCF$_3$, $R^1$-Np1-CH$_2$CH$_2$-Th3-OCF$_3$,
$R^1$-Np2-CH$_2$CH$_2$-Th3-OCF$_3$, $R^1$-Np3-CH$_2$CH$_2$-Th3-OCF$_3$, $R^1$-Np4-CH$_2$CH$_2$-Th3-OCF$_3$,
$R^1$-Cy-CH$_2$CH$_2$-Th4-OCF$_3$, $R^1$-Ph1-CH$_2$CH$_2$-Th4-OCF$_3$, $R^1$-Ph2-CH$_2$CH$_2$-Th4-OCF$_3$,
$R^1$-Ph3-CH$_2$CH$_2$-Th4-OCF$_3$, $R^1$-Np1-CH$_2$CH$_2$-Th4-OCF$_3$, $R^1$-Np2-CH$_2$CH$_2$-Th4-OCF$_3$, R¹-Np3-CH$_2$CH$_2$-Th4-OCF$_3$, R¹-Np4-CH$_2$CH$_2$-Th4-OCF$_3$, in the case in which $n^a=n^b=1$, and $n^c=n^d=0$, and Z is a fluorine atom, R¹-Cy-Cy-Th1-F, R¹-Ph1-Cy-Th1-F, R¹-Ph2-Cy-Th1-F, R¹-Ph3-Cy-Th1-F,
R¹-Np1-Cy-Th1-F, R¹-Np2-Cy-Th1-F, R¹-Np3-Cy-Th1-F, R¹-Np4-Cy-Th1-F,
R¹-Cy-Cy-Th2-F, R¹-Ph1-Cy-Th2-F, R¹-Ph2-Cy-Th2-F, R¹-Ph3-Cy-Th2-F,
R¹-Np1-Cy-Th2-F, R¹-Np2-Cy-Th2-F, R¹-Np3-Cy-Th2-F, R¹-Np4-Cy-Th2-F,
R¹-Cy-Cy-Th3-F, R¹-Ph1-Cy-Th3-F, R¹-Ph2-Cy-Th3-F, R¹-Ph3-Cy-Th3-F,
R¹-Np1-Cy-Th3-F, R¹-Np2-Cy-Th3-F, R¹-Np3-Cy-Th3-F, R¹-Np4-Cy-Th3-F,
R¹-Cy-Cy-Th4-F, R¹-Ph1-Cy-Th4-F, R¹-Ph2-Cy-Th4-F, R¹-Ph3-Cy-Th4-F,
R¹-Np1-Cy-Th4-F, R¹-Np2-Cy-Th4-F, R¹-Np3-Cy-Th4-F, R¹-Np4-Cy-Th4-F,
R¹-Cy-CH$_2$CH$_2$-Cy-Th1-F, R¹-Ph1-CH$_2$CH$_2$-Cy-Th1-F, R¹-Ph2-CH$_2$CH$_2$-Cy-Th1-F,
R¹-Ph3-CH$_2$CH$_2$-Cy-Th1-F, R¹-Np1-CH$_2$CH$_2$-Cy-Th1-F, R¹-Np2-CH$_2$CH$_2$-Cy-Th1-F,
R¹-Np3-CH$_2$CH$_2$-Cy-Th1-F, R¹-Np4-CH$_2$CH$_2$-Cy-Th1-F, R¹-Cy-CH$_2$CH$_2$-Cy-Th2-F,
R¹-Ph1-CH$_2$CH$_2$-Cy-Th2-F, R¹-Ph2-CH$_2$CH$_2$-Cy-Th2-F, R¹-Ph3-CH$_2$CH$_2$-Cy-Th2-F,
R¹-Np1-CH$_2$CH$_2$-Cy-Th2-F, R¹-Np2-CH$_2$CH$_2$-Cy-Th2-F, R¹-Np3-CH$_2$CH$_2$-Cy-Th2-F,
R¹-Np4-CH$_2$CH$_2$-Cy-Th2-F, R¹-Cy-CH$_2$CH$_2$-Cy-Th3-F, R¹-Ph1-CH$_2$CH$_2$-Cy-Th3-F,
R¹-Ph2-CH$_2$CH$_2$-Cy-Th3-F, R¹-Ph3-CH$_2$CH$_2$-Cy-Th3-F, R¹-Np1-CH$_2$CH$_2$-Cy-Th3-F,
R¹-Np2-CH$_2$CH$_2$-Cy-Th3-F, R¹-Np3-CH$_2$CH$_2$-Cy-Th3-F, R¹-Np4-CH$_2$CH$_2$-Cy-Th3-F,
R¹-Cy-CH$_2$CH$_2$-Cy-Th4-F, R¹-Ph1-CH$_2$CH$_2$-Cy-Th4-F, R¹-Ph2-CH$_2$CH$_2$-Cy-Th4-F,
R¹-Ph3-CH$_2$CH$_2$-Cy-Th4-F, R¹-Np1-CH$_2$CH$_2$-Cy-Th4-F, R¹-Np2-CH$_2$CH$_2$-Cy-Th4-F,
R¹-Np3-CH$_2$CH$_2$-Cy-Th4-F, R¹-Np4-CH$_2$CH$_2$-Cy-Th4-F,
R¹-Cy-Ph1-Th1-F, R¹-Ph1-Ph1-Th1-F, R¹-Ph2-Ph1-Th1-F, R¹-Ph3-Ph1-Th1-F,
R¹-Np1-Ph1-Th1-F, R¹-Np2-Ph1-Th1-F, R¹-Np3-Ph1-Th1-F, R¹-Np4-Ph1-Th1-F,
R¹-Cy-Ph1-Th2-F, R¹-Ph1-Ph1-Th2-F, R¹-Ph2-Ph1-Th2-F, R¹-Ph3-Ph1-Th2-F,
R¹-Np1-Ph1-Th2-F, R¹-Np2-Ph1-Th2-F, R¹-Np3-Ph1-Th2-F, R¹-Np4-Ph1-Th2-F,
R¹-Cy-Ph1-Th3-F, R¹-Ph1-Ph1-Th3-F, R¹-Ph2-Ph1-Th3-F, R¹-Ph3-Ph1-Th3-F,
R¹-Np1-Ph1-Th3-F, R¹-Np2-Ph1-Th3-F, R¹-Np3-Ph1-Th3-F, R¹-Np4-Ph1-Th3-F,
R¹-Cy-Ph1-Th4-F, R¹-Ph1-Ph1-Th4-F, R¹-Ph2-Ph1-Th4-F, R¹-Ph3-Ph1-Th4-F,
R¹-Np1-Ph1-Th4-F, R¹-Np2-Ph1-Th4-F, R¹-Np3-Ph1-Th4-F, R¹-Np4-Ph1-Th4-F,
R¹-Cy-CH$_2$CH$_2$-Ph1-Th1-F, R¹-Ph1-CH$_2$CH$_2$-Ph1-Th1-F, R¹-Ph2-CH$_2$CH$_2$-Ph1-Th1-F,
R¹-Ph3-CH$_2$CH$_2$-Ph1-Th1-F, R¹-Np1-CH$_2$CH$_2$-Ph1-Th1-F, R¹-Np2-CH$_2$CH$_2$-Ph1-Th1-F,
R¹-Np3-CH$_2$CH$_2$-Ph1-Th1-F, R¹-Np4-CH$_2$CH$_2$-Ph1-Th1-F, R¹-Cy-CH$_2$CH$_2$-Ph1-Th2-F,
R¹-Ph1-CH$_2$CH$_2$-Ph1-Th2-F, R¹-Ph2-CH$_2$CH$_2$-Ph1-Th2-F, R¹-Ph3-CH$_2$CH$_2$-Ph1-Th2-F,
R¹-Np1-CH$_2$CH$_2$-Ph1-Th2-F, R¹-Np2-CH$_2$CH$_2$-Ph1-Th2-F, R¹-Np3-CH$_2$CH$_2$-Ph1-Th2-F,
R¹-Np4-CH$_2$CH$_2$-Ph1-Th2-F, R¹-Cy-CH$_2$CH$_2$-Ph1-Th3-F, R¹-Ph1-CH$_2$CH$_2$-Ph1-Th3-F,
R¹-Ph2-CH$_2$CH$_2$-Ph1-Th3-F, R¹-Ph3-CH$_2$CH$_2$-Ph1-Th3-F, R¹-Np1-CH$_2$CH$_2$-Ph1-Th3-F,
R¹-Np2-CH$_2$CH$_2$-Ph1-Th3-F, R¹-Np3-CH$_2$CH$_2$-Ph1-Th3-F, R¹-Np4-CH$_2$CH$_2$-Ph1-Th3-F,
R¹-Cy-CH$_2$CH$_2$-Ph1-Th4-F, R¹-Ph1-CH$_2$CH$_2$-Ph1-Th4-F, R¹-Ph2-CH$_2$CH$_2$-Ph1-Th4-F,
R¹-Ph3-CH$_2$CH$_2$-Ph1-Th4-F, R¹-Np1-CH$_2$CH$_2$-Ph1-Th4-F, R¹-Np2-CH$_2$CH$_2$-Ph1-Th4-F,
R¹-Np3-CH$_2$CH$_2$-Ph1-Th4-F, R¹-Np4-CH$_2$CH$_2$-Ph1-Th4-F,
R¹-Ph1-C≡C-Ph1-Th1-F, R¹-Ph2-C≡C-Ph1-Th1-F, R¹-Ph3-C≡C-Ph1-Th1-F,
R¹-Ph1-C≡C-Ph1-Th2-F, R¹-Ph2-C≡C-Ph1-Th2-F, R¹-Ph3-C≡C-Ph1-Th2-F,
R¹-Ph1-C≡C-Ph1-Th3-F, R¹-Ph2-C≡C-Ph1-Th3-F, R¹-Ph3-C≡C-Ph1-Th3-F,
R¹-Ph1-C≡C-Ph1-Th4-F, R¹-Ph2-C≡C-Ph1-Th4-F, R¹-Ph3-C≡C-Ph1-Th4-F,
R¹-Cy-Ph2-Th1-F, R¹-Ph1-Ph2-Th1-F, R¹-Ph2-Ph2-Th1-F, R¹-Ph3-Ph2-Th1-F,
R¹-Np1-Ph2-Th1-F, R¹-Np2-Ph2-Th1-F, R¹-Np3-Ph2-Th1-F, R¹-Np4-Ph2-Th1-F,
R¹-Cy-Ph2-Th2-F, R¹-Ph1-Ph2-Th2-F, R¹-Ph2-Ph2-Th2-F, R¹-Ph3-Ph2-Th2-F,
R¹-Np1-Ph2-Th2-F, R¹-Np2-Ph2-Th2-F, R¹-Np3-Ph2-Th2-F, R¹-Np4-Ph2-Th2-F,
R¹-Cy-Ph2-Th3-F, R¹-Ph1-Ph2-Th3-F, R¹-Ph2-Ph2-Th3-F, R¹-Ph3-Ph2-Th3-F,
R¹-Np1-Ph2-Th3-F, R¹-Np2-Ph2-Th3-F, R¹-Np3-Ph2-Th3-F, R¹-Np4-Ph2-Th3-F,
R¹-Cy-Ph2-Th4-F, R¹-Ph1-Ph2-Th4-F, R¹-Ph2-Ph2-Th4-F, R¹-Ph3-Ph2-Th4-F,
R¹-Np1-Ph2-Th4-F, R¹-Np2-Ph2-Th4-F, R¹-Np3-Ph2-Th4-F, R¹-Np4-Ph2-Th4-F,
R¹-Cy-CH$_2$CH$_2$-Ph2-Th1-F, R¹-Ph1-CH$_2$CH$_2$-Ph2-Th1-F, R¹-Ph2-CH$_2$CH$_2$-Ph2-Th1-F,
R¹-Ph3-CH$_2$CH$_2$-Ph2-Th1-F, R¹-Np1-CH$_2$CH$_2$-Ph2-Th1-F, R¹-Np2-CH$_2$CH$_2$-Ph2-Th1-F,
R¹-Np3-CH$_2$CH$_2$-Ph2-Th1-F, R¹-Np4-CH$_2$CH$_2$-Ph2-Th1-F, R¹-Cy-CH$_2$CH$_2$-Ph2-Th2-F,
R¹-Ph1-CH$_2$CH$_2$-Ph2-Th2-F, R¹-Ph2-CH$_2$CH$_2$-Ph2-Th2-F, R¹-Ph3-CH$_2$CH$_2$-Ph2-Th2-F,
R¹-Np1-CH$_2$CH$_2$-Ph2-Th2-F, R¹-Np2-CH$_2$CH$_2$-Ph2-Th2-F, R¹-Np3-CH$_2$CH$_2$-Ph2-Th2-F,
R¹-Np4-CH$_2$CH$_2$-Ph2-Th2-F, R¹-Cy-CH$_2$CH$_2$-Ph2-Th3-F, R¹-Ph1-CH$_2$CH$_2$-Ph2-Th3-F,
R¹-Ph2-CH$_2$CH$_2$-Ph2-Th3-F, R¹-Ph3-CH$_2$CH$_2$-Ph2-Th3-F, R¹-Np1-CH$_2$CH$_2$-Ph2-Th3-F,
R¹-Np2-CH$_2$CH$_2$-Ph2-Th3-F, R¹-Np3-CH$_2$CH$_2$-Ph2-Th3-F, R¹-Np4-CH$_2$CH$_2$-Ph2-Th3-F,
R¹-Cy-CH$_2$CH$_2$-Ph2-Th4-F, R¹-Ph1-CH$_2$CH$_2$-Ph2-Th4-F, R¹-Ph2-CH$_2$CH$_2$-Ph2-Th4-F,
R¹-Ph3-CH$_2$CH$_2$-Ph2-Th4-F, R¹-Np1-CH$_2$CH$_2$-Ph2-Th4-F, R¹-Np2-CH$_2$CH$_2$-Ph2-Th4-F,
R¹-Np3-CH$_2$CH$_2$-Ph2-Th4-F, R¹-Np4-CH$_2$CH$_2$-Ph2-Th4-F,
R¹-Ph1-C≡C-Ph2-Th1-F, R¹-Ph2-C≡C-Ph2-Th1-F, R¹-Ph3-C≡C-Ph2-Th1-F,
R¹-Ph1-C≡C-Ph2-Th2-F, R¹-Ph2-C≡C-Ph2-Th2-F, R¹-Ph3-C≡C-Ph2-Th2-F,
R¹-Ph1-C≡C-Ph2-Th3-F, R¹-Ph2-C≡C-Ph2-Th3-F, R¹-Ph3-C≡C-Ph2-Th3-F,
R¹-Ph1-C≡C-Ph2-Th4-F, R¹-Ph2-C≡C-Ph2-Th4-F, R¹-Ph3-C≡C-Ph2-Th4-F,
R¹-Cy-Ph3-Th1-F, R¹-Ph1-Ph3-Th1-F, R¹-Ph2-Ph3-Th1-F, R¹-Ph3-Ph3-Th1-F,
R¹-Np1-Ph3-Th1-F, R¹-Np2-Ph3-Th1-F, R¹-Np3-Ph3-Th1-F, R¹-Np4-Ph3-Th1-F,
R¹-Cy-Ph3-Th2-F, R¹-Ph1-Ph3-Th2-F, R¹-Ph2-Ph3-Th2-F, R¹-Ph3-Ph3-Th2-F, R$^1$-Np1-Ph3-Th2-F, R$^1$-Np2-Ph3-Th2-F, R$^1$-Np3-Ph3-Th2-F, R$^1$-Np4-Ph3-Th2-F,
R$^1$-Cy-Ph3-Th3-F, R$^1$-Ph1-Ph3-Th3-F, R$^1$-Ph2-Ph3-Th3-F, R$^1$-Ph3-Ph3-Th3-F,
R$^1$-Np1-Ph3-Th3-F, R$^1$-Np2-Ph3-Th3-F, R$^1$-Np3-Ph3-Th3-F, R$^1$-Np4-Ph3-Th3-F,
R$^1$-Cy-Ph3-Th4-F, R$^1$-Ph1-Ph3-Th4-F, R$^1$-Ph2-Ph3-Th4-F, R$^1$-Ph3-Ph3-Th4-F,
R$^1$-Np1-Ph3-Th4-F, R$^1$-Np2-Ph3-Th4-F, R$^1$-Np3-Ph3-Th4-F, R$^1$-Np4-Ph3-Th4-F,
R$^1$-Cy-CH$_2$CH$_2$-Ph3-Th1-F, R$^1$-Ph1-CH$_2$CH$_2$-Ph3-Th1-F, R$^1$-Ph2-CH$_2$CH$_2$-Ph3-Th1-F,
R$^1$-Ph3-CH$_2$CH$_2$-Ph3-Th1-F, R$^1$-Np1-CH$_2$CH$_2$-Ph3-Th1-F, R$^1$-Np2-CH$_2$CH$_2$-Ph3-Th1-F,
R$^1$-Np3-CH$_2$CH$_2$-Ph3-Th1-F, R$^1$-Np4-CH$_2$CH$_2$-Ph3-Th1-F, R$^1$-Cy-CH$_2$CH$_2$-Ph3-Th2-F,
R$^1$-Ph1-CH$_2$CH$_2$-Ph3-Th2-F, R$^1$-Ph2-CH$_2$CH$_2$-Ph3-Th2-F, R$^1$-Ph3-CH$_2$CH$_2$-Ph3-Th2-F,
R$^1$-Np1-CH$_2$CH$_2$-Ph3-Th2-F, R$^1$-Np2-CH$_2$CH$_2$-Ph3-Th2-F, R$^1$-Np3-CH$_2$CH$_2$-Ph3-Th2-F,
R$^1$-Np4-CH$_2$CH$_2$-Ph3-Th2-F, R$^1$-Cy-CH$_2$CH$_2$-Ph3-Th3-F, R$^1$-Ph1-CH$_2$CH$_2$-Ph3-Th3-F,
R$^1$-Ph2-CH$_2$CH$_2$-Ph3-Th3-F, R$^1$-Ph3-CH$_2$CH$_2$-Ph3-Th3-F, R$^1$-Np1-CH$_2$CH$_2$-Ph3-Th3-F,
R$^1$-Np2-CH$_2$CH$_2$-Ph3-Th3-F, R$^1$-Np3-CH$_2$CH$_2$-Ph3-Th3-F, R$^1$-Np4-CH$_2$CH$_2$-Ph3-Th3-F,
R$^1$-Cy-CH$_2$CH$_2$-Ph3-Th4-F, R$^1$-Ph1-CH$_2$CH$_2$-Ph3-Th4-F, R$^1$-Ph2-CH$_2$CH$_2$-Ph3-Th4-F,
R$^1$-Ph3-CH$_2$CH$_2$-Ph3-Th4-F, R$^1$-Np1-CH$_2$CH$_2$-Ph3-Th4-F, R$^1$-Np2-CH$_2$CH$_2$-Ph3-Th4-F,
R$^1$-Np3-CH$_2$CH$_2$-Ph3-Th4-F, R$^1$-Np4-CH$_2$CH$_2$-Ph3-Th4-F,
R$^1$-Ph1-C≡C-Ph3-Th1-F, R$^1$-Ph2-C≡C-Ph3-Th1-F, R$^1$-Ph3-C≡C-Ph3-Th1-F,
R$^1$-Ph1-C≡C-Ph3-Th2-F, R$^1$-Ph2-C≡C-Ph3-Th2-F, R$^1$-Ph3-C≡C-Ph3-Th2-F,
R$^1$-Ph1-C≡C-Ph3-Th3-F, R$^1$-Ph2-C≡C-Ph3-Th3-F, R$^1$-Ph3-C≡C-Ph3-Th3-F,
R$^1$-Ph1-C≡C-Ph3-Th4-F, R$^1$-Ph2-C≡C-Ph3-Th4-F, R$^1$-Ph3-C≡C-Ph3-Th4-F,
R$^1$-Cy-Np1-Th1-F, R$^1$-Ph1-Np1-Th1-F, R$^1$-Ph2-Np1-Th1-F, R$^1$-Ph3-Np1-Th1-F,
R$^1$-Cy-Np1-Th2-F, R$^1$-Ph1-Np1-Th2-F, R$^1$-Ph2-Np1-Th2-F, R$^1$-Cy-Np1-Th3-F,
R$^1$-Ph1-Np1-Th3-F, R$^1$-Ph2-Np1-Th3-F, R$^1$-Ph3-Np1-Th3-F, R$^1$-Cy-Np1-Th4-F,
R$^1$-Ph1-Np1-Th4-F, R$^1$-Ph2-Np1-Th4-F, R$^1$-Ph3-Np1-Th4-F,
R$^1$-Cy-CH$_2$CH$_2$-Np1-Th1-F, R$^1$-Ph1-CH$_2$CH$_2$-Np1-Th1-F, R$^1$-Ph2-CH$_2$CH$_2$-Np1-Th1-F,
R$^1$-Ph3-CH$_2$CH$_2$-Np1-Th1-F, R$^1$-Cy-CH$_2$CH$_2$-Np1-Th2-F, R$^1$-Ph1-CH$_2$CH$_2$-Np1-Th2-F,
R$^1$-Ph2-CH$_2$CH$_2$-Np1-Th2-F, R$^1$-Ph3-CH$_2$CH$_2$-Np1-Th2-F, R$^1$-Cy-CH$_2$CH$_2$-Np1-Th3-F,
R$^1$-Ph1-CH$_2$CH$_2$-Np1-Th3-F, R$^1$-Ph2-CH$_2$CH$_2$-Np1-Th3-F, R$^1$-Ph3-CH$_2$CH$_2$-Np1-Th3-F,
R$^1$-Cy-CH$_2$CH$_2$-Np1-Th4-F, R$^1$-Ph1-CH$_2$CH$_2$-Np1-Th4-F, R$^1$-Ph2-CH$_2$CH$_2$-Np1-Th4-F,
R$^1$-Ph3-CH$_2$CH$_2$-Np1-Th4-F,
in the case in which n$^a$=n$^b$=1, and n$^c$=n$^d$=0, and Z is a cyano group,
R$^1$-Cy-Cy-Th1-CN, R$^1$-Ph1-Cy-Th1-CN, R$^1$-Ph2-Cy-Th1-CN, R$^1$-Ph3-Cy-Th1-CN,
R$^1$-Np1-Cy-Th1-CN, R$^1$-Np2-Cy-Th1-CN, R$^1$-Np3-Cy-Th1-CN, R$^1$-Np4-Cy-Th1-CN,
R$^1$-Cy-Cy-Th2-CN, R$^1$-Ph1-Cy-Th2-CN, R$^1$-Ph2-Cy-Th2-CN, R$^1$-Ph3-Cy-Th2-CN,
R$^1$-Np1-Cy-Th2-CN, R$^1$-Np2-Cy-Th2-CN, R$^1$-Np3-Cy-Th2-CN, R$^1$-Np4-Cy-Th2-CN,
R$^1$-Cy-Cy-Th3-CN, R$^1$-Ph1-Cy-Th3-CN, R$^1$-Ph2-Cy-Th3-CN, R$^1$-Ph3-Cy-Th3-CN,
R$^1$-Np1-Cy-Th3-CN, R$^1$-Np2-Cy-Th3-CN, R$^1$-Np3-Cy-Th3-CN, R$^1$-Np4-Cy-Th3-CN,
R$^1$-Cy-Cy-Th4-CN, R$^1$-Ph1-Cy-Th4-CN, R$^1$-Ph2-Cy-Th4-CN, R$^1$-Ph3-Cy-Th4-CN,
R$^1$-Np1-Cy-Th4-CN, R$^1$-Np2-Cy-Th4-CN, R$^1$-Np3-Cy-Th4-CN, R$^1$-Np4-Cy-Th4-CN,
R$^1$-Cy-CH$_2$CH$_2$-Cy-Th1-CN, R$^1$-Ph1-CH$_2$CH$_2$-Cy-Th1-CN, R$^1$-Ph2-CH$_2$CH$_2$-Cy-Th1-CN,
R$^1$-Ph3-CH$_2$CH$_2$-Cy-Th1-CN, R$^1$-Np1CH$_2$CH$_2$-Cy-Th1-CN, R$^1$-Np2-CH$_2$CH$_2$-Cy-Th1-CN,
R$^1$-Np3-CH$_2$CH$_2$-Cy-Th1-CN, R$^1$-Np4-CH$_2$CH$_2$-Cy-Th1-CN, R$^1$-Cy-CN$_2$CH$_2$-Cy-Th2-CN,
R$^1$-Ph1-CH$_2$CH$_2$-Cy-Th2-CN, R$^1$-Ph2-CH$_2$CH$_2$-Cy-Th1-CN, R$^1$-Ph3-CH$_2$CH$_2$-Cy-Th2-CN,
R$^1$-Np3-CH$_2$CH$_2$-Cy-Th2-CN, R$^1$-Np2-CH$_2$CH$_2$-Cy-Th2-CN, R$^1$-Np3-CH$_2$CH$_2$-Cy-Th2-CN,
R$^1$-Np4-CH$_2$CH$_2$-Cy-Th2-CN, R$^1$-Cy-CH$_2$CH$_2$-Cy-Th3-CN, R$^1$-Ph1-CH$_2$CH$_2$-Cy-Th3-CN,
R$^1$-Ph2-CH$_2$CH$_2$-Cy-Th3-CN, R$^1$-Ph3-CH$_2$CH$_2$-Cy-Th3-CN, R$^1$-Np1-CH$_2$CH$_2$-Cy-Th3-CN,
R$^1$-Np2-CH$_2$CH$_2$-Cy-Th3-CN, R$^1$-Np3-CH$_2$CH$_2$-Cy-Th3-CN, R$^1$-Np4-CH$_2$CH$_2$-Cy-Th3-CN,
R$^1$-Cy-CH$_2$CH$_2$-Cy-Th4-CN, R$^1$-Ph1-CH$_2$CH$_2$-Cy-Th3-CN, R$^1$-Ph2-CH$_2$CH$_2$-Cy-Th4-CN,
R$^1$-Ph3-CH$_2$CH$_2$-Cy-Th4-CN, R$^1$-Np1-CH$_2$CH$_2$-Cy-Th4-CN, R$^1$-Np2-CH$_2$CH$_2$-Cy-Th4-CN,
R$^1$-Np3-CH$_2$CH$_2$-Cy-Th4-CN, R$^1$-Np4-CH$_2$CH$_2$-Cy-Th4-CN,
R$^1$-Cy-Ph1-Th1-CN, R$^1$-Ph1-Ph1-Th1-CN, R$^1$-Ph2-Ph1-Th1-CN, R$^1$-Ph3-Ph1-Th1-CN,
R$^1$-Np1-Ph1-Th1-CN, R$^1$-Np2-Ph1-Th1-CN, R$^1$-Np3-Ph1-Th1-CN,
R$^1$-Np4-Ph1-Th1-CN, R$^1$-Cy-Ph1-Th2-CN, R$^1$-Ph1-Ph1-Th2-CN, R$^1$-Ph2-Ph1-Th2-CN,
R$^1$-Ph3-Ph1-Th2-CN, R$^1$-Np1-Ph1-Th2-CN, R$^1$-Np2-Ph1-Th2-CN,
R$^1$-Np3-Ph1-Th2-CN, R$^1$-Np4-Ph1-Th2-CN, R$^1$-Cy-Ph1-Th3-CN, R$^1$-Ph1-Ph1-Th3-CN,
R$^1$-Ph2-Ph1-Th3-CN, R$^1$-Ph3-Ph1-Th3-CN, R$^1$-Np1-Ph1-Th3-CN,
R$^1$-Np2-Ph1-Th3-CN, R$^1$-Np3-Ph1-Th3-CN, R$^1$-Np4-Ph1-Th3-CN, R$^1$-Cy-Ph1-Th4-CN,
R$^1$-Ph1-Ph1-Th4-CN, R$^1$-Ph2-Ph1-Th4-CN, R$^1$-Ph3-Ph1-Th4-CN,
R$^1$-Np1-Ph1-Th4-CN, R$^1$-Np2-Ph1-Th4-CN, R$^1$-Np3-Ph1-Th4-CN,
R$^1$-Np4-Ph1-Th4-CN,
R$^1$-Cy-CH$_2$CH$_2$-Ph1-Th1-CN, R$^1$-Ph1-CH$_2$CH$_2$-Ph1-Th1-CN, R$^1$-Ph2-CH$_2$CH$_2$-Ph1-Th1-CN,
R$^1$-Ph3-CH$_2$CH$_2$-Ph1-Th1-CN, R$^1$-Np1-CH$_2$CH$_2$-Ph1-Th1-CN,
R$^1$-Np2-CH$_2$CH$_2$-Ph1-Th1-CN, R$^1$-Np3-CH$_2$CH$_2$-Ph1-Th1-CN,
R$^1$-Np4-CH$_2$CH$_2$-Ph1-Th1-CN, R$^1$-Cy-CH$_2$CH$_2$-Ph1-Th2-CN,
R$^1$-Ph1-CH$_2$CH$_2$-Ph1-Th2-CN,
R$^1$-Ph2-CH$_2$CH$_2$-Ph1-Th2-CN, R$^1$-Ph3-CH$_2$CH$_2$-Ph1-Th2-CN,
R$^1$-Np1-CH$_2$CH$_2$-Ph1-Th2-CN, R$^1$-Np2-CH$_2$CH$_2$-Ph1-Th2-CN,
R$^1$-Np3-CH$_2$CH$_2$-Ph1-Th2-CN, R$^1$-Np4-CH$_2$CH$_2$-Ph1-Th2-CN,
R$^1$-Cy-CH$_2$CH$_2$-Ph1-Th3-CN,
R$^1$-Ph1-CH$_2$CH$_2$-Ph1-Th3-CN, R$^1$-Ph2-CH$_2$CH$_2$-Ph1-Th3-CN, R$^1$-Ph3-CH$_2$CH$_2$-Ph1-Th3-CN, R$^1$-Np1-CH$_2$CH$_2$-Ph1-Th3-CN, R$^1$-Np2-CH$_2$CH$_2$-Ph1-Th3-CN, R$^1$-Np3-CH$_2$CH$_2$-Ph1-Th3-CN, R$^1$-Np4-CH$_2$CH$_2$-Ph1-Th3-CN, R$^1$-Cy-CH$_2$CH$_2$-Ph1-Th4-CN, R$^1$-Ph1-CH$_2$CH$_2$-Ph1-Th4-CN, R$^1$-Ph2-CH$_2$CH$_2$-Ph1-Th4-CN, R$^1$-Ph3-CH$_2$CH$_2$-Ph1-Th4-CN, R$^1$-Np1-CH$_2$CH$_2$-Ph1-Th4-CN, R$^1$-Np2-CH$_2$CH$_2$-Ph1-Th4-CN, R$^1$-Np3-CH$_2$CH$_2$-Ph1-Th4-CN, R$^1$-Np4-CH$_2$CH$_2$-Ph1-Th4-CN, R$^1$-Ph1-C≡C-Ph1-Th1-CN, R$^1$-Ph2-C≡C-Ph1-Th1-CN, R$^1$-Ph3-C≡C-Ph1-Th1-CN, R$^1$-Ph1-C≡C-Ph1-Th2-CN, R$^1$-Ph2-C≡C-Ph1-Th2-CN, R$^1$-Ph3-C≡C-Ph1-Th2-CN, R$^1$-Ph1-C≡C-Ph1-Th3-CN, R$^1$-Ph2-C≡C-Ph1-Th3-CN, R$^1$-Ph3-C≡C-Ph1-Th3-CN, R$^1$-Ph1-C≡C-Ph1-Th4-CN, R$^1$-Ph2-C≡C-Ph1-Th4-CN, R$^1$-Ph3-C≡C-Ph1-Th4-CN, R$^1$-Cy-Ph2-Th1-CN, R$^1$-Ph1-Ph2-Th1-CN, R$^1$-Ph2-Ph2-Th1-CN, R$^1$-Ph3-Ph2-Th1-CN, R$^1$-Np1-Ph2-Th1-CN, R$^1$-Np2-Ph2-Th1-CN, R$^1$-Np3-Ph2-Th1-CN, R$^1$-Np4-Ph2-Th1-CN, R$^1$-Cy-Ph2-Th2-CN, R$^1$-Ph1-Ph2-Th2-CN, R$^1$-Ph2-Ph2-Th2-CN, R$^1$-Ph3-Ph2-Th2-CN, R$^1$-Np1-Ph2-Th2-CN, R$^1$-Np2-Ph2-Th2-CN, R$^1$-Np3-Ph2-Th2-CN, R$^1$-Np4-Ph2-Th2-CN, R$^1$-Cy-Ph2-Th3-CN, R$^1$-Ph1-Ph2-Th3-CN, R$^1$-Ph2-Ph2-Th3-CN, R$^1$-Ph3-Ph2-Th3-CN, R$^1$-Np1-Ph2-Th3-CN, R$^1$-Np2-Ph2-Th3-CN, R$^1$-Np3-Ph2-Th3-CN, R$^1$-Np4-Ph2-Th3-CN, R$^1$-Cy-Ph2-Th4-CN, R$^1$-Ph1-Ph2-Th4-CN, R$^1$-Ph2-Ph2-Th4-CN, R$^1$-Ph3-Ph2-Th4-CN, R$^1$-Np1-Ph2-Th4-CN, R$^1$-Np2-Ph2-Th4-CN, R$^1$-Np3-Ph2-Th4-CN, R$^1$-Np4-Ph2-Th4-CN, R$^1$-Cy-CH$_2$CH$_2$-Ph2-Th1-CN, R$^1$-Ph1-CH$_2$CH$_2$-Ph2-Th1-CN, R$^1$-Ph2-CH$_2$CH$_2$-Ph2-Th1-CN, R$^1$-Ph3-CH$_2$CH$_2$-Ph2-Th1-CN, R$^1$-Np1-CH$_2$CH$_2$-Ph2-Th1-CN, R$^1$-Np2-CH$_2$CH$_2$-Ph2-Th1-CN, R$^1$-Np3-CH$_2$CH$_2$-Ph2-Th1-CN, R$^1$-Np4-CH$_2$CH$_2$-Ph2-Th1-CN, R$^1$-Cy-CH$_2$CH$_2$-Ph2-Th2-CN, R$^1$-Ph1-CH$_2$CH$_2$-Ph2-Th2-CN, R$^1$-Ph2-CH$_2$CH$_2$-Ph2-Th2-CN, R$^1$-Ph3-CH$_2$CH$_2$-Ph2-Th2-CN, R$^1$-Np1-CH$_2$CH$_2$-Ph2-Th2-CN, R$^1$-Np2-CH$_2$CH$_2$-Ph2-Th2-CN, R$^1$-Np3-CH$_2$CH$_2$-Ph2-Th2-CN, R$^1$-Np4-CH$_2$CH$_2$-Ph2-Th2-CN, R$^1$-Cy-CH$_2$CH$_2$-Ph2-Th3-CN, R$^1$-Ph1-CH$_2$CH$_2$-Ph1-Th3-CN, R$^1$-Ph2-CH$_2$CH$_2$-Ph2-Th3-CN, R$^1$-Ph3-CH$_2$CH$_2$-Ph1-Th3-CN, R$^1$-Np1-CH$_2$CH$_2$-Ph2-Th3-CN, R$^1$-Np2-CH$_2$CH$_2$-Ph2-Th3-CN, R$^1$-Np3-CH$_2$CH$_2$-Ph2-Th3-CN;

R$^1$-Np4-CH$_2$CH$_2$-Ph2-Th3-CN, R$^1$-Cy-CH$_2$CH$_2$-Ph2-Th4-CN,

R$^1$-Ph1-CH$_2$CH$_2$-Ph2-Th4-CN,

R$^1$-Ph2-CH$_2$CH$_2$-Ph2-Th4-CN, R$^1$-Ph3-CH$_2$CH$_2$-Ph2-Th4-CN,

R$^1$-Np1-CH$_2$CH$_2$-Ph2-Th4-CN, R$^1$-Np2-CH$_2$CH$_2$-Ph2-Th4-CN,

R$^1$-Np3-CH$_2$CH$_2$-Ph2-Th4-CN, R$^1$-Np4-CH$_2$CH$_2$-Ph2-Th4-CN,

R$^1$-Ph1-C≡C-Ph2-Th1-CN, R$^1$-Ph2-C≡C-Ph2-Th1-CN, R$^1$-Ph3-C≡C-Ph2-Th1-CN,

R$^1$-Ph1-C≡C-Ph2-Th2-CN, R$^1$-Ph2-C≡C-Ph2-Th2-CN, R$^1$-Ph3-C≡C-Ph2-Th2-CN,

R$^1$-Ph1-C≡C-Ph2-Th3-CN, R$^1$-Ph2-C≡C-Ph2-Th3-CN, R$^1$-Ph3-C≡C-Ph2-Th3-CN,

R$^1$-Ph1-C≡C-Ph2-Th4-CN, R$^1$-Ph2-C≡C-Ph1-Th4-CN, R$^1$-Ph3-C≡C-Ph2-Th4-CN,

R$^1$-Cy-Ph3-Th1-CN, R$^1$-Ph1-Ph3-Th1-CN, R$^1$-Ph2-Ph3-Th1-CN, R$^1$-Ph3-Ph3-Th1-CN,

R$^1$-Np1-Ph3-Th1-CN, R$^1$-Np2-Ph3-Th1-CN, R$^1$-Np3-Ph3-Th1-CN,

R$^1$-Np4-Ph3-Th1-CN, R$^1$-Cy-Ph3-Th2-CN, R$^1$-Ph1-Ph3-Th2-CN, R$^1$-Ph2-Ph3-Th2-CN,

R$^1$-Ph3-Ph3-Th2-CN, R$^1$-Np1-Ph3-Th2-CN, R$^1$-Np2-Ph3-Th2-CN,

R$^1$-Np3-Ph3-Th2-CN, R$^1$-Np4-Ph3-Th2-CN, R$^1$-Cy-Ph3-Th3-CN, R$^1$-Ph1-Ph3-Th3-CN,

R$^1$-Ph2-Ph3-Th3-CN, R$^1$-Ph3-Ph3-Th3-CN, R$^1$-Np1-Ph3-Th3-CN,

R$^1$-Np2-Ph3-Th3-CN, R$^1$-Np3-Ph3-Th3-CN, R$^1$-Np4-Ph3-Th3-CN, R$^1$-Cy-Ph3-Th4-CN,

R$^1$-Ph1-Ph3-Th4-CN, R$^1$-Ph2-Ph3-Th4-CN, R$^1$-Ph3-Ph3-Th4-CN,

R$^1$-Np1-Ph3-Th4-CN, R$^1$-Np2-Ph3-Th4-CN, R$^1$-Np3-Ph3-Th4-CN,

R$^1$-Np4-Ph3-Th4-CN,

R$^1$-Cy-CH$_2$CH$_2$-Ph3-Th1-CN, R$^1$-Ph1-CH$_2$CH$_2$-Ph3-Th1-CN, R$^1$-Ph2-CH$_2$CH$_2$-Ph3-Th1-CN,

R$^1$-Ph3-CH$_2$CH$_2$-Ph3-Th1-CN, R$^1$-Np1-CH$_2$CH$_2$-Ph3-Th1-CN,

R$^1$-Np2-CH$_2$CH$_2$-Ph3-Th1-CN, R$^1$-Np3-CH$_2$CH$_2$-Ph3-Th1-CN,

R$^1$-Np4-CH$_2$CH$_2$-Ph3-Th1-CN, R$^1$-Cy-CH$_2$CH$_2$-Ph3-Th2-CN,

R$^1$-Ph1-CH$_2$CH$_2$-Ph3-Th2-CN,

R$^1$-Ph2-CH$_2$CH$_2$-Ph3-Th2-CN, R$^1$-Ph3-CH$_2$CH$_2$-Ph3-Th2-CN,

R$^1$-Np1-CH$_2$CH$_2$-Ph3-Th2-CN, R$^1$-Np2-CH$_2$CH$_2$-Ph3-Th2-CN,

R$^1$-Np3-CH$_2$CH$_2$-Ph3-Th2-CN, R$^1$-Np4-CH$_2$CH$_2$-Ph3-Th2-CN,

R$^1$-Cy-CH$_2$CH$_2$-Ph3-Th3-CN,

R$^1$-Ph1-CH$_2$CH$_2$-Ph3-Th3-CN, R$^1$-Ph2-CH$_2$CH$_2$-Ph3-Th3-CN,

R$^1$-Ph3-CH$_2$CH$_2$-Ph3-Th3-CN, R$^1$-Np1-CH$_2$CH$_2$-Ph3-Th3-CN,

R$^1$-Np2-CH$_2$CH$_2$-Ph3-Th3-CN, R$^1$-Np3-CH$_2$CH$_2$-Ph3-Th3-CN,

R$^1$-Np4-CH$_2$CH$_2$-Ph3-Th3-CN, R$^1$-Cy-CH$_2$CH$_2$-Ph3-Th4-CN,

R$^1$-Ph1-CH$_2$CH$_2$-Ph3-Th4-CN,

R$^1$-Ph2-CH$_2$CH$_2$-Ph3-Th4-CN, R$^1$-Ph3-CH$_2$CH$_2$-Ph3-Th4-CN,

R$^1$-Np1-CH$_2$CH$_2$-Ph3-Th4-CN, R$^1$-Np2-CH$_2$CH$_2$-Ph3-Th4-CN,

R$^1$-Np3-CH$_2$CH$_2$-Ph3-Th4-CN, R$^1$-Np4-CH$_2$CH$_2$-Ph3-Th4-CN,

R$^1$-Ph1-C≡C-Ph3-Th1-CN, R$^1$-Ph2-C≡C-Ph3-Th1-CN, R$^1$-Ph3-C≡C-Ph3-Th1-CN,

R$^1$-Ph1-C≡C-Ph3-Th2-CN, R$^1$-Ph2-C≡C-Ph3-Th2-CN, R$^1$-Ph3-C≡C-Ph3-Th2-CN,

R$^1$-Ph1-C≡C-Ph3-Th3-CN, R$^1$-Ph2-C≡C-Ph3-Th3-CN, R$^1$-Ph3-C≡C-Ph3-Th3-CN,

R$^1$-Ph1-C≡C-Ph3-Th4-CN, R$^1$-Ph2-C≡C-Ph3-Th4-CN, R$^1$-Ph3-C≡C-Ph3-Th4-CN,

R$^1$-Cy-Np1-Th1-CN, R$^1$-Ph1-Np1-Th1-CN, R$^1$-Ph2-Np1-Th1-CN, R$^1$-Ph3-Np1-Th1-CN,

R$^1$-Cy-Np1-Th2-CN, R$^1$-Ph1-Np1-Th2-CN, R$^1$-Ph2-Np1-Th2-CN, R$^1$-Ph3-Np1-Th2-CN,

R$^1$-Cy-Np1-Th3-CN, R$^1$-Ph1-Np1-Th3-CN, R$^1$-Ph2-Np1-Th3-CN, R$^1$-Ph3-Np1-Th3-CN,

R$^1$-Cy-Np1-Th4-CN, R$^1$-Ph1-Np1-Th4-CN, R$^1$-Ph2-Np1-Th4-CN, R$^1$-Ph3-Np1-Th4-CN,

R$^1$-Cy-CH$_2$CH$_2$-Np1-Th1-CN, R$^1$-Ph1-CH$_2$CH$_2$-Np1-Th1-CN,

R$^1$-Ph2-CH$_2$CH$_2$-Np1-Th1-CN,

R$^1$-Ph3-CH$_2$CH$_2$-Np1-Th1-CN, R$^1$-Cy-CH$_2$CH$_2$-Np1-Th2-CN,

R$^1$-Ph1-CH$_2$CH$_2$-Np1-Th2-CN,

R$^1$-Ph2-CH$_2$CH$_2$-Np1-Th2-CN, R$^1$-Ph3-CH$_2$CH$_2$-Np1-Th2-CN,

R$^1$-Cy-CH$_2$CH$_2$-Np1-Th3-CN,

R$^1$-Ph1-CH$_2$CH$_2$-Np1-Th3-CN, R$^1$-Ph2-CH$_2$CH$_2$-Np1-Th3-CN,

R$^1$-Ph3-CH$_2$CH$_2$-Np1-Th3-CN, R$^1$-Cy-CH$_2$CH$_2$-Np1-Th4-CN,

R$^1$-Ph1-CH$_2$CH$_2$-Np1-Th4-CN,

R$^1$-Ph2-CH$_2$CH$_2$-Np1-Th4-CN, R$^1$-Ph3-CH$_2$CH$_2$-Np1-Th4-CN, in the case in which $n^a=n^b=1$, and $n^c=n^d=0$, and Z is a fluorine atom, R$^1$-Cy-Cy-Th1-OCF$_3$, R$^1$-Ph1-Cy-Th1-OCF$_3$, R$^1$-Ph2-Cy-Th1-OCF$_3$, R$^1$-Ph3-Cy-Th1-OCF$_3$, R$^1$-Np1-Cy-Th1-OCF$_3$, R$^1$-Np2-Cy-Th1-OCF$_3$, R$^1$-Np3-Cy-Th1-OCF$_3$, R$^1$-Np4-Cy-Th1-OCF$_3$, R$^1$-Cy-Cy-Th2-OCF$_3$, R$^1$-Ph1-Cy-Th2-OCF$_3$, R$^1$-Ph2-Cy-Th2-OCF$_3$, R$^1$-Ph3-Cy-Th2-OCF$_3$, R$^1$-Np1-Cy-Th2-OCF$_3$, R$^1$-Np2-Cy-Th2-OCF$_3$, R$^1$-Np3-Cy-Th2-OCF$_3$, R$^1$-Np4-Cy-Th2-OCF$_3$, R$^1$-Cy-Cy-Th3-OCF$_3$, R$^1$-Ph1-Cy-Th3-OCF$_3$, R$^1$-Ph2-Cy-Th3-OCF$_3$, R$^1$-Ph3-Cy-Th3-OCF$_3$, R$^1$-Np1-Cy-Th3-OCF$_3$, R$^1$-Np2-Cy-Th3-OCF$_3$, R$^1$-Np3-Cy-Th3-OCF$_3$, R$^1$-Np4-Cy-Th3-OCF$_3$, R$^1$-Cy-Cy-Th4-OCF$_3$, R$^1$-Ph1-Cy-Th4-OCF$_3$, R$^1$-Ph2-Cy-Th4-OCF$_3$, R$^1$-Ph3-Cy-Th4-OCF$_3$, R$^1$-Np1-Cy-Th4-OCF$_3$, R$^1$-Np2-Cy-Th4-OCF$_3$, R$^1$-Np3-Cy-Th4-OCF$_3$, R$^1$-Np4-Cy-Th4-OCF$_3$, R$^1$-Cy-CH$_2$CH$_2$-Cy-Th1-OCF$_3$, R$^1$-Ph1-CH$_2$CH$_2$-Cy-Th1-OCF$_3$, R$^1$-Ph2-CH$_2$CH$_2$-Cy-Th1-OCF$_3$, R$^1$-Ph3-CH$_2$CH$_2$-Cy-Th1-OCF$_3$, R$^1$-Np1-CH$_2$CH$_2$-Cy-Th1-OCF$_3$, R$^1$-Np2-CH$_2$CH$_2$-Cy-Th1-OCF$_3$, R$^1$-Np3-CH$_2$CH$_2$-Cy-Th1-OCF$_3$, R$^1$-Np4-CH$_2$CH$_2$-Cy-Th1-OCF$_3$, R$^1$-Cy-CH$_2$CH$_2$-Cy-Th2-OCF$_3$, R$^1$-Ph1-CH$_2$CH$_2$-Cy-Th2-OCF$_3$, R$^1$-Ph2-CH$_2$CH$_2$-Cy-Th2-OCF$_3$, R$^1$-Ph3-CH$_2$CH$_2$-Cy-Th2-OCF$_3$, R$^1$-Np1-CH$_2$CH$_2$-Cy-Th2-OCF$_3$, R$^1$-Np2-CH$_2$CH$_2$-Cy-Th2-OCF$_3$, R$^1$-Np3-CH$_2$CH$_2$-Cy-Th2-OCF$_3$, R$^1$-Np4-CH$_2$CH$_2$-Cy-Th2-OCF$_3$, R$^1$-Cy-CH$_2$CH$_2$-Cy-Th3-OCF$_3$, R$^1$-Ph1-CH$_2$CH$_2$-Cy-Th3-OCF$_3$, R$^1$-Ph2-CH$_2$CH$_2$-Cy-Th3-OCF$_3$, R$^1$-Ph3-CH$_2$CH$_2$-Cy-Th3-OCF$_3$, R$^1$-Np1-CH$_2$CH$_2$-Cy-Th3-OCF$_3$, R$^1$-Np2-CH$_2$CH$_2$-Cy-Th3-OCF$_3$, R$^1$-Np3-CH$_2$CH$_2$-Cy-Th3-OCF$_3$, R$^1$-Np4-CH$_2$CH$_2$-Cy-Th3-OCF$_3$, R$^1$-Cy-CH$_2$CH$_2$-Cy-Th4-OCF$_3$, R$^1$-Ph1-CH$_2$CH$_2$-Cy-Th4-OCF$_3$, R$^1$-Ph2-CH$_2$CH$_2$-Cy-Th4-OCF$_3$, R$^1$-Ph3-CH$_2$CH$_2$-Cy-Th4-OCF$_3$, R$^1$-Np1-CH$_2$CH$_2$-Cy-Th4-OCF$_3$, R$^1$-Np2-CH$_2$CH$_2$-Cy-Th4-OCF$_3$, R$^1$-Np3-CH$_2$CH$_2$-Cy-Th4-OCF$_3$, R$^1$-Np4-CH$_2$CH$_2$-Cy-Th4-OCF$_3$, R$^1$-Cy-Ph1-Th1-OCF$_3$, R$^1$-Ph1-Ph1-Th1-OCF$_3$, R$^1$-Ph1-Ph1-Th1-OCF$_3$, R$^1$-Ph3-Ph1-Th1-OCF$_3$, R$^1$-Np1-Ph1-Th1-OCF$_3$, R$^1$-Np2-Ph1-Th1-OCF$_3$, R$^1$-Np3-Ph1-Th1-OCF$_3$, R$^1$-Np4-Ph1-Th1-OCF$_3$, R$^1$-Cy-Ph1-Th2-OCF$_3$, R$^1$-Ph1-Ph1-Th2-OCF$_3$, R$^1$-Ph2-Ph1-Th2-OCF$_3$, R$^1$-Ph3-Ph1-Th2-OCF$_3$, R$^1$-Np1-Ph1-Th2-OCF$_3$, R$^1$-Np2-Ph1-Th2-OCF$_3$, R$^1$-Np3-Ph1-Th2-OCF$_3$, R$^1$-Np4-Ph1-Th2-OCF$_3$, R$^1$-Cy-Ph1-Th3-OCF$_3$, R$^1$-Ph1-Ph1-Th3-OCF$_3$, R$^1$-Ph2-Ph1-Th3-OCF$_3$, R$^1$-Ph3-Ph1-Th3-OCF$_3$, R$^1$-Np1-Ph1-Th3-OCF$_3$, R$^1$-Np2-Ph1-Th3-OCF$_3$, R$^1$-Np3-Ph1-Th3-OCF$_3$, R$^1$-Np4-Ph1-Th3-OCF$_3$, R$^1$-Cy-Ph1-Th4-OCF$_3$, R$^1$-Ph1-Ph1-Th4-OCF$_3$, R$^1$-Ph2-Ph1-Th4-OCF$_3$, R$^1$-Ph3-Ph1-Th4-OCF$_3$, R$^1$-Np1-Ph1-Th4-OCF$_3$, R$^1$-Np2-Ph1-Th4-OCF$_3$, R$^1$-Np3-Ph1-Th4-OCF$_3$, R$^1$-Np4-Ph1-Th4-OCF$_3$, R$^1$-Cy-CH$_2$CH$_2$-Ph1-Th1-OCF$_3$, R$^1$-Ph1-CH$_2$CH$_2$-Ph1-Th1-OCF$_3$, R$^1$-Ph2-CH$_2$CH$_2$-Ph1-Th1-OCF$_3$, R$^1$-Ph3-CH$_2$CH$_2$-Ph1-Th1-OCF$_3$, R$^1$-Np1-CH$_2$CH$_2$-Ph1-Th1-OCF$_3$, R$^1$-Np2-CH$_2$CH$_2$-Ph1-Th1-OCF$_3$, R$^1$-Np3-CH$_2$CH$_2$-Ph1-Th1-OCF$_3$, R$^1$-Np4-CH$_2$CH$_2$-Ph1-Th1-OCF$_3$, R$^1$-Cy-CH$_2$CH$_2$-Ph1-Th2-OCF$_3$, R$^1$-Ph1-CH$_2$CH$_2$-Ph1-Th2-OCF$_3$, R$^1$-Ph2-CH$_2$CH$_2$-Ph1-Th2-OCF$_3$, R$^1$-Ph3-CH$_2$CH$_2$-Ph1-Th2-OCF$_3$, R$^1$-Np1-CH$_2$CH$_2$-Ph1-Th2-OCF$_3$, R$^1$-Np2-CH$_2$CH$_2$-Ph1-Th2-OCF$_3$, R$^1$-Np3-CH$_2$CH$_2$-Ph1-Th2-OCF$_3$, R$^1$-Np4-CH$_2$CH$_2$-Ph1-Th2-OCF$_3$, R$^1$-Cy-CH$_2$CH$_2$-Ph1-Th3-OCF$_3$, R$^1$-Ph1-CH$_2$CH$_2$-Ph1-Th3-OCF$_3$, R$^1$-Ph2-CH$_2$CH$_2$-Ph1-Th3-OCF$_3$, R$^1$-Ph3-CH$_2$CH$_2$-Ph1-Th3-OCF$_3$, R$^1$-Np1-CH$_2$CH$_2$-Ph1-Th3-OCF$_3$, R$^1$-Np2-CH$_2$CH$_2$-Ph1-Th3-OCF$_3$, R$^1$-Np3-CH$_2$CH$_2$-Ph1-Th3-OCF$_3$, R$^1$-Np4-CH$_2$CH$_2$-Ph1-Th3-OCF$_3$, R$^1$-Cy-CH$_2$CH$_2$-Ph1-Th4-OCF$_3$, R$^1$-Ph1-CH$_2$CH$_2$-Ph1-Th4-OCF$_3$, R$^1$-Ph2-CH$_2$CH$_2$-Ph1-Th4-OCF$_3$, R$^1$-Ph3-CH$_2$CH$_2$-Ph1-Th4-OCF$_3$, R$^1$-Np1-CH$_2$CH$_2$-Ph1-Th4-OCF$_3$, R$^1$-Np2-CH$_2$CH$_2$-Ph1-Th4-OCF$_3$, R$^1$-Np3-CH$_2$CH$_2$-Ph1-Th4-OCF$_3$, R$^1$-Np4-CH$_2$CH$_2$-Ph1-Th4-OCF$_3$, R$^1$-Ph1-C≡C-Ph1-Th1-OCF$_3$, R$^1$-Ph2-C≡C-Ph1-Th1-OCF$_3$,
R$^1$-Ph3-C≡C-Ph1-Th1-OCF$_3$, R$^1$-Ph1-C≡C-Ph1-Th2-OCF$_3$,
R$^1$-Ph2-C≡C-Ph1-Th2-OCF$_3$, R$^1$-Ph3-C≡C-Ph1-Th2-OCF$_3$,
R$^1$-Ph1-C≡C-Ph1-Th3-OCF$_3$, R$^1$-Ph2-C≡C-Ph1-Th3-OCF$_3$,
R$^1$-Ph3-C≡C-Ph1-Th3-OCF$_3$, R$^1$-Ph1-C≡C-Ph1-Th4-OCF$_3$,
R$^1$-Ph2-C≡C-Ph1-Th4-OCF$_3$, R$^1$-Ph3-C≡C-Ph1-Th4-OCF$_3$,
R$^1$-Cy-Ph2-Th1-OCF$_3$, R$^1$-Ph1-Ph2-Th1-OCF$_3$, R$^1$-Ph2-Ph2-Th1-OCF$_3$,
R$^1$-Ph3-Ph2-Th1-OCF$_3$, R$^1$-Np1-Ph2-Th1-OCF$_3$, R$^1$-Np2-Ph2-Th1-OCF$_3$,
R$^1$-Np3-Ph2-Th1-OCF$_3$, R$^1$-Np4-Ph2-Th1-OCF$_3$, R$^1$-Cy-Ph2-Th2-OCF$_3$,
R$^1$-Ph1-Ph2-Th2-OCF$_3$, R$^1$-Ph2-Ph2-Th2-OCF$_3$, R$^1$-Ph3-Ph2-Th2-OCF$_3$,
R$^1$-Np1-Ph2-Th2-OCF$_3$, R$^1$-Np2-Ph2-Th2-OCF$_3$, R$^1$-Np3-Ph2-Th2-OCF$_3$,
R$^1$-Np4-Ph2-Th2-OCF$_3$, R$^1$-Cy-Ph2-Th3-OCF$_3$, R$^1$-Ph1-Ph2-Th3-OCF$_3$,
R$^1$-Ph2-Ph2-Th3-OCF$_3$, R$^1$-Ph3-Ph2-Th3-OCF$_3$, R$^1$-Np1-Ph2-Th3-OCF$_3$,
R$^1$-Np2-Ph2-Th3-OCF$_3$, R$^1$-Np3-Ph2-Th3-OCF$_3$, R$^1$-Np4-Ph2-Th3-OCF$_3$,
R$^1$-Cy-Ph2-Th4-OCF$_3$, R$^1$-Ph1-Ph2-Th1-OCF$_3$, R$^1$-Ph2-Ph2-Th4-OCF$_3$,
R$^1$-Ph3-Ph2-Th4-OCF$_3$, R$^1$-Np2-Ph1-Th4-OCF$_3$, R$^1$-Np2-Ph2-Th4-OCF$_3$,
R$^1$-Np3-Ph2-Th4-OCF$_3$, R$^1$-Np4-Ph2-Th4-OCF$_3$,
R$^1$-Cy-CH$_2$CH$_2$-Ph2-Th1-OCF$_3$, R$^1$-Ph1-CH$_2$CH$_2$-Ph2-Th1-OCF$_3$,
R$^1$-Ph2-CH$_2$CH$_2$-Ph2-Th1-OCF$_3$, R$^1$-Ph3-CH$_2$CH$_2$-Ph2-Th1-OCF$_3$,
R$^1$-Np1-CH$_2$CH$_2$-Ph2-Th1-OCF$_3$, R$^1$-Np2-CH$_2$CH$_2$-Ph2-Th1-OCF$_3$,
R$^1$-Np3-CH$_2$CH$_2$-Ph2-Th1-OCF$_3$, R$^1$-Np4-CH$_2$CH$_2$-Ph2-Th1-OCF$_3$,
R$^1$-Cy-CH$_2$CH$_2$-Ph2-Th2-OCF$_3$, R$^1$-Ph1-CH$_2$CH$_2$-Ph2-Th2-OCF$_3$,
R$^1$-Ph2-CH$_2$CH$_2$-Ph2-Th2-OCF$_3$, R$^1$-Ph3-CH$_2$CH$_2$-Ph2-Th2-OCF$_3$,
R$^1$-Np1-CH$_2$CH$_2$-Ph2-Th3-OCF$_3$, R$^1$-Np2-CH$_2$CH$_2$-Ph2-Th2-OCF$_3$,
R$^1$-Np3-CH$_2$CH$_2$-Ph2-Th2-OCF$_3$, R$^1$-Np4-CH$_2$CH$_2$-Ph2-Th2-OCF$_3$,
R$^1$-Cy-CH$_2$CH$_2$-Ph2-Th3-OCF$_3$, R$^1$-Ph1-CH$_2$CH$_2$-Ph2-Th3-OCF$_3$,
R$^1$-Ph2-CH$_2$CH$_2$-Ph2-Th3-OCF$_3$, R$^1$-Ph3-CH$_2$CH$_2$-Ph2-Th3-OCF$_3$,
R$^1$-Np1-CH$_2$CH$_2$-Ph2-Th3-OCF$_3$, R$^1$-Np2-CH$_2$CH$_2$-Ph2-Th3-OCF$_3$,
R$^1$-Np3-CH$_2$CH$_2$-Ph2-Th3-OCF$_3$, R$^1$-Np4-CH$_2$CH$_2$-Ph2-Th3-OCF$_3$,
R$^1$-Cy-CH$_2$CH$_2$-Ph2-Th4-OCF$_3$, R$^1$-Ph1-CH$_2$CH$_2$-Ph2-Th4-OCF$_3$,
R$^1$-Ph2-CH$_2$CH$_2$-Ph2-Th4-OCF$_3$, R$^1$-Ph3-CH$_2$CH$_2$-Ph2-Th4-OCF$_3$,
R$^1$-Np1-CH$_2$CH$_2$-Ph2-Th4-OCF$_3$, R$^1$-Np2-CH$_2$CH$_2$-Ph2-Th4-OCF$_3$,
R$^1$-Np3-CH$_2$CH$_2$-Ph2-Th4-OCF$_3$, R$^1$-Np4-CH$_2$CH$_2$-Ph2-Th4-OCF$_3$,
R$^1$-Ph1-C≡C-Ph2-Th1-OCF$_3$, R$^1$-Ph2-C≡C-Ph2-Th1-OCF$_3$,
R$^1$-Ph3-C≡C-Ph2-Th1-OCF$_3$, R$^1$-Ph1-C≡C-Ph2-Th2-OCF$_3$,
R$^1$-Ph2-C≡C-Ph2-Th2-OCF$_3$, R$^1$-Ph3-C≡C-Ph2-Th2-OCF$_3$,
R$^1$-Ph1-C≡C-Ph2-Th3-OCF$_3$, R$^1$-Ph2-C≡C-Ph2-Th3-OCF$_3$,
R$^1$-Ph3-C≡C-Ph2-Th3-OCF$_3$, R$^1$-Ph1-C≡C-Ph2-Th4-OCF$_3$,
R$^1$-Ph2-C≡C-Ph2-Th4-OCF$_3$, R$^1$-Ph3-C≡C-Ph2-Th4-OCF$_3$,
R$^1$-Cy-Ph3-Th1-OCF$_3$, R$^1$-Ph1-Ph3-Th1-OCF$_3$, R$^1$-Ph2-Ph3-Th1-OCF$_3$,
R$^1$-Ph3-Ph3-Th1-OCF$_3$, R$^1$-Np1-Ph3-Th1-OCF$_3$, R$^1$-Np2-Ph3-Th1-OCF$_3$,
R$^1$-Np3-Ph3-Th1-OCF$_3$, R$^1$-Np4-Ph3-Th1-OCF$_3$, R$^1$-Cy-Ph3-Th2-OCF$_3$,
R$^1$-Ph1-Ph3-Th2-OCF$_3$, R$^1$-Ph2-Ph3-Th2-OCF$_3$, R$^1$-Ph3-Ph3-Th2-OCF$_3$,
R$^1$-Np1-Ph3-Th2-OCF$_3$, R$^1$-Np2-Ph3-Th2-OCF$_3$, R$^1$-Np3-Ph3-Th2-OCF$_3$,
R$^1$-Np4-Ph3-Th2-OCF$_3$, R$^1$-Cy-Ph3-Th3-OCF$_3$, R$^1$-Ph1-Ph3-Th3-OCF$_3$,
R$^1$-Ph2-Ph3-Th3-OCF$_3$, R$^1$-Ph3-Ph3-Th3-OCF$_3$, R$^1$-Np1-Ph3-Th3-OCF$_3$,
R$^1$-Np2-Ph3-Th3-OCF$_3$, R$^1$-Np3-Ph3-Th3-OCF$_3$, R$^1$-Np4-Ph3-Th3-OCF$_3$,
R$^1$-Cy-Ph3-Th4-OCF$_3$, R$^1$-Ph1-Ph3-Th4-OCF$_3$, R$^1$-Ph2-Ph3-Th4-OCF$_3$,
R$^1$-Ph3-Ph3-Th4-OCF$_3$, R$^1$-Np1-Ph3-Th4-OCF$_3$, R$^1$-Np2-Ph3-Th4-OCF$_3$,
R$^1$-Np3-Ph3-Th4-OCF$_3$, R$^1$-Np4-Ph3-Th4-OCF$_3$,
R$^1$-Cy-CH$_2$CH$_2$-Ph3-Th1-OCF$_3$, R$^1$-Ph1-CH$_2$CH$_2$-Ph3-Th1-OCF$_3$,
R$^1$-Ph2-CH$_2$CH$_2$-Ph3-Th1-OCF$_3$, R$^1$-Ph3-CH$_2$CH$_2$-Ph3-Th1-OCF$_3$,
R$^1$-Np1-CH$_2$CH$_2$-Ph3-Th1-OCF$_3$, R$^1$-Np2-CH$_2$CH$_2$-Ph3-Th1-OCF$_3$,
R$^1$-Np3-CH$_2$CH$_2$-Ph3-Th1-OCF$_3$, R$^1$-Np4-CH$_2$CH$_2$-Ph3-Th1-OCF$_3$,
R$^1$-Cy-CH$_2$CH$_2$-Ph3-Th2-OCF$_3$, R$^1$-Ph1-CH$_2$CH$_2$-Ph3-Th2-OCF$_3$,
R$^1$-Ph2-CH$_2$CH$_2$-Ph3-Th2-OCF$_3$, R$^1$-Ph3-CH$_2$CH$_2$-Ph3-Th2-OCF$_3$,
R$^1$-Np1-CH$_2$CH$_2$-Ph3-Th2-OCF$_3$, R$^1$-Np2-CH$_2$CH$_2$-Ph3-Th2-OCF$_3$,
R$^1$-Np3-CH$_2$CH$_2$-Ph3-Th2-OCF$_3$, R$^1$-Np4-CH$_2$CH$_2$-Ph3-Th2-OCF$_3$,
R$^1$-Cy-CH$_2$CH$_2$-Ph3-Th3-OCF$_3$, R$^1$-Ph1-CH$_2$CH$_2$-Ph3-Th3-OCF$_3$,
R$^1$-Ph2-CH$_2$CH$_2$-Ph3-Th3-OCF$_3$, R$^1$-Ph3-CH$_2$CH$_2$-Ph3-Th3-OCF$_3$,
R$^1$-Np1-CH$_2$CH$_2$-Ph3-Th3-OCF$_3$, R$^1$-Np2-CH$_2$CH$_2$-Ph3-Th3-OCF$_3$,
R$^1$-Np3-CH$_2$CH$_2$-Ph3-Th3-OCF$_3$, R$^1$-Np4-CH$_2$CH$_2$-Ph3-Th3-OCF$_3$,
R$^1$-Cy-CH$_2$CH$_2$-Ph3-Th4-OCF$_3$, R$^1$-Ph1-CH$_2$CH$_2$-Ph3-Th4-OCF$_3$,
R$^1$-Ph2-CH$_2$CH$_2$-Ph3-Th4-OCF$_3$, R$^1$-Ph3-CH$_2$CH$_2$-Ph3-Th4-OCF$_3$,
R$^1$-Np1-CH$_2$CH$_2$-Ph3-Th4-OCF$_3$, R$^1$-Np2-CH$_2$CH$_2$-Ph3-Th4-OCF$_3$,
R$^1$-Np3-CH$_2$CH$_2$-Ph3-Th4-OCF$_3$, R$^1$-Np4-CH$_2$CH$_2$-Ph3-Th4-OCF$_3$,
R$^1$-Cy-C≡C-Ph3-Th1-OCF$_3$, R$^1$-Ph1-C≡C-Ph3-Th1-OCF$_3$,
R$^1$-Ph2-C≡C-Ph3-Th1-OCF$_3$, R$^1$-Ph3-C≡C-Ph3-Th1-OCF$_3$, R$^1$-Ph1-C≡C-Ph3-Th2-OCF$_3$, R$^1$-Ph2-C≡C-Ph3-Th2-OCF$_3$,
R$^1$-Ph3-C≡C-Ph3-Th2-OCF$_3$, R$^1$-Ph1-C≡C-Ph3-Th3-OCF$_3$,
R$^1$-Ph2-C≡C-Ph3-Th3-OCF$_3$, R$^1$-Ph3-C≡C-Ph3-Th3-OCF$_3$,
R$^1$-Ph1-C≡C-Ph3-Th4-OCF$_3$, R$^1$-Ph2-C≡C-Ph3-Th4-OCF$_3$,
R$^1$-Ph3-C≡C-Ph3-Th4-OCF$_3$,
R$^1$-Cy-Np1-Th1-OCF$_3$, R$^1$-Ph1-Np1-Th1-OCF$_3$, R$^1$-Ph2-Np1-Th1-OCF$_3$,
R$^1$-Ph3-Np1-Th1-OCF$_3$, R$^1$-Np1-Np1-Th1-OCF$_3$, R$^1$-Np2-Np1-Th1-OCF$_3$,
R$^1$-Np3-Np1-Th1-OCF$_3$, R$^1$-Np4-Np1-Th1-OCF$_3$, R$^1$-Cy-Np1-Th2-OCF$_3$,
R$^1$-Ph1-Np1-Th2-OCF$_3$, R$^1$-Ph2-Np1-Th2-OCF$_3$, R$^1$-Ph3-Np1-Th2-OCF$_3$,
R$^1$-Cy-Np1-Th3-OCF$_3$, R$^1$-Ph1-Np1-Th3-OCF$_3$, R$^1$-Ph2-Np1-Th3-OCF$_3$,
R$^1$-Ph3-Np1-Th3-OCF$_3$, R$^1$-Cy-Np1-Th4-OCF$_3$, R$^1$-Ph1-Np1-Th4-OCF$_3$,
R$^1$-Ph2-Np1-Th4-OCF$_3$, R$^1$-Ph3-Np1-Th4-OCF$_3$,
R$^1$-Cy-CH$_2$CH$_2$-Np1-Th1-OCF$_3$, R$^1$-Ph1-CH$_2$CH$_2$-Np1-Th1-OCF$_3$,
R$^1$-Ph2-CH$_2$CH$_2$-Np1-Th1-OCF$_3$, R$^1$-Ph3-CH$_2$CH$_2$-Np1-Th1-OCF$_3$,
R$^1$-Cy-CH$_2$CH$_2$-Np1-Th2-OCF$_3$, R$^1$-Ph1-CH$_2$CH$_2$-Np1-Th2-OCF$_3$,
R$^1$-Ph2-CH$_2$CH$_2$-Np1-Th2-OCF$_3$, R$^1$-Ph3-CH$_2$CH$_2$-Np1-Th2-OCF$_3$,
R$^1$-Cy-CH$_2$CH$_2$-Np1-Th3-OCF$_3$, R$^1$-Ph1-CH$_2$CH$_2$-Np1-Th3-OCF$_3$,
R$^1$-Ph2-CH$_2$CH$_2$-Np1-Th3-OCF$_3$, R$^1$-Ph3-CH$_2$CH$_2$-Np1-Th3-OCF$_3$,
R$^1$-Cy-CH$_2$CH$_2$-Np1-Th4-OCF$_3$, R$^1$-Ph1-CH$_2$CH$_2$-Np1-Th4-OCF$_3$,
R$^1$-Ph2-CH$_2$CH$_2$-Np1-Th4-OCF$_3$, R$^1$-Ph3-CH$_2$CH$_2$-Np1-Th4-OCF$_3$,
in the case in which $n^a=n^b=0$, and $n^c=1$, $n^d=0$ or $n^c=0$, $n^d=1$, and Z is a fluorine atom,
R$^1$-Th1-Ph1-F, R$^1$-Th1-Ph2-F, R$^1$-Th1-Ph3-F, R$^1$-Th1-Np1-F, R$^1$-Th1-Np2-F,
R$^1$-Th1-Np3-F, R$^1$-Th1-Np4-F, R$^1$-Th2-Ph1-F, R$^1$-Th2-Ph2-F, R$^1$-Th2-Ph3-F,
R$^1$-Th2-Np1-F, R$^1$-Th2-Np2-F, R$^1$-Th2-Np3-F, R$^1$-Th2-Np4-F, R$^1$-Th3-Ph1-F,
R$^1$-Th3-Ph2-F, R$^1$-Th3-Ph3-F, R$^1$-Th3-Np1-F, R$^1$-Th3-Np2-F, R$^1$-Th3-Np3-F,
R$^1$-Th3-Np4-F, R$^1$-Th4-Ph1-F, R$^1$-Th4-Ph2-F, R$^1$-Th4-Ph3-F, R$^1$-Th4-Np1-F,
R$^1$-Th4-Np2-F, R$^1$-Th4-Np3-F, R$^1$-Th4-Np4-F,
R$^1$-Th1-CH$_2$CH$_2$-Ph1-F, R$^1$-Th1-CH$_2$CH$_2$-Ph2-F, R$^1$-Th1-CH$_2$CH$_2$-Ph3-F,
R$^1$-Th1-CH$_2$CH$_2$-Np1-F, R$^1$-Th1-CH$_2$CH$_2$-Np2-F, R$^1$-Th1-CH$_2$CH$_2$-Np3-F,
R$^1$-Th1-CH$_2$CH$_2$-Np4-F, R$^1$-Th2-CH$_2$CH$_2$-Ph1-F, R$^1$-Th2-CH$_2$CH$_2$-Ph2-F,
R$^1$-Th2-CH$_2$CH$_2$-Ph3-F, R$^1$-Th2-CH$_2$CH$_2$-Np1-F, R$^1$-Th2-CH$_2$CH$_2$-Np2-F,
R$^1$-Th2-CH$_2$CH$_2$-Np3-F, R$^1$-Th2-CH$_2$CH$_2$-Np4-F, R$^1$-Th3-CH$_2$CH$_2$-Ph1-F,
R$^1$-Th3-CH$_2$CH$_2$-Ph2-F, R$^1$-Th3-CH$_2$CH$_2$-Ph3-F, R$^1$-Th3-CH$_2$CH$_2$-Np1-F,
R$^1$-Th3-CH$_2$CH$_2$-Np2-F, R$^1$-Th3-CH$_2$CH$_2$-Np3-F, R$^1$-Th3-CH$_2$CH$_2$-Np4-F,
R$^1$-Th4-CH$_2$CH$_2$-Ph1-F, R$^1$-Th4-CH$_2$CH$_2$-Ph2-F, R$^1$-Th4-CH$_2$CH$_2$-Ph3-F,
R$^1$-Th4-CH$_2$CH$_2$-Np1-F, R$^1$-Th4-CH$_2$CH$_2$-Np2-F, R$^1$-Th4-CH$_2$CH$_2$-Np3-F,
R$^1$-Th4-CH$_2$CH$_2$-Np4-F,
R$^1$-Th1-C≡C-Ph1-F, R$^1$-Th1-C≡C-Ph2-F, R$^1$-Th1-C≡C-Ph3-F,
R$^1$-Th2-C≡C-Ph1-F, R$^1$-Th2-C≡C-Ph2-F, R$^1$-Th2-C≡C-Ph3-F,
R$^1$-Th3-C≡C-Ph1-F, R$^1$-Th3-C≡C-Ph2-F, R$^1$-Th3-C≡C-Ph3-F,
R$^1$-Th4-C≡C-Ph1-F, R$^1$-Th4-C≡C-Ph2-F,
in the case in which $n^a=n^b=0$, and $n^c=1$, $n^d=0$ or $n^c=0$, $n^d=1$, and Z is a cyano group,
R$^1$-Th1-Ph1-CN, R$^1$-Th1-Ph2-CN, R$^1$-Th1-Ph3-CN, R$^1$-Th1-Np1-CN, R$^1$-Th1-Np2-CN,
R$^1$-Th1-Np3-CN, R$^1$-Th1-Np4-CN, R$^1$-Th2-Ph1-CN, R$^1$-Th2-Ph2-CN, R$^1$-Th2-Ph3-CN,
R$^1$-Th2-Np1-CN, R$^1$-Th2-Np2-CN, R$^1$-Th2-Np3-CN, R$^1$-Th2-Np4-CN, R$^1$-Th3-Ph1-CN,
R$^1$-Th3-Ph2-CN, R$^1$-Th3-Ph3-CN, R$^1$-Th3-Np1-CN, R$^1$-Th3-Np2-CN, R$^1$-Th3-Np3-CN,
R$^1$-Th3-Np4-CN, R$^1$-Th4-Ph1-CN, R$^1$-Th4-Ph2-CN, R$^1$-Th4-Ph3-CN, R$^1$-Th4-Np1-CN,
R$^1$-Th4-Np2-CN, R$^1$-Th4-Np3-CN, R$^1$-Th4-Np4-CN,
R$^1$-Th1-CH$_2$CH$_2$-Ph1-CN, R$^1$-Th1-CH$_2$CH$_2$-Ph2-CN, R$^1$-Th1-CH$_2$CH$_2$-Ph3-CN,
R$^1$-Th1-CH$_2$CH$_2$-Np1-CN, R$^1$-Th1-CH$_2$CH$_2$-Np2-CN, R$^1$-Th1-CH$_2$CH$_2$-Np3-CN,
R$^1$-Th1-CH$_2$CH$_2$-Np4-CN, R$^1$-Th2-CH$_2$CH$_2$-Ph1-CN, R$^1$-Th2-CH$_2$CH$_2$-Ph2-CN,
R$^1$-Th2-CH$_2$CH$_2$-Ph3-CN, R$^1$-Th2-CH$_2$CH$_2$-Np1-CN, R$^1$-Th2-CH$_2$CH$_2$-Np2-CN,
R$^1$-Th2-CH$_2$CH$_2$-Np3-CN, R$^1$-Th2-CH$_2$CH$_2$-Np4-CN, R$^1$-Th3-CH$_2$CH$_2$-Ph1-CN,
R$^1$-Th3-CH$_2$CH$_2$-Ph2-CN, R$^1$-Th3-CH$_2$CH$_2$-Ph3-CN, R$^1$-Th3-CH$_2$CH$_2$-Np1-CN,
R$^1$-Th3-CH$_2$CH$_2$-Np2-CN, R$^1$-Th3-CH$_2$CH$_2$-Np3-CN, R$^1$-Th3-CH$_2$CH$_2$-Np4-CN,
R$^1$-Th4-CH$_2$CH$_2$-Ph1-CN, R$^1$-Th4-CH$_2$CH$_2$-Ph2-CN, R$^1$-Th4-CH$_2$CH$_2$-Ph3-CN,
R$^1$-Th4-CH$_2$CH$_2$-Np1-CN, R$^1$-Th4-CH$_2$CH$_2$-Np2-CN, R$^1$-Th4-CH$_2$CH$_2$-Np3-CN,
R$^1$-Th4-CH$_2$CH$_2$-Np4-CN,
R$^1$-Th1-C≡C-Ph1-CN, R$^1$-Th1-C≡C-Ph2-CN, R$^1$-Th1-C≡C-Ph3-CN,
R$^1$-Th2-C≡C-Ph1-CN, R$^1$-Th2-C≡C-Ph2-CN, R$^1$-Th2-C≡C-Ph3-CN,
R$^1$-Th3-C≡C-Ph1-CN, R$^1$-Th3-C≡C-Ph2-CN, R$^1$-Th3-C≡C-Ph3-CN,
R$^1$-Th4-C≡C-Ph1-CN, R$^1$-Th4-C≡C-Ph2-CN,
in the case in which $n^a=n^b=0$, and $n^c=1$, $n^d=0$ or $n^c=0$, $n^d=1$, and Z is a trifluoromethyl group,
R$^1$-Th1-Ph1-OCF$_3$, R$^1$-Th1-Ph2-OCF$_3$, R$^1$-Th1-Ph3-OCF$_3$, R$^1$-Th1-Np1-OCF$_3$,
R$^1$-Th1-Np2-OCF$_3$, R$^1$-Th1-Np3-OCF$_3$, R$^1$-Th1-Np4-OCF$_3$, R$^1$-Th2-Ph1-OCF$_3$,
R$^1$-Th2-Ph2-OCF$_3$, R$^1$-Th2-Ph3-OCF$_3$, R$^1$-Th2-Np1-OCF$_3$, R$^1$-Th2-Np2-OCF$_3$,
R$^1$-Th2-Np3-OCF$_3$, R$^1$-Th2-Np4-OCF$_3$, R$^1$-Th3-Ph1-OCF$_3$, R$^1$-Th3-Ph2-OCF$_3$,
R$^1$-Th3-Ph3-OCF$_3$, R$^1$-Th3-Np1-OCF$_3$, R$^1$-Th3-Np2-OCF$_3$, R$^1$-Th3-Np3-OCF$_3$,
R$^1$-Th3-Np4-OCF$_3$, R$^1$-Th4-Ph1-OCF$_3$, R$^1$-Th4-Ph2-OCF$_3$, R$^1$-Th4-Ph3-OCF$_3$,
R$^1$-Th4-Np1-OCF$_3$, R$^1$-Th4-Np2-OCF$_3$, R$^1$-Th4-Np3-OCF$_3$, R$^1$-Th4-Np4-OCF$_3$,
R$^1$-Th1-CH$_2$CH$_2$-Ph1-OCF$_3$, R$^1$-Th1-CH$_2$CH$_2$-Ph2-OCF$_3$, R$^1$-Th1-CH$_2$CH$_2$-Ph3-OCF$_3$, R¹-Th1-CH₂CH₂-Np1-OCF₃, R¹-Th1-CH₂CH₂-Np2-OCF₃, R¹-Th1-CH₂CH₂-Np3-OCF₃,
R¹-Th1-CH₂CH₂-Np4-OCF₃, R¹-Th2-CH₂CH₂-Ph1-OCF₃, R¹-Th2-CH₂CH₂-Ph2-OCF₃,
R¹-Th2-CH₂CH₂-Ph3-OCF₃, R¹-Th2-CH₂CH₂-Np1-OCF₃, R¹-Th2-CH₂CH₂-Np2-OCF₃,
R¹-Th2-CH₂CH₂-Np3-OCF₃, R¹-Th2-CH₂CH₂-Np4-OCF₃, R¹-Th3-CH₂CH₂-Ph1-OCF₃,
R¹-Th3-CH₂CH₂-Ph2-OCF₃, R¹-Th3-CH₂CH₂-Ph3-OCF₃, R¹-Th3-CH₂CH₂-Np1-OCF₃,
R¹-Th3-CH₂CH₂-Np2-OCF₃, R¹-Th3-CH₂CH₂-Np3-OCF₃, R¹-Th3-CH₂CH₂-Np4-OCF₃,
R¹-Th4-CH₂CH₂-Ph1-OCF₃, R¹-Th4-CH₂CH₂-Ph2-OCF₃, R¹-Th4-CH₂CH₂-Ph3-OCF₃,
R¹-Th4-CH₂CH₂-Np1-OCF₃, R¹-Th4-CH₂CH₂-Np2-OCF₃, R¹-Th4-CH₂CH₂-Np3-OCF₃,
R¹-Th4-CH₂CH₂-Np4-OCF₃,
R¹-Th1-C≡C-Ph1-OCF₃, R¹-Th1-C≡C-Ph2-OCF₃, R¹-Th1-C≡C-Ph3-OCF₃,
R¹-Th2-C≡C-Ph1-OCF₃, R¹-Th2-C≡C-Ph2-OCF₃, R¹-Th2-C≡C-Ph3-OCF₃,
R¹-Th3-C≡C-Ph1-OCF₃, R¹-Th3-C≡C-Ph2-OCF₃, R¹-Th3-C≡C-Ph3-OCF₃,
R¹-Th4-C≡C-Ph1-OCF₃, R¹-Th4-C≡C-Ph2-OCF₃,
in the case in which $n^a=n^b=0$, and $n^c=n^d=1$, and Z is a fluorine atom,
R¹-Th1-Cy-Ph1-F, R¹-Th1-Cy-Ph2-F, R¹-Th1-Cy-Ph3-F, R¹-Th1-Cy-Np1-F,
R¹-Th1-Cy-Np2-F, R¹-Th1-Cy-Np3-F, R¹-Th1-Cy-Np4-F, R¹-Th2-Cy-Ph1-F,
R¹-Th2-Cy-Ph2-F, R¹-Th2-Cy-Ph3-F, R¹-Th2-Cy-Np1-F, R¹-Th2-Cy-Np2-F,
R¹-Th2-Cy-Np3-F, R¹-Th2-Cy-Np4-F, R¹-Th3-Cy-Ph1-F, R¹-Th3-Cy-Ph2-F,
R¹-Th3-Cy-Ph3-F, R¹-Th3-Cy-Np1-F, R¹-Th3-Cy-Np2-F, R¹-Th3-Cy-Np3-F,
R¹-Th3-Cy-Np4-F, R¹-Th4-Cy-Ph1-F, R¹-Th4-Cy-Ph2-F, R¹-Th4-Cy-Ph3-F,
R¹-Th4-Cy-Np1-F, R¹-Th4-Cy-Np2-F, R¹-Th4-Cy-Np3-F, R¹-Th4-Cy-Np4-F,
R¹-Th1-Ph1-Ph1-F, R¹-Th1-Ph1-Ph2-F, R¹-Th1-Ph1-Ph3-F, R¹-Th1-Ph1-Np1-F,
R¹-Th1-Ph1-Np2-F, R¹-Th1-Ph1-Np3-F, R¹-Th1-Ph1-Np4-F, R¹-Th2-Ph1-Ph1-F,
R¹-Th2-Ph1-Ph2-F, R¹-Th2-Ph1-Ph3-F, R¹-Th2-Ph1-Np1-F, R¹-Th2-Ph1-Np2-F,
R¹-Th2-Ph1-Np3-F, R¹-Th2-Ph1-Np4-F, R¹-Th3-Ph1-Ph1-F, R¹-Th3-Ph1-Ph2-F,
R¹-Th3-Ph1-Ph3-F, R¹-Th3-Ph1-Np1-F, R¹-Th3-Ph1-Np2-F, R¹-Th3-Ph1-Np3-F,
R¹-Th3-Ph1-Np4-F, R¹-Th4-Ph1-Ph1-F, R¹-Th4-Ph1-Ph2-F, R¹-Th4-Ph1-Ph3-F,
R¹-Th4-Ph1-Np1-F, R¹-Th4-Ph1-Np2-F, R¹-Th4-Ph1-Np3-F, R¹-Th4-Ph1-Np4-F,
R¹-Th1-Ph2-Ph1-F, R¹-Th1-Ph2-Ph2-F, R¹-Th1-Ph2-Ph3-F, R¹-Th1-Ph2-Np1-F,
R¹-Th1-Ph2-Np2-F, R¹-Th1-Ph2-Np3-F, R¹-Th1-Ph2-Np4-F, R¹-Th2-Ph2-Ph1-F,
R¹-Th2-Ph2-Ph2-F, R¹-Th2-Ph2-Ph3-F, R¹-Th2-Ph2-Np1-F, R¹-Th2-Ph2-Np2-F,
R¹-Th2-Ph2-Np3-F, R¹-Th2-Ph2-Np4-F, R¹-Th3-Ph2-Ph1-F, R³-Th3-Ph2-Ph2-F,
R¹-Th3-Ph2-Ph3-F, R¹-Th3-Ph2-Np1-F, R¹-Th3-Ph2-Np2-F, R¹-Th3-Ph2-Np3-F,
R¹-Th3-Ph2-Np4-F, R¹-Th4-Ph2-Ph1-F, R¹-Th4-Ph2-Ph2-F, R¹-Th4-Ph2-Ph3-F,
R¹-Th4-Ph2-Np1-F, R¹-Th4-Ph2-Np2-F, R¹-Th4-Ph2-Np3-F, R¹-Th4-Ph2-Np4-F,
R¹-Th1-Ph3-Ph1-F, R¹-Th1-Ph3-Ph2-F, R¹-Th1-Ph3-Ph3-F, R¹-Th1-Ph3-Np1-F,
R¹-Th1-Ph3-Np2-F, R¹-Th1-Ph3-Np3-F, R¹-Th1-Ph3-NO-F, R¹-Th2-Ph3-Ph1-F,
R¹-Th2-Ph3-Ph2-F, R¹-Th2-Ph3-Ph3-F, R¹-Th2-Ph3-Np1-F, R¹-Th2-Ph3-Np2-F,
R¹-Th2-Ph3-Np3-F, R¹-Th2-Ph3-Np4-F, R¹-Th3-Ph3-Ph1-F, R¹-Th3-Ph3-Ph2-F,
R¹-Th3-Ph3-Ph3-F, R¹-Th3-Ph3-Np1-F, R¹-Th3-Ph3-Np2-F, R¹-Th3-Ph3-Np3-F,
R¹-Th3-Ph3-Np4-F, R¹-Th4-Ph3-Ph1-F, R¹-Th4-Ph3-Ph2-F, R¹-Th4-Ph3-Ph3-F,
R¹-Th4-Ph3-Np1-F, R¹-Th4-Ph3-Np2-F, R¹-Th4-Ph3-Np3-F, R¹-Th4-Ph3-Np4-F,
R¹-Th1-Np1-Ph1-F, R¹-Th1-Np1-Ph2-F, R¹-Th1-Np1-Ph3-F, R¹-Th2-Np1-Ph1-F,
R¹-Th2-Np1-Ph2-F, R¹-Th2-Np1-Ph3-F, R¹-Th3-Np1-Ph1-F, R¹-Th3-Np1-Ph2-F,
R¹-Th3-Np1-Ph3-F, R¹-Th4-Np1-Ph1-F, R¹-Th4-Np1-Ph2-F, R¹-Th4-Np1-Ph3-F,
R¹-Th1-Np2-Ph1-F, R¹-Th1-Np2-Ph2-F, R¹-Th1-Np2-Ph3-F, R¹-Th2-Np2-Ph1-F,
R¹-Th2-Np2-Ph2-F, R¹-Th2-Np2-Ph3-F, R¹-Th3-Np2-Ph1-F, R¹-Th3-Np2-Ph2-F,
R¹-Th3-Np2-Ph3-F, R¹-Th4-Np2-Ph1-F, R¹-Th4-Np2-Ph2-F, R¹-Th4-Np2-Ph3-F,
R¹-Th1-Np3-Ph1-F, R¹-Th1-Np3-Ph2-F, R¹-Th1-Np3-Ph3-F, R¹-Th2-Np3-Ph1-F,
R¹-Th2-Np3-Ph2-F, R¹-Th2-Np3-Ph3-F, R¹-Th3-Np3-Ph1-F, R¹-Th3-Np3-Ph2-F,
R¹-Th3-Np3-Ph3-F, R¹-Th4-Np3-Ph1-F, R¹-Th4-Np3-Ph2-F, R¹-Th4-Np3-Ph3-F,
R¹-Th1-Np4-Ph1-F, R¹-Th1-Np4-Ph2-F, R¹-Th1-Np4-Ph3-F, R¹-Th2-Np4-Ph1-F,
R¹-Th2-Np4-Ph2-F, R¹-Th2-Np4-Ph3-F, R¹-Th3-Np4-Ph1-F, R¹-Th3-Np4-Ph2-F,
R¹-Th3-Np4-Ph3-F, R¹-Th4-Np4-Ph1-F, R¹-Th4-Np4-Ph2-F, R¹-Th4-Np4-Ph3-F,
R¹-Th1-Cy-CH₂CH₂-Ph1-F, R¹-Th1-Cy-CH₂CH₂-Ph2-F, R¹-Th1-Cy-CH₂CH₂-Ph3-F,
R¹-Th1-Cy-CH₂CH₂-Np1-F, R¹-Th1-Cy-CH₂CH₂-Np2-F, R¹-Th1-Cy-CH₂CH₂-Np3-F,
R¹-Th1-Cy-CH₂CH₂-Np4-F, R¹-Th2-Cy-CH₂CH₂-Ph1-F, R¹-Th2-Cy-CH₂CH₂-Ph2-F,
R¹-Th2-Cy-CH₂CH₂-Ph3-F, R¹-Th2-Cy-CH₂CH₂-Np1-F, R¹-Th2-Cy-CH₂CH₂-Np2-F,
R¹-Th2-Cy-CH₂CH₂-Np3-F, R¹-Th2-Cy-CH₂CH₂-Np4-F, R¹-Th3-Cy-CH₂H₂-Ph1-F,
R¹-Th3-Cy-CH₂CH₂-Ph2-F, R¹-Th3-Cy-CH₂CH₂-Ph3-F, R¹-Th3-Cy-CH₂CH₂-Np1-F,
R¹-Th3-Cy-CH₂CH₂-Np2-F, R¹-Th3-Cy-CH₂CH₂-Np3-F, R¹-Th3-Cy-CH₂CH₂-Np4-F,
R¹-Th4-Cy-CH₂CH₂-Ph1-F, R¹-Th4-Cy-CH₂CH₂-Ph2-F, R¹-Th4-Cy-CH₂CH₂-Ph3-F,
R¹-Th4-Cy-CH₂CH₂-Np1-F, R¹-Th4-Cy-CH₂CH₂-Np2-F, R¹-Th4-Cy-CH₂CH₂-Np3-F,
R¹-Th4-Cy-CH₂CH₂-Np4-F, R¹-Th1-Ph1-CH₂CH₂-Ph1-F, R¹-Th1-Ph1-CH₂CH₂-Ph2-F,
R¹-Th1-Ph1-CH₂CH₂-Ph3-F, R¹-Th1-Ph1-CH₂CH₂-Np1-F, R¹-Th1-Ph1-CH₂CH₂-Np2-F,
R¹-Th1-Ph1-CH₂CH₂-Np3-F, R¹-Th1-Ph1-CH₂CH₂-Np4-F, R¹-Th2-Ph1-CH₂CH₂-Ph1-F,
R¹-Th2-Ph1-CH₂CH₂-Ph2-F, R¹-Th2-Ph1-CH₂CH₂-Ph3-F, R¹-Th2-Ph1-CH₂CH₂-Np1-F,
R¹-Th2-Ph1-CH₂CH₂-Np2-F, R¹-Th2-Ph1-CH₂CH₂-Np3-F, R¹-Th2-Ph1-CH₂CH₂-Np4-F,
R¹-Th3-Ph1-CH₂CH₂-Ph1-F, R¹-Th3-Ph1-CH₂CH₂-Ph2-F, R¹-Th3-Ph1-CH₂CH₂-Ph3-F, R$^1$-Th3-Ph1-CH$_2$CH$_2$-Np1-F, R$^1$-Th3-Ph1-CH$_2$CH$_2$-Np2-F, R$^1$-Th3-Ph1-CH$_2$CH$_2$-Np3-F,
R$^1$-Th3-Ph1-CH$_2$CH$_2$-Np4-F, R$^1$-Th4-Ph1-CH$_2$CH$_2$-Ph1-F, R$^1$-Th4-Ph1-CH$_2$CH$_2$-Ph2-F,
R$^1$-Th4-Ph1-CH$_2$CH$_2$-Ph3-F, R$^1$-Th4-Ph1-CH$_2$CH$_2$-Np1-F, R$^1$-Th4-Ph1-CH$_2$CH$_2$-Np2-F,
R$^1$-Th4-Ph1-CH$_2$CH$_2$-Np3-F, R$^1$-Th4-Ph1-CH$_2$CH$_2$-Np4-F, R$^1$-Th1-Ph2-CH$_2$CH$_2$-Ph1-F,
R$^1$-Th1-Ph2-CH$_2$CH$_2$-Ph2-F, R$^1$-Th1-Ph2-CH$_2$CH$_2$-Ph3-F, R$^1$-Th1-Ph2-CH$_2$CH$_2$-Np1-F,
R$^1$-Th1-Ph2-CH$_2$CH$_2$-Np2-F, R$^1$-Th1-Ph2-CH$_2$CH$_2$-Np3-F, R$^1$-Th1-Ph2-CH$_2$CH$_2$-Np4-F,
R$^1$-Th2-Ph2-CH$_2$CH$_2$-Ph1-F, R$^1$-Th2-Ph2-CH$_2$CH$_2$-Ph2-F, R$^1$-Th2-Ph2-CH$_2$CH$_2$-Ph3-F,
R$^1$-Th2-Ph2-CH$_2$CH$_2$-Np1-F, R$^1$-Th2-Ph2-CH$_2$CH$_2$-Np2-F, R$^1$-Th2-Ph2-CH$_2$CH$_2$-Np3-F,
R$^1$-Th2-Ph2-CH$_2$CH$_2$-Np4-F, R$^1$-Th3-Ph2-CH$_2$CH$_2$-Ph1-F, R$^1$-Th3-Ph2-CH$_2$CH$_2$-Ph2-F,
R$^1$-Th3-Ph2-CH$_2$CH$_2$-Ph3-F, R$^1$-Th3-Ph2-CH$_2$CH$_2$-Np1-F, R$^1$-Th3-Ph2-CH$_2$CH$_2$-Np2-F,
R$^1$-Th3-Ph2-CH$_2$CH$_2$-Np3-F, R$^1$-Th3-Ph2-CH$_2$CH$_2$-Np4-F, R$^1$-Th4-Ph2-CH$_2$CH$_2$-Ph1-F,
R$^1$-Th4-Ph2-CH$_2$CH$_2$-Ph2-F, R$^1$-Th4-Ph2-CH$_2$CH$_2$-Ph3-F, R$^1$-Th4-Ph2-CH$_2$CH$_2$-Np1-F,
R$^1$-Th4-Ph2-CH$_2$CH$_2$-Np2-F, R$^1$-Th4-Ph2-CH$_2$CH$_2$-Np3-F, R$^1$-Th4-Ph2-CH$_2$CH$_2$-Np4-F,
R$^1$-Th1-Ph3-CH$_2$CH$_2$-Ph1-F, R$^1$-Th1-Ph3-CH$_2$CH$_2$-Ph2-F, R$^1$-Th1-Ph3-CH$_2$CH$_2$-Ph3-F,
R$^1$-Th1-Ph3-CH$_2$CH$_2$-Np1-F, R$^1$-Th1-Ph3-CH$_2$CH$_2$-Np2-F, R$^1$-Th1-Ph3-CH$_2$CH$_2$-Np3-F,
R$^1$-Th1-Ph3-CH$_2$CH$_2$-Np4-F, R$^1$-Th2-Ph3-CH$_2$CH$_2$-Ph1-F, R$^1$-Th2-Ph3-CH$_2$CH$_2$-Ph2-F,
R$^1$-Th2-Ph3-CH$_2$CH$_2$-Ph3-F, R$^1$-Th2-Ph1-CH$_2$CH$_2$-Np1-F, R$^1$-Th2-Ph3-CH$_2$CH$_2$-Np2-F,
R$^1$-Th2-Ph3-CH$_2$CH$_2$-Np3-F, R$^1$-Th2-Ph3-CH$_2$CH$_2$-Np4-F, R$^1$-Th3-Ph3-CH$_2$CH$_2$-Ph2-F,
R$^1$-Th3-Ph3-CH$_2$CH$_2$-Ph3-F, R$^1$-Th3-Ph3-CH$_2$CH$_2$-Ph3-F, R$^1$-Th3-Ph3-CH$_2$CH$_2$-Np1-F,
R$^1$-Th3-Ph3-CH$_2$CH$_2$-Np2-F, R$^1$-Th3-Ph3-CH$_2$CH$_2$-Np3-F, R$^1$-Th3-Ph3-CH$_2$CH$_2$-Np1-F,
R$^1$-Th4-Ph3-CH$_2$CH$_2$-Ph1-F, R$^1$-Th4-Ph3-CH$_2$CH$_2$-Ph2-F, R$^1$-Th4-Ph3-CH$_2$CH$_2$-Ph3-F,
R$^1$-Th4-Ph3-CH$_2$CH$_2$-Np1-F, R$^1$-Th4-Ph3-CH$_2$CH$_2$-Np2-F, R$^1$-Th4-Ph3-CH$_2$CH$_2$-Np3-F,
R$^1$-Th4-Ph3-CH$_2$CH$_2$-Np4-F, R$^1$-Th1-Np1-CH$_2$CH$_2$-Ph1-F, R$^1$-Th1-Np1-CH$_2$CH$_2$-Ph2-F,
R$^1$-Th1-Np1-CH$_2$CH$_2$-Ph3-F, R$^1$-Th2-Np1-CH$_2$CH$_2$-Ph1-F, R$^1$-Th2-Np1-CH$_2$CH$_2$-Ph2-F,
R$^1$-Th2-Np1-CH$_2$CH$_2$-Ph3-F, R$^1$-Th3-Np1-CH$_2$CH$_2$-Ph1-F, R$^1$-Th3-Np1-CH$_2$CH$_2$-Ph2-F,
R$^1$-Th3-Np1-CH$_2$CH$_2$-Ph3-F, R$^1$-Th4-Np1-CH$_2$CH$_2$-Ph1-F, R$^1$-Th4-Np1-CH$_2$CH$_2$-Ph2-F,
R$^1$-Th4-Np1-CH$_2$CH$_2$-Ph3-F, R$^1$-Th1-Np2-CH$_2$CH$_2$-Ph1-F, R$^1$-Th1-Np2-CH$_2$CH$_2$-Ph2-F,
R$^1$-Th1-Np2-CH$_2$CH$_2$-Ph3-F, R$^1$-Th1-Np2-CH$_2$CH$_2$-Ph1-F, R$^1$-Th2-Np2-CH$_2$CH$_2$-Ph2-F,
R$^1$-Th2-Np2-CH$_2$CH$_2$-Ph3-F, R$^1$-Th3-Np2-CH$_2$CH$_2$-Ph1-F, R$^1$-Th3-Np2-CH$_2$CH$_2$-Ph2-F,
R$^1$-Th3-Np2-CH$_2$CH$_2$-Ph3-F, R$^1$-Th4-Np2-CH$_2$CH$_2$-Ph1-F, R$^1$-Th4-Np2-CH$_2$CH$_2$-Ph2-F,
R$^1$-Th4-Np2-CH$_2$CH$_2$-Ph3-F, R$^1$-Th1-Np3-CH$_2$CH$_2$-Ph1-F, R$^1$-Th1-Np3-CH$_2$CH$_2$-Ph2-F,
R$^1$-Th1-Np3-CH$_2$CH$_2$-Ph3-F, R$^1$-Th2-Np3-CH$_2$CH$_2$-Ph1-F, R$^1$-Th2-Np3-CH$_2$CH$_2$-Ph2-F,
R$^1$-Th2-Np3-CH$_2$CH$_2$-Ph3-F, R$^1$-Th3-Np3-CH$_2$CH$_2$-Ph1-F, R$^1$-Th3-Np3-CH$_2$CH$_2$-Ph2-F,
R$^1$-Th3-Np3-CH$_2$CH$_2$-Ph3-F, R$^1$-Th4-Np3-CH$_2$CH$_2$-Ph1-F, R$^1$-Th4-Np3-CH$_2$CH$_2$-Ph2-F,
R$^1$-Th4-Np3-CH$_2$CH$_2$-Ph3-F, R$^1$-Th3-Np3-CH$_2$CH$_2$-Ph1-F, R$^1$-Th3-Np4-CH$_2$CH$_2$-Ph2-F,
R$^1$-Th1-Np3-CH$_2$CH$_2$-Ph3-F, R$^1$-Th2-Np4-CH$_2$CH$_2$-Ph1-F, R$^1$-Th2-Np4-CH$_2$CH$_2$-Ph2-F,
R$^1$-Th1-Np4-CH$_2$CH$_2$-Ph3-F, R$^1$-Th3-Np4-CH$_2$CH$_2$-Ph1-F, R$^1$-Th3-Np4-CH$_2$CH$_2$-Ph2-F,
R$^1$-Th3-Np4-CH$_2$CH$_2$-Ph3-F, R$^1$-Th4-Np4-CH$_2$CH$_2$-Ph1-F, R$^1$-Th4-Np4-CH$_2$CH$_2$-Ph2-F,
R$^1$-Th4-Np4-CH$_2$CH$_2$-Ph3-F, R$^1$-Th1-CH$_2$CH$_2$-Cy-Ph1-F, R$^1$-Th1-CH$_2$CH$_2$-Cy-Ph2-F,
R$^1$-Th1-CH$_2$CH$_2$-Cy-Ph3-F, R$^1$-Th1-CH$_2$CH$_2$-Cy-Np1-F, R$^1$-Th1-CH$_2$CH$_2$-Cy-Np2-F,
R$^1$-Th1-CH$_2$CH$_2$-Cy-Np3-F, R$^1$-Th1-CH$_2$CH$_2$-Cy-Np4-F, R$^1$-Th2-CH$_2$CH$_2$-Cy-Ph1-F,
R$^1$-Th2-CH$_2$CH$_2$-Cy-Ph2-F, R$^1$-Th2-CH$_2$CH$_2$-Cy-Ph3-F, R$^1$-Th2-CH$_2$CH$_2$-Cy-Np1-F,
R$^1$-Th2-CH$_2$CH$_2$-Cy-Np2-F, R$^1$-Th2-CH$_2$CH$_2$-Cy-Np3-F, R$^1$-Th2-CH$_2$CH$_2$-Cy-Np4-F,
R$^1$-Th3-CH$_2$CH$_2$-Cy-Ph1-F, R$^1$-Th3-CH$_2$CH$_2$-Cy-Ph2-F, R$^1$-Th3-CH$_2$CH$_2$-Cy-Ph3-F,
R$^1$-Th3-CH$_2$CH$_2$-Cy-Np1-F, R$^1$-Th3-CH$_2$CH$_2$-Cy-Np2-F, R$^1$-Th3-CH$_2$CH$_2$-Cy-Np3-F,
R$^1$-Th3-CH$_2$CH$_2$-Cy-Np4-F, R$^1$-Th4-CH$_2$CH$_2$-Cy-Ph1-F, R$^1$-Th4-CH$_2$CH$_2$-Cy-Ph2-F,
R$^1$-Th4-CH$_2$CH$_2$-Cy-Ph3-F, R$^1$-Th4-CH$_2$CH$_2$-Cy-Np1-F, R$^1$-Th4-CH$_2$CH$_2$-Cy-Np2-F,
R$^1$-Th4-CH$_2$CH$_2$-Cy-Np3-F, R$^1$-Th4-CH$_2$CH$_2$-Cy-Np4-F, R$^1$-Th1-CH$_2$CH$_2$-Ph1-Ph1-F,
R$^1$-Th1-CH$_2$CH$_2$-Ph1-Ph2-F, R$^1$-Th1-CH$_2$CH$_2$-Ph1-Ph3-F, R$^1$-Th1-CH$_2$CH$_2$-Ph1-Np1-F,
R$^1$-Th1-CH$_2$CH$_2$-Ph1-Np2-F, R$^1$-Th1-CH$_2$CH$_2$-Ph1-Np3-F, R$^1$-Th1-CH$_2$CH$_2$-Ph1-Np4-F,
R$^1$-Th2-CH$_2$CH$_2$-Ph1-Ph1-F, R$^1$-Th2-CH$_2$CH$_2$-Ph1-Ph2-F, R$^1$-Th2-CH$_2$CH$_2$-Ph1-Ph3-F,
R$^1$-Th2-CH$_2$CH$_2$-Ph1-Np1-F, R$^1$-Th2-CH$_2$CH$_2$-Ph1-Np2-F, R$^1$-Th2-CH$_2$CH$_2$-Ph1-Np3-F,
R$^1$-Th2-CH$_2$CH$_2$-Ph1-Np4-F, R$^1$-Th3-CH$_2$CH$_2$-Ph1-Ph1-F, R$^1$-Th3-CH$_2$CH$_2$-Ph1-Ph2-F,
R$^1$-Th3-CH$_2$CH$_2$-Ph1-Ph3-F, R$^1$-Th3-CH$_2$CH$_2$-Ph1-Np1-F, R$^1$-Th3-CH$_2$CH$_2$-Ph1-Np2-F,
R$^1$-Th3-CH$_2$CH$_2$-Ph1-Np3-F, R$^1$-Th3-CH$_2$CH$_2$-Ph1-Np4-F, R$^1$-Th4-CH$_2$CH$_2$-Ph1-Ph1-F,
R$^1$-Th4-CH$_2$CH$_2$-Ph1-Ph2-F, R$^1$-Th4-CH$_2$CH$_2$-Ph1-Ph3-F, R$^1$-Th4-CH$_2$CH$_2$-Ph1-Np1-F,
R$^1$-Th4-CH$_2$CH$_2$-Ph1-Np2-F, R$^1$-Th4-CH$_2$CH$_2$-Ph1-Np3-F, R$^1$-Th4-CH$_2$CH$_2$-Ph1-Np4-F,
R$^1$-Th1-CH$_2$CH$_2$-Ph2-Ph1-F, R$^1$-Th1-CH$_2$CH$_2$-Ph2-Ph2-F, R$^1$-Th1-CH$_2$CH$_2$-Ph2-Ph3-F,
R$^1$-Th1-CH$_2$CH$_2$-Ph2-Np1-F, R$^1$-Th1-CH$_2$CH$_2$-Ph2-Np2-F, R$^1$-Th1-CH$_2$CH$_2$-Ph2-Np3-F,
R$^1$-Th1-CH$_2$CH$_2$-Ph2-Np4-F, R$^1$-Th2-CH$_2$CH$_2$-Ph2-Ph1-F, R$^1$-Th2-CH$_2$CH$_2$-Ph2-Ph2-F,
R$^1$-Th2-CH$_2$CH$_2$-Ph2-Ph3-F, R$^1$-Th2-CH$_2$CH$_2$-Ph2-Np1-F, R$^1$-Th2-CH$_2$CH$_2$-Ph2-Np2-F,
R$^1$-Th2-CH$_2$CH$_2$-Ph2-Np3-F, R$^1$-Th2-CH$_2$CH$_2$-Ph2-Np4-F, R$^1$-Th3-CH$_2$CH$_2$-Ph2-Ph1-F,
R$^1$-Th3-CH$_2$CH$_2$-Ph2-Ph2-F, R$^1$-Th3-CH$_2$CH$_2$-Ph2-Ph3-F, R$^1$-Th3-CH$_2$CH$_2$-Ph2-Np1-F,
R$^1$-Th3-CH$_2$CH$_2$-Ph2-Np2-F, R$^1$-Th3-CH$_2$CH$_2$-Ph2-Np3-F, R$^1$-Th3-CH$_2$CH$_2$-Ph2-Np4-F,
R$^1$-Th4-CH$_2$CH$_2$-Ph2-Ph1-F, R$^1$-Th4-CH$_2$CH$_2$-Ph2-Ph2-F, R$^1$-Th4-CH$_2$CH$_2$-Ph2-Ph3-F,
R$^1$-Th4-CH$_2$CH$_2$-Ph2-Np1-F, R$^1$-Th4-CH$_2$CH$_2$-Ph2-Np2-F, R$^1$-Th4-CH$_2$CH$_2$-Ph2-Np3-F,
R$^1$-Th4-CH$_2$CH$_2$-Ph2-Np4-F, R$^1$-Th1-CH$_2$CH$_2$-Ph3-Ph1-F, R$^1$-Th1-CH$_2$CH$_2$-Ph3-Ph2-F,
R$^1$-Th1-CH$_2$CH$_2$-Ph3-Ph3-F, R$^1$-Th1-CH$_2$CH$_2$-Ph3-Np1-F, R$^1$-Th1-CH$_2$CH$_2$-Ph3-Np2-F, R$^1$-Th1-CH$_2$CH$_2$-Ph3-Np3-F, R$^1$-Th1-CH$_2$CH$_2$-Ph3-Np4-F, R$^1$-Th2-CH$_2$CH$_2$-Ph3-Ph1-F,
R$^1$-Th2-CH$_2$CH$_2$-Ph3-Ph2-F, R$^1$-Th2-CH$_2$CH$_2$-Ph3-Ph3-F, R$^1$-Th2-CH$_2$CH$_2$-Ph3-Np1-F,
R$^1$-Th2-CH$_2$CH$_2$-Ph3-Np2-F, R$^1$-Th2-CH$_2$CH$_2$-Ph3-Np3-F, R$^1$-Th2-CH$_2$CH$_2$-Ph3-Np4-F,
R$^1$-Th3-CH$_2$CH$_2$-Ph3-Ph1-F, R$^1$-Th3-CH$_2$CH$_2$-Ph3-Ph2-F, R$^1$-Th3-CH$_2$CH$_2$-Ph3-Ph3-F,
R$^1$-Th3-CH$_2$CH$_2$-Ph3-Np1-F, R$^1$-Th3-CH$_2$CH$_2$-Ph3-Np2-F, R$^1$-Th3-CH$_2$CH$_2$-Ph3-Np3-F,
R$^1$-Th3-CH$_2$CH$_2$-Ph3-Np1-F, R$^1$-Th4-CH$_2$CH$_2$-Ph3-Ph1-F, R$^1$-Th4-CH$_2$CH$_2$-Ph3-Ph2-F,
R$^1$-Th4-CH$_2$CH$_2$-Ph3-Ph3-F, R$^1$-Th4-CH$_2$CH$_2$-Ph3-Np1-F, R$^1$-Th4-CH$_2$CH$_2$-Ph3-Np2-F,
R$^1$-Th4-CH$_2$CH$_2$-Ph3-Np3-F, R$^1$-Th4-CH$_2$CH$_2$-Ph3-Np4-F, R$^1$-Th1-CH$_2$CH$_2$-Np1-Ph1-F,
R$^1$-Th1-CH$_2$CH$_2$-Np1-Ph2-F, R$^1$-Th1-CH$_2$CH$_2$-Np1-Ph3-F, R$^1$-Th2-CH$_2$CH$_2$-Np1-Ph1-F,
R$^1$-Th3-CH$_2$CH$_2$-Np1-Ph1-F, R$^1$-Th3-CH$_2$CH$_2$-Np1-Ph3-F, R$^1$-Th3-CH$_2$CH$_2$-Np1-Ph1-F,
R$^1$-Th3-CH$_2$CH$_2$-Np1-Ph2-F, R$^1$-Th3-CH$_2$CH$_2$-Np1-Ph3-F, R$^1$-Th4-CH$_2$CH$_2$-Np1-Ph1-F,
R$^1$-Th4-CH$_2$CH$_2$-Np1-Ph2-F, R$^1$-Th4-CH$_2$CH$_2$-Np1-Ph3-F, R$^1$-Th1-CH$_2$CH$_2$-Np2-Ph1-F,
R$^1$-Th1-CH$_2$CH$_2$-Np2-Ph2-F, R$^1$-Th1-CH$_2$CH$_2$-Np2-Ph3-F, R$^1$-Th2-CH$_2$CH$_2$-Np2-Ph1-F,
R$^1$-Th3-CH$_2$CH$_2$-Np2-Ph2-F, R$^1$-Th2-CH$_2$CH$_2$-Np2-Ph3-F, R$^1$-Th3-CH$_2$CH$_2$-Np2-Ph1-F,
R$^1$-Th3-CH$_2$CH$_2$-Np2-Ph2-F, R$^1$-Th3-CH$_2$CH$_2$-Np2-Ph3-F, R$^1$-Th4-CH$_2$CH$_2$-Np2-Ph1-F,
R$^1$-Th4-CH$_2$CH$_2$-Np2-Ph2-F, R$^1$-Th4-CH$_2$CH$_2$-Np2-Ph3-F, R$^1$-Th1-CH$_2$CH$_2$-Np3-Ph1-F,
R$^1$-Th1-CH$_2$CH$_2$-Np3-Ph2-F, R$^1$-Th1-CH$_2$CH$_2$-Np3-Ph3-F, R$^1$-Th2-CH$_2$CH$_2$-Np3-Ph1-F,
R$^1$-Th2-CH$_2$CH$_2$-Np3-Ph2-F, R$^1$-Th2-CH$_2$CH$_2$-Np3-Ph3-F, R$^1$-Th3-CH$_2$CH$_2$-Np3-Ph1-F,
R$^1$-Th3-CH$_2$CH$_2$-Np3-Ph2-F, R$^1$-Th3-CH$_2$CH$_2$-Np3-Ph3-F, R$^1$-Th4-CH$_2$CH$_2$-Np3-Ph1-F,
R$^1$-Th4-CH$_2$CH$_2$-Np3-Ph2-F, R$^1$-Th4-CH$_2$CH$_2$-Np3-Ph3-F, R$^1$-Th1-CH$_2$CH$_2$-Np4-Ph1-F,
R$^1$-Th1-CH$_2$CH$_2$-Np4-Ph2-F, R$^1$-Th1-CH$_2$CH$_2$-Np4-Ph3-F, R$^1$-Th2-CH$_2$CH$_2$-Np4-Ph1-F,
R$^1$-Th2-CH$_2$CH$_2$-Np4-Ph2-F, R$^1$-Th2-CH$_2$CH$_2$-Np4-Ph3-F, R$^1$-Th3-CH$_2$CH$_2$-Np4-Ph1-F,
R$^1$-Th3-CH$_2$CH$_2$-Np4-Ph2-F, R$^1$-Th3-CH$_2$CH$_2$-Np4-Ph3-F, R$^1$-Th4-CH$_2$CH$_2$-Np4-Ph1-F,
R$^1$-Th4-CH$_2$CH$_2$-Np4-Ph2-F, R$^1$-Th4-CH$_2$CH$_2$-Np4-Ph3-F,
R$^1$-Th1-Ph1-C≡C-Ph1-F, R$^1$-Th1-Ph1-C≡C-Ph2-F, R$^1$-Th1-Ph1-C≡C-Ph3-F,
R$^1$-Th2-Ph1-C≡C-Ph1-F, R$^1$-Th2-Ph1-C≡C-Ph2-F, R$^1$-Th2-Ph1-C≡C-Ph3-F,
R$^1$-Th3-Ph1-C≡C-Ph1-F, R$^1$-Th3-Ph1-C≡C-Ph2-F, R$^1$-Th3-Ph1-C≡C-Ph3-F,
R$^1$-Th4-Ph1-C≡C-Ph1-F, R$^1$-Th4-Ph1-C≡C-Ph2-F, R$^1$-Th4-Ph1-C≡C-Ph3-F,
R$^1$-Th1-Ph2-C≡C-Ph1-F, R$^1$-Th1-Ph2-C≡C-Ph2-F, R$^1$-Th1-Ph2-C≡C-Ph3-F,
R$^1$-Th2-Ph2-C≡C-Ph1-F, R$^1$-Th2-Ph2-C≡C-Ph2-F, R$^1$-Th2-Ph2-C≡C-Ph3-F,
R$^1$-Th3-Ph2-C≡C-Ph1-F, R$^1$-Th3-Ph2-C≡C-Ph2-F, R$^1$-Th3-Ph2-C≡C-Ph3-F,
R$^1$-Th4-Ph2-C≡C-Ph1-F, R$^1$-Th4-Ph2-C≡C-Ph2-F, R$^1$-Th4-Ph2-C≡C-Ph3-F,
R$^1$-Th1-Ph3-C≡C-Ph1-F, R$^1$-Th1-Ph3-C≡C-Ph2-F, R$^1$-Th1-Ph3-C≡C-Ph3-F,
R$^1$-Th2-Ph3-C≡C-Ph1-F, R$^1$-Th2-Ph3-C≡C-Ph2-F, R$^1$-Th2-Ph3-C≡C-Ph3-F,
R$^1$-Th3-Ph3-C≡C-Ph1-F, R$^1$-Th3-Ph3-C≡C-Ph2-F, R$^1$-Th3-Ph3-C≡C-Ph3-F,
R$^1$-Th4-Ph3-C≡C-Ph1-F, R$^1$-Th4-Ph3-C≡C-Ph2-F, R$^1$-Th4-Ph3-C≡C-Ph3-F,
R$^1$-Th1-C≡C-Ph1-Ph1-F, R$^1$-Th1-C≡C-Ph1-Ph2-F, R$^1$-Th1-C≡C-Ph1-Ph3-F,
R$^1$-Th2-C≡C-Ph1-Ph1-F, R$^1$-Th2-C≡C-Ph1-Ph2-F, R$^1$-Th2-C≡C-Ph1-Ph3-F,
R$^1$-Th3-C≡C-Ph1-Ph1-F, R$^1$-Th3-C≡C-Ph1-Ph2-F, R$^1$-Th3-C≡C-Ph1-Ph3-F,
R$^1$-Th4-C≡C-Ph1-Ph1-F, R$^1$-Th4-C≡C-Ph1-Ph2-F, R$^1$-Th4-C≡C-Ph1-Ph3-F,
R$^1$-Th1-C≡C-Ph2-Ph1-F, R$^1$-Th1-C≡C-Ph2-Ph2-F, R$^1$-Th1-C≡C-Ph2-Ph3-F,
R$^1$-Th2-C≡C-Ph2-Ph1-F, R$^1$-Th2-C≡C-Ph2-Ph2-F, R$^1$-Th2-C≡C-Ph2-Ph3-F,
R$^1$-Th3-C≡C-Ph2-Ph1-F, R$^1$-Th3-C≡C-Ph2-Ph2-F, R$^1$-Th3-C≡C-Ph2-Ph3-F,
R$^1$-Th4-C≡C-Ph2-Ph1-F, R$^1$-Th4-C≡C-Ph2-Ph2-F, R$^1$-Th4-C≡C-Ph2-Ph3-F,
R$^1$-Th1-C≡C-Ph3-Ph1-F, R$^1$-Th1-C≡C-Ph3-Ph2-F, R$^1$-Th1-C≡C-Ph3-Ph3-F,
R$^1$-Th2-C≡C-Ph3-Ph1-F, R$^1$-Th2-C≡C-Ph3-Ph2-F, R$^1$-Th2-C≡C-Ph3-Ph3-F,
R$^1$-Th3-C≡C-Ph3-Ph1-F, R$^1$-Th3-C≡C-Ph3-Ph2-F, R$^1$-Th3-C≡C-Ph3-Ph3-F,
R$^1$-Th4-C≡C-Ph3-Ph1-F, R$^1$-Th4-C≡C-Ph3-Ph2-F, R$^1$-Th4-C≡C-Ph3-Ph3-F, in the case in which $n^a$=1, $n^b$=0 or $n^a$=0, $n^b$=1, and $n^c$=1, $n^d$=0 or $n^c$=0, $n^d$=1, and Z is a fluorine atom, R$^1$-Cy-Th1-Ph1-F, R$^1$-Cy-Th1-Ph2-F, R$^1$-Cy-Th1-Ph3-F, R$^1$-Cy-Th1-Np1-F,
R$^1$-Cy-Th1-Np2-F, R$^1$-Cy-Th1-Np3-F, R$^1$-Cy-Th1-Np4-F,
R$^1$-Cy-CH$_2$CH$_2$-Th1-Ph1-F, R$^1$-Cy-CH$_2$CH$_2$-Th1-Ph2-F, R$^1$-Cy-CH$_2$CH$_2$-Th1-Ph3-F,
R$^1$-Cy-CH$_2$CH$_2$-Th1-Np1-F, R$^1$-Cy-CH$_2$CH$_2$-Th1-Np2-F, R$^1$-Cy-CH$_2$CH$_2$-Th1-Np3-F,
R$^1$-Cy-CH$_2$CH$_2$-Th1-Np4-F, R$^1$-Cy-Th1-CH$_2$CH$_2$-Ph1-F, R$^1$-Cy-Th1-CH$_2$CH$_2$-Ph2-F,
R$^1$-Cy-Th1-CH$_2$CH$_2$-Ph3-F, R$^1$-Cy-Th1-CH$_2$CH$_2$-Np1-F, R$^1$-Cy-Th1-CH$_2$CH$_2$-Np2-F,
R$^1$-Cy-Th1-CH$_2$CH$_2$-Np3-F, R$^1$-Cy-Th1-CH$_2$CH$_2$-Np4-F,
R$^1$-Cy-Th1-C≡C-Ph1-F, R$^1$-Cy-Th1-C≡C-Ph2-F, R$^1$-Cy-Th1-C≡C-Ph3-F,
R$^1$-Ph1-Th1-Ph1-F, R$^1$-Ph1-Th1-Ph2-F, R$^1$-Ph1-Th1-Ph3-F, R$^1$-Ph1-Th1-Np1-F,
R$^1$-Ph1-Th1-Np2-F, R$^1$-Ph1-Th1-Np3-F, R$^1$-Ph1-Th1-Np4-F,
R$^1$-Ph1-CH$_2$CH$_2$-Th1-Ph1-F, R$^1$-Ph1-CH$_2$CH$_2$-Th1-Ph2-F, R$^1$-Ph1-CH$_2$CH$_2$-Th1-Ph3-F,
R$^1$-Ph1-CH$_2$CH$_2$-Th1-Np1-F, R$^1$-Ph1-CH$_2$CH$_2$-Th1-Np2-F, R$^1$-Ph1-CH$_2$CH$_2$-Th1-Np3-F,
R$^1$-Ph1-CH$_2$CH$_2$-Th1-Np4-F, R$^1$-Ph1-Th1-CH$_2$CH$_2$-Ph1-F, R$^1$-Ph1-Th1-CH$_2$CH$_2$-Ph2-F,
R$^1$-Ph1-Th1-CH$_2$CH$_2$-Ph3-F, R$^1$-Ph1-Th1-CH$_2$CH$_2$-Np1-F, R$^1$-Ph1-Th1-CH$_2$CH$_2$-Np2-F,
R$^1$-Ph1-Th1-CH$_2$CH$_2$-Np3-F, R$^1$-Ph1-Th1-CH$_2$CH$_2$-Np4-F,
R$^1$-Ph1-C≡C-Th1-Ph1-F, R$^1$-Ph1-C≡C-Th1-Ph2-F, R$^1$-Ph1-C≡C-Th1-Ph3-F,
R$^1$-Ph1-Th1-C≡C-Ph2-F, R$^1$-Ph1-Th1-C≡C-Ph3-F,
R$^1$-Ph2-Th1-Ph1-F, R$^1$-Ph2-Th1-Ph2-F, R$^1$-Ph2-Th1-Ph3-F, R$^1$-Ph2-Th1-Np1-F,
R$^1$-Ph2-Th1-Np2-F, R$^1$-Ph2-Th1-Np3-F, R$^1$-Ph2-Th1-Np4-F,
R$^1$-Ph2-CH$_2$CH$_2$-Th1-Ph1-F, R$^1$-Ph2-CH$_2$CH$_2$-Th1-Ph2-F, R$^1$-Ph2-CH$_2$CH$_2$-Th1-Ph3-F, R$^1$-Ph2-CH$_2$CH$_2$-Th1-Np1-F, R$^1$-Ph2-CH$_2$CH$_2$-Th1-Np2-F, R$^1$-Ph2-CH$_2$CH$_2$-Th1-Np3-F,
R$^1$-Ph2-CH$_2$CH$_2$-Th1-Np4-F, R$^1$-Ph2-Th1-CH$_2$CH$_2$-Ph1-F, R$^1$-Ph2-Th1-CH$_2$CH$_2$-Ph2-F,
R$^1$-Ph2-Th1-CH$_2$CH$_2$-Ph3-F, R$^1$-Ph2-Th1-CH$_2$CH$_2$-Np1-F, R$^1$-Ph2-Th1-CH$_2$CH$_2$-Np2-F,
R$^1$-Ph2-Th1-CH$_2$CH$_2$-Np3-F, R$^1$-Ph2-Th1-CH$_2$CH$_2$-Np4-F,
R$^1$-Ph2-C≡C-Th1-Ph1-F, R$^1$-Ph2-C≡C-Th1-Ph2-F, R$^1$-Ph2-C≡C-Th1-Ph3-F,
R$^1$-Ph2-Th1-C≡C-Ph1-F, R$^1$-Ph2-Th1-C≡C-Ph2-F, R$^1$-Ph2-Th1-C≡C-Ph3-F,
R$^1$-Ph3-Th1-Ph1-F, R$^1$-Ph3-Th1-Ph2-F, R$^1$-Ph3-Th1-Ph3-F, R$^1$-Ph3-Th1-Np1-F,
R$^1$-Ph3-Th1-Np2-F, R$^1$-Ph3-Th1-Np3-F, R$^1$-Ph3-Th1-Np4-F,
R$^1$-Ph3-CH$_2$CH$_2$-Th1-Ph1-F, R$^1$-Ph3-CH$_2$CH$_2$-Th1-Ph2-F, R$^1$-Ph3-CH$_2$CH$_2$-Th1-Ph3-F,
R$^1$-Ph3-CH$_2$CH$_2$-Th1-Np1-F, R$^1$-Ph3-CH$_2$CH$_2$-Th1-Np2-F, R$^1$-Ph3-CH$_2$CH$_2$-Th1-Np3-F,
R$^1$-Ph3-CH$_2$CH$_2$-Th1-Np4-F, R$^1$-Ph3-Th1-CH$_2$CH$_2$-Ph1-F, R$^1$-Ph3-Th1-CH$_2$CH$_2$-Ph2-F,
R$^1$-Ph3-Th1-CH$_2$CH$_2$-Ph3-F, R$^1$-Ph3-Th1-CH$_2$CH$_2$-Np1-F, R$^1$-Ph3-Th1-CH$_2$CH$_2$-Np2-F,
R$^1$-Ph3-Th1-CH$_2$CH$_2$-Np3-F, R$^1$-Ph3-T 1-CH$_2$CH$_2$-Np4-F,
R$^1$-Ph3-C≡C-Th1-Ph1-F, R$^1$-Ph3-C≡C-Th1-Ph2-F, R$^1$-Ph3-C≡C-Th1-Ph3-F,
R$^1$-Ph3-Th1-C≡C-Ph1-F, R$^1$-Ph3-Th1-C≡C-Ph2-F, R$^1$-Ph3-Th1-C≡C-Ph3-F,
R$^1$-Np1-Th1-Ph1-F, R$^1$-Np1-Th1-Ph2-F, R$^1$-Np1-Th1-Ph3-F,
R$^1$-Np1-CH$_2$CH$_2$-Th1-Ph1-F, R$^1$-Np1-CH$_2$CH$_2$-Th1-Ph2-F, R$^1$-Np1-CH$_2$CH$_2$-Th1-Ph3-F,
R$^1$-Np1-Th1-CH$_2$CH$_2$-Ph1-F, R$^1$-Np1-Th1-CH$_2$CH$_2$-Ph2-F, R$^1$-Np1-Th1-CH$_2$CH$_2$-Ph3-F,
R$^1$-Np2-Th1-Ph1-F, R$^1$-Np2-Th1-Ph2-F, R$^1$-Np2-Th1-Ph3-F,
R$^1$-Np2-CH$_2$CH$_2$-Th1-Ph1-F, R$^1$-Np2-CH$_2$CH$_2$-Th1-Ph2-F, R$^1$-Np2-CH$_2$CH$_2$-Th1-Ph3-F,
R$^1$-Np2-Th1-CH$_2$CH$_2$-Ph1-F, R$^1$-Np2-Th1-CH$_2$CH$_2$-Ph2-F, R$^1$-Np2-Th1-CH$_2$CH$_2$-Ph3-F,
R$^1$-Np3-Th1-Ph1-F, R$^1$-Np3-Th1-Ph2-F, R$^1$-Np3-Th1-Ph3-F,
R$^1$-Np3-CH$_2$CH$_2$-Th1-Ph1-F, R$^1$-Np3-CH$_2$CH$_2$-Th1-Ph2-F, R$^1$-Np3-CH$_2$CH$_2$-Th1-Ph3-F,
R$^1$-Np3-Th1-CH$_2$CH$_2$-Ph1-F, R$^1$-Np3-Th1-CH$_2$CH$_2$-Ph2-F, R$^1$-Np3-Th1-CH$_2$CH$_2$-Ph3-F,
R$^1$-Np1-Th1-Ph1-F, R$^1$-Np1-Th1-Ph2-F, R$^1$-Np1-Th1-Ph3-F,
R$^1$-Np4-CH$_2$CH$_2$-Th1-Ph1-F, R$^1$-Np4-CH$_2$CH$_2$-Th1-Ph2-F, R$^1$-Np4-CH$_2$CH$_2$-Th1-Ph3-F,
R$^1$-Np4-Th1-CH$_2$CH$_2$-Ph1-F, R$^1$-Np4-Th1-CH$_2$CH$_2$-Ph2-F, R$^1$-Np4-Th1-CH$_2$CH$_2$-Ph3-F,
R$^1$-Cy-Th2-Ph1-F, R$^1$-Cy-Th2-Ph2-F, R$^1$-Cy-Th2-Ph3-F, R$^1$-Cy-Th2-Np1-F,
R$^1$-Cy-Th2-Np2-F, R$^1$-Cy-Th2-Np3-F, R$^1$-Cy-Th2-Np4-F,
R$^1$-Cy-CH$_2$CH$_2$-Th2-Ph1-F, R$^1$-Cy-CH$_2$CH$_2$-Th2-Ph2-F, R$^1$-Cy-CH$_2$CH$_2$-Th2-Ph3-F,
R$^1$-Cy-CH$_2$CH$_2$-Th2-Np1-F, R$^1$-Cy-CH$_2$CH$_2$-Th2-Np2-F, R$^1$-Cy-CH$_2$CH$_2$-Th2-Np3-F,
R$^1$-Cy-CH$_2$CH$_2$-Th2-Np4-F, R$^1$-Cy-Th2-CH$_2$CH$_2$-Ph1-F, R$^1$-Cy-Th2-CH$_2$CH$_2$-Ph2-F,
R$^1$-Cy-Th2-CH$_2$CH$_2$-Ph3-F, R$^1$-Cy-Th2-CH$_2$CH$_2$-Np1-F, R$^1$-Cy-Th2-CH$_2$CH$_2$-Np2-F,
R$^1$-Cy-Th2-CH$_2$CH$_2$-Np3-F, R$^1$-Cy-Th2-CH$_2$CH$_2$-Np4-F,
R$^1$-Cy-Th2-C≡C-Ph1-F, R$^1$-Cy-Th2-C≡C-Ph2-F, R$^1$-Cy-Th2-C≡C-Ph3-F,
R$^1$-Ph1-Th2-Ph1-F, R$^1$-Ph1-Th2-Ph2-F, R$^1$-Ph1-Th2-Ph3-F, R$^1$-Ph1-Th2-Np1-F,
R$^1$-Ph1-Th2-Np2-F, R$^1$-Ph1-Th2-Np3-F, R$^1$-Ph1-Th2-Np4-F,
R$^1$-Ph1-CH$_2$CH$_2$-Th2-Ph1-F, R$^1$-Ph1-CH$_2$CH$_2$-Th2-Ph2-F, R$^1$-Ph1-CH$_2$CH$_2$-Th2-Ph3-F,
R$^1$-Ph1-CH$_2$CH$_2$-Th2-Np1-F, R$^1$-Ph1-CH$_2$CH$_2$-Th2-Np2-F, R$^1$-Ph1-CH$_2$CH$_2$-Th2-Np3-F,
R$^1$-Ph1-CH$_2$CH$_2$-Th2-Np4-F, R$^1$-Ph1-Th2-CH$_2$CH$_2$-Ph1-F, R$^1$-Ph1-Th2-CH$_2$CH$_2$-Ph2-F,
R$^1$-Ph1-Th2-CH$_2$CH$_2$-Ph3-F, R$^1$-Ph1-Th2-CH$_2$CH$_2$-Np1-F, R$^1$-Ph1-Th2-CH$_2$CH$_2$-Np2-F,
R$^1$-Ph1-Th2-CH$_2$CH$_2$-Np3-F, R$^1$-Ph1-Th2-CH$_2$CH$_2$-Np4-F,
R$^1$-Ph1-C≡C-Th2-Ph1-F, R$^1$-Ph1-C≡C-Th2-Ph2-F, R$^1$-Ph1-C≡C-Th2-Ph3-F,
R$^1$-Ph1-Th2-C≡C-Ph1-F, R$^1$-Ph1-Th2-C≡C-Ph2-F, R$^1$-Ph1-Th2-C≡C-Ph3-F,
R$^1$-Ph2-Th2-Ph1-F, R$^1$-Ph2-Th2-Ph2-F, R$^1$-Ph2-Th2-Ph3-F, R$^1$-Ph2-Th2-Np1-F,
R$^1$-Ph2-Th2-Np2-F, R$^1$-Ph2-Th2-Np3-F, R$^1$-Ph2-Th2-Np4-F,
R$^1$-Ph2-CH$_2$CH$_2$-Th2-Ph1-F, R$^1$-Ph2-CH$_2$CH$_2$-Th2-Ph2-F, R$^1$-Ph2-CH$_2$CH$_2$-Th2-Ph3-F,
R$^1$-Ph2-CH$_2$CH$_2$-Th2-Np1-F, R$^1$-Ph2-CH$_2$CH$_2$-Th2-Np2-F, R$^1$-Ph2-CH$_2$CH$_2$-Th2-Np3-F,
R$^1$-Ph2-CH$_2$CH$_2$-Th2-Np4-F, R$^1$-Ph2-Th2-CH$_2$CH$_2$-Ph1-F, R$^1$-Ph2-Th2-CH$_2$CH$_2$-Ph2-F,
R$^1$-Ph2-Th2-CH$_2$CH$_2$-Ph3-F, R$^1$-Ph2-Th2-CH$_2$CH$_2$-Np1-F, R$^1$-Ph2-Th2-CH$_2$CH$_2$-Np2-F,
R$^1$-Ph2-Th2-CH$_2$CH$_2$-Np3-F, R$^1$-Ph2-Th2-CH$_2$CH$_2$-Np4-F,
R$^1$-Ph2-C≡C-Th2-Ph1-F, R$^1$-Ph2-C≡C-Th2-Ph2-F, R$^1$-Ph2-C≡C-Th2-Ph3-F,
R$^1$-Ph2-Th2-C≡C-Ph1-F, R$^1$-Ph2-Th2-C≡C-Ph2-F, R$^1$-Ph2-Th2-C≡C-Ph3-F,
R$^1$-Ph3-Th2-Ph1-F, R$^1$-Ph3-Th2-Ph2-F, R$^1$-Ph3-Th2-Ph3-F, R$^1$-Ph3-Th2-Np1-F,
R$^1$-Ph3-Th2-Np2-F, R$^1$-Ph3-Th2-Np3-F, R$^1$-Ph3-Th2-Np4-F,
R$^1$-Ph3-CH$_2$CH$_2$-Th2-Ph1-F, R$^1$-Ph1-CH$_2$CH$_2$-Th1-Ph2-F, R$^1$-Th3-CH$_2$CM$_2$-Th1-Ph3-F,
R$^1$-Ph3-CH$_2$CH$_2$-Th2-Np1-F, R$^1$-Ph3-CH$_2$CH$_2$-Th2-Np2-F, R$^1$-Ph3-CH$_2$CH$_2$-Th2-Np3-F,
R$^1$-Ph3-CH$_2$CH$_2$-Th2-Np4-F, R$^1$-Ph3-Th2-CH$_2$CH$_2$-Ph1-F, R$^1$-Ph3-Th2-CH$_2$CH$_2$-Ph2-F,
R$^1$-Ph3-Th2-CH$_2$CH$_2$-Ph3-F, R$^1$-Ph3-Th2-CH$_2$CH$_2$-Np1-F, R$^1$-Ph3-Th2-CH$_2$CH$_2$-Np2-F,
R$^1$-Ph3-Th2-CH$_2$CH$_2$-Np3-F, R$^1$-Ph3-Th2-CH$_2$CH$_2$-Np4-F,
R$^1$-Ph3-C≡C-Th2-Ph1-F, R$^1$-Ph3-C≡C-Th2-Ph2-F, R$^1$-Ph3-C≡C-Th2-Ph3-F,
R$^1$-Ph3-Th2-C≡C-Ph1-F, R$^1$-Ph3-Th2-C≡C-Ph2-F, R$^1$-Ph3-Th2-C≡C-Ph3-F,
R$^1$-Np1-Th2-Ph1-F, R$^1$-Np1-Th2-Ph2-F, R$^1$-Np1-Th2-Ph3-F,
R$^1$-Np1-CH$_2$CH$_2$-Th2-Ph1-F, R$^1$-Np1-CH$_2$CH$_2$-Th2-Ph2-F, R$^1$-Np1-CH$_2$CH$_2$-Th2-Ph3-F,
R$^1$-Np1-Th2-CH$_2$CH$_2$-Ph1-F, R$^1$-Np1-Th2-CH$_2$CH$_2$-Ph2-F, R$^1$-Np1-Th2-CH$_2$CH$_2$-Ph3-F,
R$^1$-Np2-Th2-Ph1-F, R$^1$-Np2-Th2-Ph2-F, R$^1$-Np2-Th2-Ph3-F,
R$^1$-Np2-CH$_2$CH$_2$-Th2-Ph1-F, R$^1$-Np2-CH$_2$CH$_2$-Th2-Ph2-F, R$^1$-Np2-CH$_2$CH$_2$-Th2-Ph3-F,
R$^1$-Np2-Th2-CH$_2$CH$_2$-Ph1-F, R$^1$-Np2-Th2-CH$_2$CH$_2$-Ph2-F, R$^1$-Np2-Th2-CH$_2$CH$_2$-Ph3-F,
R$^1$-Np3-Th2-Ph1-F, R$^1$-Np3-Th2-Ph2-F, R$^1$-Np3-Th2-Ph3-F,
R$^1$-Np3-CH$_2$CH$_2$-Th2-Ph1-F, R$^1$-Np3-CH$_2$CH$_2$-Th2-Ph2-F, R$^1$-Np3-CH$_2$CH$_2$-Th2-Ph3-F,
R$^1$-Np3-Th2-CH$_2$CH$_2$-Ph1-F, R$^1$-Np3-Th2-CH$_2$CH$_2$-Ph2-F, R$^1$-Np3-Th2-CH$_2$CH$_2$-Ph3-F, R$^1$-Np1-Th2-Ph1-F, R$^1$-Np1-Th2-Ph2-F, R$^1$-Np1-Th2-Ph3-F,
R$^1$-Np4-CH$_2$CH$_2$-Th2-Ph1-F, R$^1$-Np4-CH$_2$CH$_2$-Th2-Ph2-F, R$^1$-Np4-CH$_2$CH$_2$-Th2-Ph3-F,
R$^1$-Np4-Th2-CH$_2$CH$_2$-Ph1-F, R$^1$-Np4-Th2-CH$_2$CH$_2$-Ph2-F, R$^1$-Np4-Th2-CH$_2$CH$_2$-Ph3-F,
R$^1$-Cy-Th3-Ph1-F, R$^1$-Cy-Th3-Ph2-F, R$^1$-Cy-Th3-Ph3-F, R$^1$-Cy-Th3-Np1-F,
R$^1$-Cy-Th3-Np2-F, R$^1$-Cy-Th3-Np3-F, R$^1$-Cy-Th3-Np4-F,
R$^1$-Cy-CH$_2$CH$_2$-Th3-Ph1-F, R$^1$-Cy-CH$_2$CH$_2$-Th3-Ph2-F, R$^1$-Cy-CH$_2$CH$_2$-Th3-Ph3-F,
R$^1$-Cy-CH$_2$CH$_2$-Th3-Np1-F, R$^1$-Cy-CH$_2$CH$_2$-Th3-Np2-F, R$^1$-Cy-CH$_2$CH$_2$-Th3-Np3-F,
R$^1$-Cy-CH$_2$CH$_2$-Th3-Np4-F, R$^1$-Cy-Th3-CH$_2$CH$_2$-Ph1-F, R$^1$-Cy-Th3-CH$_2$CH$_2$-Ph2-F,
R$^1$-Cy-Th3-CH$_2$CH$_2$-Ph3-F, R$^1$-Cy-Th3-CH$_2$CH$_2$-Np1-F, R$^1$-Cy-Th3-CH$_2$CH$_2$-Np2-F,
R$^1$-Cy-Th3-CH$_2$CH$_2$-Np3-F, R$^1$-Cy-Th3-CH$_2$CH$_2$-Np4-F,
R$^1$-Cy-Th3-C≡C-Ph1-F, R$^1$-Cy-Th3-C≡C-Ph2-F, R$^1$-Cy-Th3-C≡C-Ph3-F,
R$^1$-Ph1-Th3-Ph1-F, R$^1$-Ph1-Th3-Ph2-F, R$^1$-Ph1-Th3-Ph3-F, R$^1$-Ph1-Th3-Np1-F,
R$^1$-Ph1-Th3-Np2-F, R$^1$-Ph1-Th3-Np3-F, R$^1$-Ph1-Th3-Np4-F,
R$^1$-Ph1-CH$_2$CH$_2$-Th3-Ph1-F, R$^1$-Ph1-CH$_2$CH$_2$-Th3-Ph2-F, R$^1$-Ph1-CH$_2$CH$_2$-Th3-Ph3-F,
R$^1$-Ph1-CH$_2$CH$_2$-Th3-Np1-F, R$^1$-Ph1-CH$_2$CH$_2$-Th3-Np2-F, R$^1$-Ph1-CH$_2$CH$_2$-Th3-Np3-F,
R$^1$-Ph1-CH$_2$CH$_2$-Th3-Np4-F, R$^1$-Ph1-Th3-CH$_2$CH$_2$-Ph1-F, R$^1$-Ph1-Th3-CH$_2$CH$_2$-Ph2-F,
R$^1$-Ph1-Th3-CH$_2$CH$_2$-Ph3-F, R$^1$-Ph1-Th3-CH$_2$CH$_2$-Np1-F, R$^1$-Ph1-Th3-CH$_2$CH$_2$-Np2-F,
R$^1$-Ph1-Th3-CH$_2$CH$_2$-Np3-F, R$^1$-Ph1-Th3-CH$_2$CH$_2$-Np4-F,
R$^1$-Ph1-C≡C-Th3-Ph1-F, R$^1$-Ph1-C≡C-Th3-Ph2-F, R$^1$-Ph1-C≡C-Th3-Ph3-F,
R$^1$-Ph1-Th3-C≡C-Ph1-F, R$^1$-Ph1-Th3-C≡C-Ph2-F, R$^1$-Ph1-Th3-C≡C-Ph3-F,
R$^1$-Ph2-Th3-Ph1-F, R$^1$-Ph2-Th3-Ph2-F, R$^1$-Ph2-Th3-Ph3-F, R$^1$-Ph2-Th3-Np1-F,
R$^1$-Ph1-Th3-Np2-F, R$^1$-Ph2-Th3-Np3-F, R$^1$-Ph2-Th3-Np4-F,
R$^1$-Ph2-CH$_2$CH$_2$-Th3-Ph1-F, R$^1$-Ph2-CH$_2$CH$_2$-Th3-Ph2-F, R$^1$-Ph2-CH$_2$CH$_2$-Th3-Ph3-F,
R$^1$-Ph2-CH$_2$CH$_2$-Th3-Np1-F, R$^1$-Ph2-CH$_2$CH$_2$-Th3-Np2-F, R$^1$-Ph2-CH$_2$CH$_2$-Th3-Np3-F,
R$^1$-Ph2-CH$_2$CH$_2$-Th3-Np4-F, R$^1$-Ph2-Th3-CH$_2$CH$_2$-Ph1-F, R$^1$-Ph2-Th3-CH$_2$CH$_2$-Ph2-F,
R$^1$-Ph2-Th3-CH$_2$CH$_2$-Ph3-F, R$^1$-Ph2-Th3-CH$_2$CH$_2$-Np1-F, R$^1$-Ph2-Th3-CH$_2$CH$_2$-Np2-F,
R$^1$-Ph2-Th3-CH$_2$CH$_2$-Np3-F, R$^1$-Ph2-Th3-CH$_2$CH$_2$-Np4-F,
R$^1$-Ph2-C≡C-Th3-Ph1-F, R$^1$-Ph2-C≡C-Th3-Ph2-F, R$^1$-Ph2-C≡C-Th3-Ph3-F,
R$^1$-Ph2-Th3-C≡C-Ph1-F, R$^1$-Ph2-Th3-C≡C-Ph2-F, R$^1$-Ph2-Th3-C≡C-Ph3-F,
R$^1$-Ph3-Th3-Ph1-F, R$^1$-Ph3-Th3-Ph2-F, R$^1$-Ph3-Th3-Ph3-F, R$^1$-Ph3-Th3-Np1-F,
R$^1$-Ph3-Th3-Np2-F, R$^1$-Ph3-Th3-Np3-F, R$^1$-Ph3-Th3-Np4-F,
R$^1$-Ph3-CH$_2$CH$_2$-Th3-Ph1-F, R$^1$-Ph3-CH$_2$CH$_2$-Th3-Ph2-F, R$^1$-Ph3-CH$_2$CH$_2$-Th3-Ph3-F,
R$^1$-Ph3-CH$_2$CH$_2$-Th3-Np1-F, R$^1$-Ph3-CH$_2$CH$_2$-Th3-Np2-F, R$^1$-Ph3-CH$_2$CH$_2$-Th3-Np3-F,
R$^1$-Ph3-CH$_2$CH$_2$-Th3-Np4-F, R$^1$-Ph3-Th3-CH$_2$CH$_2$-Ph1-F, R$^1$-Ph3-Th3-CH$_2$CH$_2$-Ph2-F,
R$^1$-Ph3-Th3-CH$_2$CH$_2$-Ph3-F, R$^1$-Ph3-Th3-CH$_2$CH$_2$-Np1-F, R$^1$-Ph3-Th3-CH$_2$CH$_2$-Np2-F,
R$^1$-Ph3-Th3-CH$_2$CH$_2$-Np3-F, R$^1$-Ph3-Th3-CH$_2$CH$_2$-Np4-F,
R$^1$-Ph3-C≡C-Th3-Ph1-F, R$^1$-Ph3-C≡C-Th3-Ph2-F, R$^1$-Ph3-C≡C-Th3-Ph3-F,
R$^1$-Ph3-Th3-C≡C-Ph1-F, R$^1$-Ph3-Th3-C≡C-Ph2-F, R$^1$-Ph3-Th3-C≡C-Ph3-F,
R$^1$-Np1-Th3-Ph1-F, R$^1$-Np1-Th3-Ph2-F, R$^1$-Np1-Th3-Ph3-F,
R$^1$-Np1-CH$_2$CH$_2$-Th3-Ph1-F, R$^1$-Np1-CH$_2$CH$_2$-Th3-Ph2-F, R$^1$-Np1-CH$_2$CH$_2$-Th3-Ph3-F,
R$^1$-Np1-Th3-CH$_2$CH$_2$-Ph1-F, R$^1$-Np1-Th3-CH$_2$CH$_2$-Ph2-F, R$^1$-Np1-Th3-CH$_2$CH$_2$-Ph3-F,
R$^1$-Np2-Th3-Ph1-F, R$^1$-Np2-Th3-Ph2-F, R$^1$-Np2-Th3-Ph3-F,
R$^1$-Np2-CH$_2$CH$_2$-Th3-Ph1-F, R$^1$-Np2-CH$_2$CH$_2$-Th3-Ph2-F, R$^1$-Np2-CH$_2$CH$_2$-Th3-Ph3-F,
R$^1$-Np2-Th3-CH$_2$CH$_2$-Ph1-F, R$^1$-Np2-Th3-CH$_2$CH$_2$-Ph2-F, R$^1$-Np2-Th3-CH$_2$CH$_2$-Ph3-F,
R$^1$-Np3-Th3-Ph1-F, R$^1$-Np3-Th3-Ph2-F, R$^1$-Np3-Th3-Ph3-F,
R$^1$-Np3-CH$_2$CH$_2$-Th3-Ph1-F, R$^1$-Np3-CH$_2$CH$_2$-Th3-Ph2-F, R$^1$-Np3-CH$_2$CH$_2$-Th3-Ph3-F,
R$^1$-Np3-Th3-CH$_2$CH$_2$-Ph1-F, R$^1$-Np3-Th3-CH$_2$CH$_2$-Ph2-F, R$^1$-Np3-Th3-CH$_2$CH$_2$-Ph3-F,
R$^1$-Np1-Th3-Ph1-F, R$^1$-Np1-Th3-Ph2-F, R$^1$-Np1-Th3-Ph3-F,
R$^1$-Np4-CH$_2$CH$_2$-Th3-Ph1-F, R$^1$-Np4-CH$_2$CH$_2$-Th3-Ph2-F, R$^1$-Np4-CH$_2$CH$_2$-Th3-Ph3-F,
R$^1$-Np4-Th3-CH$_2$CH$_2$-Ph1-F, R$^1$-Np4-Th3-CH$_2$CH$_2$-Ph2-F, R$^1$-Np4-Th3-CH$_2$CH$_2$-Ph3-F,
R$^1$-Cy-Th3-Ph1-F, R$^1$-Cy-Th3-Ph2-F, R$^1$-Cy-Th3-Ph3-F, R$^1$-Cy-Th3-Np1-F,
R$^1$-Cy-Th3-Np2-F, R$^1$-Cy-Th3-Np3-F, R$^1$-Cy-Th3-Np4-F,
R$^1$-Cy-CH$_2$CH$_2$-Th3-Ph1-F, R$^1$-Cy-CH$_2$CH$_2$-Th3-Ph2-F, R$^1$-Cy-CH$_2$CH$_2$-Th3-Ph3-F,
R$^1$-Cy-CH$_2$CH$_2$-Th3-Np1-F, R$^1$-Cy-CH$_2$CH$_2$-Th3-Np2-F, R$^1$-Cy-CH$_2$CH$_2$-Th3-Np3-F,
R$^1$-Cy-CH$_2$CH$_2$-Th3-Np4-F, R$^1$-Cy-Th3-CH$_2$CH$_2$-Ph1-F, R$^1$-Cy-Th3-CH$_2$CH$_2$-Ph2-F,
R$^1$-Cy-Th3-CH$_2$CH$_2$-Ph3-F, R$^1$-Cy-Th3-CH$_2$CH$_2$-Np1-F, R$^1$-Cy-Th3-CH$_2$CH$_2$-Np2-F,
R$^1$-Cy-Th3-CH$_2$CH$_2$-Np3-F, R$^1$-Cy-Th3-CH$_2$CH$_2$-Np4-F,
R$^1$-Cy-Th3-C≡C-Ph1-F, R$^1$-Cy-Th3-C≡C-Ph2-F, R$^1$-Cy-Th3-C≡C-Ph3-F,
R$^1$-Ph1-Th3-Ph1-F, R$^1$-Ph1-Th3-Ph2-F, R$^1$-Ph1-Th3-Ph3-F, R$^1$-Ph1-Th3-Np1-F,
R$^1$-Ph1-Th3-Np2-F, R$^1$-Ph1-Th3-Np3-F, R$^1$-Ph1-Th3-Np4-F,
R$^1$-Ph1-CH$_2$CH$_2$-Th3-Ph1-F, R$^1$-Ph1-CH$_2$CH$_2$-Th3-Ph2-F, R$^1$-Ph1-CH$_2$CH$_2$-Th3-Ph3-F,
R$^1$-Ph1-CH$_2$CH$_2$-Th3-Np1-F, R$^1$-Ph1-CH$_2$CH$_2$-Th3-Np2-F, R$^1$-Ph1-CH$_2$CH$_2$-Th3-Np3-F,
R$^1$-Ph1-CH$_2$CH$_2$-Th3-Np4-F, R$^1$-Ph1-Th3-CH$_2$CH$_2$-Ph1-F, R$^1$-Ph1-Th3-CH$_2$CH$_2$-Ph2-F,
R$^1$-Ph1-Th3-CH$_2$CH$_2$-Ph3-F, R$^1$-Ph1-Th3-CH$_2$CH$_2$-Np1-F, R$^1$-Ph1-Th3-CH$_2$CH$_2$-Np2-F,
R$^1$-Ph1-Th3-CH$_2$CH$_2$-Np3-F, R$^1$-Ph1-Th3-CH$_2$CH$_2$-Np4-F,
R$^1$-Ph1-C≡C-Th3-Ph1-F, R$^1$-Ph1-C≡C-Th3-Ph2-F, R$^1$-Ph1-C≡C-Th3-Ph3-F,
R$^1$-Ph1-Th3-C≡C-Ph1-F, R$^1$-Ph1-Th3-C≡C-Ph2-F, R$^1$-Ph1-Th3-C≡C-Ph3-F,
R$^1$-Ph2-Th3-Ph1-F, R$^1$-Ph2-Th3-Ph2-F, R$^1$-Ph2-Th3-Ph3-F, R$^1$-Ph2-Th3-Np1-F,
R$^1$-Ph2-Th3-Np2-F, R$^1$-Ph2-Th3-Np3-F, R$^1$-Ph2-Th3-Np4-F,
R$^1$-Ph2-CH$_2$CH$_2$-Th3-Ph1-F, R$^1$-Ph2-CH$_2$CH$_2$-Th3-Ph2-F, R$^1$-Ph2-CH$_2$CH$_2$-Th3-Ph3-F,
R$^1$-Ph2-CH$_2$CH$_2$-Th3-Np1-F, R$^1$-Ph2-CH$_2$CH$_2$-Th3-Np2-F, R$^1$-Ph2-CH$_2$CH$_2$-Th3-Np3-F, R$^1$-Ph2-CH$_2$CH$_2$-Th3-Np4-F, R$^1$-Ph2-Th3-CH$_2$CH$_2$-Ph1-F, R$^1$-Ph2-Th3-CH$_2$CH$_2$-Ph2-F,
R$^1$-Ph2-Th3-CH$_2$CH$_2$-Ph3-F, R$^1$-Ph2-Th3-CH$_2$CH$_2$-Np1-F, R$^1$-Ph2-Th3-CH$_2$CH$_2$-Np2-F,
R$^1$-Ph2-Th3-CH$_2$CH$_2$-Np3-F, R$^1$-Ph2-Th3-CH$_2$CH$_2$-Np4-F,
R$^1$-Ph2-C≡C-Th3-Ph1-F, R$^1$-Ph2-C≡C-Th3-Ph2-F, R$^1$-Ph2-C≡C-Th3-Ph3-F,
R$^1$-Ph2-Th3-C≡C-Ph1-F, R$^1$-Ph2-Th3-C≡C-Ph2-F, R$^1$-Ph2-Th3-C≡C-Ph3-F,
R$^1$-Ph3-Th3-Ph1-F, R$^1$-Ph3-Th3-Ph2-F, R$^1$-Ph3-Th3-Ph3-F, R$^1$-Ph3-Th3-Np1-F,
R$^1$-Ph3-Th3-Np2-F, R$^1$-Ph3-Th3-Np3-F, R$^1$-Ph3-Th3-Np4-F,
R$^1$-Ph3-CH$_2$CH$_2$-Th3-Ph1-F, R$^1$-Ph3-CH$_2$CH$_2$-Th3-Ph2-F, R$^1$-Ph3-CH$_2$CH$_2$-Th3-Ph3-F,
R$^1$-Ph3-CH$_2$CH$_2$-Th3-Np1-F, R$^1$-Ph3-CH$_2$CH$_2$-Th3-Np2-F, R$^1$-Ph3-CH$_2$CH$_2$-Th3-Np3-F,
R$^1$-Ph3-CH$_2$CH$_2$-Th3-Np4-F, R$^1$-Ph3-Th3-CH$_2$CH$_2$-Ph1-F, R$^1$-Ph3-Th3-CH$_2$CH$_2$-Ph2-F,
R$^1$-Ph3-Th3-CH$_2$CH$_2$-Ph3-F, R$^1$-Ph3-Th3-CH$_2$CH$_2$-Np1-F, R$^1$-Ph3-Th3-CH$_2$CH$_2$-Np2-F,
R$^1$-Ph3-Th3-CH$_2$CH$_2$-Np3-F, R$^1$-Ph3-Th3-CH$_2$CH$_2$-Np4-F,
R$^1$-Ph3-C≡C-Th3-Ph1-F, R$^1$-Ph3-C≡C-Th3-Ph2-F, R$^1$-Ph3-C≡C-Th3-Ph3-F,
R$^1$-Ph3-Th3-C≡C-Ph1-F, R$^1$-Ph3-Th3-C≡C-Ph2-F, R$^1$-Ph3-Th3-C≡C-Ph3-F,
R$^1$-Np1-Th3-Ph1-F, R$^1$-Np1-Th3-Ph2-F, R$^1$-Np1-Th3-Ph3-F,
R$^1$-Np1-CH$_2$CH$_2$-Th3-Ph1-F, R$^1$-Np1-CH$_2$CH$_2$-Th3-Ph2-F, R$^1$-Np1-CH$_2$CH$_2$-Th3-Ph3-F,
R$^1$-Np1-Th3-CH$_2$CH$_2$-Ph1-F, R$^1$-Np1-Th3-CH$_2$CH$_2$-Ph2-F, R$^1$-Np1-Th3-CH$_2$CH$_2$-Ph3-F,
R$^1$-Np2-Th3-Ph1-F, R$^1$-Np2-Th3-Ph2-F, R$^1$-Np2-Th3-Ph3-F,
R$^1$-Np2-CH$_2$CH$_2$-Th3-Ph1-F, R$^1$-Np2-CH$_2$CH$_2$-Th3-Ph2-F, R$^1$-Np2-CH$_2$CH$_2$-Th3-Ph3-F,
R$^1$-Np2-Th3-CH$_2$CH$_2$-Ph1-F, R$^1$-Np2-Th3-CH$_2$CH$_2$-Ph2-F, R$^1$-Np2-Th3-CH$_2$CH$_2$-Ph3-F,
R$^1$-Np3-Th3-Ph1-F, R$^1$-Np3-Th3-Ph2-F, R$^1$-Np3-Th3-Ph3-F,
R$^1$-Np3-CH$_2$CH$_2$-Th3-Ph1-F, R$^1$-Np3-CH$_2$CH$_2$-Th3-Ph2-F, R$^1$-Np3-CH$_2$CH$_2$-Th3-Ph3-F,
R$^1$-Np3-Th3-CH$_2$CH$_2$-Ph1-F, R$^1$-Np3-Th3-CH$_2$CH$_2$-Ph2-F, R$^1$-Np3-Th3-CH$_2$CH$_2$-Ph3-F,
R$^1$-Np1-Th3-Ph1-F, R$^1$-Np1-Th3-Ph2-F, R$^1$-Np1-Th3-Ph3-F,
R$^1$-Np4-CH$_2$CH$_2$-Th3-Ph1-F, R$^1$-Np4-CH$_2$CH$_2$-Th3-Ph2-F, R$^1$-Np4-CH$_2$CH$_2$-Th3-Ph3-F,
R$^1$-Np4-Th3-CH$_2$CH$_2$-Ph1-F, R$^1$-Np4-Th3-CH$_2$CH$_2$-Ph2-F, R$^1$-Np4-Th3-CH$_2$CH$_2$-Ph3-F,
in the case in which $n^a$=1, $n^b$=0 or $n^a$=0, $n^b$=1, and $n^c$=1, $n^d$=0 or $n^c$=0, $n^d$=1, and Z is a cyano group,
R$^1$-Cy-Th1-Ph1-CN, R$^1$-Cy-Th1-Ph2-CN, R$^1$-Cy-Th1-Ph3-CN, R$^1$-Cy-Th1-Np1-CN,
R$^1$-Cy-Th1-Np2-CN, R$^1$-Cy-Th1-Np3-CN, R$^1$-Cy-Th1-Np4-CN,
R$^1$-Cy-CH$_2$CH$_2$-Th1-Ph1-CN, R$^1$-Cy-CH$_2$CH$_2$-Th1-Ph2-CN, R$^1$-Cy-CH$_2$CH$_2$-Th1-Ph3-CN,
R$^1$-Cy-CH$_2$CH$_2$-Th1-Np1-CN, R$^1$-Cy-CH$_2$CH$_2$-Th1-Np2-CN, R$^1$-Cy-CH$_2$CH$_2$-Th1-Np3-CN,
R$^1$-Cy-CH$_2$CH$_2$-Th1-Np4-CN, R$^1$-Cy-Th1-CH$_2$CH$_2$-Ph1-CN, R$^1$-Cy-Th1-CH$_2$CH$_2$-Ph2-CN,
R$^1$-Cy-Th1-CH$_2$CH$_2$-Ph3-CN, R$^1$-Cy-Th1-CH$_2$CH$_2$-Np1-CN, R$^1$-Cy-Th1-CH$_2$CH$_2$-Np2-CN,
R$^1$-Cy-Th1-CH$_2$CH$_2$-Np3-CN, R$^1$-Cy-Th1-CH$_2$CH$_2$-Np4-CN,
R$^1$-Cy-Th1-C≡C-Ph1-CN, R$^1$-Cy-Th1-C≡C-Ph2-CN, R$^1$-Cy-Th1-C≡C-Ph3-CN,
R$^1$-Ph1-Th1-Ph1-CN, R$^1$-Ph1-Th1-Ph2-CN, R$^1$-Ph1-Th1-Ph3-CN,
R$^1$-Ph1-Th1-Np1-CN, R$^1$-Ph1-Th1-Np2-CN, R$^1$-Ph1-Th1-Np3-CN,
R$^1$-Ph1-Th1-Np4-CN,
R$^1$-Ph1-CH$_2$CH$_2$-Th1-Ph1-CN, R$^1$-Ph1-CH$_2$CH$_2$-Th1-Ph2-CN,
R$^1$-Ph1-CH$_2$CH$_2$-Th1-Ph3-CN, R$^1$-Ph1-CH$_2$CH$_2$-Th1-Np1-CN,
R$^1$-Ph1-CH$_2$CH$_2$-Th1-Np2-CN, R$^1$-Ph1-CH$_2$CH$_2$-Th1-Np3-CN,
R$^1$-Ph1-CH$_2$CH$_2$-Th1-Np4-CN, R$^1$-Ph1-Th1-CH$_2$CH$_2$-Ph1-CN,
R$^1$-Ph1-Th1-CH$_2$CH$_2$-Ph2-CN, R$^1$-Ph1-Th1-CH$_2$CH$_2$-Ph3-CN,
R$^1$-Ph1-Th1-CH$_2$CH$_2$-Np1-CN, R$^1$-Ph1-Th1-CH$_2$CH$_2$-Np2-CN,
R$^1$-Ph1-Th1-CH$_2$CH$_2$-Np3-CN, R$^1$-Ph1-Th1-CH$_2$CH$_2$-Np4-CN,
R$^1$-Ph1-C≡C-Th1-Ph1-CN, R$^1$-Ph1-C≡C-Th1-Ph2-CN, R$^1$-Ph1-C≡C-Th1-Ph3-CN,
R$^1$-Ph1-Th1-C≡C-Ph1-CN, R$^1$-Ph1-Th1-C≡C-Ph2-CN, R$^1$-Ph1-Th1-C≡C-Ph3-CN,
R$^1$-Ph2-Th1-Ph1-CN, R$^1$-Ph2-Th1-Ph2-CN, R$^1$-Ph2-Th1-Ph3-CN,
R$^1$-Ph2-Th1-Np1-CN, R$^1$-Ph2-Th1-Np2-CN, R$^1$-Ph2-Th1-Np3-CN,
R$^1$-Ph2-Th1-Np4-CN,
R$^1$-Ph2-CH$_2$CH$_2$-Th1-Ph1-CN, R$^1$-Ph2-CH$_2$CH$_2$-Th1-Ph2-CN,
R$^1$-Ph2-CH$_2$CH$_2$-Th1-Ph3-CN, R$^1$-Ph2-CH$_2$CH$_2$-Th1-Np1-CN,
R$^1$-Ph2-CH$_2$CH$_2$-Th1-Np2-CN, R$^1$-Ph2-CH$_2$CH$_2$-Th1-Np3-CN,
R$^1$-Ph2-CH$_2$CH$_2$-Th1-Np4-CN, R$^1$-Ph2-Th1-CH$_2$CH$_2$-Ph1-CN,
R$^1$-Ph2-Th1-CH$_2$CH$_2$-Ph2-CN, R$^1$-Ph2-Th1-CH$_2$CH$_2$-Ph3-CN,
R$^1$-Ph2-Th1-CH$_2$CH$_2$-Np1-CN, R$^1$-Ph1-Th1-CH$_2$CH$_2$-Np2-CN,
R$^1$-Ph2-Th1-CH$_2$CH$_2$-Np3-CN, R$^1$-Ph2-Th1-CH$_2$CH$_2$-Np2-CN,
R$^1$-Ph2-C≡C-Th1-Ph1-CN, R$^1$-Ph2-C≡C-Th1-Ph2-CN, R$^1$-Ph2-C≡C-Th1-Ph3-CN,
R$^1$-Ph2-Th1-C≡C-Ph1-CN, R$^1$-Ph2-Th1-C≡C-Ph2-CN, R$^1$-Ph2-Th1-C≡C-Ph3-CN,
R$^1$-Ph3-Th1-Ph1-CN, R$^1$-Ph3-Th1-Ph2-CN, R$^1$-Ph3-Th1-Ph3-CN,
R$^1$-Ph3-Th1-Np1-CN, R$^1$-Ph3-Th1-Np2-CN, R$^1$-Ph3-Th1-Np3-CN,
R$^1$-Ph3-Th1-Np4-CN,
R$^1$-Ph3-CH$_2$CH$_2$-Th1-Ph1-CN, R$^1$-Ph3-CH$_2$CH$_2$-Th1-Ph2-CN,
R$^1$-Ph3-CH$_2$CH$_2$-Th1-Ph3-CN, R$^1$-Ph3-CH$_2$CH$_2$-Th1-Np1-CN,
R$^1$-Ph3-CH$_2$CH$_2$-Th1-Np2-CN, R$^1$-Ph3-CH$_2$CH$_2$-Th1-Np3-CN,
R$^1$-Ph3-CH$_2$CH$_2$-Th1-Np4-CN, R$^1$-Ph3-Th1-CH$_2$CH$_2$-Ph1-CN,
R$^1$-Ph3-Th1-CH$_2$CH$_2$-Ph2-CN, R$^1$-Ph3-Th1-CH$_2$CH$_2$-Ph3-CN,
R$^1$-Ph3-Th1-CH$_2$CH$_2$-Np1-CN, R$^1$-Ph3-Th1-CH$_2$CH$_2$-Np2-CN,
R$^1$-Ph3-Th1-CH$_2$CH$_2$-Np3-CN, R$^1$-Ph3-Th1-CH$_2$CH$_2$-Np4-CN,
R$^1$-Ph3-C≡C-Th1-Ph1-CN, R$^1$-Ph3-C≡C-Th1-Ph2-CN, R$^1$-Ph3-C≡C-Th1-Ph3-CN, R¹-Ph3-Th1-C≡C-Ph1-CN, R¹-Ph3-Th1-C≡C-Ph2-CN, R¹-Ph3-Th1-C≡C-Ph3-CN,
R¹-Np1-Th1-Ph1-CN, R¹-Np1-Th1-Ph2-CN, R¹-Np1-Th1-Ph3-CN,
R¹-Np1-CH$_2$CH$_2$-Th1-Ph1-CN, R¹-Np1-CH$_2$CH$_2$-Th1-Ph2-CN,
R¹-Np1-CH$_2$CH$_2$-Th1-Ph3-CN, R¹-Np1-Th1-CH$_2$CH$_2$-Ph1-CN,
R¹-Np1-Th1-CH$_2$CH$_2$-Ph2-CN, R¹-Np1-Th1-CH$_2$CH$_2$-Ph3-CN,
R¹-Np2-Th1-Ph1-CN, R¹-Np2-Th1-Ph2-CN, R¹-Np2-Th1-Ph3-CN,
R¹-Np2-CH$_2$CH$_2$-Th1-Ph1-CN, R¹-Np2-CH$_2$CH$_2$-Th1-Ph2-CN,
R¹-Np2-CH$_2$CH$_2$-Th1-Ph3-CN, R¹-Np2-Th1-CH$_2$CH$_2$-Ph1-CN,
R¹-Np2-Th1-CH$_2$CH$_2$-Ph2-CN, R¹-Np2-Th1-CH$_2$CH$_2$-Ph3-CN,
R¹-Np3-Th1-Ph1-CN, R¹-Np3-Th1-Ph2-CN, R¹-Np3-Th1-Ph3-CN,
R¹-Np3-CH$_2$CH$_2$-Th1-Ph1-CN, R¹-Np3-CH$_2$CH$_2$-Th1-Ph2-CN,
R¹-Np3-CH$_2$CH$_2$-Th1-Ph3-CN, R¹-Np3-Th1-CH$_2$CH$_2$-Ph1-CN,
R¹-Np3-Th1-CH$_2$CH$_2$-Ph2-CN, R¹-Np3-Th1-CH$_2$CH$_2$-Ph3-CN,
R¹-Np1-Th1-Ph1-CN, R¹-Np1-Th1-Ph2-CN, R¹-Np1-Th1-Ph3-CN,
R¹-Np4-CH$_2$CH$_2$-Th1-Ph1-CN, R¹-Np4-CH$_2$CH$_2$-Th1-Ph2-CN,
R¹-Np4-CH$_2$CH$_2$-Th1-Ph3-CN, R¹-Np4-Th1-CH$_2$CH$_2$-Ph1-CN,
R¹-Np4-Th1-CH$_2$CH$_2$-Ph2-CN, R¹-Np4-Th1-CH$_2$CH$_2$-Ph3-CN,
R¹-Cy-Th2-Ph1-CN, R¹-Cy-Th2-Ph2-CN, R¹-Cy-Th2-Ph3-CN, R¹-Cy-Th2-Np1-CN,
R¹-Cy-Th2-Np2-CN, R¹-Cy-Th2-Np3-CN, R¹-Cy-Th2-Np4-CN,
R¹-Cy-CH$_2$CH$_2$-Th2-Ph1-CN, R¹-Cy-CH$_2$CH$_2$-Th2-Ph2-CN, R¹-Cy-CH$_2$CH$_2$-Th2-Ph3-CN,
R¹-Cy-CH$_2$CH$_2$-Th2-Np1-CN, R¹-Cy-CH$_2$CH$_2$-Th2-Np2-CN, R¹-Cy-CH$_2$CH$_2$-Th2-Np3-CN,
R¹-Cy-CH$_2$CH$_2$-Th2-Np4-CN, R¹-Cy-Th2-CH$_2$CH$_2$-Ph1-CN, R¹-Cy-Th2-CH$_2$CH$_2$-Ph2-CN,
R¹-Cy-Th2-CH$_2$CH$_2$-Ph3-CN, R¹-Cy-Th2-CH$_2$CH$_2$-Np1-CN, R¹-Cy-Th2-CH$_2$CH$_2$-Np2-CN,
R¹-Cy-Th2-CH$_2$CH$_2$-Np3-CN, R¹-Cy-Th2-CH$_2$CH$_2$-Np4-CN,
R¹-Cy-Th2-C≡C-Ph1-CN, R¹-Cy-Th2-C≡C-Ph2-CN, R¹-Cy-Th2-C≡C-Ph3-CN,
R¹-Ph1-Th2-Ph1-CN, R¹-Ph1-Th2-Ph2-CN, R¹-Ph1-Th2-Ph3-CN,
R¹-Ph1-Th2-Np1-CN, R¹-Ph1-Th2-Np2-CN, R¹-Ph1-Th2-Np3-CN,
R¹-Ph1-Th2-Np4-CN,
R¹-Ph1-CH$_2$CH$_2$-Th2-Ph1-CN, R¹-Ph1-CH$_2$CH$_2$-Th2-Ph2-CN,
R¹-Ph1-CH$_2$CH$_2$-Th2-Ph3-CN, R¹-Ph1-CH$_2$CH$_2$-Th2-Np1-CN,
R¹-Ph1-CH$_2$CH$_2$-Th2-Np2-CN, R¹-Ph1-CH$_2$CH$_2$-Th2-Np3-CN,
R¹-Ph1-CH$_2$CH$_2$-Th2-Np4-CN, R¹-Ph1-Th2-CH$_2$CH$_2$-Ph1-CN,
R¹-Ph1-Th2-CH$_2$CH$_2$-Ph2-CN, R¹-Ph1-Th2-CH$_2$CH$_2$-Ph3-CN,
R¹-Ph1-Th2-CH$_2$CH$_2$-Np1-CN, R¹-Ph1-Th2-CH$_2$CH$_2$-Np2-CN,
R¹-Ph1-Th2-CH$_2$CH$_2$-Np3-CN, R¹-Ph1-Th2-CH$_2$CH$_2$-Np4-CN,
R¹-Ph1-C≡C-Th2-Ph1-CN, R¹-Ph1-C≡C-Th2-Ph2-CN, R¹-Ph1-C≡C-Th2-Ph3-CN,
R¹-Ph1-Th2-C≡C-Ph1-CN, R¹-Ph1-Th2-C≡C-Ph2-CN, R¹-Ph1-Th2-C≡C-Ph3-CN,
R¹-Ph2-Th2-Ph1-CN, R¹-Ph2-Th2-Ph2-CN, R¹-Ph2-Th2-Ph3-CN,
R¹-Ph2-Th2-Np1-CN, R¹-Ph2-Th2-Np2-CN, R¹-Ph2-Th2-Np3-CN,
R¹-Ph2-Th2-Np4-CN,
R¹-Ph2-CH$_2$CH$_2$-Th2-Ph1-CN, R¹-Ph2-CH$_2$CH$_2$-Th2-Ph2-CN,
R¹-Ph2-CH$_2$CH$_2$-Th2-Ph3-CN, R¹-Ph2-CH$_2$CH$_2$-Th2-Np1-CN,
R¹-Ph2-CH$_2$CH$_2$-Th1-Np2-CN, R¹-Ph2-CH$_2$CH$_2$-Th2-Np3-CN,
R¹-Ph2-CH$_2$CH$_2$-Th2-Np4-CN, R¹-Ph2-CH$_2$CH$_2$-Ph1-CN,
R¹-Ph2-CH$_2$CH$_2$-Ph2-CN, R¹-Ph2-CH$_2$CH$_2$-Ph3-CN,
R¹-Ph2-Th2-CH$_2$CH$_2$-Np1-CN, R¹-Ph2-Th2-CH$_2$CH$_2$-Np2-CN,
R¹-Ph2-Th2-CH$_2$CH$_2$-Np3-CN, R¹-Ph2-Th2-CH$_2$CH$_2$-Np4-CN,
R¹-Ph2-C≡C-Th2-Ph1-CN, R¹-Ph2-C≡C-Th2-Ph2-CN, R¹-Ph2-C≡C-Th2-Ph3-CN,
R¹-Ph2-Th2-C≡C-Ph1-CN, R¹-Ph2-Th2-C≡C-Ph2-CN, R¹-Ph2-Th2-C≡C-Ph3-CN,
R¹-Ph3-Th2-Ph1-CN, R¹-Ph3-Th2-Ph2-CN, R¹-Ph3-Th2-Ph3-CN,
R¹-Ph3-Th2-Np1-CN, R¹-Ph3-Th2-Np2-CN, R¹-Ph3-Th2-Np3-CN,
R¹-Ph3-Th2-Np4-CN,
R¹-Ph3-CH$_2$CH$_2$-Th2-Ph1-CN, R¹-Ph3-CH$_2$CH$_2$-Th2-Ph2-CN,
R¹-Ph3-CH$_2$CH$_2$-Th2-Ph3-CN, R¹-Ph3-CH$_2$CH$_2$-Th2-Np1-CN,
R¹-Ph3-CH$_2$CH$_2$-Th2-Np2-CN, R¹-Ph3-CH$_2$CH$_2$-Th2-Np3-CN,
R¹-Ph3-CH$_2$CH$_2$-Th2-Np4-CN, R¹-Ph3-Th2-CH$_2$CH$_2$-Ph1-CN,
R¹-Ph3-Th2-CH$_2$CH$_2$-Ph2-CN, R¹-Ph3-Th2-CH$_2$CH$_2$-Ph3-CN,
R¹-Ph3-Th2-CH$_2$CH$_2$-Np1-CN, R¹-Ph3-Th2-CH$_2$CH$_2$-Np2-CN,
R¹-Ph3-Th2-CH$_2$CH$_2$-Np3-CN, R¹-Ph3-Th2-CH$_2$CH$_2$-Np4-CN,
R¹-Ph3-C≡C-Th2-Ph1-CN, R¹-Ph3-C≡C-Th2-Ph2-CN, R¹-Ph3-C≡C-Th2-Ph3-CN,
R¹-Ph3-Th2-C≡C-Ph1-CN, R¹-Ph3-Th2-C≡C-Ph2-CN, R¹-Ph3-Th2-C≡C-Ph3-CN,
R¹-Np1-Th2-Ph1-CN, R¹-Np1-Th2-Ph2-CN, R¹-Np1-Th2-Ph3-CN,
R¹-Np1-CH$_2$CH$_2$-Th2-Ph1-CN, R¹-Np1-CH$_2$CH$_2$-Th2-Ph2-CN,
R¹-Np1-CH$_2$CH$_2$-Th2-Ph3-CN, R¹-Np1-Th2-CH$_2$CH$_2$-Ph1-CN,
R¹-Np1-Th2-CH$_2$CH$_2$-Ph2-CN, R¹-Np1-Th2-CH$_2$CH$_2$-Ph3-CN,
R¹-Np2-Th2-Ph1-CN, R¹-Np2-Th2-Ph2-CN, R¹-Np2-Th2-Ph3-CN,
R¹-Np2-CH$_2$CH$_2$-Th2-Ph1-CN, R¹-Np2-CH$_2$CH$_2$-Th2-Ph2-CN,
R¹-Np2-CH$_2$CH$_2$-Th2-Ph3-CN, R¹-Np2-Th2-CH$_2$CH$_2$-Ph1-CN,
R¹-Np2-Th2-CH$_2$CH$_2$-Ph2-CN, R¹-Np2-Th2-CH$_2$CH$_2$-Ph3-CN, R$^1$-Np3-Th2-Ph1-CN, R$^1$-Np3-Th2-Ph2-CN, R$^1$-Np3-Th2-Ph3-CN,
R$^1$-Np3-CH$_2$CH$_2$-Th2-Ph1-CN, R$^1$-Np3-CH$_2$CH$_2$-Th2-Ph2-CN,
R$^1$-Np3-CH$_2$CH$_2$-Th2-Ph3-CN, R$^1$-Np3-Th2-CH$_2$CH$_2$-Ph1-CN,
R$^1$-Np3-Th2-CH$_2$CH$_2$-Ph2-CN, R$^1$-Np3-Th2-CH$_2$CH$_2$-Ph3-CN,
R$^1$-Np1-Th2-Ph1-CN, R$^1$-Np1-Th2-Ph2-CN, R$^1$-Np1-Th2-Ph3-CN,
R$^1$-Np4-CH$_2$CH$_2$-Th2-Ph1-CN, R$^1$-Np4-CH$_2$CH$_2$-Th2-Ph2-CN,
R$^1$-Np4-CH$_2$CH$_2$-Th2-Ph3-CN, R$^1$-Np4-Th2-CH$_2$CH$_2$-Ph1-CN,
R$^1$-Np4-Th2-CH$_2$CH$_2$-Ph2-CN, R$^1$-Np4-Th2-CH$_2$CH$_2$-Ph3-CN,
R$^1$-Cy-Th3-Ph1-CN, R$^1$-Cy-Th3-Ph2-CN, R$^1$-Cy-Th3-Ph3-CN, R$^1$-Cy-Th3-Np1-CN,
R$^1$-Cy-Th3-Np2-CN, R$^1$-Cy-Th3-Np3-CN, R$^1$-Cy-Th3-Np4-CN,
R$^1$-Cy-CH$_2$CH$_2$-Th3-Ph1-CN, R$^1$-Cy-CH$_2$CH$_2$-Th3-Ph2-CN, R$^1$-Cy-CH$_2$CH$_2$-Th3-Ph3-CN,
R$^1$-Cy-CH$_2$CH$_2$-Th3-Np1-CN, R$^1$-Cy-CH$_2$CH$_2$-Th3-Np2-CN, R$^1$-Cy-CH$_2$CH$_2$-Th3-Np3-CN,
R$^1$-Cy-CH$_2$CH$_2$-Th3-Np4-CN, R$^1$-Cy-Th3-CH$_2$CH$_2$-Ph1-CN, R$^1$-Cy-Th3-CH$_2$CH$_2$-Ph2-CN,
R$^1$-Cy-Th3-CH$_2$CH$_2$-Ph3-CN, R$^1$-Cy-Th3-CH$_2$CH$_2$-Np1-CN, R$^1$-Cy-Th3-CH$_2$CH$_2$-Np2-CN,
R$^1$-Cy-Th3-CH$_2$CH$_2$-Np3-CN, R$^1$-Cy-Th3-CH$_2$CH$_2$-Np4-CN,
R$^1$-Cy-Th3-C≡C-Ph1-CN, R$^1$-Cy-Th3-C≡C-Ph2-CN, R$^1$-Cy-Th3-C≡C-Ph3-CN,
R$^1$-Ph1-Th3-Ph1-CN, R$^1$-Ph1-Th3-Ph2-CN, R$^1$-Ph1-Th3-Ph3-CN,
R$^1$-Ph1-Th3-Np1-CN, R$^1$-Ph1-Th3-Np2-CN, R$^1$-Ph1-Th3-Np3-CN,
R$^1$-Ph1-Th3-Np4-CN,
R$^1$-Ph1-CH$_2$CH$_2$-Th3-Ph1-CN, R$^1$-Ph1-CH$_2$CH$_2$-Th3-Ph2-CN,
R$^1$-Ph1-CH$_2$CH$_2$-Th3-Ph3-CN, R$^1$-Ph1-CH$_2$CH$_2$-Th3-Np1-CN,
R$^1$-Ph1-CH$_2$CH$_2$-Th3-Np2-CN, R$^1$-Ph1-CH$_2$CH$_2$-Th3-Np3-CN,
R$^1$-Ph1-CH$_2$CH$_2$-Th3-Np4-CN, R$^1$-Ph1-Th3-CH$_2$CH$_2$-Ph1-CN,
R$^1$-Ph1-Th3-CH$_2$CH$_2$-Ph2-CN, R$^1$-Ph1-Th3-CH$_2$CH$_2$-Ph3-CN,
R$^1$-Ph1-Th3-CH$_2$CH$_2$-Np1-CN, R$^1$-Ph1-Th3-CH$_2$CH$_2$-Np2-CN,
R$^1$-Ph1-Th3-CH$_2$CH$_2$-Np3-CN, R$^1$-Ph1-Th3-CH$_2$CH$_2$-Np4-CN,
R$^1$-Ph1-C≡C-Th3-Ph1-CN, R$^1$-Ph1-C≡C-Th3-Ph2-CN, R$^1$-Ph1-C≡C-Th3-Ph3-CN,
R$^1$-Ph1-Th3-C≡C-Ph1-CN, R$^1$-Ph1-Th3-C≡C-Ph2-CN, R$^1$-Ph1-Th3-C≡C-Ph3-CN,
R$^1$-Ph2-Th3-Ph1-CN, R$^1$-Ph2-Th3-Ph2-CN, R$^1$-Ph2-Th3-Ph3-CN,
R$^1$-Ph2-Th3-Np1-CN, R$^1$-Ph2-Th3-Np2-CN, R$^1$-Ph2-Th3-Np3-CN,
R$^1$-Ph2-Th3-Np4-CN,
R$^1$-Ph2-CH$_2$CH$_2$-Th3-Ph1-CN, R$^1$-Ph2-CH$_2$CH$_2$-Th3-Ph2-CN,
R$^1$-Ph2-CH$_2$CH$_2$-Th3-Ph3-CN, R$^1$-Ph2-CH$_2$CH$_2$-Th3-Np1-CN,
R$^1$-Ph2-CH$_2$CH$_2$-Th3-Np2-CN, R$^1$-Ph2-CH$_2$CH$_2$-Th3-Np3-CN,
R$^1$-Ph2-CH$_2$CH$_2$-Th3-Np4-CN, R$^1$-Ph2-Th3-CH$_2$CH$_2$-Ph1-CN,
R$^1$-Ph2-Th3-CH$_2$CH$_2$-Ph2-CN, R$^1$-Ph2-Th3-CH$_2$CH$_2$-Ph3-CN,
R$^1$-Ph2-Th3-CH$_2$CH$_2$-Np1-CN, R$^1$-Ph2-Th3-CH$_2$CH$_2$-Np2-CN,
R$^1$-Ph2-Th3-CH$_2$CH$_2$-Np3-CN, R$^1$-Ph2-Th3-CH$_2$CH$_2$-Np4-CN,
R$^1$-Ph2-C≡C-Th3-Ph1-CN, R$^1$-Ph2-C≡C-Th3-Ph2-CN, R$^1$-Ph2-C≡C-Th3-Ph3-CN,
R$^1$-Ph2-Th3-C≡C-Ph1-CN, R$^1$-Ph2-Th3-C≡C-Ph2-CN, R$^1$-Ph2-Th3-C≡C-Ph3-CN,
R$^1$-Ph3-Th3-Ph1-CN, R$^1$-Ph3-Th3-Ph2-CN, R$^1$-Ph3-Th3-Ph3-CN,
R$^1$-Ph3-Th3-Np1-CN, R$^1$-Ph3-Th3-Np2-CN, R$^1$-Ph3-Th3-Np3-CN,
R$^1$-Ph3-Th3-Np4-CN,
R$^1$-Ph3-CH$_2$CH$_2$-Th3-Ph1-CN, R$^1$-Ph3-CH$_2$CH$_2$-Th3-Ph2-CN,
R$^1$-Ph3-CH$_2$CH$_2$-Th3-Ph3-CN, R$^1$-Ph3-CH$_2$CH$_2$-Th3-Np1-CN,
R$^1$-Ph3-CH$_2$CH$_2$-Th3-Np2-CN, R$^1$-Ph3-CH$_2$CH$_2$-Th3-Np3-CN,
R$^1$-Ph3-CH$_2$CH$_2$-Th3-Np4-CN, R$^1$-Ph3-Th3-CH$_2$CH$_2$-Ph1-CN,
R$^1$-Ph3-Th3-CH$_2$CH$_2$-Ph2-CN, R$^1$-Ph3-Th3-CH$_2$CH$_2$-Ph3-CN,
R$^1$-Ph3-Th3-CH$_2$CH$_2$-Np1-CN, R$^1$-Ph3-Th3-CH$_2$CH$_2$-Np2-CN,
R$^1$-Ph3-Th3-CH$_2$CH$_2$-Np3-CN, R$^1$-Ph3-Th3-CH$_2$CH$_2$-Np4-CN,
R$^1$-Ph3-C≡C-Th3-Ph1-CN, R$^1$-Ph3-C≡C-Th3-Ph2-CN, R$^1$-Ph3-C≡C-Th3-Ph3-CN,
R$^1$-Ph3-Th3-C≡C-Ph1-CN, R$^1$-Ph3-Th3-C≡C-Ph2-CN, R$^1$-Ph3-Th3-C≡C-Ph3-CN,
R$^1$-Np1-Th3-Ph1-CN, R$^1$-Np1-Th3-Ph2-CN, R$^1$-Np1-Th3-Ph3-CN,
R$^1$-Np1-CH$_2$CH$_2$-Th3-Ph1-CN, R$^1$-Np1-CH$_2$CH$_2$-Th3-Ph2-CN,
R$^1$-Np1-CH$_2$CH$_2$-Th3-Ph3-CN, R$^1$-Np1-Th3-CH$_2$CH$_2$-Ph1-CN,
R$^1$-Np1-Th3-CH$_2$CH$_2$-Ph2-CN, R$^1$-Np1-Th3-CH$_2$CH$_2$-Ph3-CN,
R$^1$-Np2-Th3-Ph1-CN, R$^1$-Np2-Th3-Ph2-CN, R$^1$-Np2-Th3-Ph3-CN,
R$^1$-Np2-CH$_2$CH$_2$-Th3-Ph1-CN, R$^1$-Np2-CH$_2$CH$_2$-Th3-Ph2-CN,
R$^1$-Np2-CH$_2$CH$_2$-Th3-Ph3-CN, R$^1$-Np2-Th3-CH$_2$CH$_2$-Ph1-CN,
R$^1$-Np2-Th3-CH$_2$CH$_2$-Ph2-CN, R$^1$-Np2-Th3-CH$_2$CH$_2$-Ph3-CN,
R$^1$-Np3-Th3-Ph1-CN, R$^1$-Np3-Th3-Ph2-CN, R$^1$-Np3-Th3-Ph3-CN,
R$^1$-Np3-CH$_2$CH$_2$-Th3-Ph1-CN, R$^1$-Np3-CH$_2$CH$_2$-Th3-Ph2-CN,
R$^1$-Np3-CH$_2$CH$_2$-Th3-Ph3-CN, R$^1$-Np3-Th3-CH$_2$CH$_2$-Ph1-CN,
R$^1$-Np3-Th3-CH$_2$CH$_2$-Ph2-CN, R$^1$-Np3-Th3-CH$_2$CH$_2$-Ph3-CN,
R$^1$-Np1-Th3-Ph1-CN, R$^1$-Np1-Th3-Ph2-CN, R$^1$-Np1-Th3-Ph3-CN,
R$^1$-Np4-CH$_2$CH$_2$-Th3-Ph1-CN, R$^1$-Np4-CH$_2$CH$_2$-Th3-Ph2-CN,
R$^1$-Np4-CH$_2$CH$_2$-Th3-Ph3-CN, R$^1$-Np4-Th3-CH$_2$CH$_2$-Ph1-CN,
R$^1$-Np4-Th3-CH$_2$CH$_2$-Ph2-CN, R$^1$-Np4-Th3-CH$_2$CH$_2$-Ph3-CN,
R$^1$-Cy-Th3-Ph1-CN, R$^1$-Cy-Th3-Ph2-CN, R$^1$-Cy-Th3-Ph3-CN, R$^1$-Cy-Th3-Np1-CN, R¹-Cy-Th3-Np2-CN, R¹-Cy-Th3-Np3-CN, R¹-Cy-Th3-Np4-CN,
R¹-Cy-CH₂CH₂-Th3-Ph1-CN, R¹-Cy-CH₂CH₂-Th3-Ph2-CN, R¹-Cy-CH₂CH₂-Th3-Ph3-CN,
R¹-Cy-CH₂CH₂-Th3-Np1-CN, R¹-Cy-CH₂CH₂-Th3-Np2-CN, R¹-Cy-CH₂CH₂-Th3-Np3-CN,
R¹-Cy-CH₂CH₂-Th3-Np4-CN, R¹-Cy-Th3-CH₂CH₂-Ph1-CN, R¹-Cy-Th3-CH₂CH₂-Ph2-CN,
R¹-Cy-Th3-CH₂CH₂-Ph3-CN, R¹-Cy-Th3-CH₂CH₂-Np1-CN, R¹-Cy-Th3-CH₂CH₂-Np2-CN,
R¹-Cy-Th3-CH₂CH₂-Np3-CN, R¹-Cy-Th3-CH₂CH₂-Np4-CN,
R¹-Cy-Th3-C≡C-Ph1-CN, R¹-Cy-Th3-C≡C-Ph2-CN, R¹-Cy-Th3-C≡C-Ph3-CN,
R¹-Ph1-Th3-Ph1-CN, R¹-Ph1-Th3-Ph2-CN, R¹-Ph1-Th3-Ph3-CN,
R¹-Ph1-Th3-Np1-CN, R¹-Ph1-Th3-Np2-CN, R¹-Ph1-Th3-Np3-CN,
R¹-Ph1-Th3-Np4-CN,
R¹-Ph1-CH₂CH₂-Th3-Ph1-CN, R¹-Ph1-CH₂CH₂-Th3-Ph2-CN,
R¹-Ph1-CH₂CH₂-Th3-Ph3-CN, R¹-Ph1-CH₂CH₂-Th3-Np1-CN,
R¹-Ph1-CH₂CH₂-Th3-Np2-CN, R¹-Ph1-CH₂CH₂-Th3-Np3-CN,
R¹-Ph1-CH₂CH₂-Th3-Np4-CN, R¹-Ph1-Th3-CH₂CH₂-Ph1-CN,
R¹-Ph1-Th3-CH₂CH₂-Ph2-CN, R¹-Ph1-Th3-CH₂CH₂-Ph3-CN,
R¹-Ph1-Th3-CH₂CH₂-Np1-CN, R¹-Ph1-Th3-CH₂CH₂-Np2-CN,
R¹-Ph1-Th3-CH₂CH₂-Np3-CN, R¹-Ph1-Th3-CH₂CH₂-Np4-CN,
R¹-Ph1-C≡C-Th3-Ph1-CN, R¹-Ph1-C≡C-Th3-Ph2-CN, R¹-Ph1-C≡C-Th3-Ph3-CN,
R¹-Ph1-Th3-C≡C-Ph1-CN, R¹-Ph1-Th3-C≡C-Ph2-CN, R¹-Ph1-Th3-C≡C-Ph3-CN,
R¹-Ph2-Th3-Ph1-CN, R¹-Ph2-Th3-Ph2-CN, R¹-Ph2-Th3-Ph3-CN,
R¹-Ph2-Th3-Np1-CN, R¹-Ph2-Th3-Np2-CN, R¹-Ph2-Th3-Np3-CN,
R¹-Ph2-Th3-Np4-CN,
R¹-Ph2-CH₂CH₂-Th3-Ph1-CN, R¹-Ph2-CH₂CH₂-Th3-Ph2-CN,
R¹-Ph2-CH₂CH₂-Th3-Ph3-CN, R¹-Ph2-CH₂CH₂-Th3-Np1-CN,
R¹-Ph2-CH₂CH₂-Th3-Np2-CN, R¹-Ph2-CH₂CH₂-Th3-Np3-CN,
R¹-Ph2-CH₂CH₂-Th3-Np4-CN, R¹-Ph2-Th3-CH₂CH₂-Ph1-CN,
R¹-Ph2-Th3-CH₂CH₂-Ph2-CN, R¹-Ph2-Th3-CH₂CH₂-Ph3-CN,
R¹-Ph2-Th3-CH₂CH₂-Np1-CN, R¹-Ph2-Th3-CH₂CH₂-Np2-CN,
R¹-Ph2-Th3-CH₂CH₂-Np3-CN, R¹-Ph2-Th3-CH₂CH₂-Np4-CN,
R¹-Ph2-C≡C-Th3-Ph1-CN, R¹-Ph2-C≡C-Th3-Ph2-CN, R¹-Ph2-C≡C-Th3-Ph3-CN,
R¹-Ph2-Th3-C≡C-Ph1-CN, R¹-Ph2-Th3-C≡C-Ph2-CN, R¹-Ph1-Th3-C≡C-Ph3-CN,
R¹-Ph3-Th3-Ph1-CN, R¹-Ph3-Th3-Ph2-CN, R¹-Ph3-Th3-Ph3-CN,
R¹-Ph3-Th3-Np1-CN, R¹-Ph3-Th3-Np2-CN, R¹-Ph3-Th3-Np3-CN,
R¹-Ph3-Th3-Np4-CN,
R¹-Ph3-CH₂CH₂-Th3-Ph1-CN, R¹-Ph3-CH₂CH₂-Th3-Ph2-CN,
R¹-Ph3-CH₂CH₂-Th3-Ph3-CN, R¹-Ph3-CH₂CH₂-Th3-Np1-CN,
R¹-Ph3-CH₂CH₂-Th3-Np2-CN, R¹-Ph3-CH₂CH₂-Th3-Np3-CN,
R¹-Ph3-CH₂CH₂-Th3-Np4-CN, R¹-Ph3-Th3-CH₂CH₂-Ph1-CN,
R¹-Ph3-Th3-CH₂CH₂-Ph2-CN, R¹-Ph3-Th3-CH₂CH₂-Ph3-CN,
R¹-Ph3-Th3-CH₂CH₂-Np1-CN, R¹-Ph3-Th3-CH₂CH₂-Np2-CN,
R¹-Ph3-Th3-CH₂CH₂-Np3-CN, R¹-Ph3-Th3-CH₂CH₂-Np4-CN,
R¹-Ph3-C≡C-Th3-Ph1-CN, R¹-Ph3-C≡C-Th3-Ph2-CN, R¹-Ph3-C≡C-Th3-Ph3-CN,
R¹-Ph3-Th3-C≡C-Ph1-CN, R¹-Ph3-Th3-C≡C-Ph2-CN, R¹-Ph3-Th3-C≡C-Ph3-CN,
R¹-Np1-Th3-Ph1-CN, R¹-Np1-Th3-Ph2-CN, R¹-Np1-Th3-Ph3-CN,
R¹-Np1-CH₂CH₂-Th3-Ph1-CN, R¹-Np1-CH₂CH₂-Th3-Ph2-CN,
R¹-Np1-CH₂CH₂-Th3-Ph3-CN, R¹-Np1-Th3-CH₂CH₂-Ph1-CN,
R¹-Np1-Th3-CH₂CH₂-Ph2-CN, R¹-Np1-Th3-CH₂CH₂-Ph3-CN,
R¹-Np2-Th3-Ph1-CN, R¹-Np2-Th3-Ph2-CN, R¹-Np2-Th3-Ph3-CN,
R¹-Np2-CH₂CH₂-Th3-Ph1-CN, R¹-Np2-CH₂CH₂-Th3-Ph2-CN,
R¹-Np2-CH₂CH₂-Th3-Ph3-CN, R¹-Np2-Th3-CH₂CH₂-Ph1-CN,
R¹-Np2-Th3-CH₂CH₂-Ph2-CN, R¹-Np2-Th3-CH₂CH₂-Ph3-CN,
R¹-Np3-Th3-Ph1-CN, R¹-Np3-Th3-Ph2-CN, R¹-Np3-Th3-Ph3-CN,
R¹-Np3-CH₂CH₂-Th3-Ph1-CN, R¹-Np3-CH₂CH₂-Th3-Ph2-CN,
R¹-Np3-CH₂CH₂-Th3-Ph3-CN, R¹-Np3-Th3-CH₂CH₂-Ph1-CN,
R¹-Np3-Th3-CH₂CH₂-Ph2-CN, R¹-Np3-Th3-CH₂CH₂-Ph3-CN,
R¹-Np1-Th3-Ph1-CN, R¹-Np1-Th3-Ph2-CN, R¹-Np1-Th3-Ph3-CN,
R¹-Np4-CH₂CH₂-Th3-Ph1-CN, R¹-Np4-CH₂CH₂-Th3-Ph2-CN,
R¹-Np4-CH₂CH₂-Th3-Ph3-CN, R¹-Np4-Th3-CH₂CH₂-Ph1-CN,
R¹-Np4-Th3-CH₂CH₂-Ph2-CN, R¹-Np4-Th3-CH₂CH₂-Ph3-CN, in the case in which $n^a=1$, $n^b=0$ or $n^a=0$, $n^b=1$, and $n^c=1$, $n^d=0$ or $n^c=0$, $n^d=1$ and Z is a trifluoromethyl group, R¹-Cy-Th1-Ph1-CF₃, R¹-Cy-Th1-Ph2-CF₃, R¹-Cy-Th1-Ph3-CF₃, R¹-Cy-Th1-Np1-CF₃,
R¹-Cy-Th1-Np2-CF₃, R¹-Cy-Th1-Np3-CF₃, R¹-Cy-Th1-Np4-CF₃,
R¹-Cy-CH₂CH₂-Th1-Ph1-CF₃, R¹-Cy-CH₂CH₂-Th1-Ph2-CF₃, R¹-Cy-CH₂CH₂-Th1-Ph3-CF₃,
R¹-Cy-CH₂CH₂-Th1-Np1-CF₃, R¹-Cy-CH₂CH₂-Th1-Np2-CF₃,
R¹-Cy-CH₂CH₂-Th1-Np3-CF₃,
R¹-Cy-CH₂CH₂-Th1-Np4-CF₃, R¹-Cy-Th1-CH₂CH₂-Ph1-CF₃, R¹-Cy-Th1-CH₂CH₂-Ph2-CF₃,
R¹-Cy-Th1-CH₂CH₂-Ph3-CF₃, R¹-Cy-Th1-CH₂CH₂-Np1-CF₃, R¹-Cy-Th1-CH₂CH₂-Np2-CF₃,
R¹-Cy-Th1-CH₂CH₂-Np3-CF₃, R¹-Cy-Th1-CH₂CH₂-Np4-CF₃,
R¹-Cy-Th1-C≡C-Ph1-CF₃, R¹-Cy-Th1-C≡C-Ph2-CF₃, R¹-Cy-Th1-C≡C-Ph3-CF₃, R¹-Ph1-Th1-Ph1-CF₃, R¹-Ph1-Th1-Ph2-CF₃, R¹-Ph1-Th1-Ph3-CF₃,
R¹-Ph1-Th1-Np1-CF₃, R¹-Ph1-Th1-Np2-CF₃, R¹-Ph1-Th1-Np3-CF₃,
R¹-Ph1-Th1-Np4-CF₃,
R¹-Ph1-CH₂CH₂-Th1-Ph1-CF₃, R¹-Ph1-CH₂CH₂-Th1-Ph2-CF₃,
R¹-Ph1-CH₂CH₂-Th1-Ph3-CF₃, R¹-Ph1-CH₂CH₂-Th1-Np1-CF₃,
R¹-Ph1-CH₂CH₂-Th1-Np2-CF₃, R¹-Ph1-CH₂CH₂-Th1-Np3-CF₃,
R¹-Ph1-CH₂CH₂-Th1-Np4-CF₃, R¹-Ph1-Th1-CH₂CH₂-Ph1-CF₃,
R¹-Ph1-Th1-CH₂CH₂-Ph2-CF₃, R¹-Ph1-Th1-CH₂CH₂-Ph3-CF₃,
R¹-Ph1-Th1-CH₂CH₂-Np1-CF₃, R¹-Ph1-Th1-CH₂CH₂-Np2-CF₃,
R¹-Ph1-Th1-CH₂CH₂-Np3-CF₃, R¹-Ph1-Th1-CH₂CH₂-Np4-CF₃,
R¹-Ph1-C≡C-Th1-Ph1-CF₃, R¹-Ph1-C≡C-Th1-Ph2-CF₃, R¹-Ph1-C≡C-Th1-Ph3-CF₃,
R¹-Ph1-Th1-C≡C-Ph1-CF₃, R¹-Ph1-Th1-C≡C-Ph2-CF₃, R¹-Ph1-Th1-C≡C-Ph3-CF₃,
R¹-Ph2-Th1-Ph1-CF₃, R¹-Ph2-Th1-Ph2-CF₃, R¹-Ph2-Th1-Ph3-CF₃,
R¹-Ph2-Th1-Np1-CF₃, R¹-Ph2-Th1-Np2-CF₃, R¹-Ph2-Th1-Np3-CF₃,
R¹-Ph2-Th1-Np4-CF₃,
R¹-Ph2-CH₂CH₂-Th1-Ph1-CF₃, R¹-Ph2-CH₂CH₂-Th1-Ph2-CF₃,
R¹-Ph2-CH₂CH₂-Th1-Ph3-CF₃, R¹-Ph2-CH₂CH₂-Th1-Np1-CF₃,
R¹-Ph2-CH₂CH₂-Th1-Np2-CF₃, R¹-Ph2-CH₂CH₂-Th1-Np3-CF₃,
R¹-Ph2-CH₂CH₂-Th1-Np4-CF₃, R¹-Ph2-Th1-CH₂CH₂-Ph1-CF₃,
R¹-Ph2-Th1-CH₂CH₂-Ph2-CF₃, R¹-Ph1-Th2-CH₂CH₂-Ph3-CF₃,
R¹-Ph2-Th1-CH₂CH₂-Np1-CF₃, R¹-Ph2-Th1-CH₂CH₂-Np2-CF₃,
R¹-Ph2-Th1-CH₂CH₂-Np3-CF₃, R¹-Ph2-Th1-CH₂CH₂-Np4-CF₃,
R¹-Ph2-C≡C-Th1-Ph1-CF₃, R¹-Ph2-C≡C-Th1-Ph2-CF₃, R¹-Ph2-C≡C-Th1-Ph3-CF₃,
R¹-Ph2-Th1-C≡C-Ph1-CF₃, R¹-Ph2-Th1-C≡C-Ph2-CF₃, R¹-Ph2-Th1-C≡C-Ph3-CF₃,
R¹-Ph3-Th1-Ph1-CF₃, R¹-Ph3-Th1-Ph2-CF₃, R¹-Ph3-Th1-Ph3-CF₃,
R¹-Ph3-Th1-Np1-CF₃, R¹-Ph3-Th1-Np2-CF₃, R¹-Ph3-Th1-Np3-CF₃,
R¹-Ph3-Th1-Np4-CF₃,
R¹-Ph3-CH₂CH₂-Th1-Ph1-CF₃, R¹-Ph3-CH₂CH₂-Th1-Ph2-CF₃,
R¹-Ph3-CH₂CH₂-Th1-Ph3-CF₃, R¹-Ph3-CH₂CH₂-Th1-Np1-CF₃,
R¹-Ph3-CH₂CH₂-Th1-Np2-CF₃, R¹-Ph3-CH₂CH₂-Th1-Np3-CF₃,
R¹-Ph3-CH₂CH₂-Th1-Np4-CF₃, R¹-Ph3-Th1-CH₂CH₂-Ph1-CF₃,
R¹-Ph3-Th1-CH₂CH₂-Ph2-CF₃, R¹-Ph3-Th1-CH₂CH₂-Ph3-CF₃,
R¹-Ph3-Th1-CH₂CH₂-Np1-CF₃, R¹-Ph3-Th1-CH₂CH₂-Np2-CF₃,
R¹-Ph3-Th1-CH₂CH₂-Np3-CF₃, R¹-Ph3-Th1-CH₂CH₂-Np4-CF₃,
R¹-Ph3-C≡C-Th1-Ph1-CF₃, R¹-Ph3-C≡C-Th1-Ph2-CF₃, R¹-Ph3-C≡C-Th1-Ph3-CF₃,
R¹-Ph3-Th1-C≡C-Ph1-CF₃, R¹-Ph3-Th1-C≡C-Ph2-CF₃, R¹-Ph3-Th1-C≡C-Ph3-CF₃,
R¹-Np1-Th1-Ph1-CF₃, R¹-Np1-Th1-Ph2-CF₃, R¹-Np1-Th1-Ph3-CF₃,
R¹-Np1-CH₂CH₂-Th1-Ph1-CF₃, R¹-Np1-CH₂CH₂-Th1-Ph2-CF₃,
R¹-Np1-CH₂CH₂-Th1-Ph3-CF₃, R¹-Np1-Th1-CH₂CH₂-Ph1-CF₃,
R¹-Np1-Th1-CH₂CH₂-Ph2-CF₃, R¹-Np1-Th1-CH₂CH₂-Ph3-CF₃,
R¹-Np2-Th1-Ph1-CF₃, R¹-Np2-Th1-Ph2-CF₃, R¹-Np2-Th1-Ph3-CF₃,
R¹-Np2-CH₂CH₂-Th1-Ph1-CF₃, R¹-Np2-CH₂CH₂-Th1-Ph2-CF₃,
R¹-Np2-CH₂CH₂-Th1-Ph3-CF₃, R¹-Np2-Th1-CH₂CH₂-Ph1-CF₃,
R¹-Np2-Th1-CH₂CH₂-Ph2-CF₃, R¹-Np2-Th1-CH₂CH₂-Ph3-CF₃,
R¹-Np3-Th1-Ph1-CF₃, R¹-Np3-Th1-Ph2-CF₃, R¹-Np3-Th1-Ph3-CF₃,
R¹-Np3-CH₂CH₂-Th1-Ph1-CF₃, R¹-Np3-CH₂CH₂-Th1-Ph2-CF₃,
R¹-Np3-CH₂CH₂-Th1-Ph3-CF₃, R¹-Np3-Th1-CH₂CH₂-Ph1-CF₃,
R¹-Np3-Th1-CH₂CH₂-Ph2-CF₃, R¹-Np3-Th1-CH₂CH₂-Ph3-CF₃,
R¹-Np1-Th1-Ph1-CF₃, R¹-Np1-Th1-Ph2-CF₃, R¹-Np1-Th1-Ph3-CF₃,
R¹-Np4-CH₂CH₂-Th1-Ph1-CF₃, R¹-Np4-CH₂CH₂-Th1-Ph2-CF₃,
R¹-Np4-CH₂CH₂-Th1-Ph3-CF₃, R¹-Np4-Th1-CH₂CH₂-Ph1-CF₃,
R¹-Np4-Th1-CH₂CH₂-Ph2-CF₃, R¹-Np4-Th1-CH₂CH₂-Ph3-CF₃,
R¹-Cy-Th2-Ph1-CF₃, R¹-Cy-Th2-Ph2-CF₃, R¹-Cy-Th2-Ph3-CF₃, R¹-Cy-Th2-Np1-CF₃,
R¹-Cy-Th2-Np2-CF₃, R¹-Cy-Th2-Np3-CF₃, R¹-Cy-Th2-Np4-CF₃,
R¹-Cy-CH₂CH₂-Th2-Ph1-CF₃, R¹-Cy-CH₂CH₂-Th2-Ph2-CF₃, R¹-Cy-CH₂CH₂-Th2-Ph3-CF₃,
R¹-Cy-CH₂CH₂-Th2-Np1-CF₃, R¹-Cy-CH₂CH₂-Th2-Np2-CF₃,
R¹-Cy-CH₂CH₂-Th2-Np3-CF₃,
R¹-Cy-CH₂CH₂-Th2-Np4-CF₃, R¹-Cy-Th2-CH₂CH₂-Ph1-CF₃, R¹-Cy-Th2-CH₂CH₂-Ph2-CF₃,
R¹-Cy-Th2-CH₂CH₂-Ph3-CF₃, R¹-Cy-Th2-CH₂CH₂-Np1-CF₃, R¹-Cy-Th2-CH₂CH₂-Np2-CF₃,
R¹-Cy-Th2-CH₂CH₂-Np3-CF₃, R¹-Cy-Th2-CH₂CH₂-Np4-CF₃,
R¹-Cy-Th2-C≡C-Ph1-CF₃, R¹-Cy-Th2-C≡C-Ph2-CF₃, R¹-Cy-Th2-C≡C-Ph3-CF₃,
R¹-Ph1-Th2-Ph1-CF₃, R¹-Ph1-Th2-Ph2-CF₃, R¹-Ph1-Th2-Ph3-CF₃,
R¹-Ph1-Th2-Np1-CF₃, R¹-Ph1-Th2-Np2-CF₃, R¹-Ph1-Th2-Np3-CF₃,
R¹-Ph1-Th2-Np4-CF₃,
R¹-Ph1-CH₂CH₂-Th2-Ph1-CF₃, R¹-Ph1-CH₂CH₂-Th2-Ph2-CF₃,
R¹-Ph1-CH₂CH₂-Th2-Ph3-CF₃, R¹-Ph1-CH₂CH₂-Th2-Np1-CF₃,
R¹-Ph1-CH₂CH₂-Th2-Np2-CF₃, R¹-Ph1-CH₂CH₂-Th2-Np3-CF₃,
R¹-Ph1-CH₂CH₂-Th2-Np4-CF₃, R¹-Ph1-Th2-CH₂CH₂-Ph1-CF₃,
R¹-Ph1-Th2-CH₂CH₂-Ph2-CF₃, R¹-Ph1-Th2-CH₂CH₂-Ph3-CF₃,
R¹-Ph1-Th2-CH₂CH₂-Np1-CF₃, R¹-Ph1-Th2-CH₂CH₂-Np2-CF₃, R¹-Ph1-Th2-CH₂CH₂-Np3-CF₃, R¹-Ph1-Th2-CH₂CH₂-Np4-CF₃,
R¹-Ph1-C≡C-Th2-Ph1-CF₃, R¹-Ph1-C≡C-Th2-Ph2-CF₃, R¹-Ph1-C≡C-Th2-Ph3-CF₃,
R¹-Ph1-Th2-C≡C-Ph1-CF₃, R¹-Ph1-Th2-C≡C-Ph2-CF₃, R¹-Ph1-Th2-C≡C-Ph3-CF₃,
R¹-Ph2-Th2-Ph1-CF₃, R¹-Ph2-Th2-Ph2-CF₃, R¹-Ph2-Th2-Ph3-CF₃,
R¹-Ph2-Th2-Np1-CF₃, R¹-Ph2-Th2-Np2-CF₃, R¹-Ph2-Th2-Np3-CF₃,
R¹-Ph2-Th2-Np4-CF₃,
R¹-Ph2-CH₂CH₂-Th2-Ph1-CF₃, R¹-Ph2-CH₂CH₂-Th2-Ph2-CF₃,
R¹-Ph2-CH₂CH₂-Th2-Ph3-CF₃, R¹-Ph2-CH₂CH₂-Th2-Np1-CF₃,
R¹-Ph2-CH₂CH₂-Th2-Np2-CF₃, R¹-Ph2-CH₂CH₂-Th2-Np3-CF₃,
R¹-Ph2-CH₂CH₂-Th2-Np4-CF₃, R¹-Ph2-Th2-CH₂CH₂-Ph1-CF₃,
R¹-Ph2-Th2-CH₂CH₂-Ph2-CF₃, R¹-Ph2-Th2-CH₂CH₂-Ph3-CF₃,
R¹-Ph2-Th2-CH₂CH₂-Np1-CF₃, R¹-Ph2-Th2-CH₂CH₂-Np2-CF₃,
R¹-Ph2-Th2-CH₂CH₂-Np3-CF₃, R¹-Ph2-Th2-CH₂CH₂-Np4-CF₃,
R¹-Ph2-C≡C-Th2-Ph1-CF₃, R¹-Ph2-C≡C-Th2-Ph2-CF₃, R¹-Ph2-C≡C-Th2-Ph3-CF₃,
R¹-Ph2-Th2-C≡C-Ph1-CF₃, R¹-Ph2-Th2-C≡C-Ph2-CF₃, R¹-Ph2-Th2-C≡C-Ph3-CF₃,
R¹-Ph3-Th2-Ph1-CF₃, R¹-Ph3-Th2-Ph2-CF₃, R¹-Ph3-Th2-Ph3-CF₃,
R¹-Ph3-Th2-Np1-CF₃, R¹-Ph3-Th2-Np2-CF₃, R¹-Ph3-Th2-Np3-CF₃,
R¹-Ph3-Th2-Np4-CF₃,
R¹-Ph3-CH₂CH₂-Th2-Ph1-CF₃, R¹-Ph3-CH₂CH₂-Th2-Ph2-CF₃,
R¹-Ph3-CH₂CH₂-Th2-Ph3-CF₃, R¹-Ph3-CH₂CH₂-Th2-Np1-CF₃,
R¹-Ph3-CH₂CH₂-Th2-Np2-CF₃, R¹-Ph3-CH₂CH₂-Th2-Np3-CF₃,
R¹-Ph3-CH₂CH₂-Th2-Np4-CF₃, R¹-Ph3-Th2-CH₂CH₂-Ph1-CF₃,
R¹-Ph3-Th2-CH₂CH₂-Ph2-CF₃, R¹-Ph3-Th2-CH₂CH₂-Ph3-CF₃,
R¹-Ph3-Th2-CH₂CH₂-Np1-CF₃, R¹-Ph3-Th2-CH₂CH₂-Np2-CF₃,
R¹-Ph3-Th2-CH₂CH₂-Np3-CF₃, R¹-Ph3-Th2-CH₂CH₂-Np4-CF₃,
R¹-Ph3-C≡C-Th2-Ph1-CF₃, R¹-Ph3-C≡C-Th2-Ph2-CF₃, R¹-Ph3-C≡C-Th2-Ph3-CF₃,
R¹-Ph3-Th2-C≡C-Ph1-CF₃, R¹-Ph3-Th2-C≡C-Ph2-CF₃, R¹-Ph3-Th2-C≡C-Ph3-CF₃,
R¹-Np1-Th2-Ph1-CF₃, R¹-Np1-Th2-Ph2-CF₃, R¹-Np1-Th2-Ph3-CF₃,
R¹-Np1-CH₂CH₂-Th2-Ph1-CF₃, R¹-Np1-CH₂CH₂-Th2-Ph2-CF₃,
R¹-Np1-CH₂CH₂-Th2-Ph3-CF₃, R¹-Np1-Th2-CH₂CH₂-Ph1-CF₃,
R¹-Np1-Th2-CH₂CH₂-Ph2-CF₃, R¹-Np1-Th2-CH₂CH₂-Ph3-CF₃,
R¹-Np2-Th2-Ph1-CF₃, R¹-Np2-Th2-Ph2-CF₃, R¹-Np2-Th2-Ph3-CF₃,
R¹-Np2-CH₂CH₂-Th2-Ph1-CF₃, R¹-Np2-CH₂CH₂-Th2-Ph2-CF₃,
R¹-Np2-CH₂CH₂-Th2-Ph3-CF₃, R¹-Np2-Th2-CH₂CH₂-Ph1-CF₃,
R¹-Np2-Th2-CH₂CH₂-Ph2-CF₃, R¹-Np2-Th2-CH₂CH₂-Ph3-CF₃,
R¹-Np3-Th2-Ph1-CF₃, R¹-Np3-Th2-Ph2-CF₃, R¹-Np3-Th2-Ph3-CF₃,
R¹-Np3-CH₂CH₂-Th2-Ph1-CF₃, R¹-Np3-CH₂CH₂-Th2-Ph2-CF₃,
R¹-Np3-CH₂CH₂-Th2-Ph3-CF₃, R¹-Np3-Th2-CH₂CH₂-Ph1-CF₃,
R¹-Np3-Th2-CH₂CH₂-Ph2-CF₃, R¹-Np3-Th2-CH₂CH₂-Ph3-CF₃,
R¹-Np1-Th2-Ph1-CF₃, R¹-Np1-Th2-Ph2-CF₃, R¹-Np1-Th2-Ph3-CF₃,
R¹-Np4-CH₂CH₂-Th2-Ph1-CF₃, R¹-Np4-CH₂CH₂-Th2-Ph2-CF₃,
R¹-Np4-CH₂CH₂-Th2-Ph3-CF₃, R¹-Np4-Th2-CH₂CH₂-Ph1-CF₃,
R¹-Np4-Th2-CH₂CH₂-Ph2-CF₃, R¹-Np4-Th2-CH₂CH₂-Ph3-CF₃,
R¹-Cy-Th3-Ph1-CF₃, R¹-Cy-Th3-Ph2-CF₃, R¹-Cy-Th3-Ph3-CF₃, R¹-Cy-Th3-Np1-CF₃,
R¹-Cy-Th3-Np2-CF₃, R¹-Cy-Th3-Np3-CF₃, R¹-Cy-Th3-Np4-CF₃,
R¹-Cy-CH₂CH₂-Th3-Ph1-CF₃, R¹-Cy-CH₂CH₂-Th3-Ph1-CF₃, R¹-Cy-CH₂CH₂-Th3-Ph3-CF₃,
R¹-Cy-CH₂CH₂-Th3-Np1-CF₃, R¹-Cy-CH₂CH₂-Th3-Np2-CF₃,
R¹-Cy-CH₂CH₂-Th3-Np3-CF₃,
R¹-Cy-CH₂CH₂-Th3-Np4-CF₃, R¹-Cy-Th3-CH₂CH₂-Ph1-CF₃, R¹-Cy-Th3-CH₂CH₂-Ph2-CF₃,
R¹-Cy-Th3-CH₂CH₂-Ph3-CF₃, R¹-Cy-Th3-CH₂CH₂-Np1-CF₃, R¹-Cy-Th3-CH₂CH₂-Np2-CF₃,
R¹-Cy-Th3-CH₂CH₂-Np3-CF₃, R¹-Cy-Th3-CH₂CH₂-Np4-CF₃,
R¹-Cy-Th3-C≡C-Ph1-CF₃, R¹-Cy-Th3-C≡C-Ph2-CF₃, R¹-Cy-Th3-C≡C-Ph3-CF₃,
R¹-Ph1-Th3-Ph1-CF₃, R¹-Ph1-Th3-Ph2-CF₃, R¹-Ph1-Th3-Ph3-CF₃,
R¹-Ph1-Th3-Np1-CF₃, R¹-Ph1-Th3-Np2-CF₃, R¹-Ph1-Th3-Np3-CF₃,
R¹-Ph1-Th3-Np4-CF₃,
R¹-Ph1-CH₂CH₂-Th3-Ph1-CF₃, R¹-Ph1-CH₂CH₂-Th3-Ph2-CF₃,
R¹-Ph1-CH₂CH₂-Th3-Ph3-CF₃, R¹-Ph1-CH₂CH₂-Th3-Np1-CF₃,
R¹-Ph1-CH₂CH₂-Th3-Np2-CF₃, R¹-Ph1-CH₂CH₂-Th3-Np3-CF₃,
R¹-Ph1-CH₂CH₂-Th3-Np4-CF₃, R¹-Ph1-Th3-CH₂CH₂-Ph1-CF₃,
R¹-Ph1-Th3-CH₂CH₂-Ph2-CF₃, R¹-Ph1-Th3-CH₂CH₂-Ph3-CF₃,
R¹-Ph1-Th3-CH₂CH₂-Np1-CF₃, R¹-Ph1-Th3-CH₂CH₂-Np2-CF₃,
R¹-Ph1-Th3-CH₂CH₂-Np3-CF₃, R¹-Ph1-Th3-CH₂CH₂-Np4-CF₃,
R¹-Ph1-C≡C-Th3-Ph1-CF₃, R¹-Ph1-C≡C-Th3-Ph2-CF₃, R¹-Ph1-C≡C-Th3-Ph3-CF₃,
R¹-Ph1-Th3-C≡C-Ph1-CF₃, R¹-Ph1-Th3-C≡C-Ph2-CF₃, R¹-Ph1-Th3-C≡C-Ph3-CF₃,
R¹-Ph2-Th3-Ph1-CF₃, R¹-Ph2-Th3-Ph2-CF₃, R¹-Ph2-Th3-Ph3-CF₃,
R¹-Ph2-Th3-Np1-CF₃, R¹-Ph2-Th3-Np2-CF₃, R¹-Ph2-Th3-Np3-CF₃,
R¹-Ph2-Th3-Np4-CF₃,
R¹-Ph2-CH₂CH₂-Th3-Ph1-CF₃, R¹-Ph2-CH₂CH₂-Th3-Ph2-CF₃,
R¹-Ph2-CH₂CH₂-Th3-Ph3-CF₃, R¹-Ph2-CH₂CH₂-Th3-Np1-CF₃,
R¹-Ph2-CH₂CH₂-Th3-Np2-CF₃, R¹-Ph2-CH₂CH₂-Th3-Np3-CF₃, R¹-Ph2-CH₂CH₂-Th3-Np4-CF₃, R¹-Ph2-Th3-CH₂CH₂-Ph1-CF₃,
R¹-Ph2-Th3-CH₂CH₂-Ph2-CF₃, R¹-Ph2-Th3-CH₂CH₂-Ph3-CF₃,
R¹-Ph2-Th3-CH₂CH₂-Np1-CF₃, R¹-Ph2-Th3-CH₂CH₂-Np2-CF₃,
R¹-Ph2-Th3-CH₂CH₂-Np3-CF₃, R¹-Ph2-Th3-CH₂CH₂-Np4-CF₃,
R¹-Ph2-C≡C-Th3-Ph1-CF₃, R¹-Ph2-C≡C-Th3-Ph2-CF₃, R¹-Ph2-C≡C-Th3-Ph3-CF₃,
R¹-Ph2-Th3-C≡C-Ph1-CF₃, R¹-Ph2-Th3-C≡C-Ph2-CF₃, R¹-Ph2-Th3-C≡C-Ph3-CF₃,
R¹-Ph3-Th3-Ph1-CF₃, R¹-Ph3-Th3-Ph2-CF₃, R¹-Ph3-Th3-Ph3-CF₃,
R¹-Ph3-Th3-Np1-CF₃, R¹-Ph3-Th3-Np2-CF₃, R¹-Ph3-Th3-Np3-CF₃,
R¹-Ph3-Th3-Np4-CF₃,
R¹-Ph3-CH₂CH₂-Th3-Ph1-CF₃, R¹-Ph-CH₂CH₂-Th3-Ph2-CF₃,
R¹-Ph3-CH₂CH₂-Th3-Ph3-CF₃, R¹-Ph3-CH₂CH₂-Th3-Np1-CF₃,
R¹-Ph3-CH₂CH₂-Th3-Np2-CF₃, R¹-Ph3-CH₂CH₂-Th3-Np3-CF₃,
R¹-Ph3-CH₂CH₂-Th3-Np4-CF₃, R¹-Ph3-Th3-CH₂CH₂-Ph1-CF₃,
R¹-Ph3-Th3-CH₂CH₂-Ph2-CF₃, R¹-Ph3-Th3-CH₂CH₂-Ph3-CF₃,
R¹-Ph3-Th3-CH₂CH₂-Np1-CF₃, R¹-Ph3-Th3-CH₂CH₂-Np2-CF₃,
R¹-Ph3-Th3-CH₂CH₂-Np3-CF₃, R¹-Ph3-Th3-CH₂CH₂-Np4-CF₃,
R¹-Ph3-C≡C-Th3-Ph1-CF₃, R¹-Ph3-C≡C-Th3-Ph2-CF₃, R¹-Ph3-C≡C-Th3-Ph3-CF₃,
R¹-Ph3-Th3-C≡C-Ph1-CF₃, R¹-Ph3-Th3-C≡C-Ph2-CF₃, R¹-Ph3-Th3-C≡C-Ph3-CF₃,
R¹-Np1-Th3-Ph1-CF₃, R¹-Np1-Th3-Ph2-CF₃, R¹-Np1-Th3-Ph3-CF₃,
R¹-Np1-CH₂CH₂-Th3-Ph1-CF₃, R¹-Np1-CH₂CH₂-Th3-Ph2-CF₃,
R¹-Np1-CH₂CH₂-Th3-Ph3-CF₃, R¹-Np1-Th3-CH₂CH₂-Ph1-CF₃,
R¹-Np1-Th3-CH₂CH₂-Ph1-CF₃, R¹-Np1-Th3-CH₂CH₂-Ph3-CF₃,
R¹-Np2-Th3-Ph1-CF₃, R¹-Np2-Th3-Ph2-CF₃, R¹-Np2-Th3-Ph3-CF₃,
R¹-Np2-CH₂CH₂-Th3-Ph1-CF₃, R¹-Np2-CH₂CH₂-Th3-Ph2-CF₃,
R¹-Np2-CH₂CH₂-Th3-Ph3-CF₃, R¹-Np2-Th3-CH₂CH₂-Ph1-CF₃,
R¹-Np2-Th3-CH₂CH₂-Ph2-CF₃, R¹-Np2-Th3-CH₂CH₂-Ph3-CF₃,
R¹-Np3-Th3-Ph1-CF₃, R¹-Np3-Th3-Ph2-CF₃, R¹-Np3-Th3-Ph3-CF₃,
R¹-Np3-CH₂CH₂-Th3-Ph1-CF₃, R¹-Np3-CH₂CH₂-Th3-Ph2-CF₃,
R¹-Np3-CH₂CH₂-Th3-Ph3-CF₃, R¹-Np3-Th3-CH₂CH₂-Ph1-CF₃,
R¹-Np3-Th3-CH₂CH₂-Ph2-CF₃, R¹-Np3-Th3-CH₂CH₂-Ph3-CF₃,
R¹-Np1-Th3-Ph1-CF₃, R¹-Np1-Th3-Ph2-CF₃, R¹-Np1-Th3-Ph3-CF₃,
R¹-Np4-CH₂CH₂-Th3-Ph1-CF₃, R¹-Np4-CH₂CH₂-Th3-Ph2-CF₃,
R¹-Np4-CH₂CH₂-Th3-Ph3-CF₃, R¹-Np4-Th3-CH₂CH₂-Ph1-CF₃,
R¹-Np4-Th3-CH₂CH₂-Ph2-CF₃, R¹-Np4-Th3-CH₂CH₂-Ph3-CF₃, R¹-Cy-Th3-Ph1-CF₃, R¹-Cy-Th3-Ph2-CF₃, R¹-Cy-Th3-Ph3-CF₃, R¹-Cy-Th3-Np1-CF₃,
R¹-Cy-Th3-Np2-CF₃, R¹-Cy-Th3-Np3-CF₃, R¹-Cy-Th3-Np4-CF₃,
R¹-Cy-CH₂CH₂-Th3-Ph1-CF₃, R¹-Cy-CH₂CH₂-Th3-Ph2-CF₃, R¹-Cy-CH₂CH₂-Th3-Ph3-CF₃,
R¹-Cy-CH₂CH₂-Th3-Np1-CF₃, R¹-Cy-CH₂CH₂-Th3-Np2-CF₃,
R¹-Cy-CH₂CH₂-Th3-Np3-CF₃,
R¹-Cy-CH₂CH₂-Th3-Np4-CF₃, R¹-Cy-Th3-CH₂CH₂-Ph1-CF₃, R¹-Cy-Th3-CH₂CH₂-Ph2-CF₃,
R¹-Cy-Th3-CH₂CH₂-Ph3-CF₃, R¹-Cy-Th3-CH₂CH₂-Np1-CF₃, R¹-Cy-Th3-CH₂CH₂-Np2-CF₃,
R¹-Cy-Th3-CH₂CH₂-Np3-CF₃, R¹-Cy-Th3-CH₂CH₂-Np4-CF₃,
R¹-Cy-Th3-C≡C-Ph1-CF₃, R¹-Cy-Th3-C≡C-Ph2-CF₃, R¹-Cy-Th3-C≡C-Ph3-CF₃,
R¹-Ph1-Th3-Ph1-CF₃, R¹-Ph1-Th3-Ph2-CF₃, R¹-Ph1-Th3-Ph3-CF₃,
R¹-Ph1-Th3-Np1-CF₃, R¹-Ph1-Th3-Np2-CF₃, R¹-Ph1-Th3-Np3-CF₃,
R¹-Ph1-Th3-Np4-CF₃,
R¹-Ph1-CH₂CH₂-Th3-Ph1-CF₃, R¹-Ph1-CH₂CH₂-Th3-Ph1-CF₃,
R¹-Ph1-CH₂CH₂-Th3-Ph3-CF₃, R¹-Ph1-CH₂CH₂-Th3-Np1-CF₃,
R¹-Ph1-CH₂CH₂-Th3-Np2-CF₃, R¹-Ph1-CH₂CH₂-Th3-Np3-CF₃,
R¹-Ph1-CH₂CH₂-Th3-Np4-CF₃, R¹-Ph1-Th3-CH₂CH₂-Ph1-CF₃,
R¹-Ph1-Th3-CH₂CH₂-Ph2-CF₃, R¹-Ph1-Th3-CH₂CH₂-Ph3-CF₃,
R¹-Ph1-Th3-CH₂CH₂-Np1-CF₃, R¹-Ph1-Th3-CH₂CH₂-Np2-CF₃,
R¹-Ph1-Th3-CH₂CH₂-Np3-CF₃, R¹-Ph1-Th3-CH₂CH₂-Np4-CF₃,
R¹-Ph1-C≡C-Th3-Ph1-CF₃, R¹-Ph1-C≡C-Th3-Ph2-CF₃, R¹-Ph1-C≡C-Th3-Ph3-CF₃,
R¹-Ph1-Th3-C≡C-Ph1-CF₃, R¹-Ph1-Th3-C≡C-Ph2-CF₃, R¹-Ph1-Th3-C≡C-Ph3-CF₃,
R¹-Ph2-Th3-Ph1-CF₃, R¹-Ph2-Th3-Ph2-CF₃, R¹-Ph2-Th3-Ph3-CF₃,
R¹-Ph2-Th3-Np1-CF₃, R¹-Ph2-Th3-Np2-CF₃, R¹-Ph2-Th3-Np3-CF₃,
R¹-Ph2-Th3-Np4-CF₃,
R¹-Ph2-CH₂CH₂-Th3-Ph1-CF₃, R¹-Ph2-CH₂CH₂-Th3-Ph2-CF₃,
R¹-Ph2-CH₂CH₂-Th3-Ph3-CF₃, R¹-Ph2-CH₂CH₂-Th3-Np1-CF₃,
R¹-Ph2-CH₂CH₂-Th3-Np2-CF₃, R¹-Ph2-CH₂CH₂-Th3-Np3-CF₃,
R¹-Ph2-CH₂CH₂-Th3-Np4-CF₃, R¹-Ph2-Th3-CH₂CH₂-Ph1-CF₃,
R¹-Ph2-Th3-CH₂CH₂-Ph2-CF₃, R¹-Ph2-Th3-CH₂CH₂-Ph3-CF₃,
R¹-Ph2-Th3-CH₂CH₂-Np1-CF₃, R¹-Ph2-Th3-CH₂CH₂-Np2-CF₃,
R¹-Ph2-Th3-CH₂CH₂-Np3-CF₃, R¹-Ph2-Th3-CH₂CH₂-Np4-CF₃,
R¹-Ph2-C≡C-Th3-Ph1-CF₃, R¹-Ph2-C≡C-Th3-Ph2-CF₃, R¹-Ph2-C≡C-Th3-Ph3-CF₃,
R¹-Ph2-Th3-C≡C-Ph1-CF₃, R¹-Ph2-Th3-C≡C-Ph2-CF₃, R¹-Ph2-Th3-C≡C-Ph3-CF₃,
R¹-Ph3-Th3-Ph1-CF₃, R¹-Ph3-Th3-Ph2-CF₃, R¹-Ph3-Th3-Ph3-CF₃,
R¹-Ph3-Th3-Np1-CF₃, R¹-Ph3-Th3-Np2-CF₃, R¹-Ph3-Th3-Np3-CF₃, R$^1$-Ph3-Th3-Np4-CF$_3$,
R$^1$-Ph3-CH$_2$CH$_2$-Th3-Ph1-CF$_3$, R$^1$-Ph3-CH$_2$CH$_2$-Th3-Ph2-CF$_3$,
R$^1$-Ph3-CH$_2$CH$_2$-Th3-Ph3-CF$_3$, R$^1$-Ph3-CH$_2$CH$_2$-Th3-Np1-CF$_3$,
R$^1$-Ph3-CH$_2$CH$_2$-Th3-Np2-CF$_3$, R$^1$-Ph3-CH$_2$CH$_2$-Th3-Np3-CF$_3$,
R$^1$-Ph3-CH$_2$CH$_2$-Th3-Np4-CF$_3$, R$^1$-Ph3-Th3-CH$_2$CH$_2$-Ph1-CF$_3$,
R$^1$-Ph3-Th3-CH$_2$CH$_2$-Ph2-CF$_3$, R$^1$-Ph3-Th3-CH$_2$CH$_2$-Ph3-CF$_3$,
R$^1$-Ph3-Th3-CH$_2$CH$_2$-Np1-CF$_3$, R$^1$-Ph3-Th3-CH$_2$CH$_2$-Np2-CF$_3$,
R$^1$-Ph3-Th3-CH$_2$CH$_2$-Np3-CF$_3$, R$^1$-Ph3-Th3-CH$_2$CH$_2$-Np4-CF$_3$,
R$^1$-Ph3-C≡C-Th3-Ph1-CF$_3$, R$^1$-Ph3-C≡C-Th3-Ph2-CF$_3$, R$^1$-Ph3-C≡C-Th3-Ph3-CF$_3$,
R$^1$-Ph3-Th3-C≡C-Ph1-CF$_3$, R$^1$-Ph3-Th3-C≡C-Ph2-CF$_3$, R$^1$-Ph3-Th3-C≡C-Ph3-CF$_3$,
R$^1$-Np1-Th3-Ph1-CF$_3$, R$^1$-Np1-Th3-Ph2-CF$_3$, R$^1$-Np1-Th3-Ph3-CF$_3$,
R$^1$-Np1-CH$_2$CH$_2$-Th3-Ph1-CF$_3$, R$^1$-Np1-CH$_2$CH$_2$-Th3-Ph2-CF$_3$,
R$^1$-Np1-CH$_2$CH$_2$-Th3-Ph3-CF$_3$, R$^1$-Np1-Th3-CH$_2$CH$_2$-Ph1-CF$_3$,
R$^1$-Np1-Th3-CH$_2$CH$_2$-Ph2-CF$_3$, R$^1$-Np1-Th3-CH$_2$CH$_2$-Ph3-CF$_3$,
R$^1$-Np2-Th3-Ph1-CF$_3$, R$^1$-Np2-Th3-Ph2-CF$_3$, R$^1$-Np2-Th3-Ph3-CF$_3$,
R$^1$-Np2-CH$_2$CH$_2$-Th3-Ph1-CF$_3$, R$^1$-Np2-CH$_2$CH$_2$-Th3-Ph2-CF$_3$,
R$^1$-Np2-CH$_2$CH$_2$-Th3-Ph3-CF$_3$, R$^1$-Np2-Th3-CH$_2$CH$_2$-Ph1-CF$_3$,
R$^1$-Np2-Th3-CH$_2$CH$_2$-Ph2-CF$_3$, R$^1$-Np2-Th3-CH$_2$CH$_2$-Ph3-CF$_3$,
R$^1$-Np3-Th3-Ph1-CF$_3$, R$^1$-Np3-Th3-Ph2-CF$_3$, R$^1$-Np3-Th3-Ph3-CF$_3$,
R$^1$-Np3-CH$_2$CH$_2$-Th3-Ph1-CF$_3$, R$^1$-Np3-CH$_2$CH$_2$-Th3-Ph2-CF$_3$,
R$^1$-Np3-CH$_2$CH$_2$-Th3-Ph3-CF$_3$, R$^1$-Np3-Th3-CH$_2$CH$_2$-Ph1-CF$_3$,
R$^1$-Np3-Th3-CH$_2$CH$_2$-Ph2-CF$_3$, R$^1$-Np3-Th3-CH$_2$CH$_2$-Ph3-CF$_3$,
R$^1$-Np1-Th3-Ph1-CF$_3$, R$^1$-Np1-Th3-Ph2-CF$_3$, R$^1$-Np1-Th3-Ph3-CF$_3$,
R$^1$-Np4-CH$_2$CH$_2$-Th3-Ph1-CF$_3$, R$^1$-Np4-CH$_2$CH$_2$-Th3-Ph2-CF$_3$,
R$^1$-Np4-CH$_2$CH$_2$-Th3-Ph3-CF$_3$, R$^1$-Np4-Th3-CH$_2$CH$_2$-Ph1-CF$_3$,
R$^1$-Np4-Th3-CH$_2$CH$_2$-Ph2-CF$_3$, R$^1$-Np4-Th3-CH$_2$CH$_2$-Ph3-CF$_3$, In the case in which ring C is the formula (IIb),
then in the case in which $n^a=n^b=0$, and $n^c=1$, $n^d=0$ or $n^c=0$, $n^d=1$, and Z is a fluorine atom,
R$^1$-Te1-Ph1-F, R$^1$-Te1-Ph2-F, R$^1$-Te1-Ph3-F, R$^1$-Te1-Np1-F, R$^1$-Te1-Np2-F,
R$^1$-Te1-Np3-F, R$^1$-Te1-Np4-F, R$^1$-Te2-Ph1-F, R$^1$-Te2-Ph2-F, R$^1$-Te2-Ph3-F,
R$^1$-Te2-Np1-F, R$^1$-Te2-Np2-F, R$^1$-Te2-Np3-F, R$^1$-Te2-Np4-F,
R$^1$-Te1-CH$_2$CH$_2$-Ph2-F, R$^1$-Te1-CH$_2$CH$_2$-Ph3-F, R$^1$-Te1-CH$_2$CH$_2$-Np1-F,
R$^1$-Te1-CH$_2$CH$_2$-Np2-F, R$^1$-Te1-CH$_2$CH$_2$-Np3-F, R$^1$-Te1-CH$_2$CH$_2$-Np4-F,
R$^1$-Te2-CH$_2$CH$_2$-Ph1-F, R$^1$-Te2-CH$_2$CH$_2$-Ph2-F, R$^1$-Te2-CH$_2$CH$_2$-Ph3-F,
R$^1$-Te2-CH$_2$CH$_2$-Np1-F, R$^1$-Te2-CH$_2$CH$_2$-Np2-F, R$^1$-Te2-CH$_2$CH$_2$-Np3-F,
R$^1$-Te2-CH$_2$CH$_2$-Np4-F, in the case in which $n^a=n^b=0$, and $n^c=1$, $n^d=0$ or $n^c=0$, $n^d=1$, and Z is a cyano group,
R$^1$-Te1-Ph2-CN, R$^1$-Te1-Ph3-CN, R$^1$-Te1-Np1-CN, R$^1$-Te1-Np2-CN, R$^1$-Te1-Np3-CN,
R$^1$-Te1-Np4-CN, R$^1$-Te2-Ph1-CN, R$^1$-Te2-Ph2-CN, R$^1$-Te2-Ph3-CN, R$^1$-Te2-Np1-CN,
R$^1$-Te2-Np2-CN, R$^1$-Te2-Np3-CN, R$^1$-Te2-Np4-CN,
R$^1$-Te1-CH$_2$CH$_2$-Ph2-CN, R$^1$-Te1-CH$_2$CH$_2$-Ph3-CN, R$^1$-Te1-CH$_2$CH$_2$-Np1-CN,
R$^1$-Te1-CH$_2$CH$_2$-Np2-CN, R$^1$-Te1-CH$_2$CH$_2$-Np3-CN, R$^1$-Te1-CH$_2$CH$_2$-Np4-CN,
R$^1$-Te2-CH$_2$CH$_2$-Ph1-CN, R$^1$-Te2-CH$_2$CH$_2$-Ph2-CN, R$^1$-Te2-CH$_2$CH$_2$-Ph3-CN,
R$^1$-Te2-CH$_2$CH$_2$-Np1-CN, R$^1$-Te2-CH$_2$CH$_2$-Np2-CN, R$^1$-Te2-CH$_2$CH$_2$-Np3-CN,
R$^1$-Te2-CH$_2$CH$_2$-Np4-CN, in the case in which $n^a=n^b=0$, and $n^c=1$, $n^d=0$ or $n^c=0$, $n^d=1$, and Z is a trifluoromethoxy group,
R$^1$-Te1-Ph1-OCF$_3$, R$^1$-Te1-Ph2-OCF$_3$, R$^1$-Te1-Ph3-OCF$_3$, R$^1$-Te1-Np1-OCF$_3$,
R$^1$-Te1-Np2-OCF$_3$, R$^1$-Te1-Np3-OCF$_3$, R$^1$-Te1-Np4-OCF$_3$, R$^1$-Te2-Ph1-OCF$_3$,
R$^1$-Te2-Ph2-OCF$_3$, R$^1$-Te2-Ph3-OCF$_3$, R$^1$-Te2-Np1-OCF$_3$, R$^1$-Te2-Np2-OCF$_3$,
R$^1$-Te2-Np3-OCF$_3$, R$^1$-Te2-Np4-OCF$_3$,
R$^1$-Te1-CH$_2$CH$_2$-Ph2-OCF$_3$, R$^1$-Te1-CH$_2$CH$_2$-Ph3-OCF$_3$, R$^1$-Te1-CH$_2$CH$_2$-Np1-OCF$_3$,
R$^1$-Te1-CH$_2$CH$_2$-Np2-OCF$_3$, R$^1$-Te1-CH$_2$CH$_2$-Np3-OCF$_3$, R$^1$-Te1-CH$_2$CH$_2$-Np4-OCF$_3$,
R$^1$-Te2-CH$_2$CH$_2$-Ph1-OCF$_3$, R$^1$-Te2-CH$_2$CH$_2$-Ph2-OCF$_3$, R$^1$-Te2-CH$_2$CH$_2$-Ph3-OCF$_3$,
R$^1$-Te2-CH$_2$CH$_2$-Np1-OCF$_3$, R$^1$-Te2-CH$_2$CH$_2$-Np2-OCF$_3$, R$^1$-Te2-CH$_2$CH$_2$-Np3-OCF$_3$,
R$^1$-Te2-CH$_2$CH$_2$-Np4-OCF$_3$, in the case in which $n^a=1$, $n^b=0$ or $n^a=0$, $n^b=1$, and $n^c=1$, $n^d=0$ or $n^c=0$, $n^d=1$, and Z is a fluorine atom,
R$^1$-Cy-Te1-Ph1-F, R$^1$-Cy-Te1-Ph2-F, R$^1$-Cy-Te1-Ph3-F, R$^1$-Cy-Te1-Np1-F,
R$^1$-Cy-Te1-Np2-F, R$^1$-Cy-Te1-Np3-F, R$^1$-Cy-Te1-Np4-F, R$^1$-Cy-Te2-Ph1-F,
R$^1$-Cy-Te2-Ph2-F, R$^1$-Cy-Te2-Ph3-F, R$^1$-Cy-Te2-Np1-F, R$^1$-Cy-Te2-Np2-F,
R$^1$-Cy-Te2-Np3-F, R$^1$-Cy-Te2-Np4-F,
R$^1$-Cy-Te1-CH$_2$CH$_2$-Ph2-F, R$^1$-Cy-Te1-CH$_2$CH$_2$-Ph3-F, R$^1$-Cy-Te1-CH$_2$CH$_2$-Np1-F,
R$^1$-Cy-Te1-CH$_2$CH$_2$-Np2-F, R$^1$-Cy-Te1-CH$_2$CH$_2$-Np3-F, R$^1$-Cy-Te1-CH$_2$CH$_2$-Np4-F,
R$^1$-Cy-Te2-CH$_2$CH$_2$-Ph1-F, R$^1$-Cy-Te2-CH$_2$CH$_2$-Ph2-F, R$^1$-Cy-Te2-CH$_2$CH$_2$-Ph3-F,
R$^1$-Cy-Te2-CH$_2$CH$_2$-Np1-F, R$^1$-Cy-Te2-CH$_2$CH$_2$-Np2-F, R$^1$-Cy-Te2-CH$_2$CH$_2$-Np3-F,
R$^1$-Cy-Te2-CH$_2$CH$_2$-Np4-F,
R$^1$-Ph1-Te1-Ph1-F, R$^1$-Ph1-Te1-Ph2-F, R$^1$-Ph1-Te1-Ph3-F, R$^1$-Ph1-Te1-Np1-F,
R$^1$-Ph1-Te1-Np2-F, R$^1$-Ph1-Te1-Np3-F, R$^1$-Ph1-Te1-Np4-F, R$^1$-Ph1-Te2-Ph1-F,
R$^1$-Ph1-Te2-Ph2-F, R$^1$-Ph1-Te2-Ph3-F, R$^1$-Ph1-Te2-Np1-F, R$^1$-Ph1-Te2-Np2-F,
R$^1$-Ph1-Te2-Np3-F, R$^1$-Ph1-Te2-Np4-F,
R$^1$-Ph1-Te1-CH$_2$CH$_2$-Ph2-F, R$^1$-Ph1-Te1-CH$_2$CH$_2$-Ph3-F, R$^1$-Ph1-Te1-CH$_2$CH$_2$-Np1-F,
R$^1$-Ph1-Te1-CH$_2$CH$_2$-Np2-F, R$^1$-Ph1-Te1-CH$_2$CH$_2$-Np3-F, R$^1$-Ph1-Te1-CH$_2$CH$_2$-Np4-F,
R$^1$-Ph1-Te2-CH$_2$CH$_2$-Ph1-F, R$^1$-Ph1-Te2-CH$_2$CH$_2$-Ph2-F, R$^1$-Ph1-Te2-CH$_2$CH$_2$-Ph3-F,
R$^1$-Ph1-Te2-CH$_2$CH$_2$-Np1-F, R$^1$-Ph1-Te2-CH$_2$CH$_2$-Np2-F, R$^1$-Ph1-Te2-CH$_2$CH$_2$-Np3-F, R$^1$-Ph1-Te2-CH$_2$CH$_2$-Np4-F,
R$^1$-Ph2-Te1-Ph1-F, R$^1$-Ph2-Te1-Ph2-F, R$^1$-Ph2-Te1-Ph3-F, R$^1$-Ph2-Te1-Np1-F,
R$^1$-Ph2-Te1-Np2-F, R$^1$-Ph2-Te1-Np3-F, R$^1$-Ph2-Te1-Np4-F, R$^1$-Ph2-Te2-Ph1-F,
R$^1$-Ph2-Te2-Ph2-F, R$^1$-Ph2-Te2-Ph3-F, R$^1$-Ph2-Te2-Np1-F, R$^1$-Ph2-Te2-Np2-F,
R$^1$-Ph2-Te2-Np3-F, R$^1$-Ph2-Te2-Np4-F,
R$^1$-Ph2-Te1-CH$_2$CH$_2$-Ph2-F, R$^1$-Ph2-Te1-CH$_2$CH$_2$-Ph3-F, R$^1$-Ph2-Te1-CH$_2$CH$_2$-Np1-F,
R$^1$-Ph2-Te1-CH$_2$CH$_2$-Np2-F, R$^1$-Ph2-Te1-CH$_2$CH$_2$-Np3-F, R$^1$-Ph2-Te1-CH$_2$CH$_2$-Np4-F,
R$^1$-Ph2-Te2-CH$_2$CH$_2$-Ph1-F, R$^1$-Ph2-Te2-CH$_2$CH$_2$-Ph2-F, R$^1$-Ph2-Te2-CH$_2$CH$_2$-Ph3-F,
R$^1$-Ph2-Te2-CH$_2$CH$_2$-Np1-F, R$^1$-Ph2-Te2-CH$_2$CH$_2$-Np2-F, R$^1$-Ph2-Te2-CH$_2$CH$_2$-Np3-F,
R$^1$-Ph2-Te2-CH$_2$CH$_2$-Np4-F,
R$^1$-Ph3-Te1-Ph1-F, R$^1$-Ph3-Te1-Ph2-F, R$^1$-Ph3-Te1-Ph3-F, R$^1$-Ph3-Te1-Np1-F,
R$^1$-Ph3-Te1-Np2-F, R$^1$-Ph3-Te1-Np3-F, R$^1$-Ph3-Te1-Np4-F, R$^1$-Ph3-Te2-Ph1-F,
R$^1$-Ph3-Te2-Ph2-F, R$^1$-Ph3-Te2-Ph3-F, R$^1$-Ph3-Te2-Np1-F, R$^1$-Ph3-Te2-Np2-F,
R$^1$-Ph3-Te2-Np3-F, R$^1$-Ph3-Te2-Np4-F,
R$^1$-Ph3-Te1-CH$_2$CH$_2$-Ph2-F, R$^1$-Ph3-Te1-CH$_2$CH$_2$-Ph3-F, R$^1$-Ph3-Te1-CH$_2$CH$_2$-Np1-F,
R$^1$-Ph3-Te1-CH$_2$CH$_2$-Np2-F, R$^1$-Ph3-Te1-CH$_2$CH$_2$-Np3-F, R$^1$-Ph3-Te1-CH$_2$CH$_2$-Np4-F,
R$^1$-Ph3-Te2-CH$_2$CH$_2$-Ph1-F, R$^1$-Ph3-Te2-CH$_2$CH$_2$-Ph2-F, R$^1$-Ph3-Te2-CH$_2$CH$_2$-Ph3-F,
R$^1$-Ph3-Te2-CH$_2$CH$_2$-Np1-F, R$^1$-Ph3-Te2-CH$_2$CH$_2$-Np2-F, R$^1$-Ph3-Te2-CH$_2$CH$_2$-Np3-F,
R$^1$-Ph3-Te2-CH$_2$CH$_2$-Np4-F,
R$^1$-Np1-Te1-Ph1-F, R$^1$-Np1-Te1-Ph2-F, R$^1$-Np1-Te1-Ph3-F, R$^1$-Np1-Te2-Ph1-F,
R$^1$-Np1-Te2-Ph2-F, R$^1$-Np1-Te2-Ph3-F,
R$^1$-Np1-Te1-CH$_2$CH$_2$-Ph2-F, R$^1$-Np1-Te1-CH$_2$CH$_2$-Ph3-F, R$^1$-Np1-Te2-CH$_2$CH$_2$-Ph1-F,
R$^1$-Np1-Te2-CH$_2$CH$_2$-Ph2-F, R$^1$-Np1-Te2-CH$_2$CH$_2$-Ph3-F,
R$^1$-Np2-Te1-Ph1-F, R$^1$-Np2-Te1-Ph2-F, R$^1$-Np2-Te1-Ph3-F, R$^1$-Np2-Te2-Ph1-F,
R$^1$-Np2-Te2-Ph2-F, R$^1$-Np2-Te2-Ph3-F,
R$^1$-Np2-Te1-CH$_2$CH$_2$-Ph2-F, R$^1$-Np2-Te1-CH$_2$CH$_2$-Ph3-F, R$^1$-Np2-Te2-CH$_2$CH$_2$-Ph1-F,
R$^1$-Np2-Te2-CH$_2$CH$_2$-Ph2-F, R$^1$-Np2-Te2-CH$_2$CH$_2$-Ph3-F,
R$^1$-Np3-Te1-Ph1-F, R$^1$-Np3-Te1-Ph2-F, R$^1$-Np3-Te1-Ph3-F, R$^1$-Np3-Te2-Ph1-F,
R$^1$-Np3-Te2-Ph2-F, R$^1$-Np3-Te2-Ph3-F,
R$^1$-Np3-Te1-CH$_2$CH$_2$-Ph2-F, R$^1$-Np3-Te1-CH$_2$CH$_2$-Ph3-F, R$^1$-Np3-Te2-CH$_2$CH$_2$-Ph1-F,
R$^1$-Np3-Te2-CH$_2$CH$_2$-Ph2-F, R$^1$-Np3-Te2-CH$_2$CH$_2$-Ph3-F,
R$^1$-Np4-Te1-Ph1-F, R$^1$-Np4-Te1-Ph2-F, R$^1$-Np4-Te1-Ph3-F, R$^1$-Np4-Te2-Ph1-F,
R$^1$-Np4-Te2-Ph2-F, R$^1$-Np4-Te2-Ph3-F,
R$^1$-Np4-Te1-CH$_2$CH$_2$-Ph2-F, R$^1$-Np4-Te1-CH$_2$CH$_2$-Ph3-F, R$^1$-Np4-Te2-CH$_2$CH$_2$-Ph1-F,
R$^1$-Np4-Te2-CH$_2$CH$_2$-Ph2-F, R$^1$-Np4-Te2-CH$_2$CH$_2$-Ph3-F,
R$^1$-Cy-CH$_2$CH$_2$-Te1-Ph1-F,
R$^1$-Cy-CH$_2$CH$_2$-Te1-Ph2-F, R$^1$-Cy-CH$_2$CH$_2$-Te1-Ph3-F, R$^1$-Cy-CH$_2$CH$_2$-Te1-Np1-F,
R$^1$-Cy-CH$_2$CH$_2$-Te1-Np2-F, R$^1$-Cy-CH$_2$CH$_2$-Te1-Np3-F, R$^1$-Cy-CH$_2$CH$_2$-Te1-Np4-F,
R$^1$-Cy-CH$_2$CH$_2$-Te2-Ph1-F, R$^1$-Cy-CH$_2$CH$_2$-Te2-Ph2-F, R$^1$-Cy-CH$_2$CH$_2$-Te2-Ph3-F,
R$^1$-Cy-CH$_2$CH$_2$-Te2-Np1-F, R$^1$-Cy-CH$_2$CH$_2$-Te2-Np2-F, R$^1$-Cy-CH$_2$CH$_2$-Te2-Np3-F,
R$^1$-Cy-CH$_2$CH$_2$-Te2-Np4-F, R$^1$-Ph1-CH$_2$CH$_2$-Te1-Ph1-F, R$^1$-Ph1-CH$_2$CH$_2$-Te1-Ph2-F,
R$^1$-Ph1-CH$_2$CH$_2$-Te1-Ph3-F, R$^1$-Ph1-CH$_2$CH$_2$-Te1-Np1-F, R$^1$-Ph1-CH$_2$CH$_2$-Te1-Np2-F,
R$^1$-Ph1-CH$_2$CH$_2$-Te1-Np3-F, R$^1$-Ph1-CH$_2$CH$_2$-Te1-Np4-F, R$^1$-Ph1-CH$_2$CH$_2$-Te2-Ph1-F,
R$^1$-Ph1-CH$_2$CH$_2$-Te2-Ph2-F, R$^1$-Ph1-CH$_2$CH$_2$-Te2-Ph3-F, R$^1$-Ph1-CH$_2$CH$_2$-Te2-Np1-F,
R$^1$-Ph1-CH$_2$CH$_2$-Te2-Np2-F, R$^1$-Ph1-CH$_2$CH$_2$-Te2-Np3-F, R$^1$-Ph1-CH$_2$CH$_2$-Te2-Np4-F,
R$^1$-Ph2-CH$_2$CH$_2$-Te1-Ph1-F, R$^1$-Ph2-CH$_2$CH$_2$-Te1-Ph2-F, R$^1$-Ph2-CH$_2$CH$_2$-Te1-Ph3-F,
R$^1$-Ph2-CH$_2$CH$_2$-Te1-Np1-F, R$^1$-Ph2-CH$_2$CH$_2$-Te1-Np2-F, R$^1$-Ph2-CH$_2$CH$_2$-Te1-Np3-F,
R$^1$-Ph2-CH$_2$CH$_2$-Te1-Np4-F, R$^1$-Ph2-CH$_2$CH$_2$-Te2-Ph1-F, R$^1$-Ph2-CH$_2$CH$_2$-Te2-Ph2-F,
R$^1$-Ph2-CH$_2$CH$_2$-Te2-Ph3-F, R$^1$-Ph2-CH$_2$CH$_2$-Te2-Np1-F, R$^1$-Ph2-CH$_2$CH$_2$-Te2-Np2-F,
R$^1$-Ph2-CH$_2$CH$_2$-Te2-Np3-F, R$^1$-Ph2-CH$_2$CH$_2$-Te2-Np4-F,
R$^1$-Ph3-CH$_2$CH$_2$-Te1-Ph1-F,
R$^1$-Ph3-CH$_2$CH$_2$-Te1-Ph2-F, R$^1$-Ph3-CH$_2$CH$_2$-Te1-Ph3-F,
R$^1$-Ph3-CH$_2$CH$_2$-Te2-Ph1-F,
R$^1$-Ph3-CH$_2$CH$_2$-Te2-Ph2-F, R$^1$-Ph3-CH$_2$CH$_2$-Te2-Ph3-F,
R$^1$-Np1-CH$_2$CH$_2$-Te1-Ph1-F,
R$^1$-Np1-CH$_2$CH$_2$-Te1-Ph2-F, R$^1$-Np1-CH$_2$CH$_2$-Te1-Ph3-F,
R$^1$-Np1-CH$_2$CH$_2$-Te2-Ph1-F,
R$^1$-Np1-CH$_2$CH$_2$-Te2-Ph2-F, R$^1$-Np1-CH$_2$CH$_2$-Te2-Ph3-F,
R$^1$-Np2-CH$_2$CH$_2$-Te1-Ph1-F,
R$^1$-Np2-CH$_2$CH$_2$-Te1-Ph2-F, R$^1$-Np2-CH$_2$CH$_2$-Te1-Ph3-F,
R$^1$-Np2-CH$_2$CH$_2$-Te2-Ph1-F,
R$^1$-Np2-CH$_2$CH$_2$-Te2-Ph2-F, R$^1$-Np2-CH$_2$CH$_2$-Te2-Ph3-F,
R$^1$-Np3-CH$_2$CH$_2$-Te1-Ph1-F,
R$^1$-Np3-CH$_2$CH$_2$-Te1-Ph2-F, R$^1$-Np3-CH$_2$CH$_2$-Te1-Ph3-F,
R$^1$-Np3-CH$_2$CH$_2$-Te2-Ph1-F,
R$^1$-Np3-CH$_2$CH$_2$-Te2-Ph2-F, R$^1$-Np3-CH$_2$CH$_2$-Te2-Ph3-F,
R$^1$-Np4-CH$_2$CH$_2$-Te1-Ph1-F,
R$^1$-Np4-CH$_2$CH$_2$-Te1-Ph2-F, R$^1$-Np4-CH$_2$CH$_2$-Te1-Ph3-F,
R$^1$-Np4-CH$_2$CH$_2$-Te2-Ph1-F,
R$^1$-Np4-CH$_2$CH$_2$-Te2-Ph2-F, R$^1$-Np4-CH$_2$CH$_2$-Te2-Ph3-F,
R$^1$-Ph1-C≡C-Te1-Ph1-F, R$^1$-Ph1-C≡C-Te1-Ph2-F, R$^1$-Ph1-C≡C-Te1-Ph3-F,
R$^1$-Ph1-C≡C-Te2-Ph1-F, R$^1$-Ph1-C≡C-Te2-Ph2-F, R$^1$-Ph1-C≡C-Te2-Ph3-F,
R$^1$-Ph2-C≡C-Te1-Ph1-F, R$^1$-Ph2-C≡C-Te1-Ph2-F, R$^1$-Ph2-C≡C-Te1-Ph3-F,
R$^1$-Ph2-C≡C-Te2-Ph1-F, R$^1$-Ph2-C≡C-Te2-Ph2-F, R$^1$-Ph2-C≡C-Te2-Ph3-F,
R$^1$-Ph3-C≡C-Te1-Ph1-F, R$^1$-Ph3-C≡C-Te1-Ph2-F, R$^1$-Ph3-C≡C-Te1-Ph3-F,
R$^1$-Ph3-C≡C-Te2-Ph1-F, R$^1$-Ph3-C≡C-Te2-Ph2-F, R$^1$-Ph3-C≡C-Te2-Ph3-F, in the case in which n$^a$=1, n$^b$=0 or n$^a$=0, n$^b$=1, and n$^c$=1, n$^d$=0 or n$^c$=0, n$^d$=1, and Z is a cyano group,
R$^1$-Cy-Te1-Ph1-CN, R$^1$-Cy-Te1-Ph2-CN, R$^1$-Cy-Te1-Ph3-CN, R$^1$-Cy-Te1-Np1-CN,
R$^1$-Cy-Te1-Np2-CN, R$^1$-Cy-Te1-Np3-CN, R$^1$-Cy-Te1-Np4-CN, R$^1$-Cy-Te2-Ph1-CN,
R$^1$-Cy-Te2-Ph2-CN, R$^1$-Cy-Te2-Ph3-CN, R$^1$-Cy-Te2-Np1-CN, R$^1$-Cy-Te2-Np2-CN,
R$^1$-Cy-Te2-Np3-CN, R$^1$-Cy-Te2-Np4-CN,
R$^1$-Cy-Te1-CH$_2$CH$_2$-Ph2-CN, R$^1$-Cy-Te1-CH$_2$CH$_2$-Ph3-CN, R$^1$-Cy-Te1-CH$_2$CH$_2$-Np1-CN,
R$^1$-Cy-Te1-CH$_2$CH$_2$-Np2-CN, R$^1$-Cy-Te1-CH$_2$CH$_2$-Np3-CN, R$^1$-Cy-Te1-CH$_2$CH$_2$-Np4-CN,
R$^1$-Cy-Te2-CH$_2$CH$_2$-Ph1-CN, R$^1$-Cy-Te2-CH$_2$CH$_2$-Ph2-CN, R$^1$-Cy-Te2-CH$_2$CH$_2$-Ph3-CN,
R$^1$-Cy-Te2-CH$_2$CH$_2$-Np1-CN, R$^1$-Cy-Te2-CH$_2$CH$_2$-Np2-CN, R$^1$-Cy-Te2-CH$_2$CH$_2$-Np3-CN,
R$^1$-Cy-Te2-CH$_2$CH$_2$-Np4-CN, R$^1$-Ph1-Te1-Ph1-CN, R$^1$-Ph1-Te1-Ph2-CN, R$^1$-Ph1-Te1-Ph3-CN,
R$^1$-Ph1-Te1-Np1-CN, R$^1$-Ph1-Te1-Np2-CN, R$^1$-Ph1-Te1-Np3-CN,
R$^1$-Ph1-Te1-Np4-CN, R$^1$-Ph1-Te2-Ph1-CN, R$^1$-Ph1-Te2-Ph2-CN,
R$^1$-Ph1-Te2-Ph3-CN, R$^1$-Ph1-Te2-Np1-CN, R$^1$-Ph1-Te2-Np2-CN,
R$^1$-Ph1-Te2-Np3-CN, R$^1$-Ph1-Te2-Np4-CN,
R$^1$-Ph1-Te1-CH$_2$CH$_2$-Ph2-CN, R$^1$-Ph1-Te1-CH$_2$CH$_2$-Ph3-CN,
R$^1$-Ph1-Te1-CH$_2$CH$_2$-Np1-CN, R$^1$-Ph1-Te1-CH$_2$CH$_2$-Np2-CN,
R$^1$-Ph1-Te1-CH$_2$CH$_2$-Np3-CN, R$^1$-Ph1-Te1-CH$_2$CH$_2$-Np4-CN,
R$^1$-Ph1-Te2-CH$_2$CH$_2$-Ph1-CN, R$^1$-Ph1-Te2-CH$_2$CH$_2$-Ph2-CN,
R$^1$-Ph1-Te2-CH$_2$CH$_2$-Ph3-CN, R$^1$-Ph1-Te2-CH$_2$CH$_2$-Np1-CN,
R$^1$-Ph1-Te2-CH$_2$CH$_2$-Np2-CN, R$^1$-Ph1-Te2-CH$_2$CH$_2$-Np3-CN,
R$^1$-Ph1-Te2-CH$_2$CH$_2$-Np4-CN,
R$^1$-Ph2-Te1-Ph1-CN, R$^1$-Ph2-Te1-Ph2-CN, R$^1$-Ph2-Te1-Ph3-CN,
R$^1$-Ph2-Te1-Np1-CN, R$^1$-Ph2-Te1-Np2-CN, R$^1$-Ph2-Te1-Np3-CN,
R$^1$-Ph2-Te1-Np4-CN, R$^1$-Ph2-Te2-Ph1-CN, R$^1$-Ph2-Te2-Ph2-CN,
R$^1$-Ph2-Te2-Ph3-CN, R$^1$-Ph2-Te2-Np1-CN, R$^1$-Ph2-Te2-Np2-CN,
R$^1$-Ph2-Te2-Np3-CN, R$^1$-Ph2-Te2-Np4-CN,
R$^1$-Ph2-Te1-CH$_2$CH$_2$-Ph1-CN, R$^1$-Ph2-Te1-CH$_2$CH$_2$-Ph3-CN,
R$^1$-Ph2-Te1-CH$_2$CH$_2$-Np1-CN, R$^1$-Ph2-Te1-CH$_2$CH$_2$-Np2-CN,
R$^1$-Ph2-Te1-CH$_2$CH$_2$-Np3-CN, R$^1$-Ph2-Te1-CH$_2$CH$_2$-Np4-CN,
R$^1$-Ph2-Te2-CH$_2$CH$_2$-Ph1-CN, R$^1$-Ph2-Te2-CH$_2$CH$_2$-Ph2-CN,
R$^1$-Ph2-Te2-CH$_2$CH$_2$-Ph3-CN, R$^1$-Ph2-Te2-CH$_2$CH$_2$-Np1-CN,
R$^1$-Ph2-Te2-CH$_2$CH$_2$-Np2-CN, R$^1$-Ph2-Te2-CH$_2$CH$_2$-Np3-CN,
R$^1$-Ph2-Te2-CH$_2$CH$_2$-Np4-CN,
R$^1$-Ph3-Te1-Ph1-CN, R$^1$-Ph3-Te1-Ph2-CN, R$^1$-Ph3-Te1-Ph3-CN,
R$^1$-Ph3-Te1-Np1-CN, R$^1$-Ph3-Te1-Np2-CN, R$^1$-Ph3-Te1-Np3-CN,
R$^1$-Ph3-Te1-Np4-CN, R$^1$-Ph3-Te2-Ph1-CN, R$^1$-Ph3-Te2-Ph2-CN,
R$^1$-Ph3-Te2-Ph3-CN, R$^1$-Ph3-Te2-Np1-CN, R$^1$-Ph3-Te2-Np2-CN,
R$^1$-Ph3-Te2-Np3-CN, R$^1$-Ph3-Te2-Np4-CN,
R$^1$-Ph3-Te1-CH$_2$CH$_2$-Ph2-CN, R$^1$-Ph3-Te1-CH$_2$CH$_2$-Ph3-CN,
R$^1$-Ph3-Te1-CH$_2$CH$_2$-Np1-CN, R$^1$-Ph3-Te1-CH$_2$CH$_2$-Np2-CN,
R$^1$-Ph3-Te1-CH$_2$CH$_2$-Np3-CN, R$^1$-Ph3-Te1-CH$_2$CH$_2$-Np4-CN,
R$^1$-Ph3-Te2-CH$_2$CH$_2$-Ph1-CN, R$^1$-Ph3-Te2-CH$_2$CH$_2$-Ph2-CN,
R$^1$-Ph3-Te2-CH$_2$CH$_2$-Ph3-CN, R$^1$-Ph3-Te2-CH$_2$CH$_2$-Np1-CN,
R$^1$-Ph3-Te2-CH$_2$CH$_2$-Np2-CN, R$^1$-Ph3-Te2-CH$_2$CH$_2$-Np3-CN,
R$^1$-Ph3-Te2-CH$_2$CH$_2$-Np4-CN,
R$^1$-Np1-Te1-Ph1-CN, R$^1$-Np1-Te1-Ph2-CN, R$^1$-Np1-Te1-Ph3-CN,
R$^1$-Np1-Te2-Ph1-CN, R$^1$-Np1-Te2-Ph2-CN, R$^1$-Np1-Te2-Ph3-CN,
R$^1$-Np1-Te1-CH$_2$CH$_2$-Ph2-CN, R$^1$-Np1-Te1-CH$_2$CH$_2$-Ph3-CN,
R$^1$-Np1-Te2-CH$_2$CH$_2$-Ph1-CN, R$^1$-Np1-Te2-CH$_2$CH$_2$-Ph2-CN,
R$^1$-Np1-Te2-CH$_2$CH$_2$-Ph3-CN,
R$^1$-Np2-Te1-Ph1-CN, R$^1$-Np2-Te1-Ph2-CN, R$^1$-Np2-Te1-Ph3-CN,
R$^1$-Np2-Te2-Ph1-CN, R$^1$-Np2-Te2-Ph2-CN, R$^1$-Np2-Te2-Ph3-CN,
R$^1$-Np2-Te1-CH$_2$CH$_2$-Ph2-CN, R$^1$-Np2-Te1-CH$_2$CH$_2$-Ph3-CN,
R$^1$-Np2-Te2-CH$_2$CH$_2$-Ph1-CN, R$^1$-Np2-Te2-CH$_2$CH$_2$-Ph2-CN,
R$^1$-Np2-Te2-CH$_2$CH$_2$-Ph3-CN, R$^1$-Np2-Te2-CH$_2$CH$_2$-Np4-CN,
R$^1$-Np3-Te1-Ph1-CN, R$^1$-Np3-Te1-Ph2-CN, R$^1$-Np3-Te1-Ph3-CN,
R$^1$-Np3-Te2-Ph1-CN, R$^1$-Np3-Te2-Ph2-CN, R$^1$-Np3-Te2-Ph3-CN,
R$^1$-Np3-Te1-CH$_2$CH$_2$-Ph2-CN, R$^1$-Np3-Te1-CH$_2$CH$_2$-Ph3-CN,
R$^1$-Np3-Te2-CH$_2$CH$_2$-Ph1-CN, R$^1$-Np3-Te2-CH$_2$CH$_2$-Ph2-CN,
R$^1$-Np3-Te2-CH$_2$CH$_2$-Ph3-CN,
R$^1$-Np4-Te1-Ph1-CN, R$^1$-Np4-Te1-Ph2-CN, R$^1$-Np4-Te1-Ph3-CN,
R$^1$-Np4-Te2-Ph1-CN, R$^1$-Np4-Te2-Ph2-CN, R$^1$-Np4-Te2-Ph3-CN,
R$^1$-Np4-Te1-CH$_2$CH$_2$-Ph2-CN, R$^1$-Np4-Te1-CH$_2$CH$_2$-Ph3-CN,
R$^1$-Np4-Te2-CH$_2$CH$_2$-Ph1-CN, R$^1$-Np4-Te2-CH$_2$CH$_2$-Ph2-CN,
R$^1$-Np4-Te2-CH$_2$CH$_2$-Ph3-CN,
R$^1$-Cy-CH$_2$CH$_2$-Te1-Ph1-CN, R$^1$-Cy-CH$_2$CH$_2$-Te1-Ph2-CN, R$^1$-Cy-CH$_2$CH$_2$-Te1-Ph3-CN,
R$^1$-Cy-CH$_2$CH$_2$-Te1-Np1-CN, R$^1$-Cy-CH$_2$CH$_2$-Te1-Np2-CN, R$^1$-Cy-CH$_2$CH$_2$-Te1-Np3-CN,
R$^1$-Cy-CH$_2$CH$_2$-Te1-Np4-CN, R$^1$-Cy-CH$_2$CH$_2$-Te2-Ph1-CN, R$^1$-Cy-CH$_2$CH$_2$-Te2-Ph2-CN,
R$^1$-Cy-CH$_2$CH$_2$-Te2-Ph3-CN, R$^1$-Cy-CH$_2$CH$_2$-Te2-Np1-CN, R$^1$-Cy-CH$_2$CH$_2$-Te2-Np2-CN,
R$^1$-Cy-CH$_2$CH$_2$-Te2-Np3-CN, R$^1$-Cy-CH$_2$CH$_2$-Te2-Np4-CN, R$^1$-Ph1-CH$_2$CH$_2$-Te1-Ph1-CN,
R$^1$-Ph1-CH$_2$CH$_2$-Te1-Ph2-CN, R$^1$-Ph1-CH$_2$CH$_2$-Te1-Ph3-CN,
R$^1$-Ph1-CH$_2$CH$_2$-Te1-Np1-CN, R$^1$-Ph1-CH$_2$CH$_2$-Te1-Np2-CN,
R$^1$-Ph1-CH$_2$CH$_2$-Te1-Np3-CN, R$^1$-Ph1-CH$_2$CH$_2$-Te1-Np4-CN,
R$^1$-Ph1-CH$_2$CH$_2$-Te2-Ph1-CN, R$^1$-Ph1-CH$_2$CH$_2$-Te2-Ph2-CN,
R$^1$-Ph1-CH$_2$CH$_2$-Te2-Ph3-CN, R$^1$-Ph1-CH$_2$CH$_2$-Te2-Np1-CN,
R$^1$-Ph1-CH$_2$CH$_2$-Te2-Np2-CN, R$^1$-Ph1-CH$_2$CH$_2$-Te2-Np3-CN,
R$^1$-Ph1-CH$_2$CH$_2$-Te2-Np4-CN, R$^1$-Ph2-CH$_2$CH$_2$-Te1-Ph1-CN,
R$^1$-Ph2-CH$_2$CH$_2$-Te1-Ph2-CN, R$^1$-Ph2-CH$_2$CH$_2$-Te1-Ph3-CN,
R$^1$-Ph2-CH$_2$CH$_2$-Te1-Np1-CN, R$^1$-Ph2-CH$_2$CH$_2$-Te1-Np2-CN,
R$^1$-Ph2-CH$_2$CH$_2$-Te1-Np3-CN, R$^1$-Ph2-CH$_2$CH$_2$-Te1-Np4-CN,
R$^1$-Ph2-CH$_2$CH$_2$-Te2-Ph1-CN, R$^1$-Ph2-CH$_2$CH$_2$-Te2-Ph2-CN, R$^1$-Ph2-CH$_2$CH$_2$-Te2-Ph3-CN, R$^1$-Ph2-CH$_2$CH$_2$-Te2-Np1-CN,
R$^1$-Ph2-CH$_2$CH$_2$-Te2-Np2-CN, R$^1$-Ph2-CH$_2$CH$_2$-Te2-Np3-CN,
R$^1$-Ph2-CH$_2$CH$_2$-Te2-Np4-CN, R$^1$-Ph3-CH$_2$CH$_2$-Te1-Ph1-CN,
R$^1$-Ph3-CH$_2$CH$_2$-Te1-Ph2-CN, R$^1$-Ph3-CH$_2$CH$_2$-Te1-Ph3-CN,
R$^1$-Ph3-CH$_2$CH$_2$-Te1-Np1-CN, R$^1$-Ph3-CH$_2$CH$_2$-Te1-Np2-CN,
R$^1$-Ph3-CH$_2$CH$_2$-Te1-Np3-CN, R$^1$-Ph3-CH$_2$CH$_2$-Te1-Np4-CN,
R$^1$-Ph3-CH$_2$CH$_2$-Te2-Ph1-CN, R$^1$-Ph3-CH$_2$CH$_2$-Te2-Ph2-CN,
R$^1$-Ph3-CH$_2$CH$_2$-Te2-Ph3-CN, R$^1$-Ph3-CH$_2$CH$_2$-Te2-Np1-CN,
R$^1$-Ph3-CH$_2$CH$_2$-Te2-Np2-CN, R$^1$-Ph3-CH$_2$CH$_2$-Te2-Np3-CN,
R$^1$-Ph3-CH$_2$CH$_2$-Te2-Np4-CN, R$^1$-Np1-CH$_2$CH$_2$-Te1-Ph1-CN,
R$^1$-Np1-CH$_2$CH$_2$-Te1-Ph2-CN, R$^1$-Np1-CH$_2$CH$_2$-Te1-Ph3-CN,
R$^1$-Np1-CH$_2$CH$_2$-Te2-Ph1-CN, R$^1$-Np1-CH$_2$CH$_2$-Te2-Ph2-CN,
R$^1$-Np1-CH$_2$CH$_2$-Te2-Ph3-CN, R$^1$-Np2-CH$_2$CH$_2$-Te1-Ph1-CN,
R$^1$-Np2-CH$_2$CH$_2$-Te1-Ph2-CN, R$^1$-Np2-CH$_2$CH$_2$-Te1-Ph3-CN,
R$^1$-Np2-CH$_2$CH$_2$-Te2-Ph1-CN, R$^1$-Np2-CH$_2$CH$_2$-Te2-Ph2-CN,
R$^1$-Np2-CH$_2$CH$_2$-Te2-Ph3-CN, R$^1$-Np3-CH$_2$CH$_2$-Te1-Ph1-CN,
R$^1$-Np3-CH$_2$CH$_2$-Te1-Ph2-CN, R$^1$-Np3-CH$_2$CH$_2$-Te1-Ph3-CN,
R$^1$-Np3-CH$_2$CH$_2$-Te2-Ph1-CN, R$^1$-Np3-CH$_2$CH$_2$-Te2-Ph2-CN,
R$^1$-Np3-CH$_2$CH$_2$-Te2-Ph3-CN, R$^1$-Np4-CH$_2$CH$_2$-Te1-Ph1-CN,
R$^1$-Np4-CH$_2$CH$_2$-Te1-Ph2-CN, R$^1$-Np4-CH$_2$CH$_2$-Te1-Ph3-CN,
R$^1$-Np4-CH$_2$CH$_2$-Te2-Ph1-CN, R$^1$-Np4-CH$_2$CH$_2$-Te2-Ph2-CN,
R$^1$-Np4-CH$_2$CH$_2$-Te2-Ph3-CN,
in the case in which $n^a$=1, $n^b$=0 or $n^a$=0, $n^b$=1, and $n^c$=1, $n^d$=0 or $n^c$=0, $n^d$=1, and Z is a trifluoromethoxy group,
R$^1$-Cy-Te1-Ph1-OCF$_3$, R$^1$-Cy-Te1-Ph2-OCF$_3$, R$^1$-Cy-Te1-Ph3-OCF$_3$,
R$^1$-Cy-Te1-Np1-OCF$_3$, R$^1$-Cy-Te1-Np2-OCF$_3$, R$^1$-Cy-Te1-Ph3-OCF$_3$,
R$^1$-Cy-Te1-Np4-OCF$_3$, R$^1$-Cy-Te2-Ph1-OCF$_3$, R$^1$-Cy-Te2-Ph2-OCF$_3$,
R$^1$-Cy-Te2-Ph3-OCF$_3$, R$^1$-Cy-Te2-Np1-OCF$_3$, R$^1$-Cy-Te2-Np2-OCF$_3$,
R$^1$-Cy-Te2-Ph3-OCF$_3$, R$^1$-Cy-Te2-Np4-OCF$_3$,
R$^1$-Cy-Te1-CH$_2$CH$^2$-Ph2-OCF$_3$, R$^1$-Cy-Te1-CH$_2$CH$^2$-Ph3-OCF$_3$,
R$^1$-Cy-Te1-CH$_2$CH$_2$-Np1-OCF$_3$, R$^1$-Cy-Te1-CH$_2$CH$_2$-Np2-OCF$_3$,
R$^1$-Cy-Te1-CH$_2$CH$_2$-Ph3-OCF$_3$, R$^1$-Cy-Te1-CH$_2$CH$_2$-Np4-OCF$_3$,
R$^1$-Cy-Te2-CH$_2$CH$_2$-Ph1-OCF$_3$, R$^1$-Cy-Te2-CH$_2$CH$_2$-Ph2-OCF$_3$,
R$^1$-Cy-Te2-CH$_2$CH$_2$-Ph3-OCF$_3$, R$^1$-Cy-Te2-CH$_2$CH$_2$-Np1-OCF$_3$,
R$^1$-Cy-Te2-CH$_2$CH$_2$-Np2-OCF$_3$, R$^1$-Cy-Te2-CH$_2$CH$_2$-Ph3-OCF$_3$,
R$^1$-Cy-Te2-CH$_2$CH$_2$-Np4-OCF$_3$,
R$^1$-Ph1-Te1-Ph1-OCF$_3$, R$^1$-Ph1-Te1-Ph1-OCF$_3$, R$^1$-Ph1-Te1-Ph3-OCF$_3$,
R$^1$-Ph1-Te1-Np1-OCF$_3$, R$^1$-Ph1-Te1-Np2-OCF$_3$, R$^1$-Ph1-Te1-Ph3-OCF$_3$,
R$^1$-Ph1-Te1-Np4-OCF$_3$, R$^1$-Ph1-Te2-Ph1-OCF$_3$, R$^1$-Ph1-Te2-Ph2-OCF$_3$,
R$^1$-Ph1-Te2-Ph1-OCF$_3$, R$^1$-Ph1-Te2-Np1-OCF$_3$, R$^1$-Ph1-Te2-Np2-OCF$_3$,
R$^1$-Ph1-Te2-Ph3-OCF$_3$, R$^1$-Ph1-Te2-Np4-OCF$_3$,
R$^1$-Ph1-Te1-CH$_2$CH$_2$-Ph2-OCF$_3$, R$^1$-Ph1-Te1-CH$_2$CH$_2$-Ph3-OCF$_3$,
R$^1$-Ph1-Te1-CH$_2$CH$_2$-Np1-OCF$_3$, R$^1$-Ph1-Te1-CH$_2$CH$_2$-Np2-OCF$_3$,
R$^1$-Ph2-Te1-CH$_2$CH$_2$-Ph3-OCF$_3$, R$^1$-Ph1-Te1-CH$_2$CH$_2$-Np3-OCF$_3$,
R$^1$-Ph1-Te2-CH$_2$CH$_2$-Ph1-OCF$_3$, R$^1$-Ph2-Te2-CH$_2$CH$_2$-Ph3-OCF$_3$,
R$^1$-Ph1-Te2-CH$_2$CH$_2$-Ph3-OCF$_3$, R$^1$-Ph1-Te2-CH$_2$CH$_2$-Np1-OCF$_3$,
R$^1$-Ph1-Te2-CH$_2$CH$_2$-Np2-OCF$_3$, R$^1$-Ph1-Te2-CH$_2$CH$_2$-Ph3-OCF$_3$,
R$^1$-Ph1-Te2-CH$_2$CH$_2$-Np4-OCF$_3$,
R$^1$-Ph2-Te1-Ph1-OCF$_3$, R$^1$-Ph2-Te1-Ph2-OCF$_3$, R$^1$-Ph2-Te1-Ph3-OCF$_3$,
R$^1$-Ph2-Te1-Np1-OCF$_3$, R$^1$-Ph2-Te1-Np2-OCF$_3$, R$^1$-Ph2-Te1-Ph3-OCF$_3$,
R$^1$-Ph2-Te1-Np4-OCF$_3$, R$^1$-Ph2-Te2-Ph1-OCF$_3$, R$^1$-Ph2-Te2-Ph2-OCF$_3$,
R$^1$-Ph2-Te2-Ph3-OCF$_3$, R$^1$-Ph2-Te2-Np1-OCF$_3$, R$^1$-Ph2-Te2-Np2-OCF$_3$,
R$^1$-Ph2-Te2-Ph3-OCF$_3$, R$^1$-Ph2-Te2-Np4-OCF$_3$,
R$^1$-Ph1-Te1-CH$_2$CH$_2$-Ph2-OCF$_3$, R$^1$-Ph2-Te1-CH$_2$CH$_2$-Ph3-OCF$_3$,
R$^1$-Ph2-Te1-CH$_2$CH$_2$-Np1-OCF$_3$, R$^1$-Ph2-Te1-CH$_2$CH$_2$-Np2-OCF$_3$,
R$^1$-Ph2-Te1-CH$_2$CH$_2$-Ph3-OCF$_3$, R$^1$-Ph2-Te1-CH$_2$CH$_2$-Np4-OCF$_3$,
R$^1$-Ph2-Te2-CH$_2$CH$_2$-Ph1-OCF$_3$, R$^1$-Ph2-Te2-CH$_2$CH$_2$-Ph2-OCF$_3$,
R$^1$-Ph2-Te2-CH$_2$CH$_2$-Ph3-OCF$_3$, R$^1$-Ph2-Te2-CH$_2$CH$_2$-Np1-OCF$_3$,
R$^1$-Ph2-Te2-CH$_2$CH$_2$-Np2-OCF$_3$, R$^1$-Ph2-Te2-CH$_2$CH$_2$-Ph3-OCF$_3$,
R$^1$-Ph2-Te2-CH$_2$CH$_2$-Np4-OCF$_3$,
R$^1$-Ph3-Te1-Ph1-OCF$_3$, R$^1$-Ph3-Te1-Ph2-OCF$_3$, R$^1$-Ph3-Te1-Ph3-OCF$_3$,
R$^1$-Ph3-Te1-Np1-OCF$_3$, R$^1$-Ph3-Te1-Np2-OCF$_3$, R$^1$-Ph3-Te1-Ph3-OCF$_3$,
R$^1$-Ph3-Te1-Np4-OCF$_3$, R$^1$-Ph3-Te2-Ph1-OCF$_3$, R$^1$-Ph3-Te2-Ph2-OCF$_3$,
R$^1$-Ph3-Te2-Ph3-OCF$_3$, R$^1$-Ph3-Te2-Np1-OCF$_3$, R$^1$-Ph3-Te2-Np2-OCF$_3$,
R$^1$-Ph3-Te2-Ph3-OCF$_3$, R$^1$-Ph3-Te2-Np4-OCF$_3$,
R$^1$-Ph3-Te1-CH$_2$CH$_2$-Ph2-OCF$_3$, R$^1$-Ph3-Te1-CH$_2$CH$_2$-Ph3-OCF$_3$,
R$^1$-Ph3-Te1-CH$_2$CH$_2$-Np1-OCF$_3$, R$^1$-Ph3-Te1-CH$_2$CH$_2$-Np2-OCF$_3$,
R$^1$-Ph3-Te1-CH$_2$CH$_2$-Ph3-OCF$_3$, R$^1$-Ph3-Te1-CH$_2$CH$_2$-Np4-OCF$_3$,
R$^1$-Ph3-Te2-CH$_2$CH$_2$-Ph1-OCF$_3$, R$^1$-Ph3-Te2-CH$_2$CH$_2$-Ph2-OCF$_3$,
R$^1$-Ph3-Te2-CH$_2$CH$_2$-Ph3-OCF$_3$, R$^1$-Ph3-Te2-CH$_2$CH$_2$-Np1-OCF$_3$,
R$^1$-Ph3-Te2-CH$_2$CH$_2$-Np2-OCF$_3$, R$^1$-Ph3-Te2-CH$_2$CH$_2$-Ph3-OCF$_3$,
R$^1$-Ph3-Te2-CH$_2$CH$_2$-Np4-OCF$_3$,
R$^1$-Np1-Te1-Ph1-OCF$_3$, R$^1$-Np1-Te1-Ph2-OCF$_3$, R$^1$-Np1-Te1-Ph3-OCF$_3$, R¹-Np1-Te1-Ph3-OCF₃, R¹-Np1-Te2-Ph1-OCF₃, R¹-Np1-Te2-Ph2-OCF₃,
R¹-Np1-Te2-Ph3-OCF₃, R¹-Np1-Te2-Ph3-OCF₃,
R¹-Np1-Te1-CH₂CH₂-Ph2-OCF₃, R¹-Np1-Te1-CH₂CH₂-Ph3-OCF₃,
R¹-Np1-Te1-CH₂CH₂-Np1-OCF₃, R¹-Np1-Te1-CH₂CH₂-Np2-OCF₃,
R¹-Np1-Te1-CH₂CH₂-Ph3-OCF₃, R¹-Np1-Te2-CH₂CH₂-Ph1-OCF₃,
R¹-Np1-Te2-CH₂CH₂-Ph2-OCF₃, R¹-Np1-Te2-CH₂CH₂-Ph3-OCF₃,
R¹-Np1-Te2-CH₂CH₂-Ph3-OCF₃,
R¹-Np2-Te1-Ph1-OCF₃, R¹-Np2-Te1-Ph2-OCF₃, R¹-Np2-Te1-Ph3-OCF₃,
R¹-Np2-Te1-Ph3-OCF₃, R¹-Np2-Te1-Np4-OCF₃, R¹-Np2-Te2-Ph1-OCF₃,
R¹-Np2-Te2-Ph2-OCF₃, R¹-Np2-Te2-Ph3-OCF₃, R¹-Np2-Te2-Ph3-OCF₃,
R¹-Np2-Te2-Np4-OCF₃,
R¹-Np2-Te1-CH₂CH₂-Ph2-OCF₃, R¹-Np2-Te1-CH₂CH₂-Ph3-OCF₃,
R¹-Np2-Te1-CH₂CH₂-Ph3-OCF₃, R¹-Np2-Te1-CH₂CH₂-Np4-OCF₃,
R¹-Np2-Te2-CH₂CH₂-Ph1-OCF₃, R¹-Np2-Te2-CH₂CH₂-Ph2-OCF₃,
R¹-Np2-Te2-CH₂CH₂-Ph3-OCF₃,
R¹-Ph3-Te1-Ph1-OCF₃, R¹-Ph3-Te1-Ph2-OCF₃, R¹-Ph3-Te1-Ph3-OCF₃,
R¹-Ph3-Te1-Np1-OCF₃, R¹-Ph3-Te1-Np2-OCF₃, R¹-Ph3-Te1-Ph3-OCF₃,
R¹-Ph3-Te1-Np4-OCF₃, R¹-Ph3-Te2-Ph1-OCF₃, R¹-Ph3-Te2-Ph2-OCF₃,
R¹-Ph3-Te2-Ph3-OCF₃, R¹-Ph3-Te2-Np1-OCF₃, R¹-Ph3-Te2-Np2-OCF₃,
R¹-Ph3-Te2-Ph3-OCF₃, R¹-Ph3-Te2-Np4-OCF₃,
R¹-Ph3-Te1-CH₂CH₂-Ph2-OCF₃, R¹-Ph3-Te1-CH₂CH₂-Ph3-OCF₃,
R¹-Ph3-Te1-CH₂CH₂-Np1-OCF₃, R¹-Ph3-Te1-CH₂CH₂-Np2-OCF₃,
R¹-Ph3-Te1-CH₂CH₂-Np4-OCF₃, R¹-Ph3-Te1-CH₂CH₂-Np4-OCF₃,
R¹-Ph3-Te2-CH₂CH₂-Ph1-OCF₃, R¹-Ph3-Te2-CH₂CH₂-Ph2-OCF₃,
R¹-Ph3-Te2-CH₂CH₂-Ph3-OCF₃, R¹-Ph3-Te2-CH₂CH₂-Np1-OCF₃,
R¹-Ph3-Te2-CH₂CH₂-Np2-OCF₃, R¹-Ph3-Te2-CH₂CH₂-Ph3-OCF₃,
R¹-Ph3-Te2-CH₂CH₂-Np4-OCF₃,
R¹-Np4-Te1-Ph1-OCF₃, R¹-Np4-Te1-Ph2-OCF₃, R¹-Np4-Te1-Ph3-OCF₃,
R¹-Np4-Te1-Np1-OCF₃, R¹-Np4-Te1-Np2-OCF₃, R¹-Np4-Te1-Ph3-OCF₃,
R¹-Np4-Te1-Np4-OCF₃, R¹-Np4-Te2-Ph1-OCF₃, R¹-Np4-Te2-Ph2-OCF₃,
R¹-Np4-Te2-Ph3-OCF₃, R¹-Np4-Te2-Np1-OCF₃, R¹-Np4-Te2-Np2-OCF₃,
R¹-Np4-Te2-Ph3-OCF₃, R¹-Np4-Te2-Np4-OCF₃,
R¹-Np4-Te1-CH₂CH₂-Ph2-OCF₃, R¹-Np4-Te1-CH₂CH₂-Ph3-OCF₃,
R¹-Np4-Te2-CH₂CH₂-Ph1-OCF₃, R¹-Np4-Te2-CH₂CH₂-Ph2-OCF₃,
R¹-Np4-Te2-CH₂CH₂-Ph3-OCF₃, R¹-Cy-CH₂CH₂-Te1-Ph1-OCF₃,
R¹-Cy-CH₂CH₂-Te1-Ph2-OCF₃, R¹-Cy-CH₂CH₂-Te1-Ph3-OCF₃,
R¹-Cy-CH₂CH₂-Te1-Np1-OCF₃, R¹-Cy-CH₂CH₂-Te1-Np2-OCF₃,
R¹-Cy-CH₂CH₂-Te1-Ph3-OCF₃, R¹-Cy-CH₂CH₂-Te1-Np4-OCF₃,
R¹-Cy-CH₂CH₂-Te2-Ph1-OCF₃, R¹-Cy-CH₂CH₂-Te2-Ph2-OCF₃,
R¹-Cy-CH₂CH₂-Te2-Ph3-OCF₃, R¹-Cy-CH₂CH₂-Te2-Np1-OCF₃,
R¹-Cy-CH₂CH₂-Te2-Np2-OCF₃, R¹-Cy-CH₂CH₂-Te2-Ph3-OCF₃,
R¹-Cy-CH₂CH₂-Te2-Np4-OCF₃, R¹-Ph1-CH₂CH₂-Te1-Ph1-OCF₃,
R¹-Ph1-CH₂CH₂-Te1-Ph2-OCF₃, R¹-Ph1-CH₂CH₂-Te1-Ph3-OCF₃,
R¹-Ph1-CH₂CH₂-Te1-Np1-OCF₃, R¹-Ph1-CH₂CH₂-Te1-Np2-OCF₃,
R¹-Ph1-CH₂CH₂-Te1-Ph3-OCF₃, R¹-Ph1-CH₂CH₂-Te1-Np4-OCF₃,
R¹-Ph1-CH₂CH₂-Te2-Ph1-OCF₃, R¹-Ph1-CH₂CH₂-Te2-Ph2-OCF₃,
R¹-Ph1-CH₂CH₂-Te2-Ph3-OCF₃, R¹-Ph1-CH₂CH₂-Te2-Np1-OCF₃,
R¹-Ph1-CH₂CH₂-Te2-Np2-OCF₃, R¹-Ph1-CH₂CH₂-Te2-Ph3-OCF₃,
R¹-Ph1-CH₂CH₂-Te2-Np4-OCF₃, R¹-Ph2-CH₂CH₂-Te1-Ph1-OCF₃,
R¹-Ph2-CH₂CH₂-Te1-Ph2-OCF₃, R¹-Ph2-CH₂CH₂-Te1-Ph3-OCF₃,
R¹-Ph2-CH₂CH₂-Te1-Np1-OCF₃, R¹-Ph2-CH₂CH₂-Te1-Np2-OCF₃,
R¹-Ph2-CH₂CH₂-Te1-Ph3-OCF₃, R¹-Ph2-CH₂CH₂-Te1-Np4-OCF₃,
R¹-Ph2-CH₂CH₂-Te2-Ph1-OCF₃, R¹-Ph2-CH₂CH₂-Te2-Ph2-OCF₃,
R¹-Ph2-CH₂CH₂-Te2-Ph3-OCF₃, R¹-Ph2-CH₂CH₂-Te2-Np1-OCF₃,
R¹-Ph2-CH₂CH₂-Te2-Np2-OCF₃, R¹-Ph2-CH₂CH₂-Te2-Ph3-OCF₃,
R¹-Ph2-CH₂CH₂-Te2-Np4-OCF₃, R¹-Ph3-CH₂CH₂-Te1-Ph1-OCF₃,
R¹-Ph3-CH₂CH₂-Te1-Ph2-OCF₃, R¹-Ph3-CH₂CH₂-Te1-Ph3-OCF₃,
R¹-Ph3-CH₂CH₂-Te1-Np1-OCF₃, R¹-Ph3-CH₂CH₂-Te1-Np2-OCF₃,
R¹-Ph3-CH₂CH₂-Te1-Ph3-OCF₃, R¹-Ph3-CH₂CH₂-Te1-Np4-OCF₃,
R¹-Ph3-CH₂CH₂-Te2-Ph1-OCF₃, R¹-Ph3-CH₂CH₂-Te2-Ph2-OCF₃,
R¹-Ph3-CH₂CH₂-Te2-Ph3-OCF₃, R¹-Ph3-CH₂CH₂-Te2-Np1-OCF₃,
R¹-Ph3-CH₂CH₂-Te2-Np2-OCF₃, R¹-Ph3-CH₂CH₂-Te2-Ph3-OCF₃,
R¹-Ph3-CH₂CH₂-Te2-Np4-OCF₃, R¹-Np1-CH₂CH₂-Te1-Ph1-OCF₃,
R¹-Np1-CH₂CH₂-Te1-Ph2-OCF₃, R¹-Np1-CH₂CH₂-Te1-Ph3-OCF₃,
R¹-Np1-CH₂CH₂-Te1-Np1-OCF₃, R¹-Np1-CH₂CH₂-Te1-Np2-OCF₃,
R¹-Np1-CH₂CH₂-Te1-Ph3-OCF₃, R¹-Np1-CH₂CH₂-Te1-Np4-OCF₃,
R¹-Np1-CH₂CH₂-Te2-Ph1-OCF₃, R¹-Np1-CH₂CH₂-Te2-Ph2-OCF₃,
R¹-Np1-CH₂CH₂-Te2-Ph3-OCF₃, R¹-Np2-CH₂CH₂-Te1-Ph1-OCF₃,
R¹-Np2-CH₂CH₂-Te1-Ph2-OCF₃, R¹-Np2-CH₂CH₂-Te1-Ph3-OCF₃,
R¹-Np2-CH₂CH₂-Te1-Np1-OCF₃, R¹-Np2-CH₂CH₂-Te1-Np2-OCF₃,
R¹-Np2-CH₂CH₂-Te1-Ph3-OCF₃, R¹-Np2-CH₂CH₂-Te1-Np4-OCF₃, R¹-Np2-CH₂CH₂-Te2-Ph1-OCF₃, R¹-Np2-CH₂CH₂-Te2-Ph2-OCF₃,
R¹-Np2-CH₂CH₂-Te2-Ph3-OCF₃, R¹-Ph3-CH₂CH₂-Te1-Ph1-OCF₃,
R¹-Ph3-CH₂CH₂-Te1-Ph2-OCF₃, R¹-Ph3-CH₂CH₂-Te1-Ph3-OCF₃,
R¹-Ph3-CH₂CH₂-Te1-Np1-OCF₃, R¹-Ph3-CH₂CH₂-Te1-Np2-OCF₃,
R¹-Ph3-CH₂CH₂-Te1-Ph3-OCF₃, R¹-Ph3-CH₂CH₂-Te1-Np4-OCF₃,
R¹-Ph3-CH₂CH₂-Te2-Ph1-OCF₃, R¹-Ph3-CH₂CH₂-Te2-Ph2-OCF₃,
R¹-Ph3-CH₂CH₂-Te2-Ph3-OCF₃, R¹-Ph3-CH₂CH₂-Te2-Np1-OCF₃,
R¹-Ph3-CH₂CH₂-Te2-Np2-OCF₃, R¹-Ph3-CH₂CH₂-Te2-Ph3-OCF₃,
R¹-Ph3-CH₂CH₂-Te2-Np4-OCF₃, R¹-Np4-CH₂CH₂-Te1-Ph1-OCF₃,
R¹-Np4-CH₂CH₂-Te1-Ph2-OCF₃, R¹-Np4-CH₂CH₂-Te1-Ph3-OCF₃,
R¹-Np4-CH₂CH₂-Te2-Ph1-OCF₃, R¹-Np4-CH₂CH₂-Te2-Ph2-OCF₃,
R¹-Np4-CH₂CH₂-Te2-Ph3-OCF₃, R¹-Np4-CH₂CH₂-Te2-Ph3-OCF₃,
R¹-Ph1-C≡C-Te1-Ph1-OCF₃, R¹-Ph1-C≡C-Te1-Ph2-OCF₃,
R¹-Ph1-C≡C-Te1-Ph3-OCF₃, R¹-Ph1-C≡C-Te1-Np1-OCF₃,
R¹-Ph1-C≡C-Te1-Np2-OCF₃, R¹-Ph1-C≡C-Te1-Ph3-OCF₃,
R¹-Ph1-C≡C-Te1-Np4-OCF₃, R¹-Ph1-C≡C-Te2-Ph1-OCF₃,
R¹-Ph1-C≡C-Te2-Ph2-OCF₃, R¹-Ph1-C≡C-Te2-Ph3-OCF₃,
R¹-Ph1-C≡C-Te2-Np1-OCF₃, R¹-Ph1-C≡C-Te2-Np2-OCF₃,
R¹-Ph1-C≡C-Te2-Ph3-OCF₃, R¹-Ph1-C≡C-Te2-Np4-OCF₃,
R¹-Ph2-C≡C-Te1-Ph1-OCF₃, R¹-Ph2-C≡C-Te1-Ph2-OCF₃,
R¹-Ph2-C≡C-Te1-Ph3-OCF₃, R¹-Ph2-C≡C-Te1-Np1-OCF₃,
R¹-Ph2-C≡C-Te1-Np2-OCF₃, R¹-Ph2-C≡C-Te1-Ph3-OCF₃,
R¹-Ph2-C≡C-Te1-Np1-OCF₃, R¹-Ph2-C≡C-Te2-Ph1-OCF₃,
R¹-Ph2-C≡C-Te2-Ph2-OCF₃, R¹-Ph2-C≡C-Te2-Ph3-OCF₃,
R¹-Ph2-C≡C-Te2-Np1-OCF₃, R¹-Ph2-C≡C-Te2-Np2-OCF₃,
R¹-Ph2-C≡C-Te2-Ph3-OCF₃, R¹-Ph1-C≡C-Te2-Np4-OCF₃,
R¹-Ph3-C≡C-Te1-Ph1-OCF₃, R¹-Ph3-C≡C-Te1-Ph1-OCF₃,
R¹-Ph3-C≡C-Te1-Ph3-OCF₃, R¹-Ph3-C≡C-Te1-Np3-OCF₃,
R¹-Ph3-C≡C-Te1-Np2-OCF₃, R¹-Ph3-C≡C-Te1-Ph3-OCF₃,
R¹-Ph3-C≡C-Te1-Np4-OCF₃, R¹-Ph3-C≡C-Te2-Ph1-OCF₃,
R¹-Ph3-C≡C-Te2-Ph2-OCF₃, R¹-Ph3-C≡C-Te2-Ph3-OCF₃,
R¹-Ph3-C≡C-Te2-Np1-OCF₃, R¹-Ph3-C≡C-Te2-Np2-OCF₃,
R¹-Ph3-C≡C-Te2-Ph3-OCF₃, R¹-Ph3-C≡C-Te2-Np4-OCF₃,
R¹-Ph3-C≡C-Te1-Ph1-OCF₃, R¹-Ph3-C≡C-Te1-Ph2-OCF₃,
R¹-Ph3-C≡C-Te1-Ph3-OCF₃, R¹-Ph3-C≡C-Te1-Np1-OCF₃,
R¹-Ph3-C≡C-Te1-Np2-OCF₃, R¹-Ph3-C≡C-Te1-Ph3-OCF₃,
R¹-Ph3-C≡C-Te1-Np4-OCF₃, R¹-Ph3-C≡C-Te2-Ph1-OCF₃,
R¹-Ph3-C≡C-Te2-Ph2-OCF₃, R¹-Ph3-C≡C-Te2-Ph3-OCF₃,
R¹-Ph3-C≡C-Te2-Np1-OCF₃, R¹-Ph3-C≡C-Te2-Np2-OCF₃,
R¹-Ph3-C≡C-Te2-Ph3-OCF₃, R¹-Ph3-C≡C-Te2-Np4-OCF₃, in the case in which $n^a=n^b=0$, and $n^c=n^d=1$, and Z is a fluorine atom, R¹-Te1-Cy-Ph1-F, R¹-Te1-Cy-Ph2-F, R¹-Te1-Cy-Ph3-F, R¹-Te1-Cy-Np1-F,
R¹-Te1-Cy-Np2-F, R¹-Te1-Cy-Np3-F, R¹-Te1-Cy-Np4-F, R¹-Te2-Cy-Ph1-F,
R¹-Te2-Cy-Ph2-F, R¹-Te2-Cy-Ph3-F, R¹-Te2-Cy-Np1-F, R¹-Te2-Cy-Np2-F,
R¹-Te2-Cy-Np3-F, R¹-Te2-Cy-Np4-F,
R¹-Te1-Cy-CH₂CH₂-Ph2-F, R¹-Te1-Cy-CH₂CH₂-Ph3-F, R¹-Te1-Cy-CH₂CH₂-Np1-F,
R¹-Te1-Cy-CH₂CH₂-Np2-F, R¹-Te1-Cy-CH₂CH₂-Np3-F, R¹-Te1-Cy-CH₂CH₂-Np4-F,
R¹-Te2-Cy-CH₂CH₂-Ph1-F, R¹-Te2-Cy-CH₂CH₂-Ph2-F, R¹-Te2-Cy-CH₂CH₂-Ph3-F,
R¹-Te2-Cy-CH₂CH₂-Np1-F, R¹-Te2-Cy-CH₂CH₂-Np2-F, R¹-Te2-Cy-CH₂CH₂-Np3-F,
R¹-Te2-Cy-CH₂CH₂-Np4-F, R¹-Te1-CH₂CH₂-Cy-Ph1-F, R¹-Te1-CH₂CH₂-Cy-Ph2-F,
R¹-Te1-CH₂CH₂-Cy-Ph3-F, R¹-Te1-CH₂CH₂-Cy-Np1-F, R¹-Te1-CH₂CH₂-Cy-Np2-F,
R¹-Te1-CH₂CH₂-Cy-Np3-F, R¹-Te1-CH₂CH₂-Cy-Np4-F, R¹-Te2-CH₂CH₂-Cy-Ph1-F,
R¹-Te2-CH₂CH₂-Cy-Ph2-F, R¹-Te2-CH₂CH₂-Cy-Ph3-F, R¹-Te2-CH₂CH₂-Cy-Np1-F,
R¹-Te2-CH₂CH₂-Cy-Np2-F, R¹-Te2-CH₂CH₂-Cy-Np3-F, R¹-Te2-CH₂CH₂-Cy-Np4-F,
R¹-Te1-Ph1-Ph1-F, R¹-Te1-Ph1-Ph2-F, R¹-Te1-Ph1-Ph3-F, R¹-Te1-Ph1-Np1-F,
R¹-Te1-Ph1-Np2-F, R¹-Te1-Ph1-Np3-F, R¹-Te1-Ph1-Np4-F, R¹-Te2-Ph1-Ph1-F,
R¹-Te2-Ph1-Ph2-F, R¹-Te2-Ph1-Ph3-F, R¹-Te2-Ph1-Np1-F, R¹-Te2-Ph1-Np2-F,
R¹-Te2-Ph1-Np3-F, R¹-Te2-Ph1-Np4-F,
R¹-Te1-Ph1-CH₂CH₂-Ph2-F, R¹-Te1-Ph1-CH₂CH₂-Ph3-F, R¹-Te1-Ph1-CH₂CH₂-Np1-F,
R¹-Te1-Ph1-CH₂CH₂-Np2-F, R¹-Te1-Ph1-CH₂CH₂-Np3-F, R¹-Te1-Ph1-CH₂CH₂-Np4-F,
R¹-Te2-Ph1-CH₂CH₂-Ph1-F, R¹-Te2-Ph1-CH₂CH₂-Ph2-F, R¹-Te2-Ph1-CH₂CH₂-Ph3-F,
R¹-Te2-Ph1-CH₂CH₂-Np1-F, R¹-Te2-Ph1-CH₂CH₂-Np2-F, R¹-Te2-Ph1-CH₂CH₂-Np3-F,
R¹-Te2-Ph1-CH₂CH₂-Np4-F,
R¹-Te1-Ph1-C≡C-Ph2-F, R¹-Te1-Ph1-C≡C-Ph3-F, R¹-Te1-Ph1-C≡C-Np1-F,
R¹-Te1-Ph1-C≡C-Np2-F, R¹-Te1-Ph1-C≡C-Np3-F, R¹-Te1-Ph1-C≡C-Np4-F,
R¹-Te2-Ph1-C≡C-Ph1-F, R¹-Te2-Ph1-C≡C-Ph2-F, R¹-Te2-Ph1-C≡C-Ph3-F,
R¹-Te2-Ph1-C≡C-Np1-F, R¹-Te2-Ph1-C≡C-Np2-F, R¹-Te2-Ph1-C≡C-Np3-F,
R¹-Te2-Ph1-C≡C-Np4-F,
R¹-Te1-Ph2-Ph1-F, R¹-Te1-Ph2-Ph2-F, R¹-Te1-Ph2-Ph3-F, R¹-Te1-Ph2-Np1-F,
R¹-Te1-Ph2-Np2-F, R¹-Te1-Ph2-Np3-F, R¹-Te1-Ph2-Np4-F, R¹-Te2-Ph2-Ph1-F, R¹-Te2-Ph2-Ph2-F, R¹-Te2-Ph2-Ph3-F, R¹-Te2-Ph2-Np1-F, R¹-Te2-Ph2-Np2-F,
R¹-Te2-Ph2-Np3-F, R¹-Te2-Ph2-Np4-F,
R¹-Te1-Ph2-CH₂CH₂-Ph2-F, R¹-Te1-Ph2-CH₂CH₂-Ph3-F, R¹-Te1-Ph2-CH₂CH₂-Np1-F,
R¹-Te1-Ph2-CH₂CH₂-Np2-F, R¹-Te1-Ph2-CH₂CH₂-Np3-F, R¹-Te1-Ph2-CH₂CH₂-Np4-F,
R¹-Te2-Ph2-CH₂CH₂-Ph1-F, R¹-Te2-Ph2-CH₂CH₂-Ph2-F, R¹-Te2-Ph2-CH₂CH₂-Ph3-F,
R¹-Te2-Ph2-CH₂CH₂-Np1-F, R¹-Te2-Ph2-CH₂CH₂-Np2-F, R¹-Te2-Ph2-CH₂CH₂-Np3-F,
R¹-Te2-Ph2-CH₂CH₂-Np4-F,
R¹-Te1-Ph2-C≡C-Ph2-F, R¹-Te1-Ph2-C≡C-Ph3-F, R¹-Te2-Ph2-C≡C-Ph1-F,
R¹-Te2-Ph2-C≡C-Ph2-F, R¹-Te2-Ph2-C≡C-Ph3-F,
R¹-Te1-Ph3-Ph1-F, R¹-Te1-Ph3-Ph2-F, R¹-Te1-Ph3-Ph3-F, R¹-Te1-Ph3-Np1-F,
R¹-Te1-Ph3-Np2-F, R¹-Te1-Ph3-Np3-F, R¹-Te1-Ph3-Np4-F, R¹-Te2-Ph3-Ph1-F,
R¹-Te2-Ph3-Ph2-F, R¹-Te2-Ph3-Ph3-F, R¹-Te2-Ph3-Np1-F, R¹-Te2-Ph3-Np2-F,
R¹-Te2-Ph3-Np3-F, R¹-Te2-Ph3-Np4-F,
R¹-Te1-Ph3-CH₂CH₂-Ph2-F, R¹-Te1-Ph3-CH₂CH₂-Ph3-F, R¹-Te1-Ph3-CH₂CH₂-Np1-F,
R¹-Te1-Ph3-CH₂CH₂-Np2-F, R¹-Te1-Ph3-CH₂CH₂-Np3-F, R¹-Te1-Ph3-CH₂CH₂-Np4-F,
R¹-Te2-Ph3-CH₂CH₂-Ph1-F, R¹-Te2-Ph3-CH₂CH₂-Ph1-F, R¹-Te2-Ph3-CH₂CH₂-Ph3-F,
R¹-Te2-Ph3-CH₂CH₂-Np1-F, R¹-Te2-Ph3-CH₂CH₂-Np2-F, R¹-Te2-Ph3-CH₂CH₂-Np3-F,
R¹-Te2-Ph3-CH₂CH₂-Np4-F,
R¹-Te1-Ph3-C≡C-Ph2-F, R¹-Te1-Ph3-C≡C-Ph3-F, R¹-Te2-Ph3-C≡C-Ph1-F,
R¹-Te2-Ph3-C≡C-Ph2-F, R¹-Te2-Ph3-C≡C-Ph3-F,
R¹-Te1-Np1-Ph1-F, R¹-Te1-Np1-Ph2-F, R¹-Te1-Np1-Ph3-F, R¹-Te2-Np1-Ph1-F,
R¹-Te2-Np1-Ph2-F, R¹-Te2-Np1-Ph3-F,
R¹-Te1-Np1-CH₂CH₂-Ph2-F, R¹-Te1-Np1-CH₂CH₂-Ph3-F, R¹-Te2-Np1-CH₂CH₂-Ph1-F,
R¹-Te2-Np1-CH₂CH₂-Ph2-F, R¹-Te2-Np1-CH₂CH₂-Ph3-F,
R¹-Te1-Np2-Ph1-F, R¹-Te1-Np2-Ph2-F, R¹-Te1-Np2-Ph3-F, R¹-Te2-Np2-Ph1-F,
R¹-Te2-Np2-Ph2-F, R¹-Te2-Np2-Ph3-F,
R¹-Te1-Np2-CH₂CH₂-Ph2-F, R¹-Te1-Np2-CH₂CH₂-Ph3-F, R¹-Te2-Np2-CH₂CH₂-Ph1-F,
R¹-Te2-Np2-CH₂CH₂-Ph2-F, R¹-Te2-Np2-CH₂CH₂-Ph3-F,
R¹-Te1-Np3-Ph1-F, R¹-Te1-Np3-Ph2-F, R¹-Te1-Np3-Ph3-F, R¹-Te2-Np3-Ph1-F,
R¹-Te2-Np3-Ph2-F, R¹-Te2-Np3-Ph3-F,
R¹-Te1-Np3-CH₂CH₂-Ph2-F, R¹-Te1-Np3-CH₂CH₂-Ph3-F, R¹-Te2-Np3-CH₂CH₂-Ph1-F,
R¹-Te2-Np3-CH₂-Ph2-F, R¹-Te2-Np3-CH₂CH₂-Ph3-F,
R¹-Te1-Np4-Ph1-F, R¹-Te1-Np4-Ph2-F, R¹-Te1-Np4-Ph3-F, R¹-Te2-Np4-Ph1-F,
R¹-Te2-Np4-Ph2-F, R¹-Te2-Np4-Ph3-F,
R¹-Te1-Np4-CH₂CH₂-Ph2-F, R¹-Te1-Np4-CH₂CH₂-Ph3-F, R¹-Te1-Np4-CH₂CH₂-Ph1-F,
R¹-Te2-Np4-CH₂CH₂-Ph2-F, R¹-Te2-Np4-CH₂CH₂-Ph3-F,
R¹-Te1-CH₂CH₂-Ph1-Ph1-F, R¹-Te1-CH₂CH₂-Ph1-Ph2-F, R¹-Te1-CH₂CH₂-Ph1-Ph3-F,
R¹-Te1-CH₂CH₂-Ph1-Np1-F, R¹-Te1-CH₂CH₂-Ph1-Np2-F, R¹-Te1-CH₂CH₂-Ph1-Np3-F,
R¹-Te1-CH₂CH₂-Ph1-Np4-F, R¹-Te2-CH₂CH₂-Ph1-Ph1-F, R¹-Te2-CH₂CH₂-Ph1-Ph2-F,
R¹-Te2-CH₂CH₂-Ph1-Ph3-F, R¹-Te2-CH₂CH₂-Ph1-Np1-F, R¹-Te2-CH₂CH₂-Ph1-Np2-F,
R¹-Te2-CH₂CH₂-Ph1-Np3-F, R¹-Te2-CH₂CH₂-Ph1-Np4-F, R¹-Te1-CH₂CH₂-Ph2-Ph1-F, R¹-Te1-CH₂CH₂-Ph2-Ph2-F, R¹-Te1-CH₂CH₂-Ph2-Ph3-F, R¹-Te1-CH₂CH₂-Ph2-Np1-F,
R¹-Te1-CH₂CH₂-Ph2-Np2-F, R¹-Te1-CH₂CH₂-Ph2-Np3-F, R¹-Te1-CH₂CH₂-Ph2-Np4-F,
R¹-Te2-CH₂CH₂-Ph2-Ph1-F, R¹-Te2-CH₂CH₂-Ph2-Ph2-F, R¹-Te2-CH₂CH₂-Ph2-Ph³-F,
R¹-Te2-CH₂CH₂-Ph2-Np1-F, R¹-Te2-CH₂CH₂-Ph2-Np2-F, R¹-Te2-CH₂CH₂-Ph2-Np3-F,
R¹-Te2-CH₂CH₂-Ph2-Np4-F, R¹-Te1-CH₂CH₂-Ph3-Ph1-F, R¹-Te1-CH₂CH₂-Ph3-Ph2-F,
R¹-Te1-CH₂CH₂-Ph3-Ph3-F, R¹-Te1-CH₂CH₂-Ph3-Np1-F, R¹-Te1-CH₂CH₂-Ph3-Np2-F,
R¹-Te1-CH₂CH₂-Ph3-Np3-F, R¹-Te1-CH₂CH₂-Ph3-Np4-F, R¹-Te2-CH₂CH₂-Ph3-Ph1-F,
R¹-Te2-CH₂CH₂-Ph3-Ph2-F, R¹-Te2-CH₂CH₂-Ph3-Ph3-F, R¹-Te2-CH₂CH₂-Ph3-Np1-F,
R¹-Te2-CH₂CH₂-Ph3-Np2-F, R¹-Te2-CH₂CH₂-Ph3-Np3-F, R¹-Te2-CH₂CH₂-Ph3-Np4-F,
R¹-Te1-CH₂CH₂-Np1-Ph1-F, R¹-Te1-CH₂CH₂-Np1-Ph2-F, R¹-Te1-CH₂CH₂-Np1-Ph3-F,
R¹-Te2-CH₂CH₂-Np1-Ph1-F, R¹-Te2-CH₂CH₂-Np1-Ph2-F, R³-Te2-CH₂CH₂-Np1-Ph3-F,
R¹-Te1-CH₂CH₂-Np2-Ph1-F, R¹-Te1-CH₂CH₂-Np2-Ph2-F, R¹-Te1-CH₂CH₂-Np2-Ph3-F,
R¹-Te2-CH₂CH₂-Np2-Ph1-F, R¹-Te2-CH₂CH₂-Np2-Ph2-F, R¹-Te2-CH₂CH₂-Np2-Ph³-F,
R¹-Te1-CH₂CH₂-Np2-CH₂CH₂-Ph2-F, R¹-Te1-CH₂CH₂-Np2-CH₂CH₂-Ph3-F,
R¹-Te2-CH₂CH₂-Np2-CH₂CH₂-Ph1-F, R¹-Te2-CH₂CH₂-Np2-CH₂CH₂-Ph2-F,
R¹-Te2-CH₂CH₂-Np2-CH₂CH₂-Ph3-F,
R¹-Te1-CH₂CH₂-Np3-Ph1-F, R¹-Te1-CH₂CH₂-Np3-Ph2-F, R¹-Te1-CH₂CH₂-Np3-Ph3-F,
R¹-Te2-CH₂CH₂-Np3-Ph1-F, R¹-Te2-CH₂CH₂-Np3-Ph2-F, R¹-Te2-CH₂CH₂-Np3-Ph3-F,
R¹-Te1-CH₂CH₂-Np4-Ph1-F, R¹-Te1-CH₂CH₂-Np4-Ph2-F, R¹-Te1-CH₂CH₂-Np4-Ph3-F,
R¹-Te1-C≡C-Ph1-Ph1-F, R¹-Te1-C≡C-Ph1-Ph2-F, R¹-Te1-C≡C-Ph1-Ph3-F,
R¹-Te2-C≡C-Ph1-Ph1-F, R¹-Te2-C≡C-Ph1-Ph2-F, R¹-Te2-C≡C-Ph1-Ph3-F,
R¹-Te1-C≡C-Ph2-Ph1-F, R¹-Te1-C≡C-Ph2-Ph2-F, R¹-Te1-C≡Ph1-Ph3-F,
R¹-Te2-C≡C-Ph2-Ph1-F, R¹-Te2-C≡C-Ph2-Ph2-F, R¹-Te2-C≡C-Ph2-Ph3-F,
R¹-Te1-C≡C-Ph3-Ph1-F, R¹-Te1-C≡C-Ph3-Ph2-F, R¹-Te1-C≡C-Ph3-Ph3-F,
R¹-Te2-C≡C-Ph3-Ph1-F, R¹-Te2-C≡C-Ph3-Ph2-F, R¹-Te2-C≡C-Ph3-Ph3-F,
in the case in which $n^a=n^b=0$, and $n^c=n^d=1$, and Z is a cyano group,
R¹-Te1-Cy-Ph1-CN, R¹-Te1-Cy-Ph2-CN, R¹-Te1-Cy-Ph3-CN, R¹-Te1-Cy-Np1-CN,
R¹-Te1-Cy-Np2-CN, R¹-Te1-Cy-Np3-CN, R¹-Te1-Cy-Np4-CN, R¹-Te2-Cy-Ph1-CN,
R¹-Te2-Cy-Ph2-CN, R¹-Te2-Cy-Ph3-CN, R¹-Te2-Cy-Np1-CN, R¹-Te2-Cy-Np2-CN,
R¹-Te2-Cy-Np3-CN, R¹-Te2-Cy-Np4-CN,
R¹-Te1-Cy-CH₂CH₂-Ph2-CN, R¹-Te1-Cy-CH₂CH₂-Ph3-CN, R¹-Te1-Cy-CH₂CH₂-Np1-CN,
R¹-Te1-Cy-CH₂CH₂-Np2-CN, R¹-Te1-Cy-CH₂CH₂-Np3-CN, R¹-Te1-Cy-CH₂CH₂-Np4-CN,
R¹-Te2-Cy-CH₂CH₂-Ph1-CN, R¹-Te2-Cy-CH₂CH₂-Ph2-CN, R¹-Te2-Cy-CH₂CH₂-Ph3-CON,
R¹-Te2-Cy-CH₂CH₂-Np1-CN, R¹-Te2-Cy-CH₂CH₂-Np2-CN, R¹-Te2-Cy-CH₂CH₂-Np3-CN,
R¹-Te2-Cy-CH₂CH₂-Np4-CN, R¹-Te1-CH₂CH₂-Cy-Ph1-CN, R¹-Te1-CH₂CH₂-Cy-Ph2-CN, R¹-Te1-CH₂CH₂-Cy-Ph3-CN, R¹-Te1-CH₂CH₂-Cy-Np1-CN, R¹-Te1-CH₂CH₂-Cy-Np2-CN,
R¹-Te1-CH₂CH₂-Cy-Np3-CN, R¹-Te1-CH₂CH₂-Cy-Np4-CN, R¹-Te2-CH₂CH₂-Cy-Ph1-CN,
R¹-Te2-CH₂CH₂-Cy-Ph2-CN, R¹-Te2-CH₂CH₂-Cy-Ph3-CN, R¹-Te2-CH₂CH₂-Cy-Np1-CN,
R¹-Te2-CH₂CH₂-Cy-Np2-CN, R¹-Te2-CH₂CH₂-Cy-Np3-CN, R¹-Te2-CH₂CH₂-Cy-Np4-CN,
R¹-Te1-CH₂CH₂-Cy-CH₂CH₂-Ph2-CN,
R¹-Te1-Ph1-Ph1-CN, R¹-Te1-Ph1-Ph2-CN, R¹-Te1-Ph1-Ph3-CN,
R¹-Te1-Ph1-Np1-CN, R¹-Te1-Ph1-Np2-CN, R¹-Te1-Ph1-Np3-CN,
R¹-Te1-Ph1-Np4-CN, R¹-Te2-Ph1-Ph1-CN, R¹-Te2-Ph1-Ph2-CN,
R¹-Te2-Ph1-Ph3-CN, R¹-Te2-Ph1-Np1-CN, R¹-Te2-Ph1-Np2-CN,
R¹-Te2-Ph1-Np3-CN, R¹-Te2-Ph1-Np4-CN,
R¹-Te1-Ph1-CH₂CH₂-Ph2-CN, R¹-Te1-Ph1-CH₂CH₂-Ph3-CN,
R¹-Te1-Ph1-CH₂CH₂-Np1-CN, R¹-Te1-Ph1-CH₂CH₂-Np2-CN,
R¹-Te1-Ph1-CH₂CH₂-Np3-CN, R¹-Te1-Ph1-CH₂CH₂-Np4-CN,
R¹-Te2-Ph1-CH₂CH₂-Ph1-CN, R¹-Te2-Ph1-CH₂CH₂-Ph2-CN,
R¹-Te2-Ph1-CH₂CH₂-Ph3-CN, R¹-Te2-Ph1-CH₂CH₂-Np2-CN,
R¹-Te2-Ph1-CH₂CH₂-Np2-CN, R¹-Te2-Ph1-CH₂CH₂-Np3-CN,
R¹-Te2-Ph1-CH₂CH₂-Np4-CN,
R¹-Te1-Ph1-C≡C-Ph2-CN, R¹-Te1-Ph1-C≡C-Ph3-CN, R¹-Te2-Ph1-C≡C-Ph1-CN,
R¹-Te2-Ph1-C≡C-Ph2-CN, R¹-Te2-Ph1-C≡C-Ph3-CN,
R¹-Te1-Ph2-Ph1-CN, R¹-Te1-Ph2-Ph2-CN, R¹-Te1-Ph2-Ph3-CN,
R¹-Te1-Ph2-Np1-CN, R¹-Te1-Ph2-Np2-CN, R¹-Te1-Ph2-Np3-CN,
R¹-Te1-Ph2-Np4-CN, R¹-Te2-Ph2-Ph1-CN, R¹-Te2-Ph2-Ph2-CN,
R¹-Te2-Ph2-Ph3-CN, R¹-Te2-Ph2-Np1-CN, R¹-Te2-Ph2-Np2-CN,
R¹-Te2-Ph2-Np3-CN, R¹-Te2-Ph2-Np4-CN,
R¹-Te1-Ph2-CH₂CH₂-Ph2-CN, R¹-Te1-Ph2-CH₂CH₂-Ph3-CN,
R¹-Te1-Ph2-CH₂CH₂-Np1-CN, R¹-Te1-Ph2-CH₂CH₂-Np2-CN,
R¹-Te1-Ph2-CH₂CH₂-Np3-CN, R¹-Te1-Ph2-CH₂CH₂-Np4-CN,
R¹-Te2-Ph2-CH₂CH₂-Ph1-CN, R¹-Te2-Ph2-CH₂CH₂-Ph2-CN,
R¹-Te2-Ph2-CH₂CH₂-Ph3-CN, R¹-Te2-Ph2-CH₂CH₂-Np1-CN,
R¹-Te2-Ph2-CH₂CH₂-Np2-CN, R¹-Te2-Ph2-CH₂CH₂-Np3-CN,
R¹-Te2-Ph2-CH₂CH₂-Np4-CN,
R¹-Te1-Ph2-C≡C-Ph2-CN, R¹-Te1-Ph2-C≡C-Ph3-CN, R¹-Te2-Ph2-C≡C-Ph1-CN,
R¹-Te2-Ph2-C≡C-Ph2-CN, R¹-Te2-Ph2-C≡C-Ph3-CN,
R¹-Te1-Ph3-Ph1-CN, R¹-Te1-Ph3-Ph2-CN, R¹-Te1-Ph3-Ph3-CN,
R¹-Te1-Ph3-Np1-CN, R¹-Te1-Ph3-Np2-CN, R¹-Te1-Ph3-Np3-CN,
R¹-Te1-Ph3-Np4-CN, R¹-Te2-Ph3-Ph1-CN, R¹-Te2-Ph3-Ph2-CN,
R¹-Te2-Ph3-Ph3-CN, R¹-Te2-Ph3-Np1-CN, R¹-Te2-Ph3-Np2-CN,
R¹-Te2-Ph3-Np3-CN, R¹-Te2-Ph3-Np4-CN,
R¹-Te1-Ph3-CH₂CH₂-Ph2-CN, R¹-Te1-Ph3-CH₂CH₂-Ph3-CN,
R¹-Te1-Ph3-CH₂CH₂-Np1-CN, R¹-Te1-Ph3-CH₂CH₂-Np2-CN,
R¹-Te1-Ph3-CH₂CH₂-Np3-CN, R¹-Te1-Ph3-CH₂CH₂-Np4-CN,
R¹-Te2-Ph3-CH₂CH₂-Ph1-CN, R¹-Te2-Ph3-CH₂CH₂-Ph2-CN,
R¹-Te2-Ph3-CH₂CH₂-Ph3-CN, R¹-Te2-Ph3-CH₂CH₂-Np1-CN,
R¹-Te2-Ph3-CH₂CH₂-Np2-CN, R¹-Te2-Ph3-CH₂CH₂-Np3-CN,
R¹-Te2-Ph3-CH₂CH₂-Np4-CN,
R¹-Te1-Ph3-C≡C-Ph2-CN, R¹-Te1-Ph3-C≡C-Ph3-CN,
R¹-Te1-Np1-Ph1-CN, R¹-Te1-Np1-Ph2-CN, R¹-Te1-Np1-Ph3-CN,
R¹-Te1-Np1-CH₂CH₂-Ph2-CN, R¹-Te1-Np1-CH₂CH₂-Ph3-CN,
R¹-Te2-Np1-CH₂CH₂-Ph1-CN, R¹-Te2-Np1-CH₂CH₂-Ph2-CN,
R¹-Te2-Np1-CH₂CH₂-Ph3-CN,
R¹-Te1-Np2-Ph1-CN, R¹-Te1-Np2-Ph2-CN, R¹-Te1-Np2-Ph3-CN,
R¹-Te2-Np2-Ph1-CN, R¹-Te2-Np2-Ph2-CN, R¹-Te2-Np2-Ph3-CN,
R¹-Te1-Np2-CH₂CH₂-Ph2-CN, R¹-Te1-Np2-CH₂CH₂-Ph3-CN,
R¹-Te2-Np2-CH₂CH₂-Ph1-CN, R¹-Te2-Np2-CH₂CH₂-Ph2-CN,
R¹-Te2-Np2-CH₂CH₂-Ph3-CN,
R¹-Te1-Np3-Ph1-CN, R¹-Te1-Np3-Ph2-CN, R¹-Te1-Np3-Ph3-CN,
R¹-Te2-Np3-Ph1-CN, R¹-Te2-Np3-Ph2-CN, R¹-Te2-Np3-Ph3-CN,
R¹-Te1-Np3-CH₂CH₂-Ph2-CN, R¹-Te1-Np3-CH₂CH₂-Ph3-CN,
R¹-Te2-Np3-CH₂CH₂-Ph1-CN, R¹-Te2-Np3-CH₂CH₂-Ph2-CN,
R¹-Te2-Np3-CH₂CH₂-Ph3-CN,
R¹-Te1-Np4-Ph1-CN, R¹-Te1-Np4-Ph2-CN, R¹-Te1-Np4-Ph3-CN,
R¹-Te2-Np4-Ph1-CN, R¹-Te2-Np4-Ph2-CN, R¹-Te2-Np4-Ph3-CN,
R¹-Te1-Np4-CH₂CH₂-Ph2-CN, R¹-Te1-Np4-CH₂CH₂-Ph3-CN,
R¹-Te2-Np4-CH₂CH₂-Ph1-CN, R¹-Te2-Np4-CH₂CH₂-Ph2-CN,
R¹-Te1-CH₂CH₂-Ph1-Ph1-CN, R¹-Te1-CH₂CH₂-Ph1-Ph2-CN,
R¹-Te1-CH₂CH₂-Ph1-Ph3-CN, R¹-Te1-CH₂CH₂-Ph1-Np1-CN,
R¹-Te1-CH₂CH₂-Ph1-Np2-CN, R¹-Te1-CH₂CH₂-Ph1-Np3-CN,
R¹-Te1-CH₂CH₂-Ph1-Np4-CN, R¹-Te2-CH₂CH₂-Ph1-Ph1-CN,
R¹-Te2-CH₂CH₂-Ph1-Ph2-CN, R¹-Te2-CH₂CH₂-Ph1-Ph3-CN,
R¹-Te2-CH₂CH₂-Ph1-Np1-CN, R¹-Te2-CH₂CH₂-Ph1-Np2-CN,
R¹-Te2-CH₂CH₂-Ph1-Np3-CN, R¹-Te2-CH₂CH₂-Ph1-Np4-CN,
R¹-Te1-CH₂CH₂-Ph2-Ph1-CN, R¹-Te1-CH₂CH₂-Ph2-Ph2-CN,
R¹-Te1-CH₂CH₂-Ph2-Ph3-CN, R¹-Te1-CH₂CH₂-Ph2-Np1-CN,
R¹-Te1-CH₂CH₂-Ph2-Np2-CN, R¹-Te1-CH₂CH₂-Ph2-Np3-CN, R¹-Te1-CH₂CH₂-Ph2-Np4-CN, R¹-Te2-CH₂CH₂-Ph2-Ph1-CN,
R¹-Te2-CH₂CH₂-Ph2-Ph2-CN, R¹-Te2-CH₂CH₂-Ph2-Ph3-CN,
R¹-Te2-CH₂CH₂-Ph2-Np1-CN, R¹-Te2-CH₂CH₂-Ph2-Np2-CN,
R¹-Te2-CH₂CH₂-Ph2-Np3-CN, R¹-Te2-CH₂CH₂-Ph2-Np4-CN,
R¹-Te1-CH₂CH₂-Ph3-Ph1-CN, R¹-Te1-CH₂CH₂-Ph3-Ph2-CN,
R¹-Te1-CH₂CH₂-Ph3-Ph3-CN, R¹-Te1-CH₂CH₂-Ph3-Np1-CN,
R¹-Te1-CH₂CH₂-Ph3-Np2-CN, R¹-Te1-CH₂CH₂-Ph3-Np3-CN,
R¹-Te1-CH₂CH₂-Ph3-Np4-CN, R¹-Te2-CH₂CH₂-Ph3-Ph1-CN,
R¹-Te2-CH₂CH₂-Ph3-Ph2-CN, R¹-Te2-CH₂CH₂-Ph3-Ph3-CN,
R¹-Te2-CH₂CH₂-Ph3-Np1-CN, R¹-Te2-CH₂CH₂-Ph3-Np2-CN,
R¹-Te2-CH₂CH₂-Ph3-Np3-CN, R¹-Te2-CH₂CH₂-Ph3-Np4-CN,
R¹-Te1-CH₂CH₂-Np1-Ph1-CN, R¹-Te1-CH₂CH₂-Np1-Ph2-CN,
R¹-Te1-CH₂CH₂-Np1-Ph3-CN, R¹-Te2-CH₂CH₂-Np1-Ph1-CN,
R¹-Te2-CH₂CH₂-Np1-Ph2-CN, R¹-Te2-CH₂CH₂-Np1-Ph3-CN,
R¹-Te1-CH₂CH₂-Np2-Ph1-CN, R¹-Te1-CH₂CH₂-Np2-Ph2-CN,
R¹-Te1-CH₂CH₂-Np2-Ph3-CN, R¹-Te2-CH₂CH₂-Np2-Ph1-CN,
R¹-Te2-CH₂CH₂-Np2-Ph2-CN, R¹-Te2-CH₂CH₂-Np2-Ph3-CN,
R¹-Te1-CH₂CH₂-Np3-Ph1-CN, R¹-Te1-CH₂CH₂-Np3-Ph2-CN,
R¹-Te1-CH₂CH₂-Np3-Ph3-CN, R¹-Te2-CH₂CH₂-Np3-Ph1-CN,
R¹-Te2-CH₂CH₂-Np3-Ph2-CN, R¹-Te2-CH₂CH₂-Np3-Ph3-CN,
R¹-Te1-CH₂CH₂-Np4-Ph1-CN, R¹-Te1-CH₂CH₂-Np4-Ph2-CN,
R¹-Te1-CH₂CH₂-Np4-Ph3-CN, R¹-Te2-CH₂CH₂-Np4-Ph1-CN,
R¹-Te2-CH₂CH₂-Np4-Ph2-CN, R¹-Te2-CH₂CH₂-Np4-Ph3-CN,
R¹-Te1-C≡C-Ph1-Ph1-CN, R¹-Te1-C≡C-Ph1-Ph2-CN, R¹-Te1-Ce-Ph1-Ph3-CN,
R¹-Te2-C≡C-Ph1-Ph1-CN, R¹-Te2-C≡C-Ph1-Ph2-CN, R¹-Te2-C≡C-Ph1-Ph3-CN,
R¹-Te1-C≡C-Ph2-Ph1-CN, R¹-Te1-C≡C-Ph2-Ph2-CN, R¹-Te1-C≡C-Ph2-Ph3-CN,
R¹-Te2-C≡C-Ph2-Ph1-CN, R¹-Te2-C≡C-Ph2-Ph2-CN, R¹-Te2-C≡C-Ph2-Ph3-CN,
R¹-Te1-C≡C-Ph3-Ph1-CN, R¹-Te1-C≡C-Ph3-Ph2-CN, R¹-Te1-C≡C-Ph3-Ph3-CN,
R¹-Te2-C≡C-Ph3-Ph1-CN, R¹-Te2-C≡C-Ph3-Ph2-CN, R¹-Te2-C≡C-Ph3-Ph3-CN,
in the case in which $n^a=n^b=0$, and $n^c=n^d=1$, and Z is a trifluoromethoxy group,
R¹-Te1-Cy-Ph1-OCF₃, R¹-Te1-Cy-Ph2-OCF₃, R¹-Te1-Cy-Ph3-OCF₃,
R¹-Te1-Cy-Np1-OCF₃, R¹-Te1-Cy-Np2-OCF₃, R¹-Te1-Cy-Np3-OCF₃,
R¹-Te1-Cy-Np4-OCF₃, R¹-Te2-Cy-Ph1-OCF₃, R¹-Te2-Cy-Ph2-OCF₃,
R¹-Te2-Cy-Ph3-OCF₃, R¹-Te2-Cy-Np1-OCF₃, R¹-Te2-Cy-Np2-OCF₃,
R¹-Te2-Cy-Np3-OCF₃, R¹-Te2-Cy-Np4-OCF₃,
R¹-Te1-Cy-CH₂CH₂-Ph2-OCF₃, R¹-Te1-Cy-CH₂CH₂-Ph3-OCF₃,
R¹-Te1-Cy-CH₂CH₂-Np1-OCF₃, R¹-Te1-Cy-CH₂CH₂-Np2-OCF₃,
R¹-Te1-Cy-CH₂CH₂-Np3-OCF₃, R¹-Te1-Cy-CH₂CH₂-Np2-OCF₃,
R¹-Te2-Cy-CH₂CH₂-Ph3-OCF₃, R¹-Te2-Cy-CH₂CH₂-Ph4-OCF₃,
R¹-Te2-Cy-CH₂CH₂-Ph3-OCF₃, R¹-Te2-Cy-CH₂CH₂-Np1-OCF₃,
R¹-Te2-Cy-CH₂CH₂-Np2-OCF₃, R¹-Te2-Cy-CH₂CH₂-Np3-OCF₃,
R¹-Te2-Cy-CH₂CH₂-Np2-OCF₃, R¹-Te2-CH₂CH₂-Cy-Ph1-OCF₃,
R¹-Te2-C≡CH₂CH₂-Cy-Ph2-OCF₃, R¹-Te1-CH₂CH₂-Cy-Ph1-OCF₃,
R¹-Te1-CH₂CH₂-Cy-Np1-OCF₃, R¹-Te1-CH₂CH₂-Cy-Np2-OCF₃,
R¹-Te1-CH₂CH₂-Cy-Np3-OCF₃, R¹-Te1-CH₂CH₂-Cy-Np2-OCF₃,
R¹-Te2-CH₂CH₂-Cy-Ph1-OCF₃, R¹-Te2-CH₂CH₂-Cy-Ph2-OCF₃,
R¹-Te2-CH₂CH₂-Cy-Ph3-OCF₃, R¹-Te2-CH₂CH₂-Cy-Np1-OCF₃,
R¹-Te2-CH₂CH₂-Cy-Np2-OCF₃, R¹-Te2-CH₂CH₂-Cy-Np3-OCF₃,
R¹-Te2-CH₂CH₂-Cy-Np4-OCF₃,
R¹-Te1-Ph1-Ph1-OCF₃, R¹-Te1-Ph1-Ph2-OCF₃, R¹-Te1-Ph1-Ph3-OCF₃,
R¹-Te1-Ph1-Np1-OCF₃, R¹-Te1-Ph1-Np2-OCF₃, R¹-Te1-Ph1-Np3-OCF₃,
R¹-Te1-Ph1-Np4-OCF₃, R¹-Te2-Ph1-Ph1-OCF₃, R¹-Te2-Ph1-Ph2-OCF₃,
R¹-Te2-Ph1-Ph3-OCF₃, R¹-Te2-Ph1-Np1-OCF₃, R¹-Te2-Ph1-Np2-OCF₃,
R¹-Te2-Ph1-Np3-OCF₃, R¹-Te2-Ph1-Np4-OCF₃,
R¹-Te1-Ph1-CH₂CH₂-Ph2-OCF₃, R¹-Te1-Ph1-CH₂CH₂-Ph3-OCF₃,
R¹-Te1-Ph1-CH₂CH₂-Np1-OCF₃, R¹-Te1-Ph1-CH₂CH₂-Np2-OCF₃,
R¹-Te1-Ph1-CH₂CH₂-Np3-OCF₃, R¹-Te1-Ph1-CH₂CH₂-Np4-OCF₃,
R¹-Te2-Ph1-CH₂CH₂-Ph1-OCF₃, R¹-Te2-Ph1-CH₂CH₂-Ph2-OCF₃,
R¹-Te2-Ph1-CH₂CH₂-Ph3-OCF₃, R¹-Te2-Ph1-CH₂CH₂-Np1-OCF₃,
R¹-Te2-Ph1-CH₂CH₂-Np2-OCF₃, R¹-Te2-Ph1-CH₂CH₂-Np3-OCF₃,
R¹-Te2-Ph1-CH₂CH₂-Np4-OCF₃,
R¹-Te1-Ph1-C≡C-Ph2-OCF₃, R¹-Te1-Ph1-C≡C-Ph3-OCF₃,
R¹-Te2-Ph1-C≡C-Ph1-OCF₃, R¹-Te2-Ph1-C≡C-Ph2-OCF₃,
R¹-Te2-Ph1-C≡C-Ph3-OCF₃,
R¹-Te1-Ph2-Ph1-OCF₃, R¹-Te1-Ph2-Ph2-OCF₃, R¹-Te1-Ph2-Ph3-OCF₃,
R¹-Te1-Ph2-Np1-OCF₃, R¹-Te1-Ph2-Np2-OCF₃, R¹-Te1-Ph2-Np3-OCF₃,
R¹-Te1-Ph2-Np4-OCF₃, R¹-Te2-Ph2-Ph1-OCF₃, R¹-Te2-Ph2-Ph2-OCF₃,
R¹-Te2-Ph2-Ph3-OCF₃, R¹-Te2-Ph2-Np1-OCF₃, R¹-Te2-Ph2-Np2-OCF₃,
R¹-Te2-Ph2-Np3-OCF₃, R¹-Te2-Ph2-Np4-OCF₃,
R¹-Te1-Ph2-CH₂CH₂-Ph2-OCF₃, R¹-Te1-Ph2-CH₂CH₂-Ph3-OCF₃,
R¹-Te1-Ph2-CH₂CH₂-Np1-OCF₃, R¹-Te1-Ph2-CH₂CH₂-Np2-OCF₃, R¹-Te1-Ph2-CH₂CH₂-Np3-OCF₃, R¹-Te1-Ph2-CH₂CH₂-Np4-OCF₃,
R¹-Te2-Ph2-CH₂CH₂-Ph1-OCF₃, R¹-Te2-Ph2-CH₂CH₂-Ph2-OCF₃,
R¹-Te2-Ph2-CH₂CH₂-Ph3-OCF₃, R¹-Te2-Ph2-CH₂CH₂-Np1-OCF₃,
R¹-Te2-Ph2-CH₂CH₂-Np2-OCF₃, R¹-Te2-Ph2-CH₂CH₂-Np3-OCF₃,
R¹-Te2-Ph2-CH₂CH₂-Np4-OCF₃,
R¹-Te1-Ph2-C≡C-Ph2-OCF₃, R¹-Te1-Ph2-C≡C-Ph3-OCF₃,
R¹-Te2-Ph2-C≡C-Ph1-OCF₃, R¹-Te2-Ph2-C≡C-Ph2-OCF₃,
R¹-Te2-Ph2-C≡C-Ph3-OCF₃,
R¹-Te1-Ph3-Ph1-OCF₃, R¹-Te1-Ph3-Ph2-OCF₃, R¹-Te1-Ph3-Ph3-OCF₃,
R¹-Te1-Ph3-Np1-OCF₃, R¹-Te1-Ph3-Np2-OCF₃, R¹-Te1-Ph3-Np3-OCF₃,
R¹-Te1-Ph3-Np4-OCF₃, R¹-Te2-Ph3-Ph1-OCF₃, R¹-Te2-Ph3-Ph2-OCF₃,
R¹-Te2-Ph3-Ph3-OCF₃, R¹-Te2-Ph3-Np1-OCF₃, R¹-Te2-Ph3-Np2-OCF₃,
R¹-Te2-Ph3-Np3-OCF₃, R¹-Te2-Ph3-Np4-OCF₃,
R¹-Te1-Ph3-CH₂CH₂-Ph2-OCF₃, R¹-Te1-Ph3-CH₂CH₂-Ph3-OCF₃,
R¹-Te1-Ph3-CH₂CH₂-Np1-OCF₃, R¹-Te1-Ph3-CH₂CH₂-Np2-OCF₃,
R¹-Te1-Ph3-CH₂CH₂-Np3-OCF₃, R¹-Te1-Ph3-CH₂CH₂-Np4-OCF₃,
R¹-Te2-Ph3-CH₂CH₂-Ph1-OCF₃, R¹-Te2-Ph3-CH₂CH₂-Ph2-OCF₃,
R¹-Te2-Ph3-CH₂CH₂-Ph3-OCF₃, R¹-Te2-Ph3-CH₂CH₂-Np1-OCF₃,
R¹-Te2-Ph3-CH₂CH₂-Np2-OCF₃, R¹-Te2-Ph3-CH₂CH₂-Np3-OCF₃,
R¹-Te2-Ph3-CH₂CH₂-Np4-OCF₃,
R¹-Te1-Ph3-C≡C-Ph2-OCF₃, R¹-Te1-Ph3-C≡C-Ph3-OCF₃,
R¹-Te2-Ph3-C≡C-Ph1-OCF₃, R¹-Te2-Ph3-C≡C-Ph2-OCF₃,
R¹-Te2-Ph3-C≡C-Ph3-OCF₃,
R¹-Te1-Np1-Ph1-OCF₃, R¹-Te1-Np1-Ph2-OCF₃, R¹-Te1-Np1-Ph3-OCF₃,
R¹-Te2-Np1-Ph1-OCF₃, R¹-Te2-Np1-Ph2-OCF₃, R¹-Te2-Np1-Ph3-OCF₃,
R¹-Te1-Np1-CH₂CH₂-Ph2-OCF₃, R¹-Te1-Np1-CH₂CH₂-Ph3-OCF₃,
R¹-Te2-Np1-CH₂CH₂-Ph1-OCF₃, R¹-Te2-Np1-CH₂CH₂-Ph2-OCF₃,
R¹-Te2-Np1-CH₂CH₂-Ph3-OCF₃,
R¹-Te1-Np2-Ph1-OCF₃, R¹-Te1-Np2-Ph2-OCF₃, R¹-Te1-Np2-Ph3-OCF₃,
R¹-Te2-Np2-Ph1-OCF₃, R¹-Te2-Np2-Ph2-OCF₃, R¹-Te2-Np2-Ph3-OCF₃,
R¹-Te1-Np2-CH₂CH₂-Ph2-OCF₃, R¹-Te1-Np2-CH₂CH₂-Ph3-OCF₃,
R¹-Te2-Np2-CH₂CH₂-Ph1-OCF₃, R¹-Te2-Np2-CH₂CH₂-Ph2-OCF₃,
R¹-Te2-Np2-CH₂CH₂-Ph3-OCF₃,
R¹-Te1-Np3-Ph1-OCF₃, R¹-Te1-Np3-Ph2-OCF₃, R¹-Te1-Np3-Ph3-OCF₃,
R¹-Te2-Np3-Ph1-OCF₃, R¹-Te2-Np3-Ph2-OCF₃, R¹-Te2-Np3-Ph3-OCF₃,
R¹-Te1-Np3-CH₂CH₂-Ph1-OCF₃, R¹-Te1-Np3-CH₂CH₂-Ph3-OCF₃,
R¹-Te2-Np3-CH₂CH₂-Ph2-OCF₃, R¹-Te2-Np3-CH₂CH₂-Ph2-OCF₃,
R¹-Te2-Np3-CH₂CH₂-Ph3-OCF₃,
R¹-Te1-Np4-Ph1-OCF₃, R¹-Te1-Np4-Ph2-OCF₃, R¹-Te1-Np4-Ph3-OCF₃,
R¹-Te2-Np1-Ph1-OCF₃, R¹-Te2-Np4-Ph2-OCF₃, R¹-Te2-Np4-Ph3-OCF₃,
R¹-Te1-Np4-CH₂CH₂-Ph2-OCF₃, R¹-Te1-Np4-CH₂CU₂-Ph3-OCF₃,
R¹-Te2-Np4-CH₂CH₂-Ph1-OCF₃, R¹-Te2-Np4-CH₂CH₂-Ph2-OCF₃,
R¹-Te2-Np4-CH₂CH₂-Ph3-OCF₃,
R¹-Te1-CH₂CH₂-Ph1-Ph1-OCF₃, R¹-Te1-CH₂CH₂-Ph1-Ph2-OCF₃,
R¹-Te1-CH₂CH₂-Ph1-Ph3-OCF₃, R¹-Te1-CH₂CH₂-Ph1-Np1-OCF₃,
R¹-Te1-CH₂CH₂-Ph1-Np2-OCF₃, R¹-Te1-CH₂CH₂-Ph1-Np3-OCF₃,
R¹-Te1-CH₂CH₂-Ph1-Np4-OCF₃, R¹-Te2-CH₂CH₂-Ph1-Ph1-OCF₃,
R¹-Te2-CH₂CH₂-Ph1-Ph2-OCF₃, R¹-Te2-CH₂CH₂-Ph1-Ph3-OCF₃,
R¹-Te2-CH₂CH₂-Ph1-Np1-OCF₃, R¹-Te2-CH₂CH₂-Ph1-Np2-OCF₃,
R¹-Te2-CH₂CH₂-Ph1-Np3-OCF₃, R¹-Te2-CH₂CH₂-Ph1-Np4-OCF₃,
R¹-Te1-CH₂CH₂-Ph2-Ph1-OCF₃, R¹-Te1-CH₂CH₂-Ph2-Ph2-OCF₃,
R¹-Te1-CH₂CH₂-Ph2-Ph3-OCF₃, R¹-Te1-CH₂CH₂-Ph2-Np1-OCF₃,
R¹-Te1-CH₂CH₂-Ph2-Np2-OCF₃, R¹-Te1-CH₂CH₂-Ph2-Np3-OCF₃,
R¹-Te1-CH₂CH₂-Ph2-Np4-OCF₃, R¹-Te2-CH₂CH₂-Ph2-Ph1-OCF₃,
R¹-Te2-CH₂CH₂-Ph2-Ph2-OCF₃, R¹-Te2-CH₂CH₂-Ph2-Ph3-OCF₃,
R¹-Te2-CH₂CH₂-Ph2-Np1-OCF₃, R¹-Te2-CH₂CH₂-Ph2-Np2-OCF₃,
R¹-Te2-CH₂CH₂-Ph2-Np3-OCF₃, R¹-Te2-CH₂CH₂-Ph2-Np4-OCF₃,
R¹-Te1-CH₂CH₂-Ph3-Ph1-OCF₃, R¹-Te1-CH₂CH₂-Ph3-Ph2-OCF₃,
R¹-Te1-CH₂CH₂-Ph3-Ph3-OCF₃, R¹-Te2-CH₂CH₂-Ph3-Ph1-OCF₃,
R¹-Te2-CH₂CH₂-Ph3-Ph2-OCF₃, R¹-Te2-CH₂CH₂-Ph3-Ph3-OCF₃,
R¹-Te2-CH₂CH₂-Ph3-Np1-OCF₃, R¹-Te2-CH₂CH₂-Ph3-Np2-OCF₃,
R¹-Te2-CH₂CH₂-Ph3-Np3-OCF₃, R¹-Te2-CH₂CH₂-Ph3-Np4-OCF₃,
R¹-Te1-CH₂CH₂-Np1-Ph1-OCF₃, R¹-Te1-CH₂CH₂-Np1-Ph2-OCF₃,
R¹-Te1-CH₂CH₂-Np1-Ph3-OCF₃, R¹-Te2-CH₂CH₂-Np1-Ph1-OCF₃,
R¹-Te2-CH₂CH₂-Np1-Ph2-OCF₃, R¹-Te2-CH₂CH₂-Np1-Ph3-OCF₃,
R¹-Te1-CH₂CH₂-Np2-Ph1-OCF₃, R¹-Te1-CH₂CH₂-Np2-Ph2-OCF₃,
R¹-Te1-CH₂CH₂-Np2-Ph3-OCF₃, R¹-Te2-CH₂CH₂-Np2-Ph1-OCF₃,
R¹-Te2-CH₂CH₂-Np2-Ph2-OCF₃, R¹-Te2-CH₂CH₂-Np2-Ph3-OCF₃,
R¹-Te1-CH₂CH₂-Np3-Ph1-OCF₃, R¹-Te1-CH₂CH₂-Np3-Ph2-OCF₃,
R¹-Te1-CH₂CH₂-Np3-Ph3-OCF₃, R¹-Te2-CH₂CH₂-Np3-Ph1-OCF₃,
R¹-Te2-CH₂CH₂-Np3-Ph2-OCF₃, R¹-Te2-CH₂CH₂-Np3-Ph3-OCF₃,
R¹-Te1-CH₂CH₂-Np4-Ph1-OCF₃, R¹-Te1-CH₂CH₂-Np4-Ph2-OCF₃, R$^1$-Te1-CH$_2$CH$_2$-Np4-Ph3-OCF$_3$, R$^1$-Te2-CH$_2$CH$_2$-Np4-Ph1-OCF$_3$,
R$^1$-Te2-CH$_2$CH$_2$-Np4-Ph2-OCF$_3$, R$^1$-Te2-CH$_2$CH$_2$-Np4-Ph3-OCF$_3$,
R$^1$-Te1-C≡C-Ph1-Ph1-OCF$_3$, R$^1$-Te1-C≡C-Ph1-Ph2-OCF$_3$,
R$^1$-Te1-C≡C-Ph1-Ph3-OCF$_3$, R$^1$-Te2-C≡C-Ph1-Ph1-OCF$_3$,
R$^1$-Te2-C≡C-Ph1-Ph2-OCF$_3$, R$^1$-Te2-C≡C-Ph1-Ph3-OCF$_3$,
R$^1$-Te1-C≡C-Ph2-Ph1-OCF$_3$, R$^1$-Te1-C≡C-Ph2-Ph2-OCF$_3$,
R$^1$-Te1-C≡C-Ph2-Ph3-OCF$_3$, R$^1$-Te2-C≡C-Ph2-Ph1-OCF$_3$,
R$^1$-Te2-C≡C-Ph2-Ph2-OCF$_3$, R$^1$-Te2-C≡C-Ph2-Ph3-OCF$_3$,
R$^1$-Te1-C≡C-Ph3-Ph1-OCF$_3$, R$^1$-Te1-C≡C-Ph3-Ph2-OCF$_3$,
R$^1$-Te1-C≡C-Ph3-Ph3-OCF$_3$, R$^1$-Te2-C≡C-Ph3-Ph1-OCF$_3$,
R$^1$-Te2-C≡C-Ph3-Ph2-OCF$_3$, R$^1$-Te2-C≡C-Ph3-Ph3-OCF$_3$,
R$^1$-Te1-C≡C-Ph3-CH$_2$CH$_2$-Ph2-OCF$_3$, R$^1$-Te1-C≡C-Ph3-CH$_2$CH$_2$-Ph3-OCF$_3$, The compounds of the general formula (I) can be produced by a variety of synthetic methods depending on the selection of the group R, the linkage groups La, Lb, Lc and Ld, the polar group Z, the ring A, the ring B, the ring C, the ring D and the ring E, and n$^a$, n$^b$, n$^c$ and n$^d$, and representative examples of these synthetic methods are presented below.

The case in which ring C is the formula (IIa)

In the case in which n$^b$=1, n$^c$=n$^d$=0, the linkage group La is a single bond, —CH$_2$CH$_2$—, —CH(CH$_3$)CH$_2$—, —CH$_2$CH(CH$_3$)—, —CH(CH$_3$)CH(CH$_3$)— or —CF$_2$CF$_2$—, and the linkage group Lb is a single bond, synthesis can be completed in accordance with the following schemes.

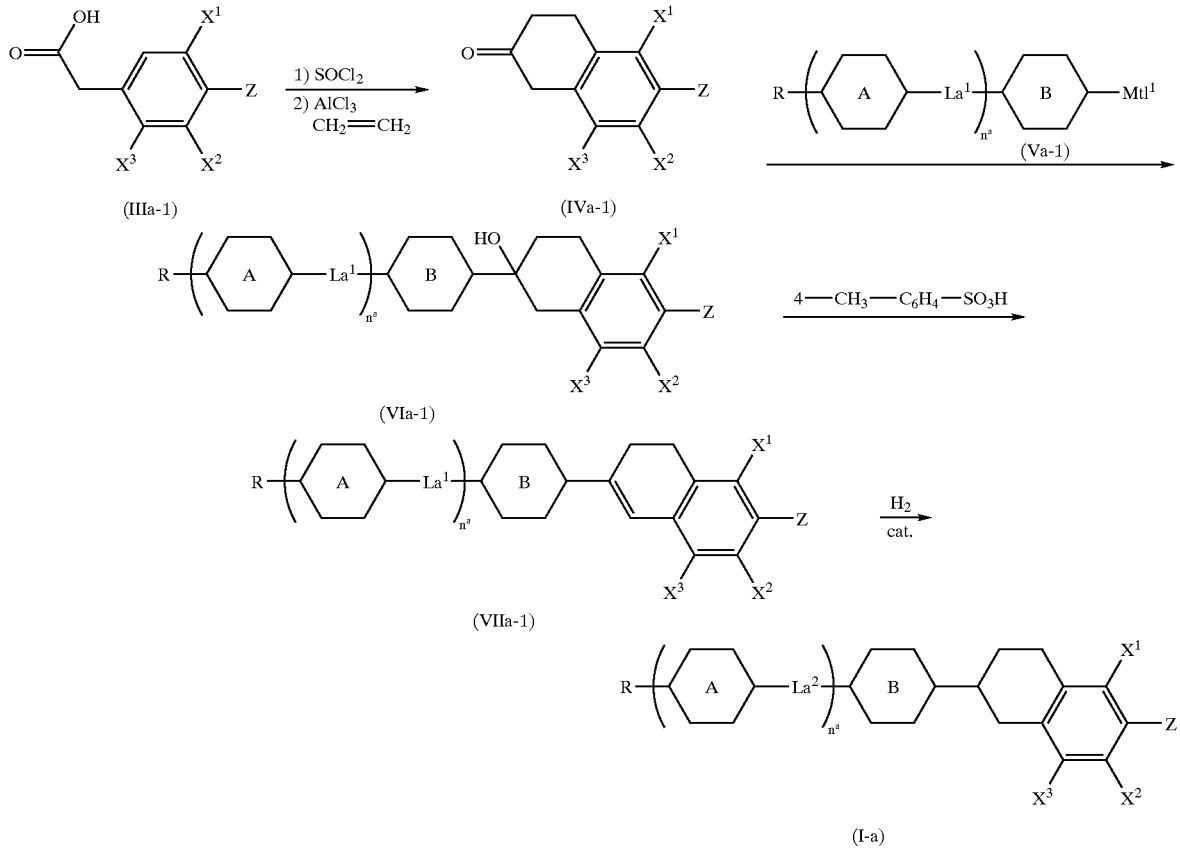

(wherein, K, the polar group Z, the ring A, the ring B, n$^a$, X$^1$, X$^2$ and X$^3$ have the same meaning as described above for the general formula (I), La$^1$ represents a single bond, —CH$_2$CH$_2$—, —CH=CH$_2$—, —C≡C—, —CH(CH$_3$)CH$_2$—, —CH$_2$CH(CH$_3$)—, —CH(CH$_3$)CH(CH$_3$)— or —CF$_2$CF$_2$—, La$^2$ represents a single bond, —CH$_2$CH$_2$—, —CH(CH$_3$)CH$_2$—, —CH$_2$CH(CH$_3$)—, —CH(CH$_3$)CH (CH$_3$)— or —CF$_2$CF$_2$—, and Mtl$^1$ represents a metal ion such as Li, BrMg, or IMg.)

That is, by using thionyl chloride or the like to convert the phenylacetic acid represented by the general formula (IIIa-1) into an acid chloride, and subsequently conducting a reaction with ethylene in the presence of aluminum chloride, a tetralone derivative represented by the general formula (IVa-1) can be prepared. By reacting this derivative with a lithium or magnesium reagent represented by the general formula (Va-1), either in or out of the presence of a metal salt such as cerium chloride or manganese chloride and a Lewis acid, an alcohol represented by the general formula (VIa-1) is obtained, and by heating this alcohol in the presence of an acid catalyst such as p-toluenesulfonic acid, a dihydronaphthalene compound represented by the general formula (VIIa-1) is obtained. Subsequent hydrogenation of this dihydronaphthalene compound in the presence of a metal catalyst such as Pd—C, Rh—C, Pt—C or Pd(OH)$_2$ or the like, yields the target compound represented by the general formula (I-a).

The lithium or magnesium reagent represented by the general formula (Va-1) is a compound frequently used in liquid crystal production, and can be easily produced from the corresponding halide or the like.

As shown in the schemes below, by replacing the lithium or magnesium reagent represented by the general formula (Va-1) with an acetylide represented by the general formula (Va-2), a compound represented by the general formula (I-b) can be produced.

general formula (I), La$^1$ represents a single bond, —CH$_2$CH$_2$—, —CH=CH—, —C≡C—, —CH(CH$_3$)CH$_2$—, —CH$_2$CH(CH$_3$)—, —CH(CH$_3$)CH(CH$_3$)— or —CF$_2$CF$_2$—, La$^2$ represents a single bond, —CH$_2$CH$_2$—, —CH(CH$_3$)CH$_2$—, —CH$_2$CH(CH$_3$)—, —CH(CH$_3$)CH(CH$_3$)— or —CF$_2$CF$_2$—, and Mtl$^1$ represents a metal ion such as Li, BrMg, or IMg.)

Furthermore, as shown in the schemes below, the compound represented by the general formula (I-b) can also be prepared by reacting the tetralone derivative represented by the general formula (IVa-1) with an ylide represented by the

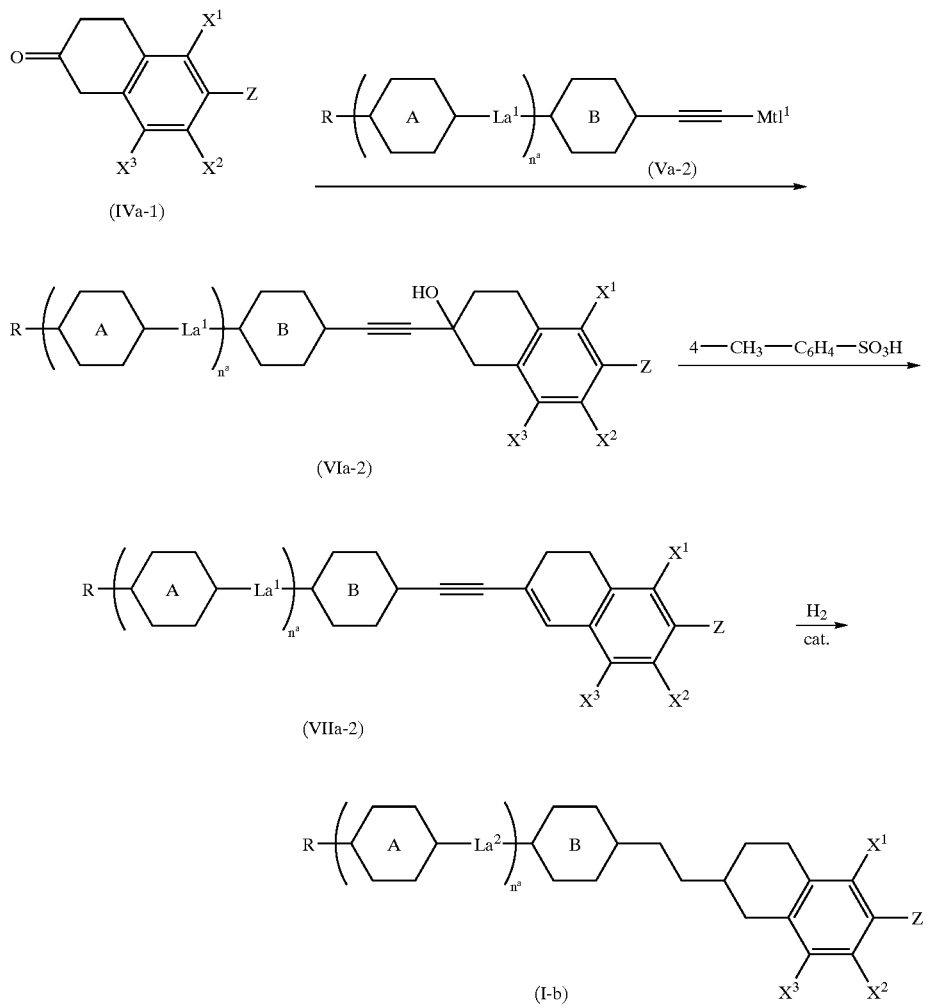

(wherein, R, the polar group Z, the ring A, the ring B, n$^a$, X$^1$, X$^2$ and X$^3$ have the same meaning as described above for the general formula (Vb-1), and then reducing the thus obtained compound (VIIb-2).

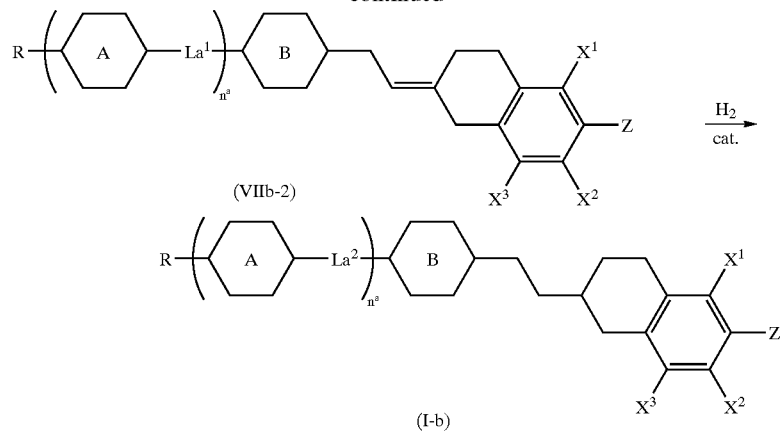

(wherein, R, the polar group Z, the ring A, the ring B, $n^a$, $X^1$, $X^2$ and $X^3$ have the same meaning as described above for the general formula (I), $La^1$ represents a single bond, —$CH_2CH_2$—, —CH=CH—, —C≡C—, —CH($CH_3$)$CH_2$—, —$CH_2$CH($CH_3$)—, —CH($CH_3$)CH($CH_3$)— or —$CF_2CF_2$—, and $La^2$ represents a single bond, —$CH_2CH_2$—, —CH($CH_3$)$CH_2$—, —$CH_2$CH($CH_3$)—, —CH($CH_3$)CH($CH_3$)— or —$CF_2CF_2$—.)

In addition, the compounds represented by the general formulas (I-b) and (I-c) can also be produced by a method shown in the schemes below.

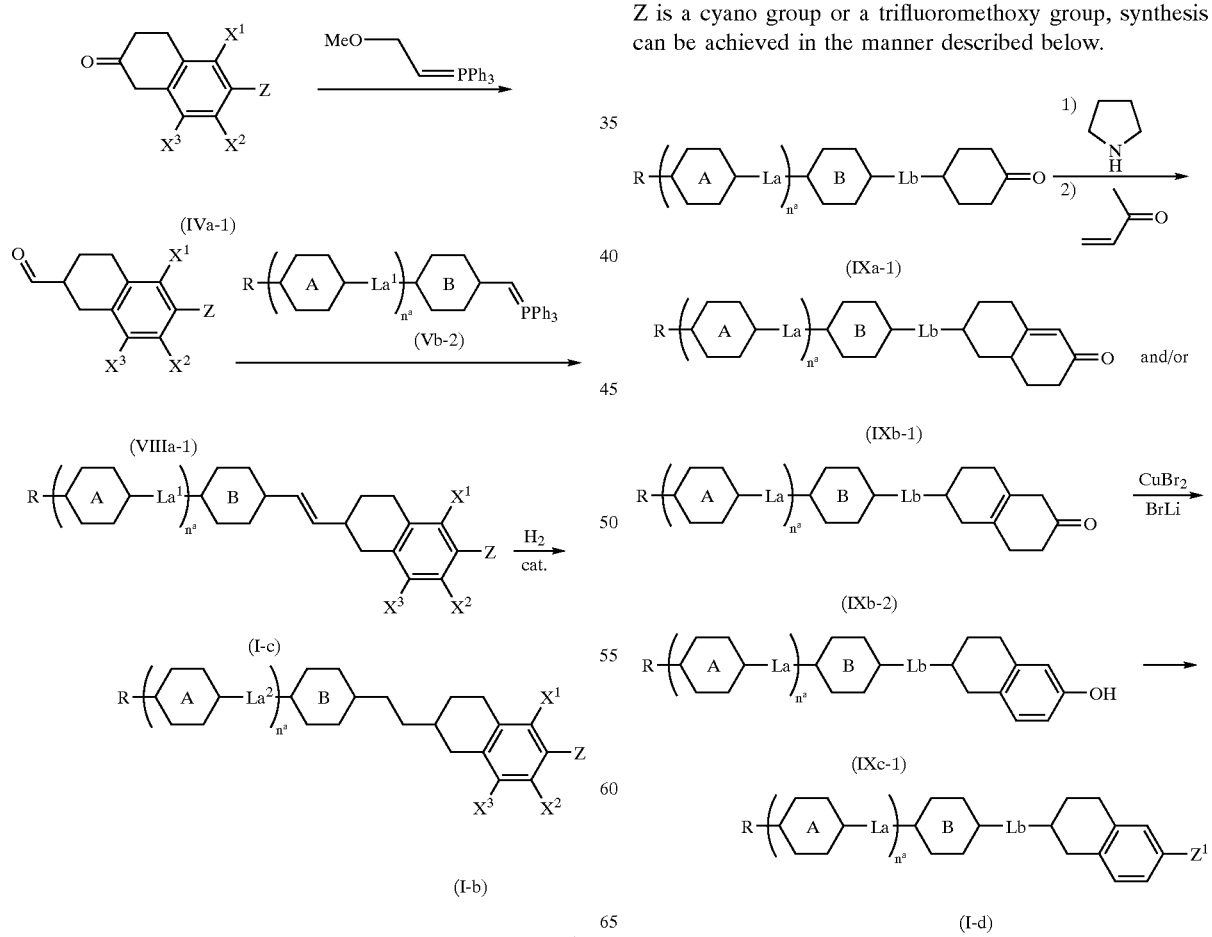

(wherein, R, the polar group Z, the ring A, the ring B, $n^a$, $X^1$, $X^2$ and $X^3$ have the same meaning as described above for the general formula (I), $La^1$ represents a single bond, —$CH_2CH_2$—, —CH=CH—, —C≡C—, —CH($CH_3$)$CH_2$—, —$CH_2$CH($CH_3$)—, —CH($CH_3$)CH($CH_3$)— or —$CF_2CF_2$—, and $La^2$ represents a single bond, —$CH_2CH_2$—, —CH($CH_3$)$CH_2$—, —$CH_2$CH($CH_3$)—, —CH($CH_3$)CH($CH_3$)— or —$CF_2CF_2$—.)

In the case in which $n^b=1$, $n^c=n^d=0$, the ring C is the formula (IIa), and $X^1$, $X^2$ and $X^3$ are hydrogen atoms, and Z is a cyano group or a trifluoromethoxy group, synthesis can be achieved in the manner described below.

(wherein, R, La, Lb, the ring A, the ring B and $n^a$ have the same meaning as described above for the general formula (I), and $Z^1$ represents a cyano group or a trifluoromethoxy group.)

That is, by subjecting a cyclohexanone derivative represented by the general formula (IXa-1) to a dehydration reaction with pyrrolidine, subsequent reaction with methyl vinyl ketone, and then treatment with an acid, a mixture of the octahydronaphthalene derivatives represented by the general formulas (IXb-1) and (IXb-2) can be obtained. By subjecting this mixture to an oxidation using copper(II) bromide or lithium bromide, a compound represented by the general formula (IXc-1) can be obtained. Following conversion of the hydroxyl group to a triflate, if the compound is reacted with copper cyanide, then a compound of the general formula (I-d) in which the $Z^1$ group is a cyano group can be obtained. Furthermore, if the phenol derivative represented by the general formula (IXc-1) is reacted with carbon tetrachloride, and subsequently reacted with potassium fluoride, then a compound of the general formula (I-d) in which the $Z^1$ group is a trifluoromethoxy group can be obtained.

In addition, by producing the compound of the general formula (Xa-1) from the formula (IIIa-2), in the same manner as for the production of the compound of the general formula (I-a), and subsequently performing a lithiation using a base such as butyllithium or lithium diisopropylamide or the like, and then reacting the product with carbon dioxide, the carboxylic acid derivative represented by the general formula (Xb-1) can be obtained. By converting this carboxylic acid to an acid chloride, and subsequently to an amide using ammonia gas, and then subjecting the product to the action of a dehydration agent, a compound represented by the general formula (I-e) can be obtained.

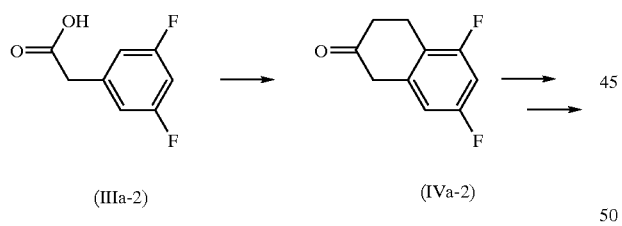

(IIIa-2)          (IVa-2)

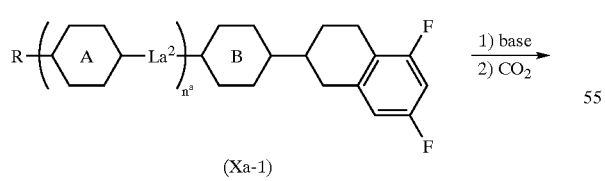

(Xa-1)

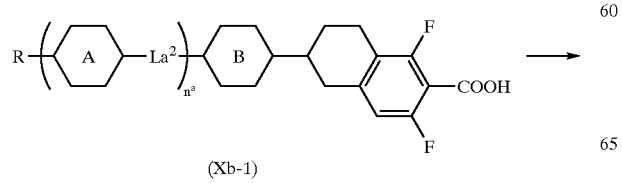

(Xb-1)

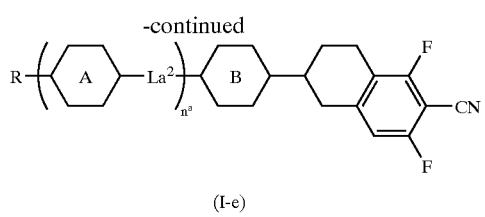

(I-e)

(wherein, R, the ring A, the ring B and $n^a$ have the same meaning as described above for the general formula (I), and $La^2$ represents a single bond, —$CH_2CH_2$—, —$CH(CH_3)CH_2$—, —$CH_2CH(CH_3)$—, —$CH(CH_3)CH(CH_3)$— or —$CF_2CF_2$—.)

Furthermore, by lithiating the compound represented by the general formula (Xa-1), and carrying out a subsequent reaction with trimethyl borate, and then with hydrogen peroxide, a compound represented by the general formula (IXc-2) can be prepared. The compound represented by the general formula (I-f) can be derived from this compound in the same manner as was described for the compound represented by the general formula (IXc-1).

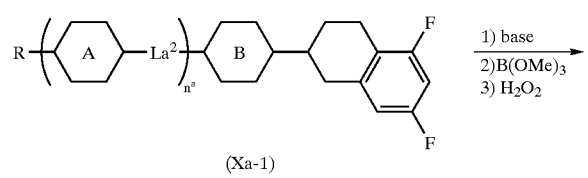

(Xa-1)

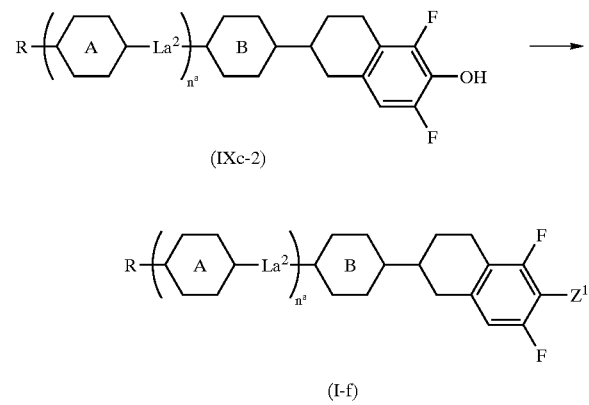

(IXc-2)

(I-f)

(wherein, R, the ring A, the ring B and $n^a$ have the same meaning as described above for the general formula (I), $La^2$ represents a single bond, —$CH_2CH_2$—, —$CH(CH_3)CH_2$—, —$CH_2CH(CH_3)$—, —$CH(CH_3)CH(CH_3)$— or —$CF_2CF_2$—, and $Z^1$ represents a cyano group or a trifluoromethoxy group.)

In the case in which $n^d=1$, $n^c=0$, the ring C is the formula (IIa), and the linkage group Lb is a single bond, synthesis can be achieved in the manner described below.

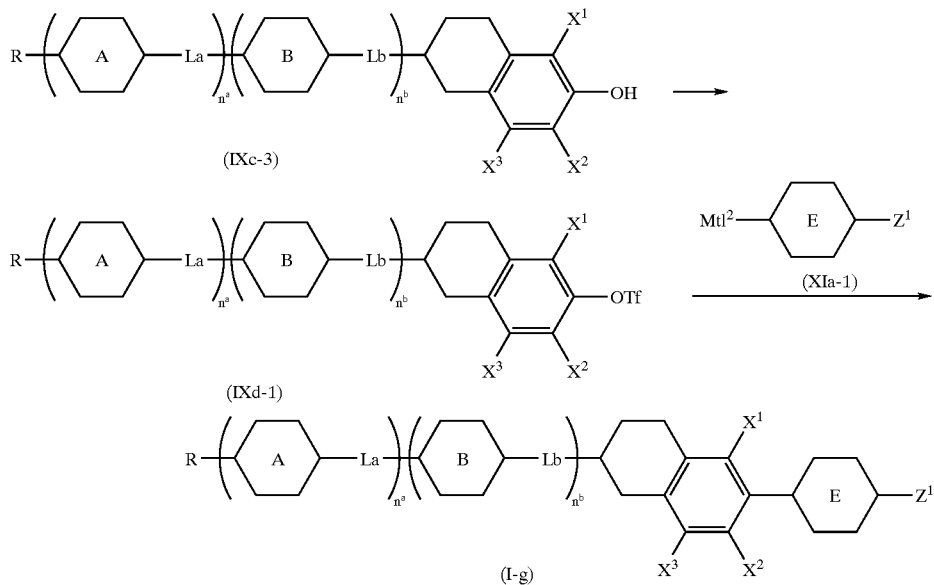

(wherein, R, the ring A, the ring B, the ring E, $n^a$, $n^b$, $X^1$, $X^2$ and $X^3$ have the same meaning as described above for the general formula (I), $Z^1$ represents a fluorine atom or a trifluoromethoxy group, Tf represents a trifluoromethanesulfonyl group, and $Mtl^2$ represents Li, ClMg, BrMg, IMg or $(HO)_2B$.)

That is, reacting a compound represented by the general formula (IXc-3), which can be prepared in the same manner as the compounds represented by the general formulas (IXc-1) and (IXc-2), with trifluoromethanesulfonic anhydride or trifluoromethanesulfonyl chloride or the like, in the presence of a base such as pyridine , diethylamine or triethylamine, and in a solvent such as dichloromethane or chloroform yields a triflate represented by the general formula (IXd-1). By reacting this triflate with a compound represented by the general formula (XIa-1) in the presence of a transition metal catalyst such as tetrakis (triphenylphosphine)palladium(0) or tetrakis (triphenylphosphine)nickel(0), a compound represented by the general formula (I-g) can be synthesized.

Furthermore, by reacting the compound represented by the general formula (IXd-1) with an acetylene compound represented by the general formula (XIb-1), in the presence of cuprous iodide and a transition metal catalyst such as dichlorobis(triphenylphosphine)palladium or tetrakis (triphenylphosphine)palladium(0), a compound represented by the general formula (I-h) can be prepared.

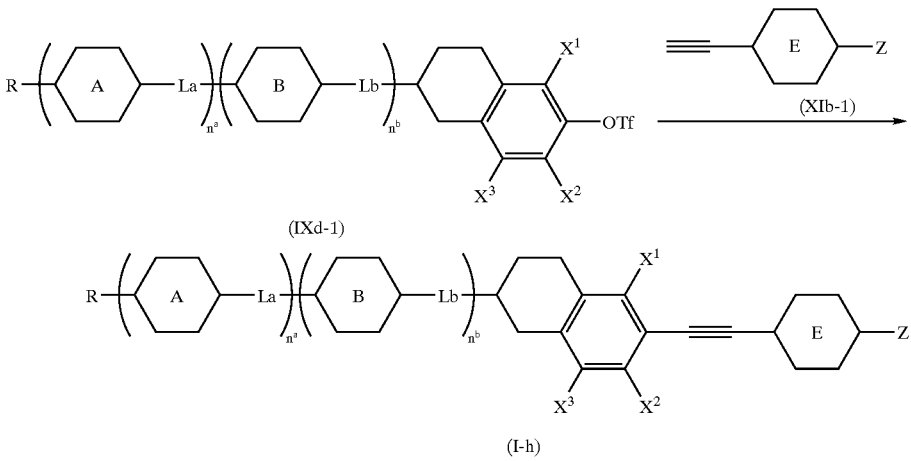

(wherein, R, the polar group Z, the ring A, the ring B, the ring E, $n^a$, $n^b$, $X^1$, $X^2$ and $X^3$ have the same meaning as described above for the general formula (I), and Tf represents a trifluoromethanesulfonyl group.)

Furthermore, reacting a compound represented by the general formula (IXb-3), which can be prepared in the same manner as the compounds represented by the general formulas (IXb-1) and (IXb-2), with an aryl lithium or magnesium reagent represented by the general formula (XIa-2), followed by dehydration, yields a compound represented by the general formula (XIIa-1), which upon subsequent oxidation with an oxidizing agent such as 2,3-dichloro-5,6-dicyano-1,4-benzoquinone or bromine or the like, yields a compound represented by the general formula (I-i).

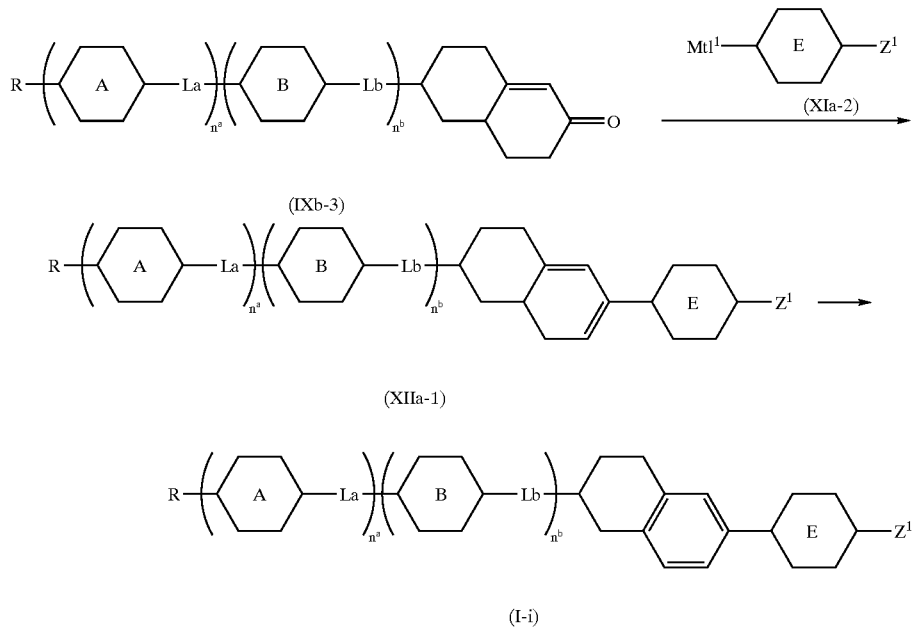

(wherein, R, the ring A, the ring B, the ring E, $n^a$ and $n^b$ have the same meaning as described above for the general formula (I), $Z^1$ represents a fluorine atom or a trifluoromethoxy group, and $Mtl^1$ represents Li, ClMg, BrMg, or IMg.)

The case in which ring C is the formula (IIb)

In the case in which $n^a=n^b=n^c=0$, $n^d=1$, and the linkage group Ld is a single bond, synthesis can be achieved in the manner described below.

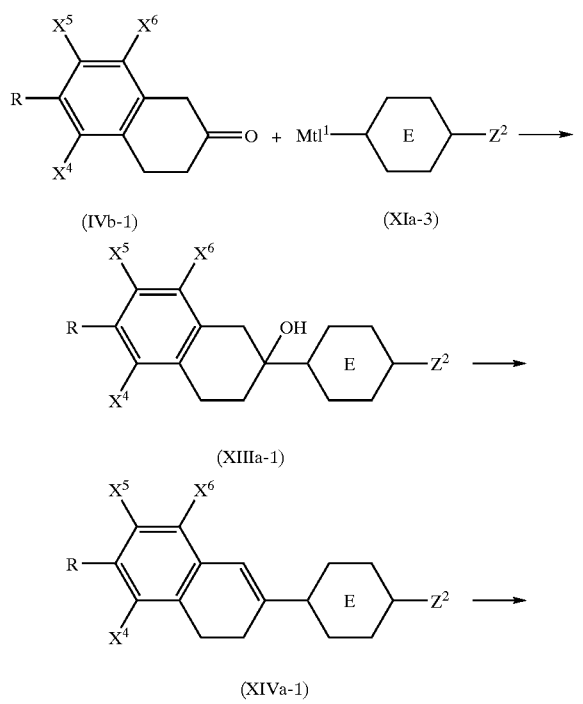

-continued

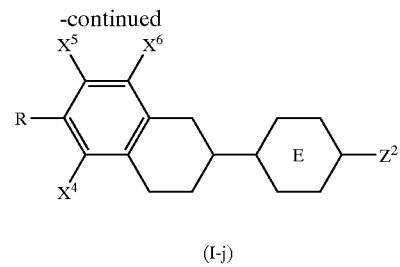

(wherein, R, $X^4$, $X^5$, $X^6$ and the ring E have the same meaning as described above for the general formula (I), $Z^2$ represents a fluorine atom, a chlorine atom, a trifluoromethyl group, a trifluoromethoxy group or a difluoromethoxy group, and $Mtl^1$ represents a metal ion such as Li, ClMg, BrMg, or IMg.) That is, by reacting a ketone represented by the general formula (IVb-1) with an aryl lithium or magnesium reagent represented by the general formula (XIa-3) either in or out of the presence of a metal salt such as cerium chloride or manganese chloride and a Lewis acid, an alcohol represented by the general formula (XIIIa-1) can be obtained, and subsequent heating in the presence of an acid catalyst such as p-toluenesulfonic acid, yields a dihydronaphthalene compound represented by the general formula (XIVa-1), which can be subsequently hydrogenated in the presence of a metal catalyst such as Pd—C, Rh—C, Pt—C or Pd(OH)$_2$ or the like to obtain the target compound represented by the general formula (I-j).

The compound (IVb-1) can be prepared by a variety of different methods, although as shown by the schemes below, a representative method comprises conversion of a phenylacetic acid derivative represented by the general formula (IIIb-1) to an acid chloride, and a subsequent reaction with ethylene in the presence of aluminum chloride.

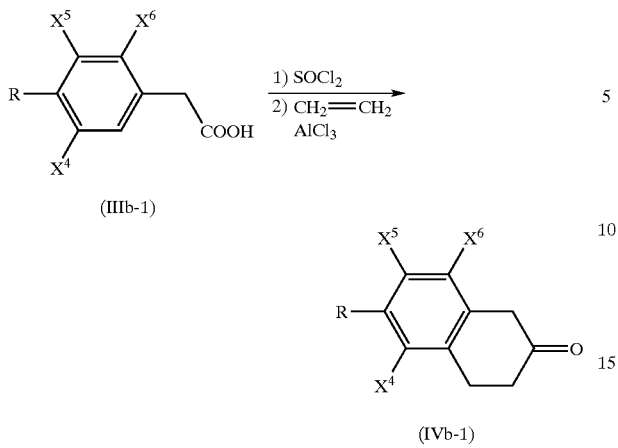

(wherein, R, $X^4$, $X^5$ and $X^6$ have the same meaning as described above for the general formula (I).)

Furthermore, in the case in which $X^4$, $X^5$ and $X^6$ are all hydrogen atoms, then as shown in the schemes below, a compound represented by the general formula (IVb-2) can be synthesized by hydrogenating a naphthol derivative represented by the general formula (XVa-1) in the presence of a transition metal catalyst such as palladium, rhodium, platinum or ruthenium, followed by subsequent oxidation, where necessary.

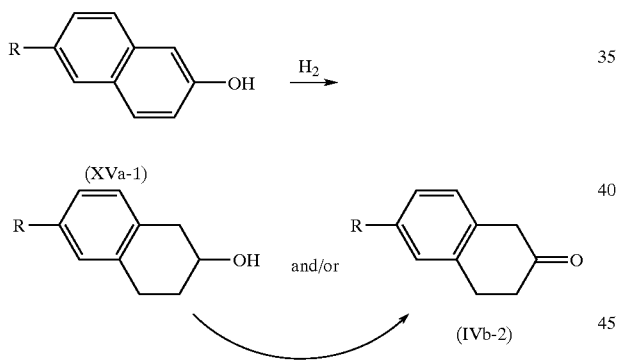

(wherein, R has the same meaning as described for the general formula (I).)

Furthermore as shown in the schemes below, subjecting octahydronaphthalenedione monoacetal, which can be synthesized by reacting 1,4-cyclohexanedione monoacetal with an amine such as pyrrolidine followed by reaction with methyl vinyl ketone, to the action of an organometallic reagent represented by $R^1$—$Mtl^1$, and performing a subsequent dehydration reaction, yields an octahydronaphthalenone acetal. By aromatizing this compound, either using a metal catalyst such as palladium, rhodium, ruthenium or platinum as a dehydrogenation catalyst, or using the action of an oxidizing agent such as 2,3-dichloro-5,6-dicyano-1,4-benzoquinone, or using a material such as sulfur, bromine or iodine, and subsequently converting the acetal to a ketone, a compound represented by the general formula (IVb-3) can be synthesized.

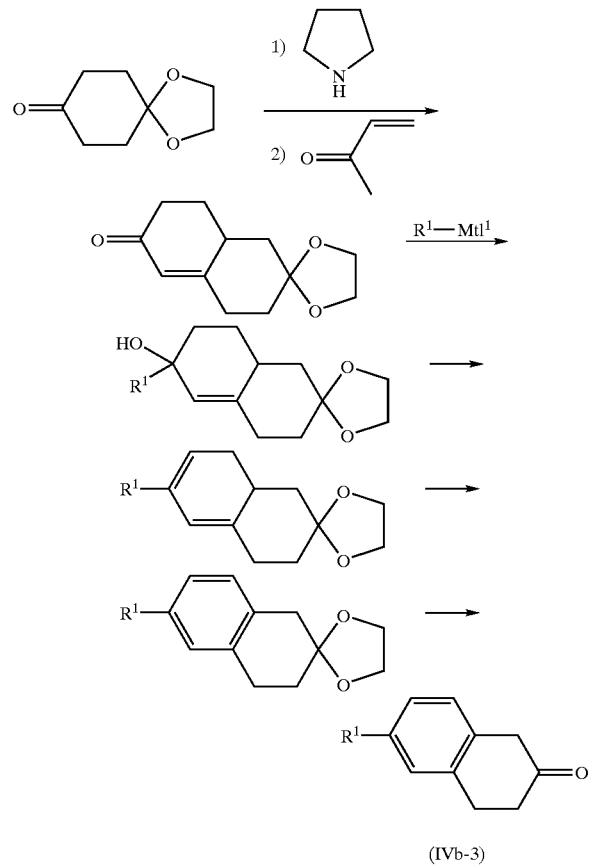

(wherein, $R^1$ represents a saturated alkyl group of 1 to 20 carbon atoms which may incorporate a branched chain and which may be substituted with 1 to 7 fluorine atoms or alkoxyl groups of 1 to 7 carbon atoms.)

In the case in which $n^a=n^b=n^c=0$, $n^d=1$, and the linkage group Ld is —$CH_2CH_2$—, synthesis can be achieved in the manner described below.

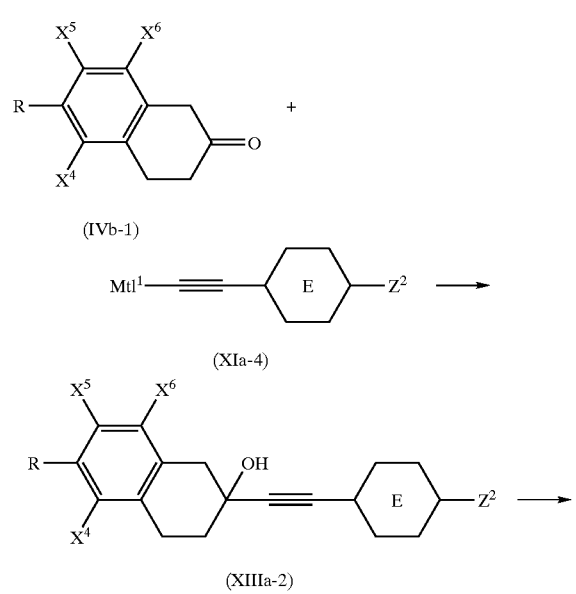

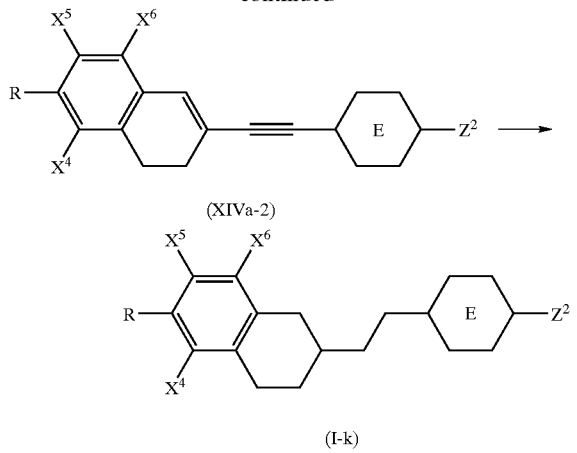

(XIVa-2)

(I-k)

(wherein, R, $X^4$, $X^5$, $X^6$ and the ring E have the same meaning as described above for the general formula (I), $Z^2$ represents a fluorine atom, a chlorine atom, a trifluoromethyl group, a trifluoromethoxy group or a difluoromethoxy group, and $Mtl^1$ represents a metal ion such as Li, ClMg, BrMg, or IMg.)

That is, by reacting the ketone represented by the general formula (IVb-1) with an aryl lithium or magnesium reagent represented by the general formula (XIa-4) either in or out of the presence of a metal salt such as cerium chloride or manganese chloride and a Lewis acid, an alcohol represented by the general formula (XIIIa-2) can be obtained, and subsequent heating in the presence of an acid catalyst such as p-toluenesulfonic acid, yields a dihydronaphthalene compound represented by the general formula (XIVa-2), which can be subsequently hydrogenated in the presence of a metal catalyst such as Pd—C, Rh—C, Pt—C or Pd(OH)$_2$ or the like to obtain the target compound represented by the general formula (I-k).

Furthermore, if compounds represented by (XIa-5) and (XIa-6) are used instead of the compounds (XIa-3) and (XIa-4) shown above, then compounds represented by the general formulas (I-l) and (I-m) can be prepared.

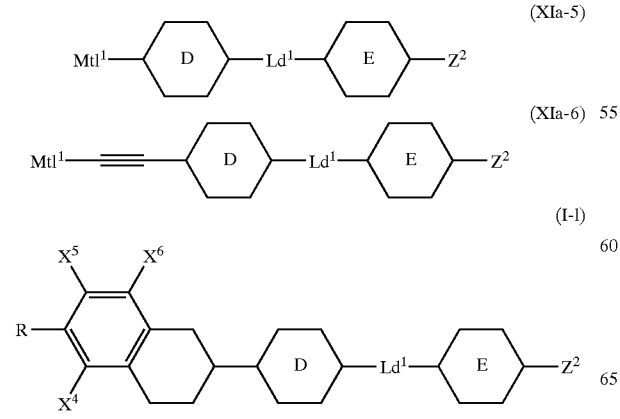

(XIa-5)

(XIa-6)

(I-l)

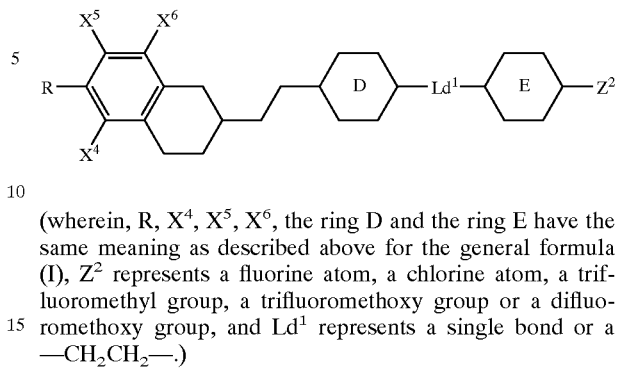

(I-m)

(wherein, R, $X^4$, $X^5$, $X^6$, the ring D and the ring E have the same meaning as described above for the general formula (I), $Z^2$ represents a fluorine atom, a chlorine atom, a trifluoromethyl group, a trifluoromethoxy group or a difluoromethoxy group, and $Ld^1$ represents a single bond or a —CH$_2$CH$_2$—.)

In addition, as shown by the schemes below, by reacting the compound represented by the general formula (IVb-1) with an ylide compound represented by the general formula (Vc-1), and then hydrogenating the thus obtained olefin compound (XVIa-1), a compound represented by the general formula (I-n) can be produced.

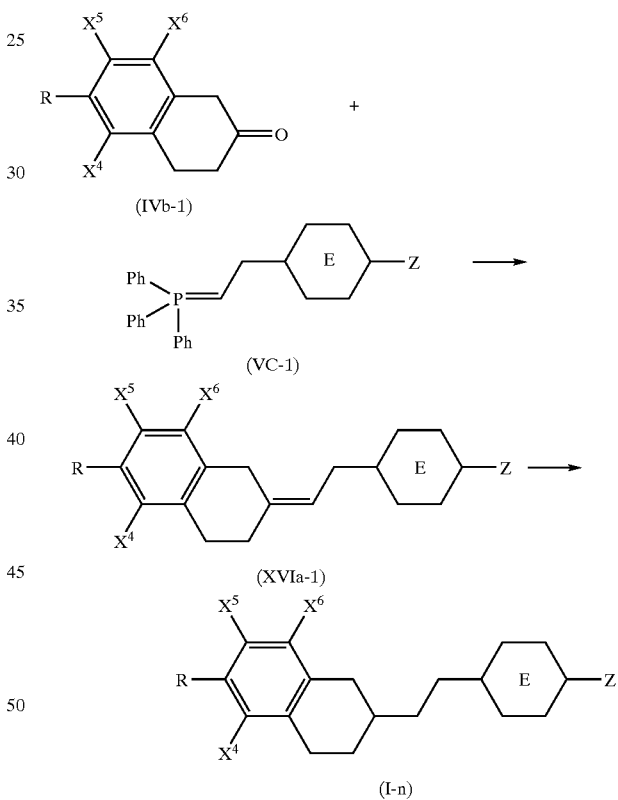

(IVb-1)

(VC-1)

(XVIa-1)

(I-n)

(wherein, R, $X^4$, $X^5$, $X^6$, the ring E and Z have the same meaning as described above for the general formula (I).)

In addition, as shown by the schemes below, by reacting the tetrahydronaphthalenone represented by the general formula (IVb-1) with an ylide compound prepared from a methoxymethyl phosphonium salt, and treating the thus obtained product with acid, an aldehyde represented by the general formula (VIIIb-1) can be obtained. By reacting this aldehyde with an ylide compound represented by the formula (Vc-2), and hydrogenating the thus produced olefin (I-o), a compound represented by the general formula (I-n) can be prepared.

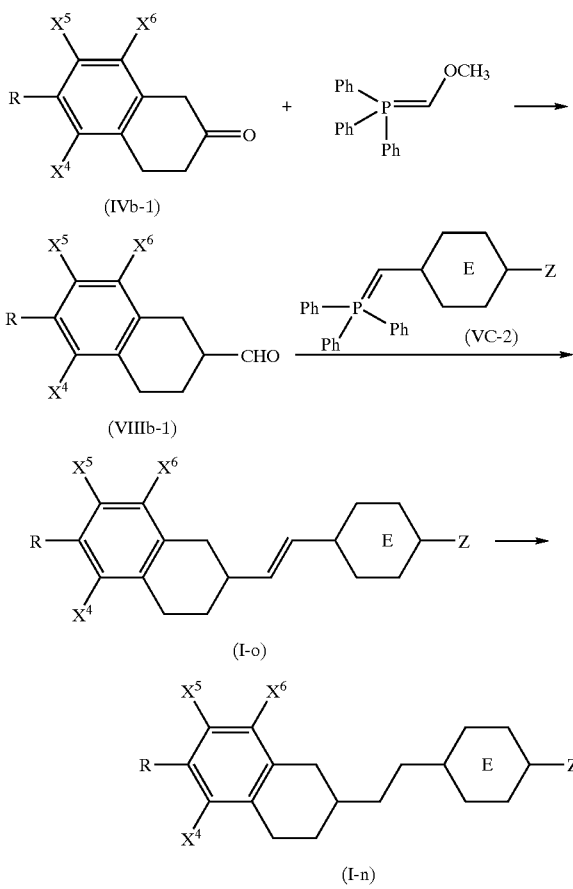

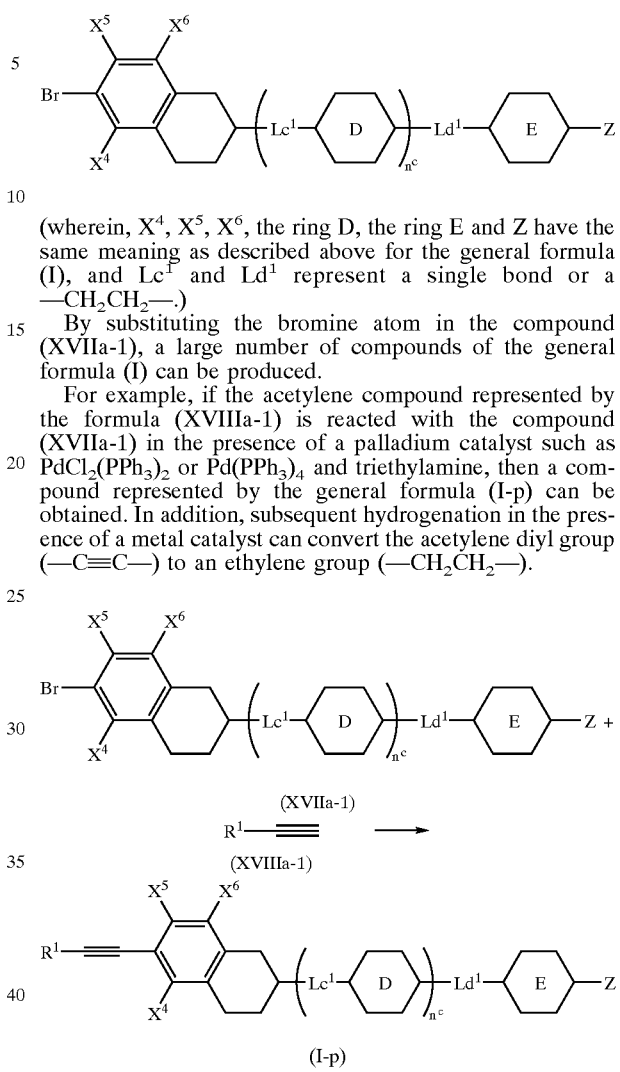

(wherein, $X^4$, $X^5$, $X^6$, the ring D, the ring E and Z have the same meaning as described above for the general formula (I), and $Lc^1$ and $Ld^1$ represent a single bond or a —$CH_2CH_2$—.)

By substituting the bromine atom in the compound (XVIIa-1), a large number of compounds of the general formula (I) can be produced.

For example, if the acetylene compound represented by the formula (XVIIIa-1) is reacted with the compound (XVIIa-1) in the presence of a palladium catalyst such as $PdCl_2(PPh_3)_2$ or $Pd(PPh_3)_4$ and triethylamine, then a compound represented by the general formula (I-p) can be obtained. In addition, subsequent hydrogenation in the presence of a metal catalyst can convert the acetylene diyl group (—C≡C—) to an ethylene group (—$CH_2CH_2$—).

(wherein, R, $X^4$, $X^5$, $X^6$, the ring E and Z have the same meaning as described above for the general formula (I).)

In the method described above, by using the compound (IVb-2) in place of (IVb-1), a compound represented by the general formula (XVIIa) can be produced.

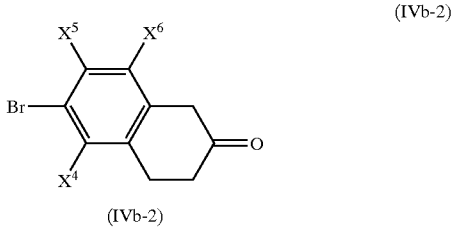

(wherein, $X^4$, $X^5$, $X^6$, the ring D, the ring E and Z have the same meaning as described above for the general formula (I), $R^1$ represents a saturated or an unsaturated alkyl group of 1 to 18 carbon atoms which may incorporate a branched chain and which may be substituted with 1 to 7 fluorine atoms or alkoxyl groups of 1 to 7 carbon atoms, and Lc and $Ld^1$ represent a single bond or a —$CH_2CH_2$—.)

In addition, by altering the compound (XVIIIa-1) to (XVIIIa-2), a compound represented by the general formula (I-q) can be produced. Subsequent hydrogenation of this compound in the presence of a metal catalyst can also be used to convert the acetylene diyl group (—C≡C—) to an ethylene group (—$CH_2CH_2$—).

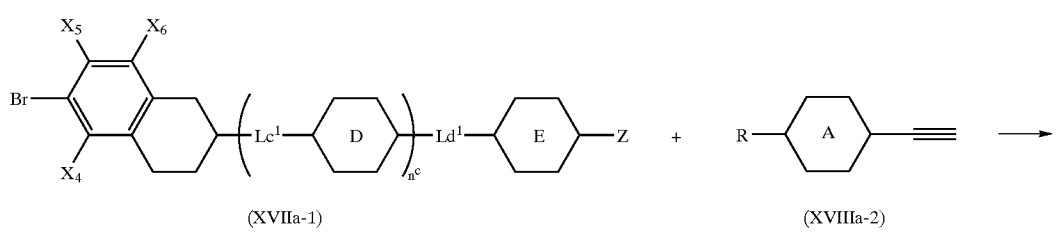

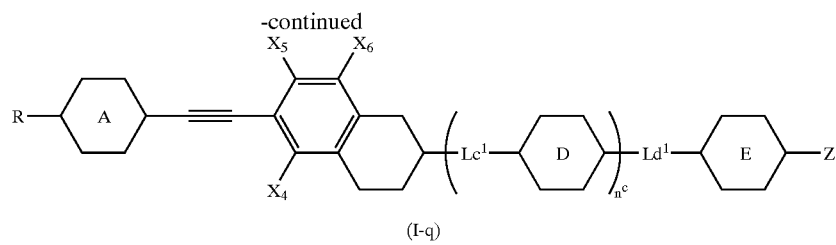

(I-q)

(wherein, R, $X^4$, $X^5$, $X^6$, the ring A, the ring D, the ring E and Z have the same meaning as described above for the general formula (I), and $Lc^1$ and $Ld^1$ represent a single bond or a $CH_2CH_2$—.)

Furthermore, by reacting the organometallic reagent represented by (XIb-1) with the compound (XVIIa-1) in the presence of a nickel or a palladium catalyst, a compound represented by the general formula (I-r) can be produced.

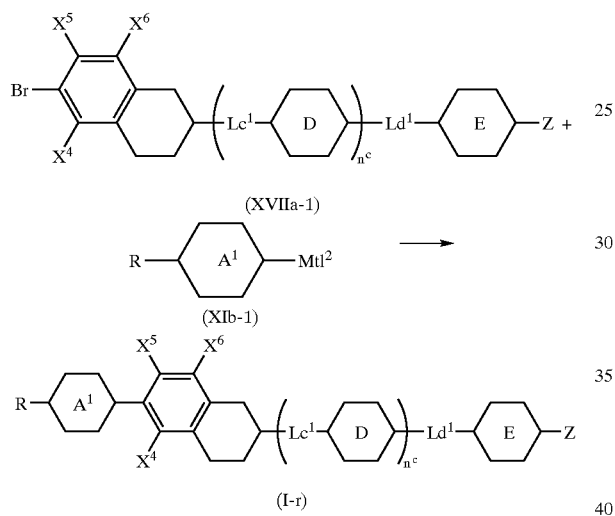

(wherein, R, $X^4$, $X^5$, $X^6$, the ring D, the ring E and Z have the same meaning as described above for the general formula (I), the ring $A^1$ represents a 1,4-phenylene group which may be substituted with one or two fluorine atoms and a naphthalene-2,6-diyl group which may be substituted with one or two fluorine atoms, $Lc^1$ and $Ld^1$ represent a single bond or a —$CH_2CH_2$—, and $Mtl^2$ represents Li, ClMg, BrMg, IMg or $(HO)_2B$.)

Representative examples of the compounds represented by the general formula (I) produced using the methods described above are shown below.

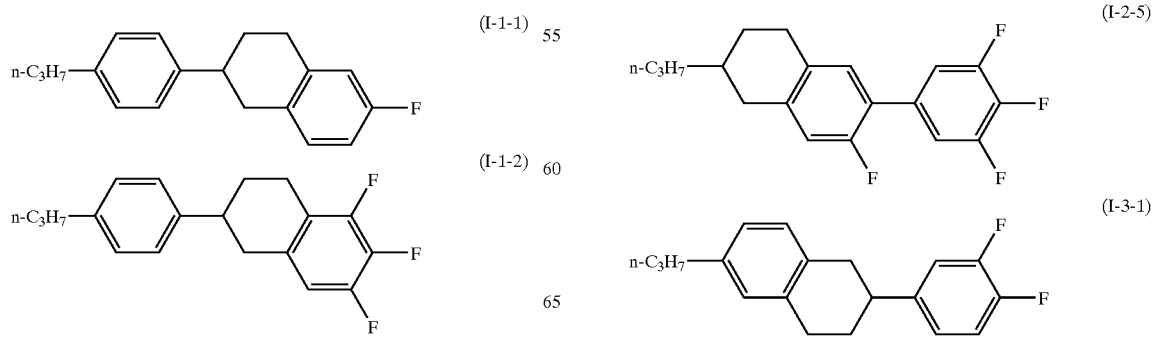

-continued

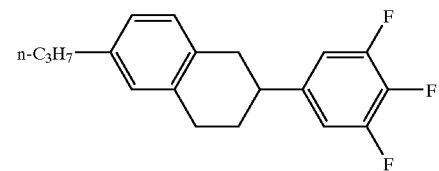
(I-3-2)

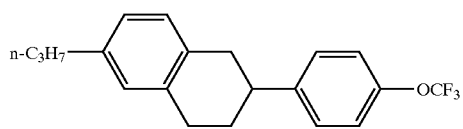
(I-3-3)

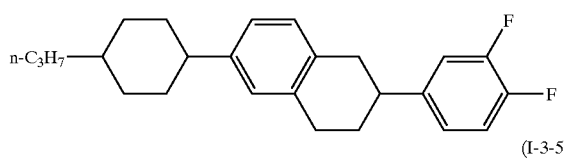
(I-3-4)

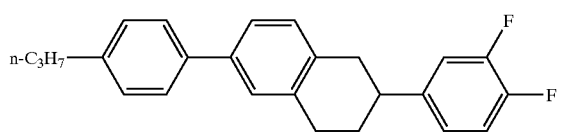
(I-3-5)

The present invention also provides a liquid crystal composition comprising at least one compound represented by the general formula (I) as a constituent.

In a liquid crystal composition comprising at least one compound represented by the general formula (I) as a constituent, provided the composition shows liquid crystallinity, any other compound may be incorporated into the composition in addition to the compound represented by the general formula (I), although as a first constituent the composition should comprise at least one compound represented by the general formula (I), and in addition should also preferably comprise at least one constituent from the second through fourth constituents described below.

Namely, the second constituent is a so-called fluorine system (halogen system) p-type liquid crystal compound, and comprises a compound represented by the general formulas (A1) to (A3) shown below.

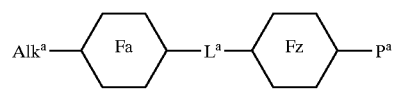
(A1)

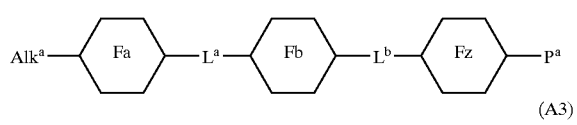
(A2)

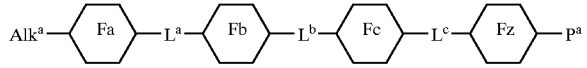
(A3)

wherein $Alk^a$ represents an alkyl group of 1 to 12 carbon atoms, which may be either a straight chain or contain methyl or ethyl branches, may contain a 3 to 6 membered ring structure, may have any particular —CH$_2$— structure within the group replaced by a —O—, —CH=CH—, —CH=CF—, —CF=CH—, —CF=CF— or —C≡C—, and may have any particular hydrogen atom within the group substituted with a fluorine atom or a trifluoromethoxy group, although straight chain alkyl groups of 2 to 7 carbon atoms, straight chain 1-alkenyl groups of 2 to 7 carbon atoms, straight chain 3-alkenyl groups of 4 to 7 carbon atoms, and alkyl groups of 1 to 5 carbon atoms in which the terminal is substituted with an alkoxyl group of 1 to 3 carbon atoms are preferred. Furthermore, in those cases in which branching leads to an asymmetric carbon atom, either optically active compounds or racemic mixtures may be used.

The ring Fa, the ring Fb and the ring Fc each represent independently a trans-1,4-cyclohexylene group, a transdecahydronaphthalene-trans-2,6-diyl group, a 1,4-phenylene group which may be substituted with one or more fluorine atoms, a naphthalene-2,6-diyl group which may be substituted with one or more fluorine atoms, a tetrahydronaphthalene-2,6-diyl group which may be substituted with one or more fluorine atoms, a 1,4-cylohexenylene group which may be substituted with a fluorine atom, a 1,3-dioxane-trans-2,5-diyl group, a pyrimidine-2,5-diyl group or a pyridine-2,5-diyl group, although a trans-1,4-cyclohexylene group, a transdecahydronaphthalene-trans-2,6-diyl group, a naphthalene-2,6-diyl group which may be substituted with a fluorine atom or a 1,4-phenylene group which may be substituted with one or two fluorine atoms are preferred. Particularly in those cases in which the ring Fb is a trans-1,4-cyclohexylene group or a transdecahydronaphthalene-trans-2,6-diyl group, it is preferable that the ring Fa is a trans-1,4-cyclohexylene group, and in those cases in which the ring Fc is a trans-1,4-cyclohexylene group or a transdecahydronaphthalene-trans-2,6-diyl group, it is preferable that the ring Fb and the ring Fa are trans-1,4-cyclohexylene groups. Furthermore in (A3), it is preferable that the ring Fa is a trans-1,4-cyclohexylene group.

$L^a$, $L^b$ and $L^c$ are linkage groups, and each represent, independently, a single bond, an ethylene group (—CH$_2$CH$_2$—), a 1,2-propylene group (—CH(CH$_3$)CH$_2$— and —CH$_2$CH(CH$_3$)—), a 1,4-butylene group, —COO—, —OCO—, —OCF$_2$—, —CF$_2$O—, —CH=CH—, —CH=CF—, —CF=CH—, —CF=CF—, —C≡C— or —CH=N—N=CH—, although a single bond, an ethylene group, a 1,4-butylene group, —COO—, —OCF$_2$—, —CF$_2$O—, —CF=CF— or —C≡C— are preferred, and a single bond or an ethylene group are particularly desirable. Furthermore it is preferable that at least one of these linkage groups in (A2), and at least two of the linkage groups in (A3) are single bonds.

The ring Fz is an aromatic ring, and can be represented by the general formulas (Ga) to (Gc) shown below.

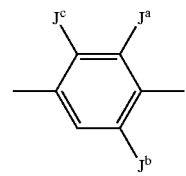
(Ga)

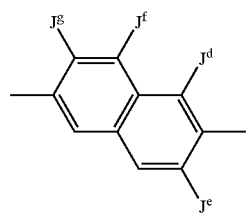
(Gb)

-continued

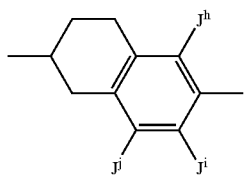
(Gc)

wherein, $J^a$ to $J^j$ each represent independently a hydrogen atom or a fluorine atom, although in (Ga) it is preferable that at least one of $J^a$ and $J^b$ is a fluorine atom, and in (Gb) it is preferable that at least one of $J^d$ to $J^f$ is a fluorine atom, with the structure in which $J^f$ is a fluorine atom being particularly desirable.

The terminal group $P^a$ represents a fluorine atom, a chlorine atom, a trifluoromethoxy group, a difluoromethoxy group, or an alkoxyl group, alkyl group, alkenyl group or alkenyloxy group of 2 or 3 carbon atoms substituted with a trifluoromethyl group or a difluoromethyl group or 2 or more fluorine atoms, although a fluorine atom, a trifluoromethoxy group or a difluoromethoxy group are preferred, and a fluorine atom is particularly desirable.

Furthermore, compounds of the general formula (I) of the present invention are not included in (A1) to (A3).

The third constituent is a so-called cyano system p-type liquid crystal compound, and comprises a compound represented by the general formulas (B1) to (B3) shown below.

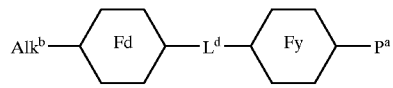
(B1)

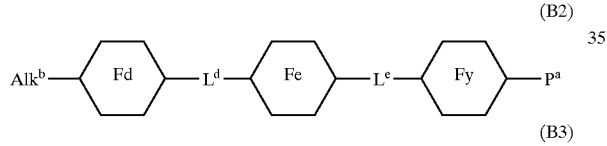
(B2)

(B3)

wherein $Alk^b$ represents an alkyl group of 1 to 12 carbon atoms, which may be either a straight chain or contain methyl or ethyl branches, may contain a 3 to 6 membered ring structure, may have any particular —$CH_2$— structure within the group replaced by a —O—, —CH=CH—, —CH=CF—, —CF=CH—, —CF=CF— or —C≡C—, and may have any particular hydrogen atom within the group substituted with a fluorine atom or a trifluoromethoxy group, although straight chain alkyl groups of 2 to 7 carbon atoms, straight chain 1-alkenyl groups of 2 to 7 carbon atoms, straight chain 3-alkenyl groups of 4 to 7 carbon atoms, and alkyl groups of 1 to 5 carbon atoms in which the terminal is substituted with an alkoxyl group of 1 to 3 carbon atoms are preferred. Furthermore, in those cases in which branching leads to an asymmetric carbon atom, either optically active compounds or racemic mixtures may be used.

The ring Fd, the ring Fe and the ring Ff each represent independently a trans-1,4-cyclohexylene group, a transdecahydronaphthalene-trans-2,6-diyl group, a 1,4-phenylene group which may be substituted with one or more fluorine atoms, a naphthalene-2,6-diyl group which may be substituted with one or more fluorine atoms, a tetrahydronaphthalene-2,6-diyl group which may be substituted with one or more fluorine co atoms, a 1,4-cyclohexenylene group which may be substituted with a fluorine atom, a 1,3-dioxane-trans-2,5-diyl group, a pyrimidine-2,5-diyl group or a pyridine-2,5-diyl group, although a trans-1,4-cyclohexylene group, a transdecahydronaphthalene-trans-2,6-diyl group, a naphthalene-2,6-diyl group which may be substituted with a fluorine atom or a 1,4-phenylene group which may be substituted with one or two fluorine atoms are preferred. Particularly in those cases in which the ring Fe is a trans-1,4-cyclohexylene group or a transdecahydronaphthalene-trans-2,6-diyl group, it is preferable that the ring Fd is a trans-1,4-cyclohexylene group, and in those cases in which the ring Ff is a trans-1,4-cyclohexylene group or a transdecahydronaphthalene-trans-2,6-diyl group, it is preferable that the ring Fd and the ring Fe are trans-1,4-cyclohexylene groups. Furthermore in (B3), it is preferable that the ring Fd is a trans-1,4-cyclohexylene group.

$L^d$, $L^e$ and $L^f$ are linkage groups, and each represent, independently, a single bond, an ethylene group (—$CH_2CH_2$—), a 1,2-propylene group (—CH($CH_3$)$CH_2$— and —$CH_2$CH($CH_3$)—), a 1,4-butylene group, —COO—, —OCO—, —$OCF_2$—, —$CF_2O$—, —CH=CH—, —CH=CF—, —CF=CH—, —CF=CF—, —C≡C—, —$OCH_2$—, —$CH_2O$— or —CH=N—N=CH—, although a single bond, an ethylene group, —COO—, —$OCF_2$—, —$CF_2O$—, —CF=CF— or —C≡C— are preferred, and a single bond, an ethylene group or a —COO— are particularly desirable. Furthermore it is preferable that at least one of these linkage groups in (B2), and at least two of the linkage groups in (B3) are single bonds.

The ring Fy is an aromatic ring, and can be represented by the general formulas (Gd) to (Gf) shown below.

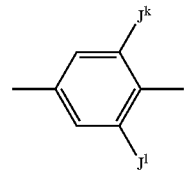
(Gd)

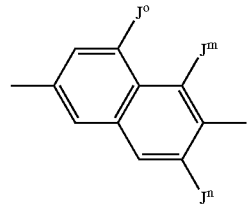
(Ge)

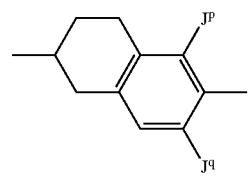
(Gf)

wherein, $J^k$ to $J^q$ each represent independently a hydrogen atom or a fluorine atom, although in (Ge) it is preferable that $J^n$ and $J^o$ are hydrogen atoms.

The terminal group pa represents a cyano group (—CN), a cyanato group (—OCN) or a —C≡CCN group, although a cyano group is preferred.

Furthermore, compounds of the general formula (I) of the present invention are not included in (B1) to (B3).

The fourth constituent is a so-called n-type liquid crystal compound in which the dielectric anisotropy is approximately zero, or a value below zero, and comprises a compound represented by the general formulas (C1) to (C3) shown below.

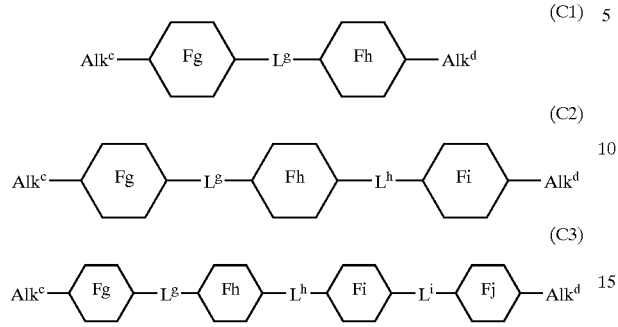

(C1)

(C2)

(C3)

wherein $Alk^c$ and $Alk^d$ each represent, independently, an alkyl group of 1 to 12 carbon atoms, which may be either a straight chain or contain methyl or ethyl branches, may contain a 3 to 6 membered ring structure, may have any particular —$CH_2$— structure within the group replaced by a —O—, —CH=CH—, —CH=CF—, —CF=CH—, —CF=CF— or —C≡C—, and may have any particular hydrogen atom within the group substituted with a fluorine atom or a trifluoromethoxy group, although straight chain alkyl groups of 1 to 7 carbon atoms, straight chain 1-alkenyl groups of 2 to 7 carbon atoms, straight chain 3-alkenyl groups of 4 to 7 carbon atoms, straight chain alkoxyl groups of 1 to 3 carbon atoms and straight chain alkyl groups of 1 to 5 carbon atoms in which the terminal is substituted with an alkoxyl group of 1 to 3 carbon atoms are preferred, and moreover, compounds in which at least one of $Alk^c$ and $Alk^d$ represent a straight chain alkyl group of 1 to 7 carbon atoms, a straight chain 1-alkenyl group of 2 to 7 carbon atoms, or a straight chain 3-alkenyl group of 4 to 7 carbon atoms are particularly desirable.

The ring Fg, the ring Fh, the ring Fi and the ring Fj each represent independently a trans-1,4-cyclohexylene group, a transdecahydronaphthalene-trans-2,6-diyl group, a 1,4-phenylene group which may be substituted with one or two fluorine atoms or methyl groups, a naphthalene-2,6-diyl group which may be substituted with one or more fluorine atoms, a tetrahydronaphthalene-2,6-diyl group which may be substituted with one or two fluorine atoms, a 1,4-cyclohexenylene group which may be substituted with one or two fluorine atoms, a 1,3-dioxane-trans-2,5-diyl group, a pyrimidine-2,5-diyl group or a pyridine-2,5-diyl group, although in each compound it is preferable that there be no more than one transdecahydronaphthalene-trans-2,6-diyl group, naphthalene-2,6-diyl group which may be substituted with one or more fluorine atoms, tetrahydronaphthalene-2,6-diyl group which may be substituted with one or two fluorine atoms, 1,4-cyclohexenylene group which may be substituted with a fluorine atom, 1,3-dioxane-trans-2,5-diyl group, pyrimidine-2,5-diyl group or pyridine-2,5-diyl group, and that the other rings in such cases should preferably be a trans-1,4-cyclohexylene group or a 1,4-phenylene group which may be substituted with one or two fluorine atoms or methyl groups.

$L^g$, $L^h$ and $L^i$ are linkage groups, and each represent, independently, a single bond, an ethylene group (—$CH_2CH_2$—), a 1,2-propylene group (—$CH(CH_3)CH_2$— and —$CH_2CH(CH_3)$—), a 1,4-butylene group, —COO—, —OCO—, —$OCF_2$—, —$CF_2O$—, —CH=CH—, —CH=CF—, —CF=CH—, —CF=CF—, —C≡C—, or —CH=N—N=CH—, although a single bond, an ethylene group, a 1,4-butylene group, —COO—, —OCO—, —$OCF_2$—, —$CF_2O$—, —CF=CF—, —C≡C—, or —CH=N—N=CH— are preferred, and it is also preferable that at least one of these linkage groups in (C2), and at least two of the linkage groups in (C3) are single bonds.

Preferred forms for (C1) can be represented by the general formulas (C1a) to (C1h) shown below.

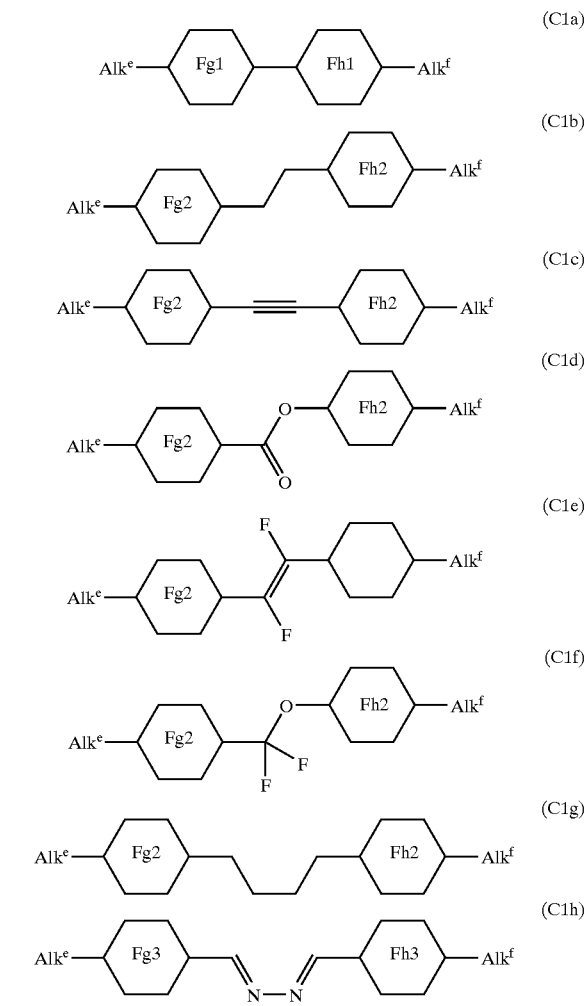

In each of the formulas above, $Alk^e$ and $Alk^f$ each represent, independently, a straight chain alkyl group of 1 to 7 carbon atoms, a straight chain 1-alkenyl group of 2 to 7 carbon atoms, a straight chain 3-alkenyl group of 4 to 7 carbon atoms, a straight chain alkoxyl group of 1 to 3 carbon atoms or a straight chain alkyl groups of 1 to 5 carbon atoms in which the terminal is substituted with an alkoxyl group of 1 to 3 carbon atoms, although at least one of $Alk^e$ and $Alk^f$ represents a straight chain alkyl group of 1 to 7 carbon atoms, a straight chain 1-alkenyl group of 2 to 7 carbon atoms, or a straight chain 3-alkenyl group of 4 to 7 carbon atoms. In those cases in which the rings Fg1 to Fg3 are aromatic, the corresponding $ALk^e$ excludes 1-alkenyl groups and alkoxyl groups, and in those cases in which the rings Fh1 to Fh3 are aromatic, the corresponding $ALk^f$ excludes 1-alkenyl groups and alkoxyl groups.

The ring Fg1 and the ring Fh1 each represent independently a trans-1,4-cyclohexylene group, a transdecahydronaphthalene-trans-2,6-diyl group, a 1,4-phenylene group which may be substituted with one or two fluorine atoms or methyl groups, a naphthalene-2,6-diyl group which may be substituted with one or more fluorine atoms, a tetrahydronaphthalene-2,6-diyl group which may be substituted with one or two fluorine atoms, a 1,4-cyclohexenylene group which may be substituted with one or two fluorine atoms, a 1,3-dioxane-trans-2,5-diyl group, a pyrimidine-2,5-diyl group or a pyridine-2,5-diyl group, although in each compound it is preferable that there be no more than one transdecahydronaphthalene-trans-2,6-diyl group, naphthalene-2,6-diyl group which may be substituted with one or more fluorine atoms, tetrahydronaphthalene-2,6-diyl group which may be substituted with one or two fluorine atoms, 1,4-cyclohexenylene group which may be substituted with a fluorine atom, 1,3-dioxane-trans-2,5-diyl group, pyrimidine-2,5-diyl group or pyridine-2,5-diyl group, and that the other ring in such cases should preferably be a trans-1,4-cyclohexylene group or a 1,4-phenylene group which may be substituted with one or two fluorine atoms or methyl groups. The ring Fg2 and the ring Fh2 each represent independently a trans-1,4-cyclohexylene group, a transdecahydronaphthalene-trans-2,6-diyl group, a 1,4-phenylene group which may be substituted with one or two fluorine atoms or methyl groups, a naphthalene-2,6-diyl group which may be substituted with one or more fluorine atoms, or a tetrahydronaphthalene-2,6-diyl group which may be substituted with one or two fluorine atoms, although in each compound it is preferable that there be no more than one transdecahydronaphthalene-trans-2,6-diyl group, naphthalene-2,6-diyl group which may be substituted with one or more fluorine atoms, or tetrahydronaphthalene-2,6-diyl group which may be substituted with one or two fluorine atoms, and that the other ring in such cases should preferably be a trans-1,4-cyclohexylene group or a 1,4-phenylene group which may be substituted with one or two fluorine atoms or methyl groups. The ring Fg3 and the ring Fh3 each represent independently a 1,4-phenylene group which may be substituted with one or two fluorine atoms or methyl groups, a naphthalene-2,6-diyl group which may be substituted with one or more fluorine atoms, or a tetrahydronaphthalene-2,6-diyl group which may be substituted with one or two fluorine atoms, although in each compound it is preferable that there be no more than one naphthalene-2,6-diyl group which may be substituted with one or more fluorine atoms or one tetrahydronaphthalene-2,6-diyl group which may be substituted with one or two fluorine atoms.

Preferred forms for (C2) can be represented by the general formula (C2a) to (C2m) shown below.

(C2a)

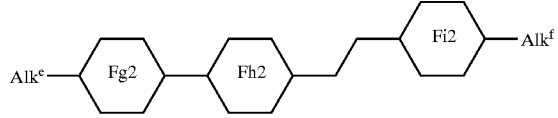
(C2b)

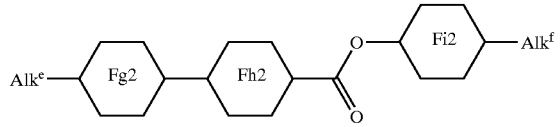
(C2c)

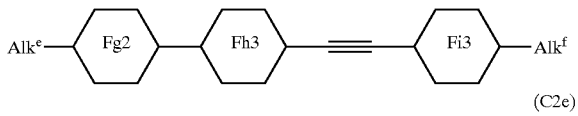
(C2d)

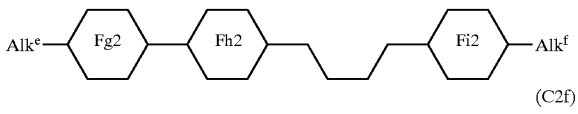
(C2e)

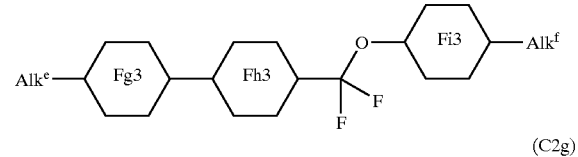
(C2f)

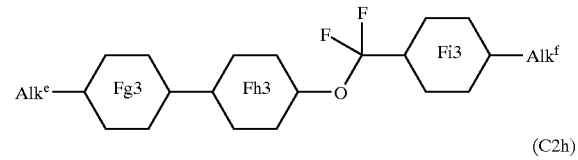
(C2g)

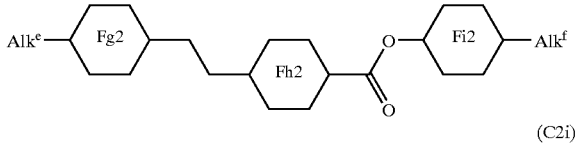
(C2h)

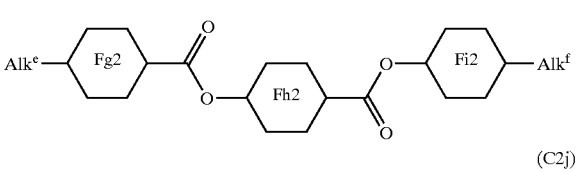
(C2i)

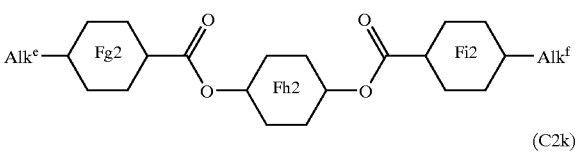
(C2j)

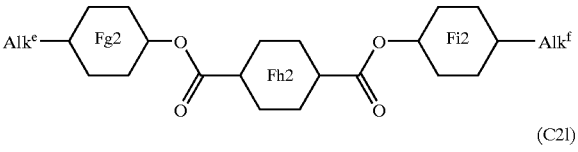
(C2k)

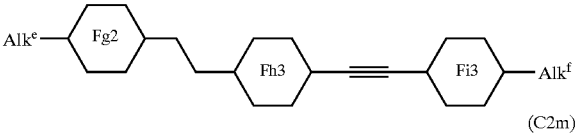
(C2l)

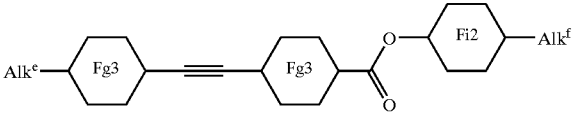
(C2m)

In each of the formulas above, the ring Fg1, ring Fg2, ring Fg3, ring Fh1, ring Fh2 and the ring Fh3 each represent the same meaning as that described above, and the ring Fi1 represents the same meaning as the ring Fg1, the ring Fi2 the same as the ring Fg2, and the ring Fi3 the same as the ring Fg3. Furthermore, in each of the compounds listed above, it is preferable that there be no more than one transdecahydronaphthalene-trans-2,6-diyl group, naphthalene-2,6-diyl group which may be substituted with one or more fluorine atoms, tetrahydronaphthalene-2,6-diyl group which may be substituted with one or two fluorine atoms, 1,4-cyclohexenylene group which may be substituted with a fluorine atom, 1,3-dioxane-trans-2,5-diyl group, pyrimidine-2,5-diyl group or pyridine-2,5-diyl group, and that the other rings in such cases should preferably be a trans-1,4-cyclohexylene group or a 1,4-phenylene group which may be substituted with one or two fluorine atoms or methyl groups.

Preferred forms for (C3) can be represented by the general formulas (C3a) to (C3f) shown below.

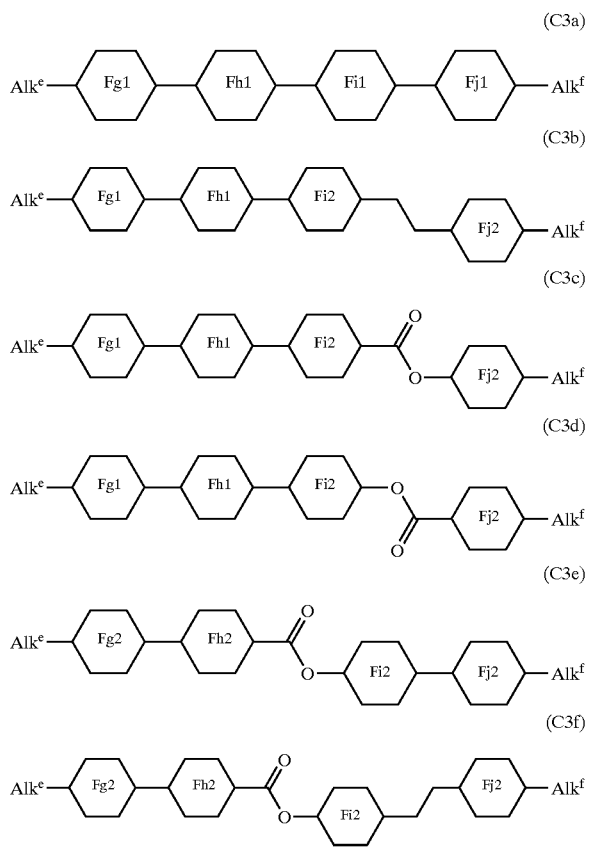

In each of the formulas above, the ring Fg1, ring Fg2, ring Fh1, ring Fh2, ring Fi1 and the ring Fi2 each represent the same meaning as that described above, and the ring Fj1 represents the same meaning as the ring Fg1, and the ring Fj2 the same as the ring Fg2. Furthermore, in each of the compounds listed above, it is preferable that there be no more than one transdecahydronaphthalene-trans-2,6-diyl group, naphthalene-2,6-diyl group which may be substituted with one or more fluorine atoms, tetrahydronaphthalene-2,6-diyl group which may be substituted with one or two fluorine atoms, 1,4-cyclohexenylene group which may be substituted with a fluorine atom, 1,3-dioxane-trans-2,5-diyl group, pyrimidine-2,5-diyl group or pyridine-2,5-diyl group, and that the other rings in such cases should preferably be a trans-1,4-cyclohexylene group or a 1,4-phenylene group which may be substituted with one or two fluorine atoms or methyl groups.

As will be shown in the examples described below, when a practical liquid crystal composition with a nematic phase upper limit temperature of 117° C. is prepared using the aforementioned compounds, and 20% by weight of a compound represented by the general formula (I) is added, the compound represented by the general formula (I) displays superior solubility with respect to the host liquid crystal composition, and it is clear that the liquid crystal phase can be exhibited over a very wide temperature range.

In addition, when the voltage holding rate of this composition was measured, the results before and after heating and after ultraviolet light irradiation were quite high and similar to those of the host liquid crystal composition.

In this manner, a compound of the present invention shows superior liquid crystallinity, and superior co-solubility with currently used liquid crystal compounds and liquid crystal compositions. Furthermore, the temperature range over which liquid crystallinity is shown is broad, the threshold voltage is low, and in terms of preparing a liquid crystal composition capable of high speed response, the compound displays superior results to conventional compounds.

Consequently, compounds of the general formula (I) can be suitably used in mixtures with other nematic liquid crystal compounds, for electric field effect type display cells of TN and STN type cells, and are particularly applicable to liquid crystal materials with a broad temperature range for which low voltage driving is possible. Furthermore of the compounds represented by the general formula (I), those compounds which incorporate no cyano groups or ester linkages offer a large specific resistance and a high voltage holding rate, and so may also be used as constituents in active matrix driven liquid crystal materials. In addition, use of the compounds of the general formula (I) is not limited to nematic liquid crystals, and application as a low viscosity material essential for realizing the high speed response of ferroelectric liquid crystals and antiferroelectric liquid crystals can also be expected.

EXAMPLES

As follows is a description of specific examples of the present invention, with a detailed description of the advantages offered by a tetrahydronaphthalene derivative of the present invention and a production method thereof, and a liquid crystal composition comprising a tetrahydronaphthalene derivative of the present invention as a constituent, although the purport and range of application of the present invention is of course not limited to these examples.

Example 1

Synthesis of 2-(4-propylphenyl)-6-fluoro-1,2,3,4-tetrahydronaphthalene (I-1-1)

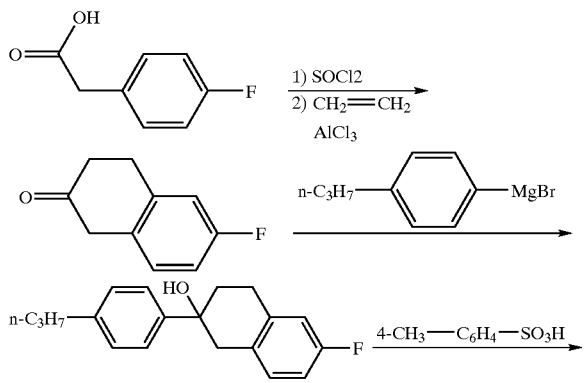

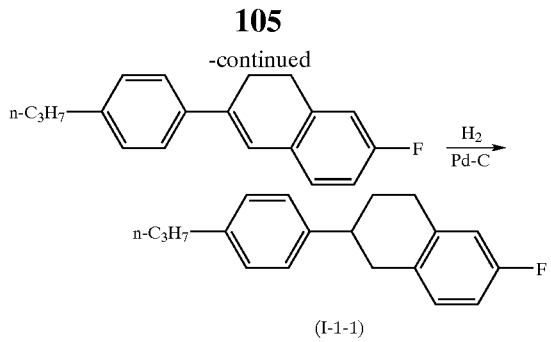

(I-1-1)

(1-1) Synthesis of 6-fluoro-3,4-dihydro-2(1H)-naphthalenone

To a solution of 30 g of 4-fluorophenylacetic acid and 48.9 g of thionyl chloride in 60 ml of 1,2-dichloroethane was added a catalytic quantity of pyridine, and the solution was then refluxed for 5 hours under an atmosphere of nitrogen. Following removal of the 1,2-dichloroethane, the product was added dropwise to an ice cooled suspension of 48.6 g of aluminum chloride in 200 ml of dichloromethane. Following stirring for 30 minutes, ethylene gas was blown into the reaction vessel, and after a further 5 hours of stirring, dilute hydrochloric acid was added, and following separation of the organic layer, the aqueous layer was extracted with toluene. The toluene extract was combined with the organic layer and washed subsequently with water, a saturated aqueous solution of sodium bicarbonate, water, and a saturated aqueous solution of sodium chloride, and was then dried over anhydrous sodium sulfate and the solvent removed by evaporation, and subsequently purified by distillation (75° C., 2 Torr) to obtain 19.4 g of 6-fluoro-3,4-dihydro-2(1H)-naphthalenone.

IR 1723, 1617 m 1596 cm$^1$.

$^1$H NMR (CDCl$_3$) δ 7.1–6.9 (m, 3H), 3.6 (s, 2H), 3.0–2.5 (m, 4H).

$^{13}$C NMR (CDCl$_3$) δ 210, 160, 139, 130, 129, 115, 114, 44, 38, 28.

MS m/z 164, 149, 135, 122, 115, 109, 101, 96, 83, 75, 63, 57.

(1-2) Synthesis of 2-(4-propylphenyl)-6-fluoro-1,2,3,4-tetrahydronaphthalene (I-1-1)

3.5 g of magnesium was suspended in 4 ml of tetrahydrofuran (THF), and a solution of 25.7 g of 4-propylbromobenzene in 100 ml of THF was then added dropwise to the suspension over an approximately 30 minute period at such a rate that the THF refluxed gently. The mixture was then stirred for a further 1 hour, and a solution of 9.4 g of 6-fluoro-3,4-dihydro-2(1H)-naphthalenone obtained from (1-1) in 80 ml of THF was then added dropwise to the mixture over a 30 minute period. Following stirring for a further 1 hour, 50 ml of 10% hydrochloric acid was added. 100 ml of hexane was then added, the organic layer was separated, and the aqueous layer was extracted with a further 100 ml of hexane which was combined with the organic layer. The combined organic extract was then washed with water, a saturated aqueous solution of sodium bicarbonate, and a saturated aqueous solution of sodium chloride, and was then dried over anhydrous sodium sulfate. The solvent was then removed by evaporation, 100 ml of toluene and 2.0 g of p-toluenesulfonic acid monohydrate were added, and the mixture was heated at 110° C. with stirring while evaporated water was separated and removed. When the evaporation of water had ceased, the temperature was reduced to room temperature, 50 ml of water was added, and the organic layer was separated. The organic layer was washed with a saturated aqueous solution of sodium bicarbonate, water, and a saturated aqueous solution of sodium chloride, and was then dried over anhydrous sodium sulfate. The solvent was removed by evaporation, and the whole residue was dissolved in 200 ml of ethyl acetate. 2.0 g of 5% palladium-carbon (wet) was then added, and the mixture was stirred in an autoclave under a hydrogen pressure of 4 Kg/cm$^2$. After stirring for 5 hours at room temperature, the catalyst was removed by filtration through celite, the solvent was removed by evaporation, and the residue was purified by silica gel column chromatography (hexane), and was recrystallized twice from ethanol to obtain 17.2 g of white crystals of 2-(4-propylphenyl)-6-fluoro-1,2,3,4-tetrahydronaphthalene.

Example 2

Synthesis of 2-(4-propylphenyl)-5,6,7-trifluoro-1,2,3,4-tetrahydronaphthalene (I-1-2)

Under the same conditions as those described for the example 1, using 3,4,5-trifluorophenylacetic acid instead of 4-fluorophenylacetic acid yielded 2-(4-propylphenyl)-5,6,7-trifluoro-1,2,3,4-tetrahydronaphthalene.

Example 3

Synthesis of 2-(4-propylphenyl)-5,7-difluoro-6-cyano-1,2,3,4-tetrahydronaphthalene

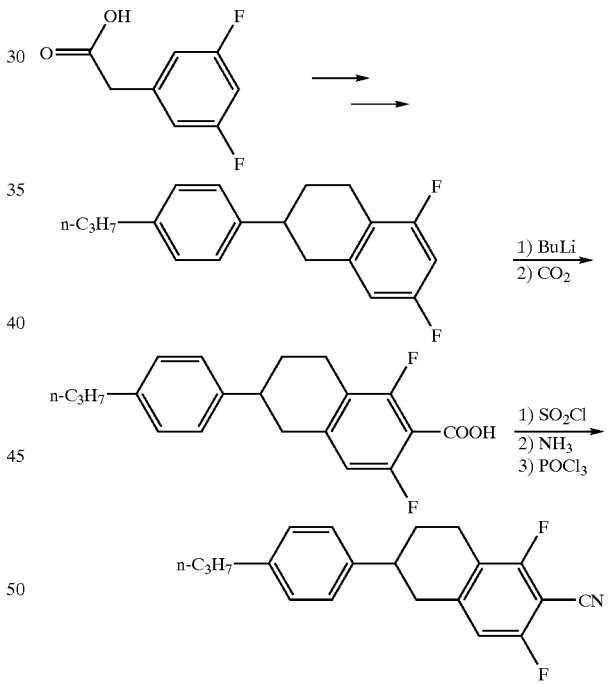

Under the same conditions as those described for the example 1, using 3,5-difluorophenylacetic acid instead of 4-fluorophenylacetic acid yielded 2-(4-propylphenyl)-5,7-difluoro-1,2,3,4-tetrahydronaphthalene. 10 g of this 2-(4-propylphenyl)-5,7-difluoro-1,2,3,4-tetrahydronaphthalene was lithiated using butyllithium, converted to a benzoic acid by blowing carbon dioxide into the reaction vessel, subsequently converted to an acid chloride with thionyl chloride, and an amide then synthesized by blowing ammonia gas into the reaction mixture was dissolved in 40 ml of DMF, 2.5 ml of phosphorus oxychloride was added, and the reaction was allowed to proceed for 2 hours at 25° C. The reaction liquid was poured into water with ice, dilute hydrochloric acid was added, and the water layer was extracted with toluene. The toluene extract was combined with the organic layer, and following washing with water, a saturated aqueous solution of sodium bicarbonate, water and a saturated aqueous solution of sodium chloride, was dried over anhydrous sodium sulfate. The crude product was purified using silica gel column chromatography (hexane/dichloromethane=6/4), and then recrystallized from ethanol to yield 6.3 g of 2-(4-propylphenyl)-5,7-difluoro-6-cyano-1,2,3,4-tetrahydronaphthalene.

Example 4

Synthesis of 2-[2-(trans-4-propylcyclohexyl)ethyl]-6-fluoro-1,2,3,4-tetrahydronaphthalene (I-1-3)

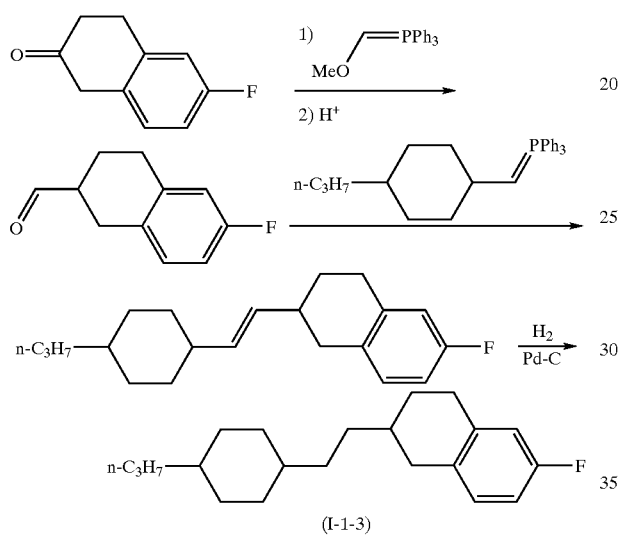

(4-1) Synthesis of 6-fluoro-1,2,3,4-tetrahydronaphthalene-2-carbaldehyde

A solution of 50 g of 6-fluoro-3,4-dihydro-2(1H)-naphthalenone obtained from (1-1) in 250 ml THF was added dropwise, at a temperature of 0° C., to a Wittig reagent prepared from 156.6 g of methoxymethyltriphenylphosphonium chloride and 51.3 g of potassium t-butoxide in ice cooled THF. After 1 hour of reaction, the mixture was returned to room temperature, water was added, and the organic layer was concentrated. Hexane was then added to dissolve the residue, the insoluble triphenylphosphine oxide was removed by filtration, and the product was washed in a 1/1 solvent mixture of methanol and water. The crude product obtained by concentrating the hexane layer was dissolved in 250 ml of THF, 250 ml of dilute hydrochloric acid was added, and the mixture was refluxed for 3 hours. Toluene was then added, and following washing with water, the product was dried over anhydrous sodium sulfate and the solvent removed by evaporation to yield 46.7 g of 6-fluoro-1,2,3,4-tetrahydronaphthalene-2-carbaldehyde.

(4-2) Synthesis of 2-[2-(trans-4-propylcyclohexyl)ethyl]-6-fluoro-1,2,3,4-tetrahydronaphthalene (I-1-3)

A solution comprising all of the 6-fluoro-1,2,3,4-tetrahydronaphthalene-2-carbaldehyde obtained from (4-1) dissolved in 250 ml THF was added dropwise, at a temperature of 0° C., to a Wittig reagent prepared from 188.7 g of 2-(trans-4-propylcyclohexyl)methyltriphenylphosphonium bromide and 44.1 g of potassium t-butoxide in ice cooled THF. After 1 hour of reaction, the mixture was returned to room temperature, water was added, and the organic layer was concentrated. Hexane was then added to dissolve the residue, the insoluble triphenylphosphine oxide was removed by filtration, and the product was washed in a 1/1 solvent mixture of methanol and water. The crude product obtained by concentrating the hexane layer was dissolved in 200 ml of ethyl acetate, 10 g of 5% palladium-carbon (wet) was added, and the mixture was stirred in an autoclave under a hydrogen pressure of 4 Kg/cm². After stirring for 5 hours at room temperature, the catalyst was removed by filtration through celite, the solvent was removed by evaporation, and the residue was purified by silica gel column chromatography (hexane), and two separate recrystallizations from ethanol to obtain 50.7 g of white crystals of 2-[2-(trans-4-propylcyclohexyl)ethyl]-6-fluoro-1,2,3,4-tetrahydronaphthalene (I-1-3).

Example 5

Synthesis of 2-[2-(trans-4-propylcyclohexyl)ethyl]-5,6,7-trifluoro-1,2,3,4-tetrahydronaphthalene (I-1-4)

Under the same conditions as those described for the example 4, using the 5,6,7-trifluoro-3,4-dihydro-2(1H)-naphthalenone synthesized in the example 2 instead of 6-fluoro-3,4-dihydro-2(1H)-naphthalenone yielded 2-[2-(trans-4-propylcyclohexyl)ethyl]-5,6,7-trifluoro-1,2,3,4-tetrahydronaphthalene.

Example 6

Synthesis of 2-propyl-6-(3,4-difluorophenyl)-1,2,3,4-tetrahydronaphthalene (I-2-1)

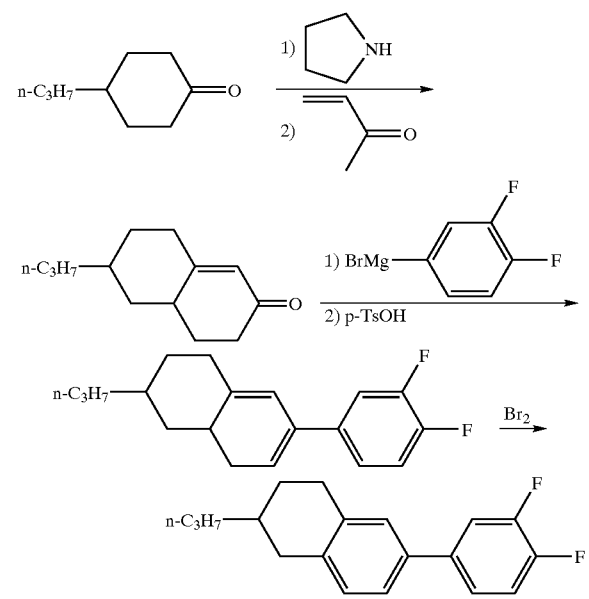

(6-1) Synthesis of 6-propyl-4,4a,5,6,7,8-hexahydro-3H-naphthalen-2-one 212 g of 4-propylcyclohexanone and 200 ml of pyrrolidine was dissolved in 600 ml of toluene, and the mixture was heated with stirring for 3 hours, and any azeotropically distilled water was removed. Excess pyrrolidine was then removed by azeotropic distillation with toluene, to obtain 1-(4-propylcyclohexa-1-en-1-yl)-pyrrolidine. The crude product was cooled, as is, to room temperature, a further 800 ml of toluene was added, the mixture was cooled in a water bath, and 120 ml of methyl vinyl ketone was added dropwise over a period of 1 hour at a temperature of 25° C. or lower. Following completion of the addition, the mixture was immediately heated and refluxed for 20 hours. The solution was then cooled to room temperature, a buffer solution of pH 5 prepared from 63 g of sodium acetate, 120 ml of acetic acid and 140 ml of water was added, and the reflux was continued for a further 4 hours. After the solution had been cooled to room temperature, the organic layer was separated and washed with water and a saturated aqueous solution of sodium chloride. The organic layer was then dried over anhydrous sodium sulfate, and the solvent removed by evaporation to obtain 320 g of a crude product of 6-propyl-4,4a,5,6,7,8-hexahydro-3H-naphthalen-2-one.

(6-2) Synthesis of 2-propyl-6-(3,4-difluorophenyl)-1,2,3,4,8,8a-hexahydronaphthalene 27.1 g of magnesium was suspended in 70 ml of tetrahydrofuran (THF), and a solution of 195.7 g of 3,4-difluorobromobenzene dissolved in 800 ml of THF was then added dropwise with the mixture under conditions of heated reflux. Following stirring for a further one hour, a solution of 150 g of the 6-propyl-4,4a,5,6,7,8-hexahydro-3H-naphthalen-2-one obtained from (6-1) above in 600 ml of THF was added dropwise, with continuous stirring and with the reaction mixture cooled in a water bath. Following stirring for a further two hours, the mixture was cooled in an ice bath, and 1000 ml of 10% hydrochloric acid was added. The product was then extracted with toluene, washed subsequently with water, and a saturated aqueous solution of sodium chloride, and was then dried over anhydrous magnesium sulfate. Subsequently, the crude product obtained by removal of the solvent by evaporation was redissolved in 1200 ml of toluene, 14.9 g of p-toluenesulfonic acid was added, and the mixture was heated with stirring for 3 hours and any azeotropically distilled water was removed. After the solution had been cooled to room temperature, the toluene layer was washed subsequently with water and a saturated aqueous solution of sodium chloride, and then dried over anhydrous magnesium sulfate, before the solvent was removed by evaporation to obtain 250 g of a crude product of 2-propyl-6-(3,4-difluorophenyl)-1,2,3,4,8,8a-hexahydronaphthalene.

(6-3) Synthesis of 2-propyl-6-(3,4-difluorophenyl)-1,2,3,4-tetrahydronaphthalene All of the crude 2-propyl-6-(3,4-difluorophenyl)-1,2,3,4,8,8a-hexahydronaphthalene obtained from (6-2) above was dissolved in 1200 ml of methylene chloride, the solution was cooled in an ice bath, and 44.2 ml of bromine was then added dropwise with stirring, with the stirring continued for a further 3 hours following completion of the addition. Subsequently, an aqueous solution of sodium hydrogen sulfite was added, and following 30 minutes of vigorous stirring, the methylene chloride layer was washed with a saturated aqueous solution of sodium chloride, dried over anhydrous magnesium sulfate, and concentrated to obtain a crude product of 2-propyl-6-(3,4-difluorophenyl)-1,2,3,4-tetrahydronaphthalene. This crude product was subsequently purified by silica gel column chromatography (hexane), and then dissolved in 800 ml of ethyl acetate, and stirred for 6 hours in an autoclave with 20 g of 5% palladium-carbon, under a hydrogen atmosphere of 4 Kg/cm². Following filtration, the solvent was removed by evaporation, and from the 230 g of crude product thus obtained, 20 g was purified by silica gel column chromatography (hexane), and then recrystallized 3 times from ethanol to obtain 6.5 g of white crystals of 2-propyl-6-(3,4-difluorophenyl)-1,2,3,4-tetrahydronaphthalene.

Example 7

Synthesis of 2-propyl-6-(3,4,5-trifluorophenyl)-1,2,3,4-tetrahydronaphthalene (I-2-2)

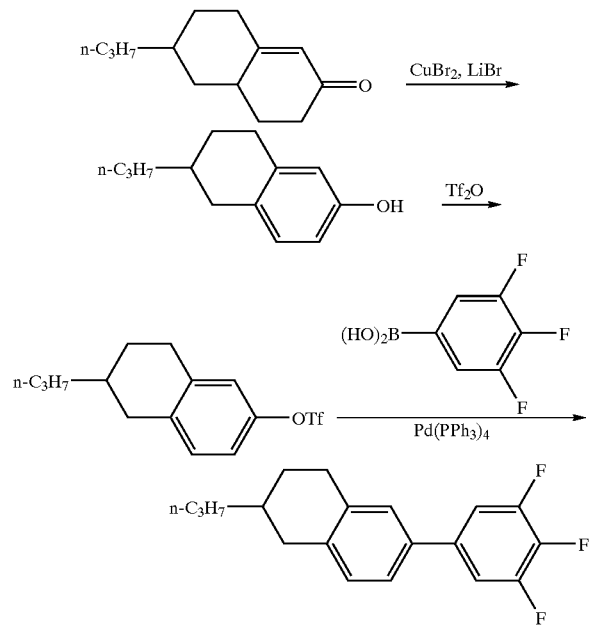

(7-1) Synthesis of 2-propyl-1,2,3,4-tetrahydro-6-naphthol 5 g of 6-propyl-4,4a,5,6,7,8-hexahydro-3H-naphthalen-2-one obtained from (6-1) was dissolved in 10 ml of acetonitrile, and a solution of 11.6 g of copper(II) bromide and 2.3 g of lithium bromide in 50 ml of acetonitrile was then added dropwise at room temperature. Following stirring of the reaction mixture for a further two hours, the solvent was removed by evaporation, and the residue was redissolved in ethyl acetate and filtered to remove any insoluble components. The solution was then washed with water and a saturated aqueous solution of sodium chloride. Following drying over anhydrous sodium sulfate, the solvent was removed by evaporation to obtain a crude product of 2-propyl-1,2,3,4-tetrahydro-6-naphthol.

(7-2) Synthesis of 2-propyl-1,2,3,4-tetrahydronaphthalen-6-yl trifluoromethanesulfonate The crude 2-propyl-1,2,3,4-tetrahydro-6-naphthol obtained from (7-1) was dissolved in 20 ml of dichloromethane, 4.7 ml of anhydrous trifluoromethanesulfonic acid was then added and suspended, and the mixture was cooled to 5° C. 4.6 ml of pyridine was then added dropwise with vigorous stirring, and the mixture then stirred for a further one hour. 20 ml of water was then added, the reaction was halted, and the organic layer was separated off. The aqueous layer was extracted with 20 ml of dichloromethane, which was combined with the organic layer, and the combined organic layer was then washed with dilute hydrochloric acid, a saturated aqueous solution of sodium bicarbonate, water, and then a saturated aqueous solution of sodium chloride, and subsequently dried over anhydrous sodium sulfate. Following removal of the solvent by evaporation, the crude product was purified by silica gel column chromatography (hexane) to obtain 3.8 g of 2-propyl-1,2,3,4-tetrahydronaphthalen-6-yl trifluoromethanesulfonate.

(7-3) Synthesis of 2-propyl-6-(3,4,5-trifluorophenyl)-1,2,3,4-tetrahydronaphthalene A mixture of 3.8 g of the produced 2-propyl-1,2,3,4-tetrahydronaphthalen-6-yl trifluoromethanesulfonate, 3.0 g of 3,4,5-trifluorophenylboric acid (this compound was produced by reacting a Grignard reagent prepared from 3,4,5-trifluorobromobenzene and magnesium, with trimethoxy borane, and then performing a hydrolysis with dilute hydrochloric acid), 0.13 g of tetrakis(triphenylphosphine) palladium(0), and 3.6 g of potassium phosphate in 20 ml of dimethyl formamide (DMF) was stirred for 10 hours at 80° C. The mixture was subsequently cooled to room temperature, 20 ml of water was added, the mixture was extracted with toluene, and the organic layer was washed subsequently with water and then a saturated aqueous solution of sodium chloride, and subsequently dried over anhydrous sodium sulfate. The crude product obtained by removal of the solvent by evaporation was purified by silica gel column chromatography (hexane) and then recrystallized 3 times from ethanol to obtain 0.5 g of 2-propyl-6-(3,4,5-trifluorophenyl)-1,2,3,4-tetrahydronaphthalene.

Example 8

Synthesis of 2-(trans-4-propylcyclohexyl)-6-(3,4,5-trifluorophenyl)-1,2,3,4-tetrahydronaphthalene (I-2-3)

obtained from (8-1) above and 14 g of 2,3-dichloro-5,6-dicyano-1,4-benzoquinone (DDQ) in 80 ml of toluene was stirred for 3 hours at room temperature. Water and toluene were then added, the mixture was filtered, and the toluene layer was then separated and washed subsequently in water and a saturated aqueous solution of sodium chloride, before being dried over anhydrous magnesium sulfate. Following removal of the solvent by evaporation, the residue was purified by silica gel column chromatography (hexane) to obtain 21.1 g of a crude product. All of this crude product was subsequently dissolved in 80 ml of ethyl acetate, and then stirred for 6 hours in an autoclave with 4 g of 5% palladium-carbon, under a hydrogen atmosphere of 4 Kg/cm$^2$. Following filtration, the solvent was removed by evaporation, and the crude product thus obtained was purified by silica gel column chromatography (hexane), and then recrystallized 3 times from ethanol/toluene to obtain 6.2 g of 2-(4-propylcyclohexyl)-6-(3,4,5-trifluorophenyl)-1,2,3,4-tetrahydronaphthalene.

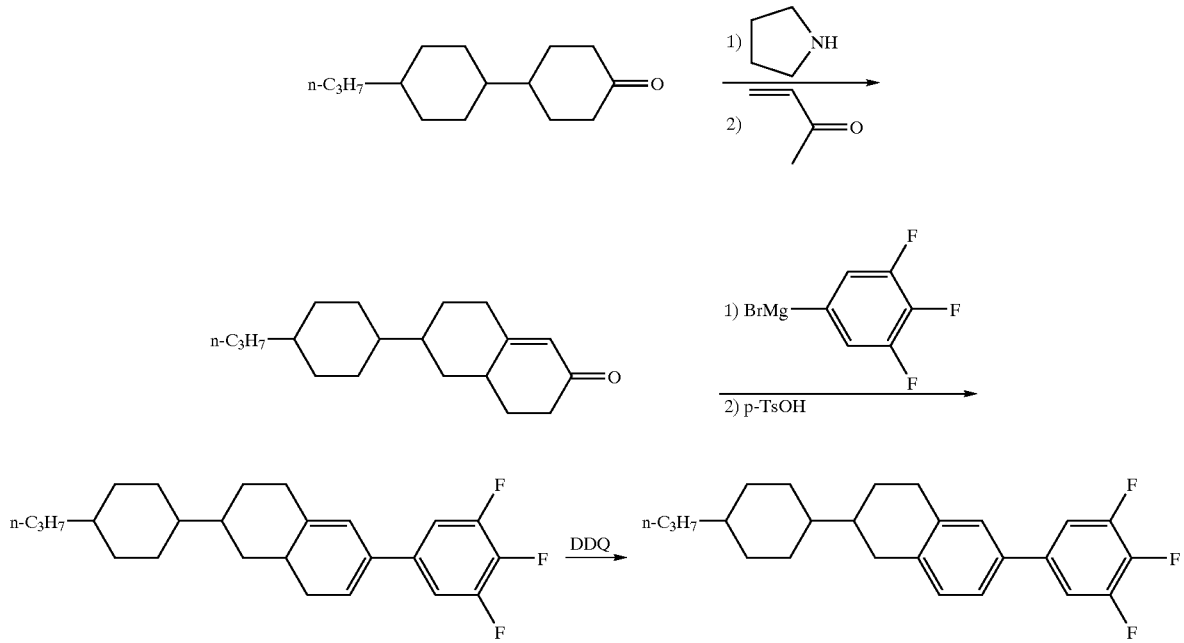

(8-1) Synthesis of 2-(4-propylcyclohexyl)-6-(3,4,5-trifluorophenyl)-1,2,3,4,8,8a-hexahydronaphthalene A synthesis was performed in the same manner as (6-1) of the example 6, with the exception of using 4-(4-propylcyclohexyl)-cyclohexanone instead of 4-propylcyclohexanone, and yielded 6-(4-propylcyclohexyl)-4,4a,5,6,7,8-hexahydro-3H-naphthalen-2-one. Subsequently, the synthesis was continued in the same manner as (6-2), with the exception of using 3,4,5-trifluorobromobenzene instead of 3,4-difluorobromobenzene, and yielded 2-(4-propylcyclohexyl)-6-(3,4,5-trifluorophenyl)-1,2,3,4,8,8a-hexahydronaphthalene.

(8-2) Synthesis of 2-(4-propylcyclohexyl)-6-(3,4,5-trifluorophenyl)-1,2,3,4-tetrahydronaphthalene A mixture of 20 g of 2-(4-propylcyclohexyl)-6-(3,4,5-trifluorophenyl)-1,2,3,4,8,8a-hexahydronaphthalene

Example 9

Synthesis of 2-propyl-6-(4-cyano-3,5-difluorophenyl)-1,2,3,4-tetrahydronaphthalene (I-2-4)

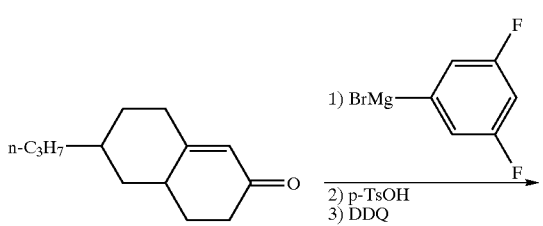

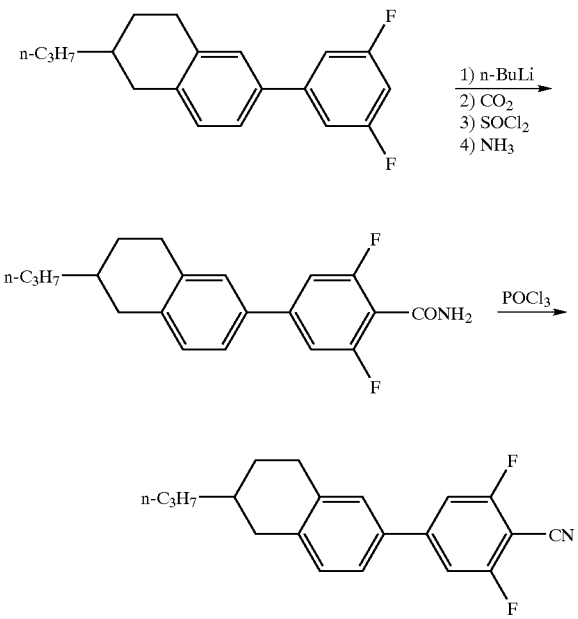

(9-1) Synthesis of 2-propyl-6-(3,5-difluorophenyl)-1,2,3,4-tetrahydronaphthalene A synthesis was performed in the same manner as (6-2) of the example 6, with the exception of replacing 3,4-difluorobromobenzene with 3,5-difluorobromobenzene, and yielded 212.5 g of 2-propyl-6-(3,5-difluorophenyl)-1,2,3,4,8,8a-hexahydronaphthalene from 200 g of 6-propyl-4,4a,5,6,7,8-hexahydro-3H-naphthalen-2-one. Subsequently, the synthesis was continued in the same manner as (8-2), and an additional vacuum distillation then carried out, to obtain 112 g of 2-propyl-6-(3,5-difluorophenyl)-1,2,3,4-tetrahydronaphthalene.

(9-2) Synthesis of 2-propyl-6-(3,5-difluoro-4-carbamoylphenyl)-1,2,3,4-tetrahydronaphthalene 27.1 g of the 2-propyl-6-(3,5-difluorophenyl)-1,2,3,4-tetrahydronaphthalene obtained in (9-1) above was dissolved in 120 ml of THF, and with the solution cooled to −50° C., 68.9 ml of a 1.51 M hexane solution of n-butyllithium was added dropwise. Carbon dioxide gas was then blown through the solution, and then water was added and the product was extracted with ethyl acetate. The organic layer was then washed subsequently with water and a saturated aqueous solution of sodium chloride, and then dried over anhydrous magnesium sulfate. Following removal of the solvent by evaporation, the crude product was redissolved in 80 ml of 1,2-dichloroethane and 8.2 ml of thionyl chloride was added. Following the dropwise addition of a catalytic quantity of pyridine, the solution was stirred for 2 hours at 50° C. and any excess thionyl chloride and the 1,2-dichloroethane were removed by evaporation. The residue was dissolved in 100 ml of methylene chloride, and ammonia gas was blown into the solution at room temperature, with stirring, and when the heat generation had ceased, water was added, the product was extracted with ethyl acetate, and the organic layer was washed subsequently with water and a saturated aqueous solution of sodium chloride, before being dried over anhydrous magnesium sulfate. The solvent was removed by evaporation and yielded a crude product of 2-propyl-6-(3,5-difluoro-4-carbamoylphenyl)-1,2,3,4-tetrahydronaphthalene.

(9-3) Synthesis of 2-propyl-6-(4-cyano-3,5-difluorophenyl)-1,2,3,4-tetrahydronaphthalene All of the crude product of 2-propyl-6-(3,5-difluoro-4-carbamoylphenyl)-1,2,3,4-tetrahydronaphthalene obtained in (9-2) above was dissolved in 120 ml of DMF, 13 ml of phosphorus oxychloride was added, and the reaction was allowed to proceed for 2 hours at 25° C. The reaction liquid was then poured into water with ice, dilute hydrochloric acid was added, and the water layer was extracted with toluene. The toluene extract was combined with the organic layer, and following washing with water, a saturated aqueous solution of sodium bicarbonate and a saturated aqueous solution of sodium chloride, was dried over anhydrous sodium sulfate. The crude product was purified using silica gel column chromatography (toluene) followed by alumina column chromatography (toluene), further purified by activated carbon treatment in an acetone solution, and then recrystallized seven times from ethanol to obtain 4.0 g of 2-propyl-6-(4-cyano-3,5-difluorophenyl)-1,2,3,4-tetrahydronaphthalene.

Example 10

Synthesis of 2-propyl-5-fluoro-6-(3,4,5-trifluorophenyl)-1,2,3,4-tetrahydronaphthalene, and 2-propyl-7-fluoro-6-(3,4,5-trifluorophenyl)-1,2,3,4-tetrahydronaphthalene (I-2-5)

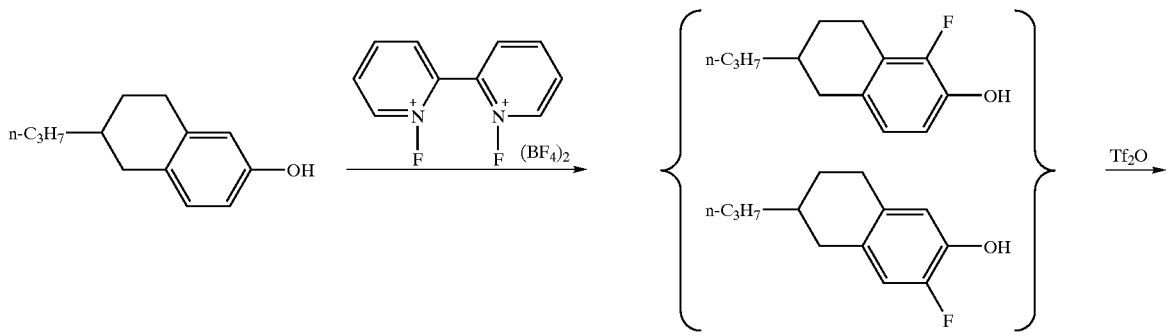

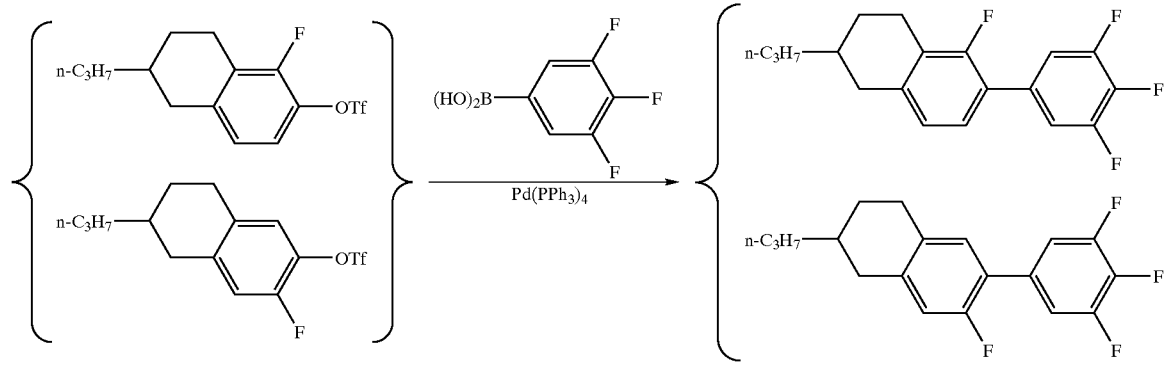

(10-1) Synthesis of 2-propyl-5-fluoro-1,2,3,4-tetrahydro-6-naphthol, and 2-propyl-7-fluoro-1,2,3,4-tetrahydro-6-naphthol 200 g of the 2-propyl-1,2,3,4-tetrahydro-6-naphthol obtained in (7-1) was dissolved in 1000 ml of dichloromethane, 5 g of sodium trifluoromethanesulfonate was added, and the mixture was stirred vigorously. 243 g of N,N'-difluoro-2,2'-bipyridinium bistetrafluoroborate was gradually added to the reaction mixture, and the resulting mixture was stirred for a further 5 hours at room temperature. Water, and then a 10% aqueous solution of sodium hydroxide were added, any excess fluorinating reagent was decomposed, and following restoration to an acidic state by addition of dilute hydrochloric acid, the organic layer was separated. The aqueous layer was extracted with dichloromethane, the extract was combined with the separated organic layer, and this combined organic extract was washed with water and a saturated aqueous solution of sodium chloride, before being dried over anhydrous sodium sulfate. The crude product obtained by removal of the solvent by evaporation was separated and purified by silica gel column chromatography (toluene), to obtain 57.0 g of 2-propyl-5-fluoro-1,2,3,4-tetrahydro-6-naphthol, and 85.5 g of 2-propyl-7-fluoro-1,2,3,4-tetrahydro-6-naphthol.

(10-2) Synthesis of 2-propyl-5-fluoro-6-(3,4,5-trifluorophenyl)-1,2,3,4-tetrahydronaphthalene, and 2-propyl-7-fluoro-6-(3,4,5-trifluorophenyl)-1,2,3,4-tetrahydronaphthalene Syntheses were performed in the same manner as (7-2) and (7-3), with the exception of using the 2-propyl-5-fluoro-1,2,3,4-tetrahydro-6-naphthol and the 2-propyl-7-fluoro-1,2,3,4-tetrahydro-6-naphthol obtained in (10-1) above instead of the 2-propyl-1,2,3,4-tetrahydro-6-naphthol in (7-2), and yielded 35 g of 2-propyl-5-fluoro-6-(3,4,5-trifluorophenyl)-1,2,3,4-tetrahydronaphthalene, and 53 g of 2-propyl-7-fluoro-6-(3,4,5-trifluorophenyl)-1,2,3,4-tetrahydronaphthalene respectively.

Example 11

Synthesis of 2-propyl-6-(3,4,5-trifluorophenyl) ethynyl-1,2,3,4-tetrahydronaphthalene

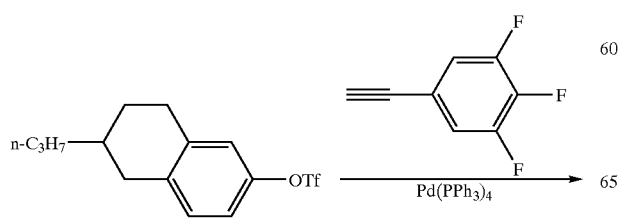

A mixture of 50 g of the 2-propyl-1,2,3,4-tetrahydronaphthalen-6-yl trifluoromethanesulfonate obtained in (7-2), 33.9 g of (3,4,5-trifluorophenyl)acetylene, 3.6 g of tetrakis(triphenylphosphine)palladium(0), and 51.4 g of potassium phosphate in 200 ml of DMF was stirred for 10 hours at 80° C. The mixture was subsequently cooled to room temperature, water was added, the mixture was extracted with toluene, and the organic layer was washed subsequently with water and a saturated aqueous solution of sodium chloride, and subsequently dried over anhydrous sodium sulfate. The crude product obtained by removal of the solvent by evaporation was purified by silica gel column chromatography (hexane) and then recrystallized 3 times from ethanol to obtain 32.6 g of 2-propyl-6-(3,4,5-trifluorophenyl)ethynyl-1,2,3,4-tetrahydronaphthalene.

Example 12

Synthesis of 6-propyl-2-(3,4,5-trifluorophenyl)-1,2,3,4-tetrahydronaphthalene (I-3-2)

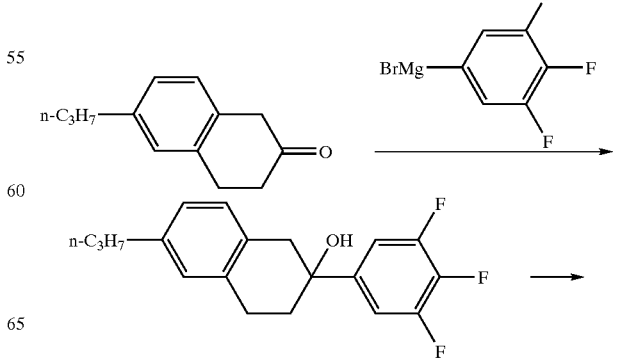

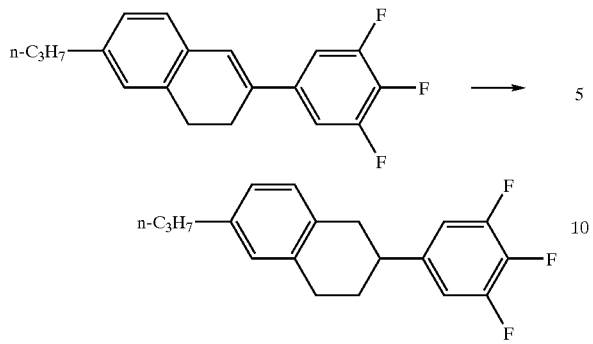

A Grignard reagent was prepared by the dropwise addition of a solution of 30 g of 3,4,5-trifluorobromobenzene in 100 ml of tetrahydrofuran to 4.0 g of magnesium. Following addition of 150 ml of toluene to this reagent, approximately 100 ml of solvent was removed under reduced pressure, at room temperature. The mixture was then heated to 60° C., and a solution of 25 g of 6-propyl-1,2,3,4-tetrahydronaphthalen-2-one in 50 ml of toluene was added dropwise over a period of 20 minutes. The resulting mixture was stirred for a further 30 minutes, returned to room temperature, and then poured into a 10% hydrochloric acid solution. The organic layer was washed with a saturated aqueous solution of sodium chloride, dried over anhydrous sodium sulfate, and then concentrated. The thus obtained residue was purified by silica gel column chromatography (hexane/ethyl acetate=6/1) and yielded 29 g of 2-hydroxy-6-propyl-2-(3,4,5-trifluorophenyl)-1,2,3,4-tetrahydronaphthalene. To this product was added 100 ml of toluene and 3 g of p-toluenesulfonic acid, and the resulting mixture was stirred with heating for one hour. The reaction solution was then cooled and concentrated, and the residue purified by silica gel column chromatography (hexane) to obtain 26 g of 6-propyl-2-(3,4,5-trifluorophenyl)-3,4-dihydronaphthalene. To this product was added 50 ml of ethanol, 50 ml of ethyl acetate and 3 g of 5% palladium-carbon, and the resulting mixture was stirred under an atmosphere of hydrogen for 2 hours at room temperature. The reaction mixture was filtered through celite, and the filtrate concentrated by removal of the solvent. The residue was purified by silica gel column chromatography (hexane), and yielded 26 g of 6-propyl-2-(3,4,5-trifluorophenyl)-1,2,3,4-tetrahydronaphthalene. This compound displayed a purity of 99% when analyzed by gas chromatography, and had a molecular weight of 304.

Example 13

Synthesis of 2-(3,4-difluorophenyl)-6-propyl-1,2,3,4-tetrahydronaphthalene (I-3-1)

A synthesis was performed under the same conditions as the example 12, with the exception of using 3,4-difluorobromobenzene instead of 3,4,5-trifluorobromobenzene, and yielded 2-(3,4-difluorophenyl)-6-propyl-1,2,3,4-tetrahydronaphthalene. Purity 99%, molecular weight 286.

Example 14

Synthesis of 6-propyl-2-(4-trifluoromethoxyphenyl)-1,2,3,4-tetrahydronaphthalene (I-3-3)

A synthesis was performed under the same conditions as the example 12, with the exception of using 4-trifluoromethoxybromobenzene instead of 3,4,5-trifluorobromobenzene, and yielded 6-propyl-2-(4-trifluoromethoxyphenyl)-1,2,3,4-tetrahydronaphthalene. Purity 99%, molecular weight 334.

Example 15

Synthesis of 2-(3,4-difluorophenyl)-6-(trans-4-propylcyclohexyl)-1,2,3,4-tetrahydronaphthalene (I-34)

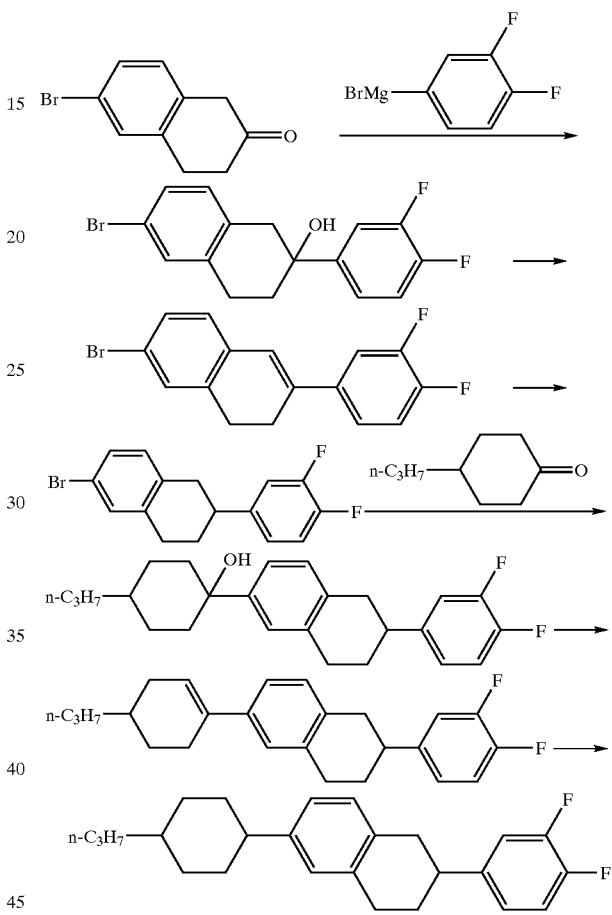

A Grignard reagent was prepared by the dropwise addition of a solution of 25 g of 3,4-difluorobromobenzene in 100 ml of tetrahydrofuran to 3.5 g of magnesium. The reagent mixture was filtered through a glass filter, and following the addition of 150 ml of toluene to the filtrate, approximately 100 ml of solvent was removed under reduced pressure, at room temperature. The mixture was then heated to 60° C., and a solution of 27 g of 6-bromo-1,2,3,4-tetrahydronaphthalen-2-one in 50 ml of toluene was added dropwise over a period of 20 minutes. The resulting mixture was stirred for a further 30 minutes, returned to room temperature, and then poured into a 10% hydrochloric acid solution. The organic layer was washed with a saturated aqueous solution of sodium chloride, dried over anhydrous sodium sulfate, and then concentrated. The thus obtained residue was purified by silica gel column chromatography (hexane/ethyl acetate=6/1) and yielded 29 g of 6-bromo-2-(3,4-difluorophenyl)-2-hydroxy-1,2,3,4-tetrahydronaphthalene. To this product was added 100 ml of toluene and 3 g of p-toluenesulfonic acid, and the resulting mixture was stirred with heating for one hour. The reaction solution was then cooled and concentrated, and the residue purified by silica gel column chromatography (hexane) to obtain 26 g of 6-bromo-2-(3,4-difluorophenyl)-3,4-dihydronaphthalene. To this product was added 50 ml of ethanol, 50 ml of ethyl acetate and 3 g of 5% rhodium-carbon, and the resulting mixture was stirred under an atmosphere of hydrogen for 2 hours at room temperature. The reaction mixture was then filtered through celite, and the filtrate concentrated by removal of the solvent. The residue was purified by silica gel column chromatography (hexane), and yielded 26 g of 6-bromo-2-(3,4-difluorophenyl)-1,2,3,4-tetrahydronaphthalene. A Grignard reagent was then prepared by the dropwise addition of a solution of this 26 g of 6-bromo-2-(3,4-difluorophenyl)-1,2,3,4-tetrahydronaphthalene in 70 ml of tetrahydrofuran to 2.3 g of magnesium. A solution of 13.5 g of 4-propylcyclohexanone in 30 ml of tetrahydrofuran was then added dropwise to this reagent. The resulting mixture was stirred for a further 30 minutes, and then poured into a 10% hydrochloric acid solution. The organic layer was washed with a saturated aqueous solution of sodium chloride, dried over anhydrous sodium sulfate, and then concentrated. The thus obtained residue was purified by silica gel column chromatography (hexane/ethyl acetate=6/1) and yielded 23 g of 2-(3,4-difluorophenyl)-2-hydroxy-6-(trans-4-propylcyclohexyl)-1,2,3,4-tetrahydronaphthalene. To this product was added 80 ml of toluene and 2 g of p-toluenesulfonic acid, and the resulting mixture was stirred with heating for one hour. The reaction solution was then cooled and concentrated, and the residue purified by silica gel column chromatography (hexane) to obtain 26 g of 2-(3,4-difluorophenyl)-6-(trans-4-propylcyclohexyl)-3,4-dihydronaphthalene. To this product was added 30 ml of ethanol, 50 ml of ethyl acetate and 2 g of 5% palladium-carbon, and the resulting mixture was stirred under an atmosphere of hydrogen for 2 hours at room temperature. The reaction mixture was then filtered through celite, and the filtrate concentrated by removal of the solvent. 50 ml of dimethyl formamide and 5.5 g of potassium t-butoxide were then added to the residue, and the mixture was stirred for 2 hours at 70° C. 10% hydrochloric acid was then added to the reaction mixture, which was then extracted with toluene, and the extracted organic layer was then washed with a saturated aqueous solution of sodium chloride, dried over anhydrous sodium sulfate and concentrated by removal of the solvent. The residue was purified by silica gel column chromatography (hexane), and then recrystallized from ethanol, and yielded 20 g of 2-(3,4-difluorophenyl)-6-(trans-4-propylcyclohexyl)-1,2,3,4-tetrahydronaphthalene. This compound displayed a purity of 99.8% when analyzed by gas chromatography, and had a molecular weight of 368.

Example 16

Synthesis of 2-(3,4-difluorophenyl)-6-(4-propylphenyl)-1,2,3,4-tetrahydronaphthalene (I-3-5)

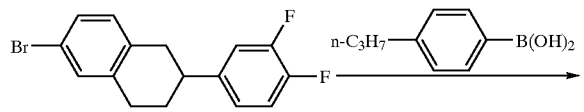
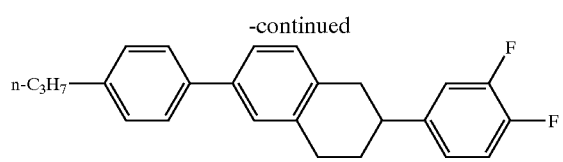

A solution of 4.5 g of 4-propylphenylboric acid obtained by reaction of a Grignard reagent prepared from 4-propylbromobenzene and magnesium with trimethoxy borane and subsequent hydrolysis with dilute hydrochloric acid, 5.0 g of 6-bromo-2-(3,4-difluorophenyl)-1,2,3,4-tetrahydronaphthalene synthesized in the example 15, 0.3 g of tetrakis(triphenylphosphine)palladium(0), and 3.0 g of potassium phosphate in 30 ml of dimethyl formamide was stirred for 10 hours at 80° C. The mixture was subsequently cooled to room temperature, water was added, and the mixture was extracted with toluene. The organic layer was washed with a saturated aqueous solution of sodium chloride, dried over anhydrous sodium sulfate, and then concentrated. The residue was purified by silica gel column chromatography (hexane) and then recrystallized from ethanol, and yielded 4 g of 2-(3,4-difluorophenyl)-6-(4-propylphenyl)-1,2,3,4-tetrahydronaphthalene. This compound displayed a purity of 99.7% when analyzed by gas chromatography, and had a molecular weight of 362.

Example 17

Preparation 1 of a Liquid Crystal Composition

The versatile host liquid crystal (H), which has a broad temperature range, is of low viscosity, and can be used in active matrix driving, was prepared.

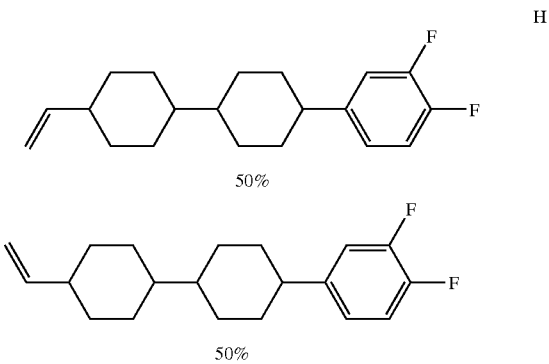

(wherein, the cyclohexane rings represent trans forms). This host liquid crystal (H) exhibits a nematic phase at 116.7° C. or lower, and has a melting point of 11° C. The physical property values of this composition, and the measured value at 20° C. of the threshold voltage (Vth) of a TN cell (cell thickness: 4.5 μm) prepared using this composition were as shown below.

Nematic phase upper limit temperature ($T_{N-I}$): 116.7° C.
Dielectric anisotropy (Δε): 4.80
Threshold voltage (Vth): 1.88 V
Response time (τ): 21.5 ms Next, when a liquid crystal composition (M-1) was prepared from 80% of this host liquid crystal (H) and 20% of the compound (I-1-2) of the present invention obtained in the example 2, the liquid crystal phase upper limit temperature ($T_{N-I}$) was 72.3° C. The value of $T_{N-I}$ was also measured after leaving the composition (M-1) to stand for 20 hours at a temperature of 150° C., but no variation was observed from the value prior to heating. Furthermore, the composition was also irradiated with ultraviolet radiation for 20 hours, but no change was observed in the value of $T_{N-I}$. When the voltage holding ratio of this composition was measured it exhibited a high value similar to that of the host liquid crystal (H), at the time of preparation, following heating, and following irradiation with ultraviolet radiation.

Next, a liquid crystal element was prepared by using the composition (M-1) to fill a TN cell with a cell thickness of 4.6 μm, and measurement of the electrooptical characteristics of the element revealed the values shown below.

Dielectric anisotropy (Δε): 5.20
Threshold voltage (Vth): 1.51 V
Response time (τ): 29.3 ms Consequently, addition of 20% of the compound (I-1-2) enabled the fall in the nematic phase upper limit temperature ($T_{N-I}$) to be limited to 44° C., while the threshold voltage (Vth) could be reduced by 0.37 V. In addition, the increase in the response time could be suppressed to 8 ms. Furthermore, even after standing for 1 week at 0° C., crystal precipitation did not occur. Moreover, when the composition was crystallized by rapid cooling and the melting point ($T_{C-N}$) was then measured, it was found to be 13° C., which is almost the same as the host liquid crystal (H), indicating that the compound (I-1-2) dissolves readily in the host liquid crystal.

Next, the voltage holding rates of this element were measured at room temperature and at 80° C., and both were extremely favorable, indicating that this element can be adequately used for active matrix driving.

Example 18

Preparation 2 of a Liquid Crystal Composition

A liquid crystal composition (M-2) was prepared in the same manner as the example 17, using the compound (I-2-3) of the present invention obtained in the example 8 instead of the compound (I-1-2), and adding 20% of this compound to the host liquid crystal (H). This composition exhibited a nematic phase upper limit temperature ($T_{N-I}$) of 118.1° C. The value of $T_{N-I}$ was also measured after leaving the composition (M-2) to stand for 20 hours at a temperature of 150° C., but no variation was observed from the value prior to heating. Furthermore, the composition was also irradiated with ultraviolet radiation for 20 hours, but no change was observed in the value of $T_{N-I}$. When the voltage holding ratio of this composition was measured it exhibited a high value similar to that of the host liquid crystal (H), at the time of preparation, following heating, and following irradiation with ultraviolet radiation.

Next, a liquid crystal element was prepared by using the composition (M-2) to fill a TN cell with a cell thickness of 6.0 Elm, and measurement of the electrooptical characteristics of the element revealed the values shown below.

Dielectric anisotropy (Δε): 5.50
Threshold voltage (Vth): 1.92 V
Response time (τ): 34.2 ms Consequently, addition of 20% of the compound (I-2-3) enabled the nematic phase temperature range to be widened, while the threshold voltage (Vth) was reduced by 0.22 V. In addition, the increase in the response time could be suppressed to 9 ms.

Example 19

Preparation 3 of a Liquid Crystal Composition

A liquid crystal composition (M-3) was prepared in the same manner as the example 17, using 20% of the compound (I-3-2) of the present invention obtained in the example 12 instead of the compound (I-1-2), and the liquid crystal phase upper limit temperature ($T_{N-I}$) of this composition was 74° C. The value of $T_{N-I}$ was also measured after leaving the composition (M-3) to stand for 20 hours at a temperature of 150° C., but no variation was observed from the value prior to heating. Furthermore, the composition was also irradiated with ultraviolet radiation for 20 hours, but no change was observed in the value of $T_{N-I}$. When the voltage holding ratio of this composition was measured it exhibited a high value similar to that of the host liquid crystal (H), at the time of preparation, following heating, and following irradiation with ultraviolet radiation.

Next, a liquid crystal element was prepared by using the composition (M-3) to fill a TN cell with a cell thickness of 6.0 μm, and measurement of the electrooptical characteristics of the element revealed the values shown below.

Dielectric anisotropy (Δε): 5.50
Threshold voltage (Vth): 1.55 V
Response time (τ): 30.5 ms Consequently, addition of 20% of the compound (I-3-2) enabled the fall in the nematic phase upper limit temperature ($T_{N-I}$) to be limited to 46° C., while the threshold voltage (Vth) could be reduced by 0.33 V. In addition, the increase in the response time could be suppressed to 9 ms. Furthermore, even after standing for 1 week at 0° C., crystal precipitation did not occur. Moreover, when the composition was crystallized by rapid cooling and the melting point ($T_{C-N}$) was then measured, it was found to be 12° C., which is almost the same as the host liquid crystal (H), indicating that the compound (I-3-2) dissolves readily in the host liquid crystal.

Next, the voltage holding rates of this element were measured at room temperature and at 80° C., and both were extremely favorable, indicating that this element can be adequately used for active matrix driving.

Comparative Example 1

A liquid crystal composition (M-4) was prepared in the same manner as the example 17, using trans-4-propyl-(3,4, 5-trifluorophenyl)cyclohexane instead of the compound (I-1-2), and adding 20% of this compound to the host liquid crystal (H). This composition exhibited a nematic phase upper limit temperature ($T_{N-I}$) of 70° C., and the liquid crystallinity was considerably low.

The physical property values of this composition, together with the electrooptical properties of an element prepared in the same manner as that described above are as shown below.

Nematic phase upper limit temperature ($T_{N-I}$): 70.0° C.
Dielectric anisotropy (Δε): 5.60
Threshold voltage (Vth): 1.58 V
Response time (τ): 30.0 ms
Birefringence (Δn): 0.080

INDUSTRIAL APPLICABILITY

A tetrahydronaphthalene derivative provided in the present invention shows superior liquid crystallinity and co-solubility with conventional liquid crystal compounds and compositions. Furthermore, addition of such a compound enables the threshold voltage to be significantly reduced with almost no deleterious effect on the response. In addition, a compound of the present invention can also be easily produced industrially, is colorless, and is chemically stable. Consequently, liquid crystal compositions containing such a compound are extremely useful as liquid crystals, and are particularly suitable for liquid crystal displays requiring a wide operating temperature range, low voltage driving and a quick response.

What is claimed is:

1. A tetrahydronaphthalene derivative represented by a general formula (I)

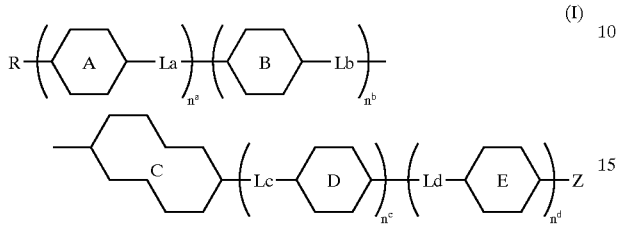

(wherein, R represents a saturated or unsaturated alkyl group or alkoxyl group of 1 to 20 carbon atoms which may incorporate a branched chain and may be substituted with 1 to 7 fluorine atoms or alkoxyl groups of 1 to 7 carbon atoms; linkage groups La, Lb, Lc and Ld each represent independently a single bond, —$CH_2CH_2$—, —CH=CH—, —CH($CH_3$)$CH_2$—, —$CH_2$CH($CH_3$)—, —CH($CH_3$)CH($CH_3$)—, —$CF_2CF_2$—, —CF=CF—, —$CH_2$O—, —O$CH_2$—, —OCH($CH_3$), —CH($CH_3$)O—, —C≡C—, —$CF_2$O—, —O$CF_2$—, —COO—, —OCO—, —COS— or —SCO—; Z represents a fluorine atom, chlorine atom, cyano group, cyanato group, trifluoromethoxy group or a difluoromethoxy group; ring A, ring B and ring D each represent independently a trans-1,4-cyclohexylene group, a trans-decahydronaphthalene-2,6-diyl group, a trans-1,3-dioxane-2,4-diyl group, or a 1,4-phenylene group which may be substituted with one or two fluorine atoms, a pyridine-2,5-diyl group, a pyrimidine-2,5-diyl group, a pyrazine-2,5-diyl group, a pyridazine-3,6-diyl group, and a naphthalene-2,6-diyl group which may be substituted with one or two fluorine atoms; ring E represents independently a 1,4-phenylene group which may be substituted with one or two fluorine atoms, and a naphthalene-2,6-diyl group which may be substituted with one or two fluorine atoms, ring C represents either one of a general formula (IIa) and a general formula (IIb)

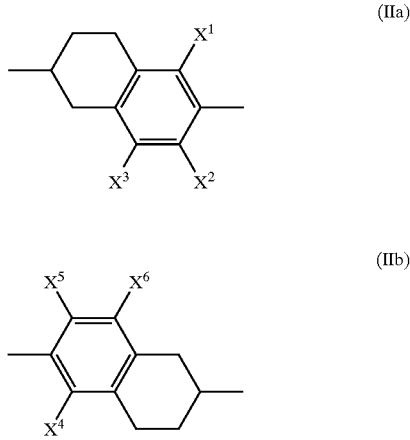

(wherein, $X^1$, $X^2$, $X^3$, $X^4$, $X^5$ and $X^6$ each represent independently a hydrogen atom or a fluorine atom); and $n^a$, $n^b$, $n^c$ and $n^d$ each represent independently either 0 or 1;

although, in a case in which $n^c$=1 and $n^d$=0, ring D represents a 1,4-phenylene group which may be substituted with one or two fluorine atoms and/or a naphthalene-2,6-diyl group which may be substituted with one or two fluorine atoms;

in a case in which Z is a cyano group, R is an unsubstituted and saturated alkyl group or alkoxyl group, $n^a$=$n^c$=$n^d$=0 and $n^b$=1, or $n^b$=$n^c$=$n^d$=0 and $n^a$=1, ring A and ring B are 1,4-phenylene groups, La and Lb are single bonds, and ring C is said general formula (IIa), then at least one of $X^1$, $X^2$ and $X^3$ represents a fluorine atom;

in a case in which Z is a cyano group, R is an unsubstituted and saturated alkyl group or alkoxyl group, $n^a$=$n^b$=$n^c$=0 and $n^d$=1, or $n^a$=$n^b$=$n^d$=0 and $n^c$=1, ring E and ring D are 1,4-phenylene groups, Lc and Ld are single bonds, —O$CH_2$— or —COO— linkages, and ring C is said general formula (IIa), then at least one of $X^1$, $X^2$ and $X^3$ represents a fluorine atom;

in a case in which Z is a cyano group, R is an unsubstituted and saturated alkyl group or alkoxyl group, $n^a$=$n^b$=$n^c$=0 and $n^d$=1, or $n^a$=$n^b$=$n^d$=0 and $n^c$=1, ring E and ring D are 1,4-phenylene groups, Lc and Ld are single bonds or —COO— linkages, and ring C is said general formula (IIb), then at least one of $X^4$, $X^5$ and $X^6$ represents a fluorine atom;

in a case in which Z is a fluorine atom, R is an unsubstituted and saturated alkyl group or alkoxyl group, $n^a$=$n^b$=$n^c$=0 and $n^d$=1, or $n^a$=$n^b$=$n^d$=0 and $n^c$=1, ring E and ring D are 1,4-phenylene groups, Lc and Ld are —COO— linkages, and ring C is said general formula (IIb), then at least one of $X^4$, $X^5$ and $X^6$ represents a fluorine atom;

and in a case in which ring C is said general formula (IIb), at least one of $n^c$ and $n^d$ is 1).

2. A tetrahydronaphthalene derivative according to claim 1, wherein in said general formula (I), ring C is represented by said formula (IIa).

3. A tetrahydronaphthalene derivative according to claim 1, wherein in said general formula (I), ring C is represented by said formula (IIb).

4. A tetrahydronaphthalene derivative according to claim 1, wherein in said general formula (I), either one of $n^a$ and $n^b$ is 0.

5. A tetrahydronaphthalene derivative according to claim 1, wherein in said general formula (I), either one of $n^c$ and $n^d$ is 0.

6. A tetrahydronaphthalene derivative according to claim 1, wherein in said general formula (I), $n^a$=$n^b$=0.

7. A tetrahydronaphthalene derivative according to claim 1, wherein in said general formula (I), $n^c$=$n^d$=0.

8. A tetrahydronaphthalene derivative according to claim 1, wherein in said general formula (I), at least one of $n^a$, $n^b$, $n^c$ and $n^d$ is 1.

9. A tetrahydronaphthalene derivative according to claim 1, wherein in said general formula (I), said linkage groups La, Lb, Lc and Ld are each selected independently from a group consisting of a single bond, —$CH_2CH_2$—, and —C≡C—.

10. A tetrahydronaphthalene derivative according to claim 1, wherein in said general formula (I), said linkage groups La, Lb, Lc and Ld are each selected independently from a group consisting of a single bond and —$CH_2CH_2$—.

11. A tetrahydronaphthalene derivative according to claim 1, wherein in said general formula (I), said linkage groups La, Lb, Lc and Ld are each a single bond.

12. A tetrahydronaphthalene derivative according to claim 1, wherein in said general formula (I), ring A, ring B and ring D are each independently selected from a group consisting of a trans-1,4-cyclohexylene group, a trans-decahydronaphthalene-2,6-diyl group, a trans-1,3-dioxane-2,4-diyl group, a 1,4-phenylene group which may be substituted with one or two fluorine atoms, and a naphthalene-2,6-diyl group which may be substituted with one or two fluorine atoms.

13. A tetrahydronaphthalene derivative according to claim 1, wherein in said general formula (I), Z is a fluorine atom.

14. A tetrahydronaphthalene derivative according to claim 1, wherein in said general formula (I), Z is a cyano group.

15. A tetrahydronanhthalene derivative represented by a general formula (I)

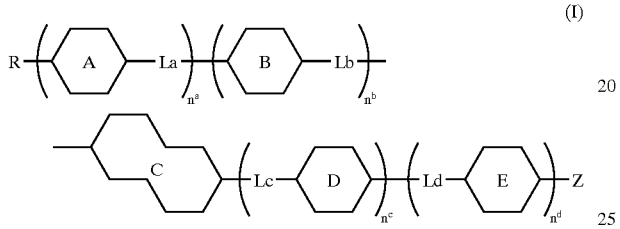

(wherein, R represents a saturated or unsaturated alkyl group or alkoxyl group of 1 to 20 carbon atoms which may incorporate a branched chain and may be substituted with 1 to 7 fluorine atoms or alkoxyl groups of 1 to 7 carbon atoms; linkage groups La, Lb, Lc and Ld each represent independently a single bond, —CH$_2$CH$_2$—, —CH=CH—, —CH(CH$_3$)CH$_2$—, —CH$_2$CH(CH$_3$)—, —CH(CH$_3$)CH(CH$_3$)—, —CF$_2$CF$_2$—, —CF=CF—, —CH$_2$O—, —OCH$_2$—, —OCH(CH$_3$)—, —CH(CH$_3$)O—, —C≡C—, —CF$_2$O—, —OCF$_2$—, —COO—, —OCO—, —COS— or —SCO—; Z represents a fluorine atom, chlorine atom, cyano group, cyanato group, trifluoromethoxy group or a difluoromethoxy group; ring A, rind B and ring D each represent independently a trans-1,4-cyclohexylene group, a trans-decahydronaphthalene-2,6-diyl group, a trans-1,3-dioxane-2,4-diyl group, or a 1,4-phenylene group which may be substituted with one or two fluorine atoms, a pyridine-2,5-diyl group, a pyrimidine-2,5-diyl group, a pyrazine-2,5-diyl group, a pyridazine-3,6-diyl group, and a naphthalene-2,6-diyl group which may be substituted with one or two fluorine atoms; ring E represents independently a 1,4-phenylene group which may be substituted with one or two fluorine atoms, and a naphthalene-2,6-diyl group which may be substituted with one or two fluorine atoms, ring C represents either one of a general formula (IIa) and a general formula (IIb)

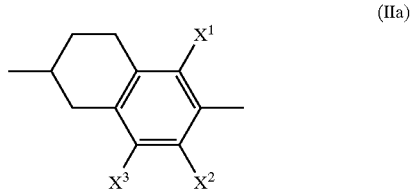

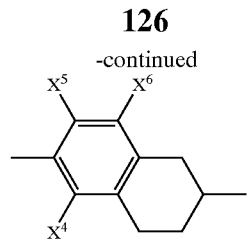

(wherein, $X^1$, $X^2$, $X^3$, $X^4$, $X^5$ and $X^6$ each represent independently a hydrogen atom or a fluorine atom): and $n^a$, $n^b$, $n^c$ and $n^d$ each represent independently either 0 or 1;

although, in a case in which $n^c$=1 and $n^d$=0, ring D represents a 1,4-phenylene group which may be substituted with one or two fluorine atoms and/or a naphthalene-2,6-diyl group which may be substituted with one or two fluorine atoms;

in a case in which Z is a cyano group, R is an unsubstituted and saturated alkyl group or alkoxyl group, $n^a$=$n^c$=$n^d$=0 and $n^b$=1, or $n^b$=$n^c$=$n^d$=0 and $n^a$=1, ring A and ring B are 1,4-phenylene groups, La and Lb are single bonds, and ring C is said general formula (IIa), then at least one of $X^1$, $X^2$ and $X^3$ represents a fluorine atom;

in a case in which Z is a cyano group, R is an unsubstituted and saturated alkyl group or alkoxyl group, $n^a$=$n^b$=$n^c$=0 and $n^d$=1, or $n^a$=$n^b$=$n^d$=0 and $n^c$=1, ring E and ring D are 1,4-phenylene groups, Lc and Ld are single bonds or —COO— linkages, and ring C is said general formula (IIa), then at least one of $X^1$, $X^2$ and $X^3$ represents a fluorine atom;

in a case in which Z is a cyano group, R is an unsubstituted and saturated alkyl group or alkoxyl group, $n^a$=$n^b$=$n^c$=0 and $n^d$=1, or $n^a$=$n^b$=$n^d$=0 and $n^c$=1, ring E and ring D are 1,4-phenylene groups, Lc and Ld are single bonds or —COO— linkages, and ring C is said general formula (IIb), then at least one of $X^4$, $X^5$ and $X^6$ represents a fluorine atom;

in a case in which Z is a fluorine atom, R is an unsubstituted and saturated alkyl group or alkoxyl group $n^a$=$n^b$=$n^c$=0 and $n^d$=1, or $n^a$=$n^b$=$n^d$=0 and $n^c$=1, ring E and ring D are 1,4-phenylene groups, Lc and Ld are —COO— linkages, and ring C is said general formula (IIb), then at least one of $X^4$, $X^5$ and $X^6$ represents a fluorine atom;

and in a case in which ring C is said general formula (IIb), at least one of $n^c$ and $n^d$ is 1), wherein in said general formula (I), Z is a trifluoromethoxy group.

16. A tetrahydronaphthalene derivative according to claim 1, wherein in said general formula (I), R is a saturated or unsaturated alkyl group of 1 to 20 carbon atoms which may incorporate a branched chain and may be substituted with 1 to 7 fluorine atoms or alkoxyl groups of 1 to 7 carbon atoms.

17. A tetrahydronaphthalene derivative according to claim 1, wherein in said general formula (I), R is a saturated or unsaturated straight chain alkyl group of 1 to 20 carbon atoms.

18. A tetrahydronaphthalene derivative according to claim 1, wherein in said general formula (I), $X^3$, $X^4$ and $X^5$ in said formula (IIa) and said formula (IIb) are hydrogen atoms.

19. A tetrahydronaphthalene derivative according to claim 1, wherein in said general formula (I), $X^2$ in said formula (IIa) is a hydrogen atom and $X^1$ is a fluorine atom.

20. A tetrahydronaphthalene derivative according to claim 1, wherein in said general formula (I), $X^1$ in said formula (IIa) is a hydrogen atom and $X^2$ is a fluorine atom.

21. A tetrahydronaphthalene derivative according to claim 1 which shows liquid crystallinity.

22. A tetrahydronaphthalene derivative according to claim 1 which shows a nematic phase.

23. A tetrahydronaphthalene derivative according to claim 1 which upon addition to a nematic liquid crystal composition shows a nematic phase.

24. A liquid crystal composition containing at least one compound of said general formula (I) according to any one of claims 1 through 23.

25. A liquid crystal composition according to claim 24 which can be used for active matrix driving.

26. A liquid crystal element comprising a liquid crystal composition according to claim 25 as a structural element.

27. An active matrix driven liquid crystal display element utilizing a liquid crystal composition according to claim 25.

* * * * *